(12) United States Patent
Gauthier et al.

(10) Patent No.: US 10,577,419 B2
(45) Date of Patent: *Mar. 3, 2020

(54) KIR3DL2 BINDING AGENTS

(71) Applicant: INNATE PHARMA, Marseilles (FR)

(72) Inventors: Laurent Gauthier, Marseilles (FR);
Simon Kollnberger, Headington (GB);
Benjamin Rossi, Marseilles (FR);
Hélène Sicard, Marseilles (FR); Carine Paturel, Marcy l'Étoile (FR);
Stéphanie Cornen, Marseilles (FR);
Stéphanie Zerbib, Marseilles (FR)

(73) Assignee: INNATE PHARMA, Marseilles (FR)

( * ) Notice: Subject to any disclaimer, the term of this patent is extended or adjusted under 35 U.S.C. 154(b) by 646 days.

This patent is subject to a terminal disclaimer.

(21) Appl. No.: 14/662,349

(22) Filed: Mar. 19, 2015

(65) Prior Publication Data

US 2015/0232556 A1     Aug. 20, 2015

Related U.S. Application Data

(63) Continuation-in-part of application No. PCT/EP2013/069302, filed on Sep. 17, 2013.

(60) Provisional application No. 61/702,834, filed on Sep. 19, 2012.

(51) Int. Cl.
| | | |
|---|---|---|
| *C07K 16/28* | (2006.01) | |
| *G01N 33/569* | (2006.01) | |
| *A61K 39/00* | (2006.01) | |

(52) U.S. Cl.
CPC ... *C07K 16/2803* (2013.01); *G01N 33/56966* (2013.01); *G01N 33/56972* (2013.01); *A61K 2039/505* (2013.01); *C07K 2317/33* (2013.01); *C07K 2317/34* (2013.01); *C07K 2317/565* (2013.01); *C07K 2317/732* (2013.01); *C07K 2317/734* (2013.01); *C07K 2317/76* (2013.01); *C07K 2317/77* (2013.01); *G01N 2333/70503* (2013.01); *G01N 2800/24* (2013.01); *G01N 2800/52* (2013.01); *G01N 2800/7095* (2013.01)

(58) Field of Classification Search
None
See application file for complete search history.

(56) References Cited

U.S. PATENT DOCUMENTS

| | | |
|---|---|---|
| 7,399,595 B2 | 7/2008 | Bensussan et al. |
| 7,919,085 B2 | 4/2011 | Bensussan et al. |
| 8,268,308 B2 | 9/2012 | Bensussan et al. |
| 8,518,655 B2 | 8/2013 | Bensussan et al. |
| 9,181,341 B2 | 11/2015 | Anfossi et al. |
| 9,828,427 B2 | 11/2017 | Anfossi et al. |
| 10,174,112 B2 | 1/2019 | Bonnafous et al. |
| 10,246,510 B2 | 4/2019 | Gauthier et al. |
| 10,280,222 B2 | 5/2019 | Gauthier et al. |
| 2012/0064081 A1 | 3/2012 | Anfossi et al. |
| 2019/0127463 A1 | 5/2019 | Bonnafous et al. |
| 2019/0248895 A1 | 8/2019 | Paturel et al. |
| 2019/0276536 A1 | 9/2019 | Gauthier et al. |

FOREIGN PATENT DOCUMENTS

| | | | | |
|---|---|---|---|---|
| WO | WO 02/50122 | 6/2002 | | |
| WO | WO 2010/081890 | 7/2010 | | |
| WO | WO-2010081890 A1 * | 7/2010 | ......... | C07K 16/2803 |
| WO | WO-2012047294 A2 * | 4/2012 | ......... | C07K 16/2833 |

OTHER PUBLICATIONS

Robert W. Bahr, Deputy Commissioner for Patent Examination Policy, Feb. 22, 2018, 2 pages. (Year: 2018).*
Edwards et al. (J. Mol. Biol. (2003) 334, 103-118. (Year: 2003).*
Lloyd et al., Protein Engineering, Design & Selection vol. 22 No. 3 pp. 159-168, 2009. (Year: 2009).*
Meyer et al. (British Journal of Haematology, 2018, 180, 808-820). (Year: 2018).*
Damschroder et al. (Mol Immunol. Aug. 2004;41(10):985-1000). (Year: 2004).*
Bowness et al. (J Immunol. Feb. 15, 2011;186(4):2672-80, and supplemental pp. 1-5). (Year: 2011).*
Kollnberger et al. (Eur. J. Immunol. 2007. 37: 1313-1322). (Year: 2007).*
Hatano et al. (J Immunol 2015; 194:1591-1601 and supplemental pp. 1-4). (Year: 2015).*
Ridley et al. (Arthritis & Rheumatology vol. 68, No. 4, Apr. 2016, pp. 901-914). (Year: 2016).*
Harlow et al. (Antibodies, A Laboratory Manual, Cold Spring Harbor laboratory, 1988, pp. 37-47). (Year: 1988).*
Pende, D. et al. "The Natural Killer Cell Receptor Specific for HLA-A Allotypes: A Novel Member of the p58/p70 Family of Inhibitory Receptors That Is Characterized by Three Immunoglobulin-like Domains and Is Expressed as a 140-kD Disulphide-linked Dimer" *Journal of Experimental Medicine*, Aug. 1, 1996, pp. 505-518, vol. 184, No. 2.
Brando, C. et al. "Receptors and lytic mediators regulating anti-tumor activity by the leukemic killer T cell line TALL-104" *Journal of Leukocyte Biology*, Aug. 2005, pp. 359-371, vol. 78, No. 2.
Bagot, M. et al. "Les lymphomes T epidermotropes comme modeles de progression tumorale" *Medicine/Sciences*, Feb. 2006, pp. 192-196, vol. 22, No. 2.
Marie-Cardine, A. et al. "Novel therapeutic and diagnostic antibodies against KIR3DL2, a unique tumor antigen overexpressed on subtypes of T cell lymphomas" *Journal of ImmunoTherapy of Cancer*, Nov. 7, 2013, p. P45, vol. 1, Suppl. 1.
Claims as filed for U.S. Appl. No. 16/398,472, dated Apr. 30, 2019, pp. 1-4.

* cited by examiner

*Primary Examiner* — Zachary S Skelding
(74) *Attorney, Agent, or Firm* — Saliwanchik, Lloyd & Eisenschenk

(57) ABSTRACT

The present invention relates to methods for the treatment of cancer and inflammatory disease using antibodies (e.g. monoclonal antibodies), antibody fragments, and derivatives thereof that specifically bind KIR3DL2. The invention also relates to antibodies, cells producing such antibodies; methods of making such antibodies; fragments, variants, and derivatives of the antibodies; pharmaceutical compositions comprising the same.

10 Claims, 23 Drawing Sheets
(11 of 23 Drawing Sheet(s) Filed in Color)
Specification includes a Sequence Listing.

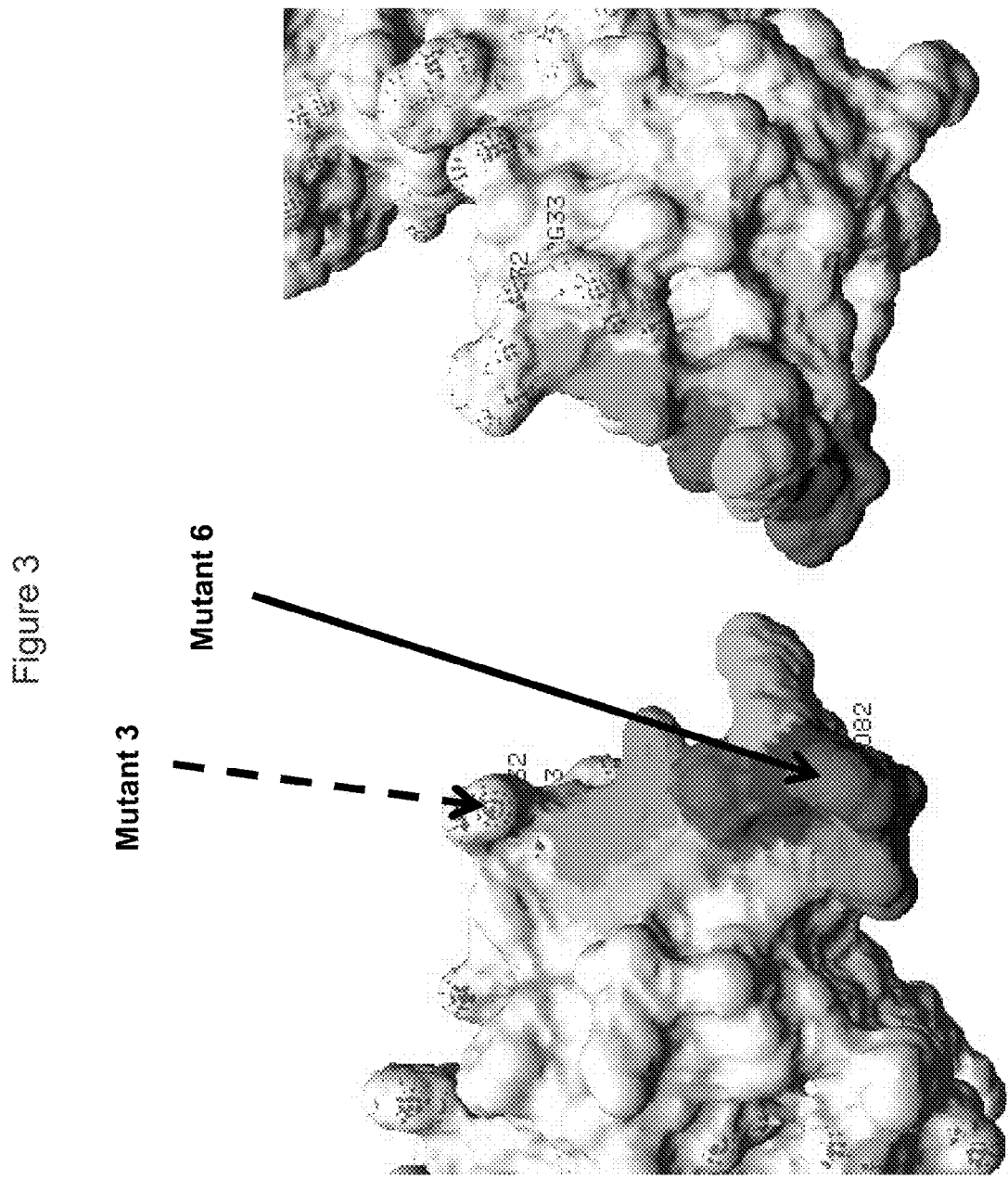

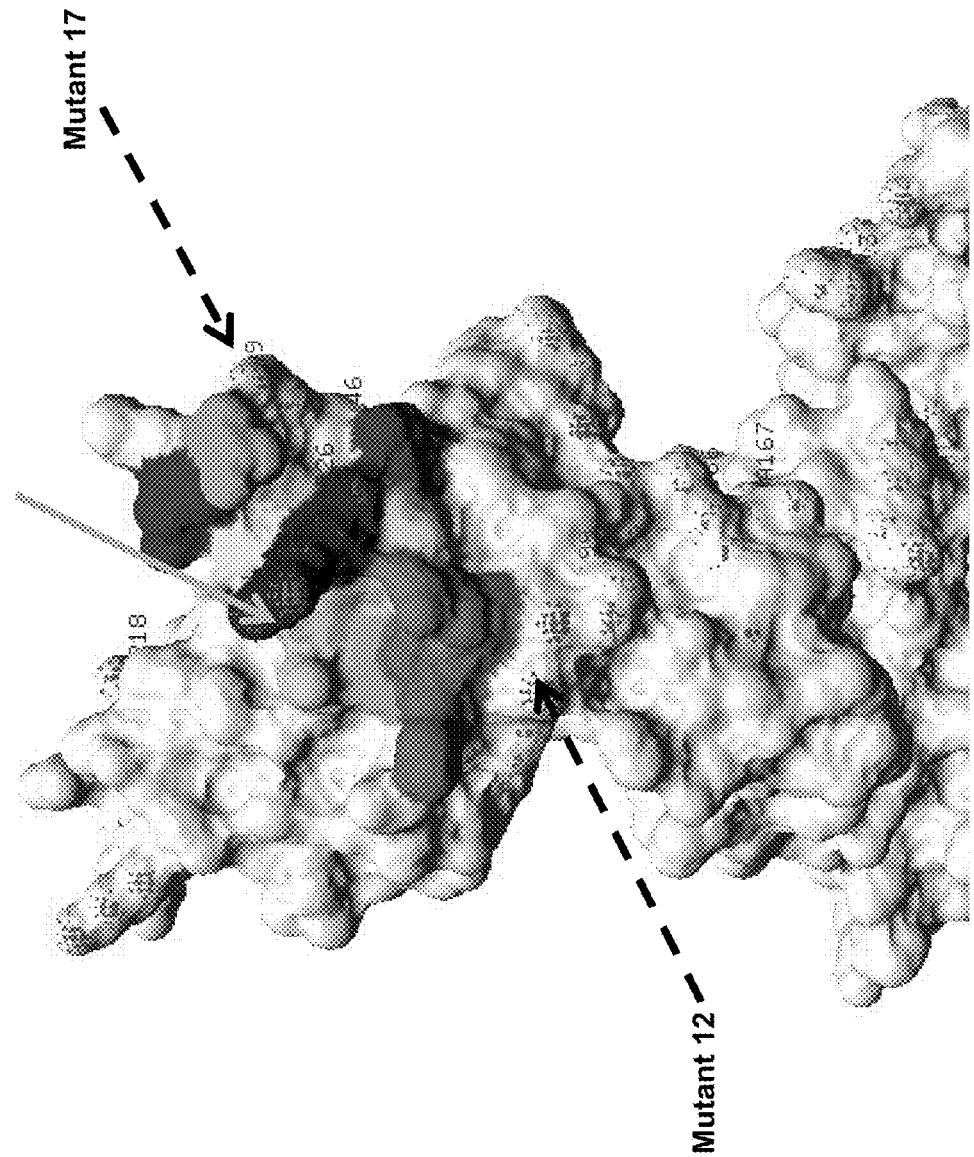

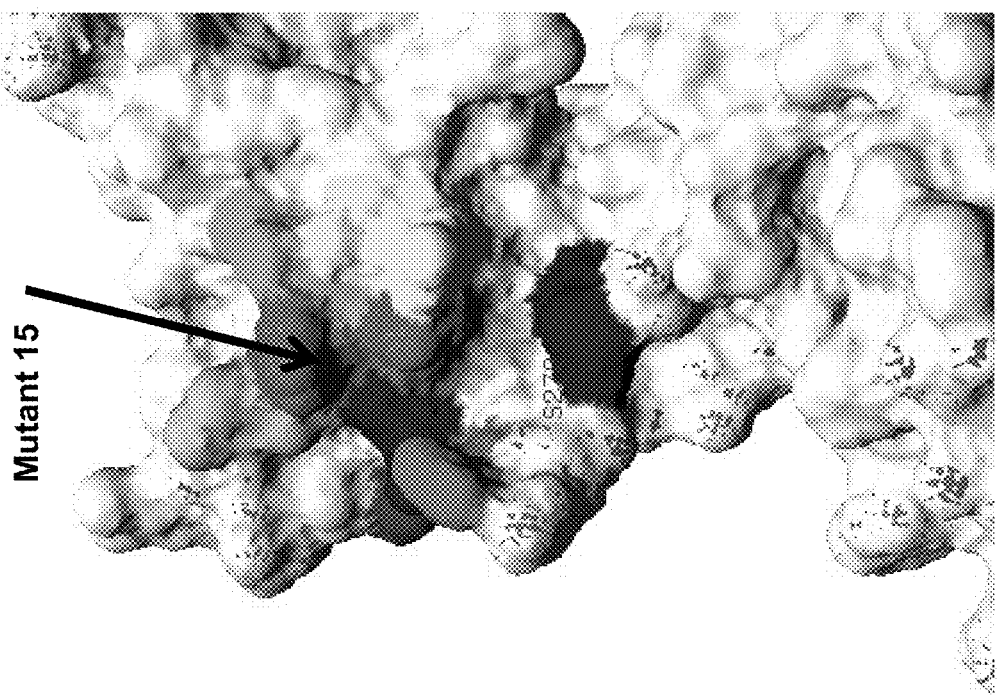

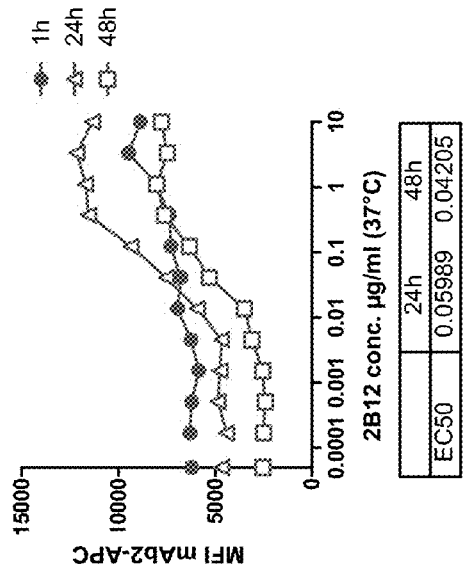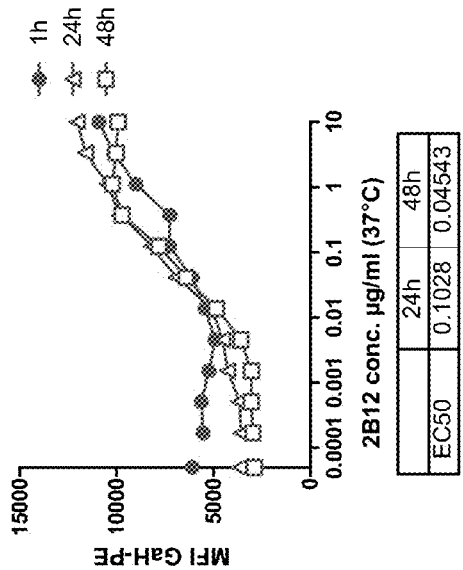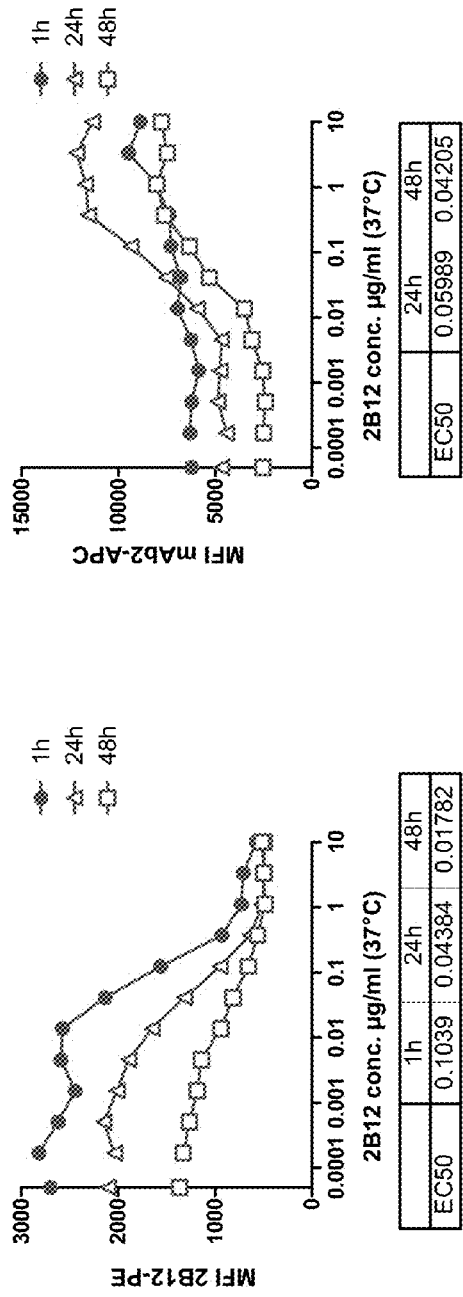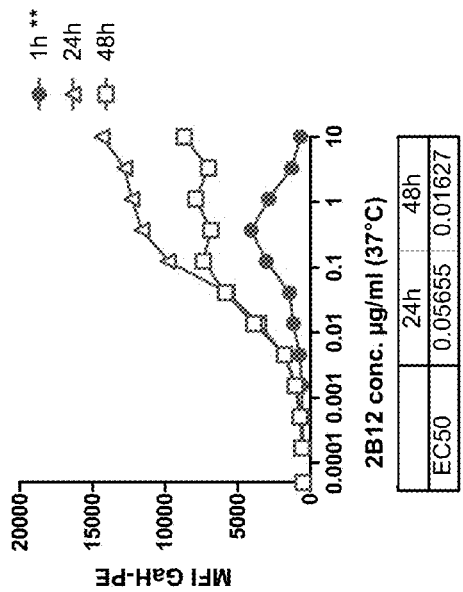
Figure 6C

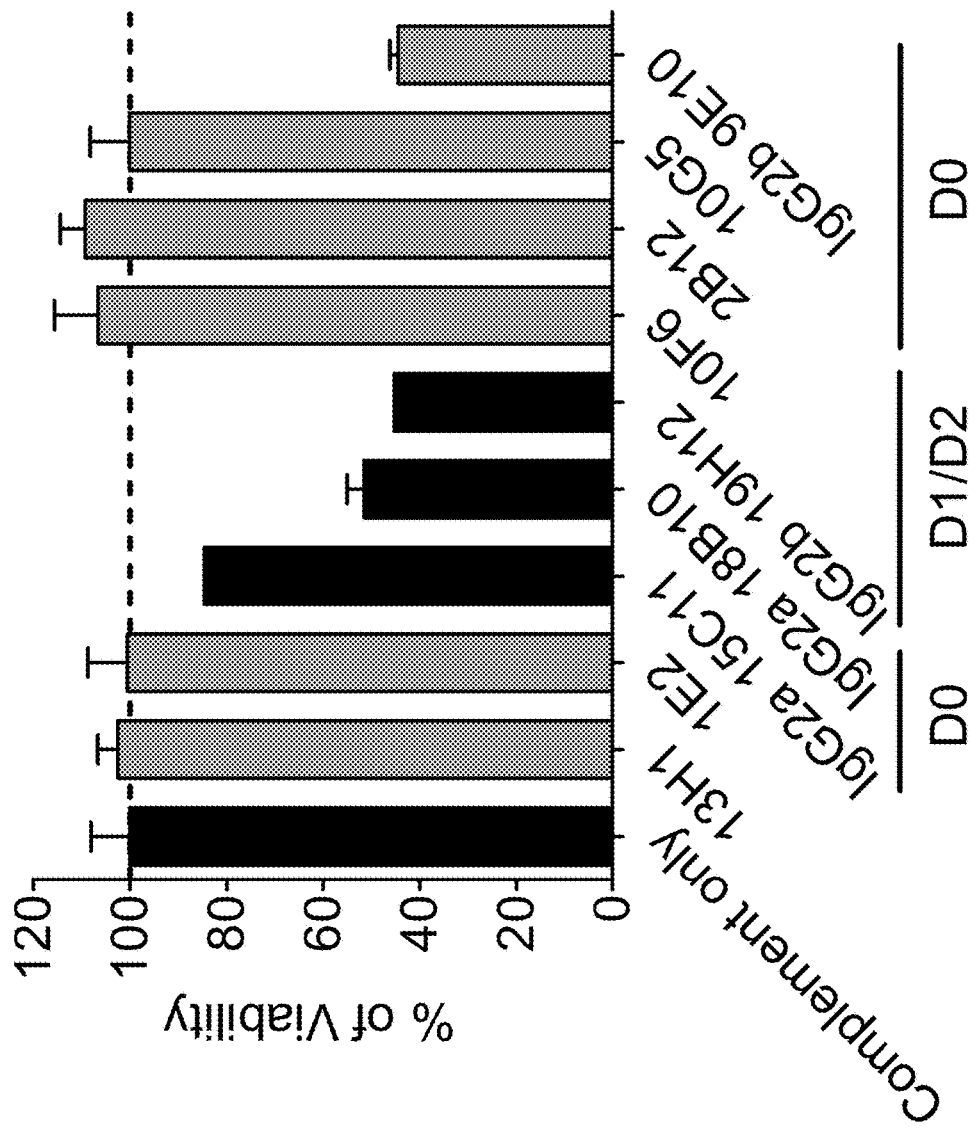

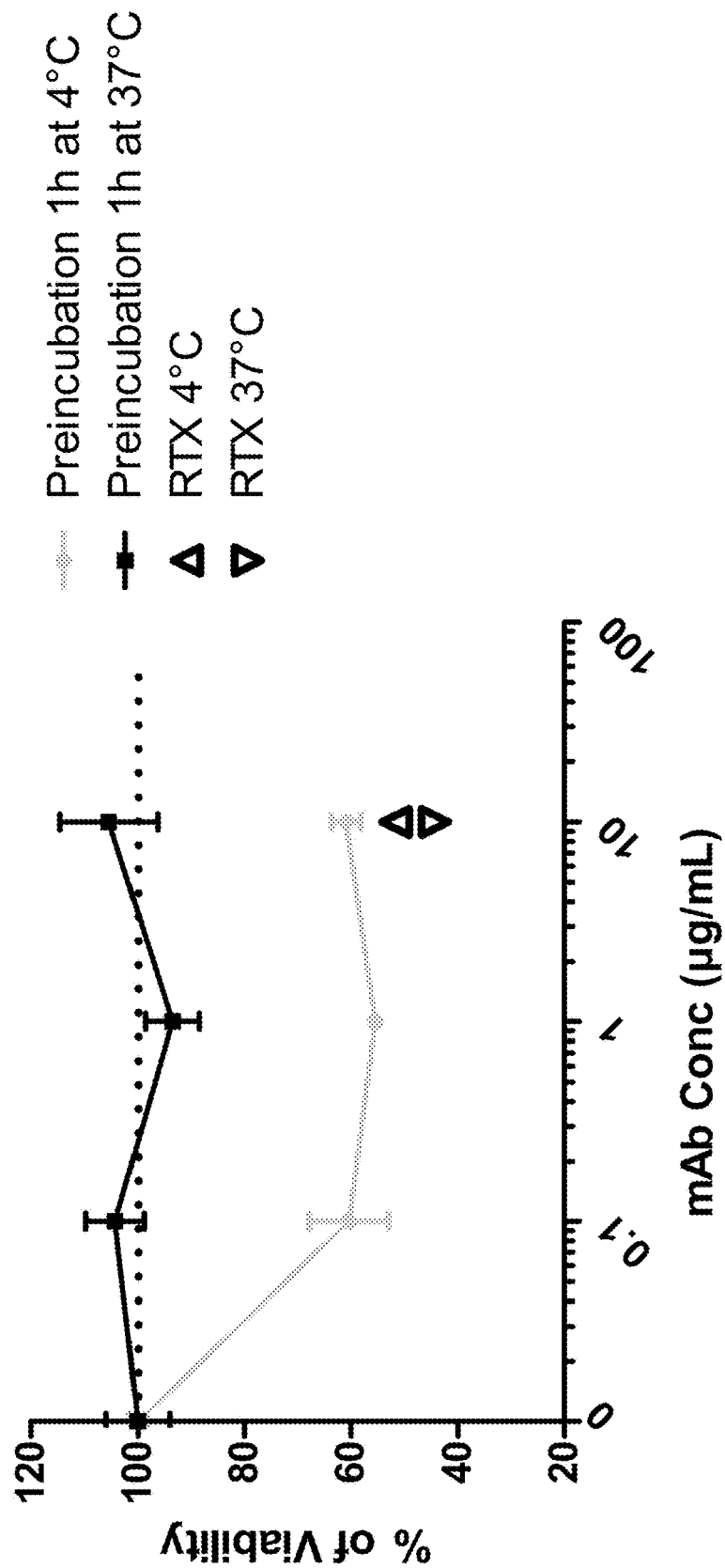

KIR3DL2 BINDING AGENTS

CROSS-REFERENCE TO RELATED APPLICATIONS

This application is a continuation-in-part of International Application No.PCT/EP2013/069302 filed Sep. 17, 2013, which claims the benefit of U.S. Provisional Application No. 61/702,834, filed Sep. 19, 2012, the disclosures of which are incorporated herein by reference in their entireties; including any drawings.

FIELD OF THE INVENTION

The present invention provides antigen-binding proteins capable of binding to KIR3DL2 polypeptides. The antibodies have increased activity in the treatment of disorders characterized by KIR3DL2-expressing cells, particularly CD4+ T cells, including malignancies such as Mycosis Fungoides and Sézary Syndrome, and KIR3DL2-expressing autoimmune disorders.

REFERENCE TO SEQUENCE LISTING

The Sequence Listing for this application is labeled "Seq-List-replace.txt" which was created on Dec. 26, 2017 and is 91 KB. The entire content of the sequence listing is incorporated herein by reference in its entirety.

BACKGROUND

Killer immunoglobulin-like receptors (KIR) are a family of receptors that, along with C-type lectin receptors (CD94-NKG2), are used by human NK cells and T-lymphocyte subsets to specifically recognize MHC class I molecules. Certain inhibitory and activating KIR have highly similar extracellular domains and are recognized by the same monoclonal antibody, e.g. KIR2DL1 and KIR2DS1 are both recognized by EB6, and 2DL2 and 2DS2 by GL183. Three criteria (number of extracellular Ig-like domains (domains D0, D1, D2), cytoplasmic tail length, and sequence analogy) have been used to categories the KIR proteins into 13 groups, namely KIR3DL1-2, KIR3DS1, KIR2DL1-5, and KIR2DS1-5. The nomenclature 2D for 2 domains or 3D for 3 domains give the number of Ig-like domains; receptors with either long or short cytoplasmic domains are further classified as L or S. (Pascal V. et al., 2007 J. Immunol. 179:1625-1633) The inhibitory receptors possess long (L) cytoplasmic tails (i.e., KIR2DL or KIR3DL) containing a canonical MM that becomes tyrosine phosphorylated upon KIR engagement of their HLA class I ligands. The phosphorylated mM recruits the Src homology 2 domain containing protein tyrosine phosphatases Src homology 2 domain-containing phosphatase 1 and/or Src homology 2 domain-containing phosphatase 2, which dephosphorylate cellular substrates, thus aborting the NK activation signal, i.e., sparing target cells with appropriate self-MHC class I expression. Receptors with short (S) cytoplasmic tails lack ITIMs (i.e., KIR2DS or KIR3DS). These activating KIR contain a charged residue within their transmembrane domain facilitating interaction with the signaling chain KARAP/DAP12. Engagement of the KIR2DS family of receptors has been shown to lead to a cascade of KARAP/DAP12-mediated signaling events culminating in increased NK cell cytolytic activity and the production of proinflammatory cytokines such as IFN-7 (Pascal et al. 2007) J. Immunol. 179: 1625-1633). Mature NK cells are predicted to acquire at least one inhibitory receptor specific for a self-MHC class I molecule, which generally functionally prevails over potentially auto-reactive activating molecules. It is proposed that the response of NK cells represents the integrated outcome of both activating and inhibitory signaling by KIR and other receptors.

KIR3DL2 has been studied as a target for the treatment of malignancies involving CD4+ T cells that express KIR3DL2 receptors, particularly CD4+ T cells, including malignancies such as Mycosis Fungoides and Sézary Syndrome (see, e.g. PCT publications WO2010/081890 and WO002/50122).

A ligand of KIR3DL2, HLA-B27, is strongly associated with the Spondyloarthritis (SpA) a group of debilitating inflammatory arthritic disorders typified by Ankylosing Spondylitis (AS). Genome wide association studies have strongly implicated genes involved in the regulation of IL-17 produced by Th17 cells in SpA (Reveille, et al. (2011) *Nat Genet* 43:761-767.). IL17 has been implicated in diverse autoimmune disorders including SpA (Shen, et al. (2009) *Arthritis Rheum* 60:1647-1656; Wendling, et al. (2007) *Joint Bone Spine* 74:304-305). HLA-B27 (B27) is expressed at the surface of antigen expressing cells (APC) in disease both as classical β2m-associated heterotrimers and non-canonical β2m-free disulphide bonded heavy chain dimers (termed B27$_2$) (Bird, et al. (2003) *Eur J Immunol* 33:748-759; Kollnberger, et al. (2002) *Arthritis Rheum* 46:2972-2982). B27 dimers but not B27 heterotrimers are ligands for the killer cell immunoglobulin-like receptor KIR3DL2 (Kollnberger et al. (2002)). The three immunoglobulin-like domains D0 D1 and D2 of KIR3DL2 are involved in binding ligand. KIR3DL2 ligation by B27 dimers promotes the survival of Th17 and NK cell subsets (Bowness, et al. (2011) *Journal of immunology* 186:2672-2680; Chan, et al. (2005) *Arthritis Rheum* 52:3586-3595). It has been shown that that there are increased proportions of pathogenic Th17 and NK cell subsets expressing KIR3DL2 in patients with SpA Bowness et al. (2011) and Chan et al. (2005). Studies strongly suggest that KIR3DL2-B27 interactions have a central role to play in SpA and that KIR3DL2 is a promising therapeutic target.

The existence of antibodies reactive against various KIR3D polypeptides have been reported. The existence of two anti-KIR3DL2 antibodies have been reported: Q241 and Q66 (Pende, et al. (1996) J Exp Med 184:505-518). However, these two antibodies are of the IgM isotype (pentamers) and are not readily suited to pharmaceutical use; furthermore, if their variable regions were placed in the context of a bivalent IgG type antibody, their affinity would be expected to be low. Cells referred to as "AZ158" producing a further antibody was reported (Parolini, S., et al. (2002) In Leucocyte typing VII. D. Mason, editor. Oxford University Press, Oxford. 415-417; PCT publication WO2010/081890). Antibody 5.133 is available from Miltenty Biotech (Auburn Calif.). Both antibodies AZ158 and 5.133 bind KIR3DL2 as well as KIR3DL1 (and further the highly homologous KIR3DS1). KIR3DL2 and KIR3DL1 share relatively high amino acid identity and various HLA ligands that bind KIR3DL2 are also recognized by KIR3DL1. Despite immunizations that gave rise to AZ158, Q241 and Q66, there is a need for improved antibodies in therapeutic and other applications.

SUMMARY OF THE INVENTION

In one aspect, the present invention results, inter alia, from the discovery that KIR3DL2 can internalize when bound to an antibody. We in turn identify a range of anti-KIR3DL2 mAbs that do not internalize. It is demonstrated that KIR3DL2 internalization strongly hampers ADCC-based approaches. In addition, the antibodies are selective for human KIR3DL2 and do not bind the closely related human KIR3DL1 and/or human KIR3DS1 receptors.

We further provide anti-KIR3DL2 antibodies that are capable of causing an increase of cell surface KIR3DL2 polypeptide available for binding by an anti-KIR3DL2 antibody, notably on malignant cells. The antibodies may, in one embodiment, increase the level of expression of KIR3DL2 polypeptides on the cell surface (e.g. of malignant cells). The antibodies may, in one embodiment, increase the amount or number of KIR3DL2 polypeptides on the cell surface available for binding by an anti-KIR3DL antibody. The antibodies may, in one embodiment, stabilize and/or cause accumulation of KIR3DL2 polypeptides present on the cell surface, e.g., they may decrease receptor cycling or internalization of KIR3DL2 polypeptides. Antibodies that increase cell surface KIR3DL2, e.g. on pathogenic CD4+ T cells, have increased potency because they permit a greater number of antibodies to be bound to a KIR3DL2-expressing cell (e.g. target cell, malignant cell). In one embodiment, provided is an isolated monoclonal antibody that binds a KIR3DL2 polypeptide on the surface of a KIR3DL2-expressing cell, wherein the antibody causes an increase of the amount or numbers of KIR3DL2 polypeptides detectable at the cell surface after being in contact with cells (in vivo or in vitro) for at least 1 hour, 3 hours, 6 hours, 12 hours or 24 hours. The increase can be in comparison to a control antibody, e.g. an isotype control, or another antibody that binds KIR3DL2 (e.g. an antibody that has a different heavy and/or light chain variable region amino acid sequence).

Here we also provide anti-KIR3DL2 antibodies that inhibit B27 dimer interactions with KIR3DL2. Notably, ligand blockade can be achieved without causing receptor internalization. We also provide antibodies that selectively block KIR3DL2-HLA B27 interactions without blocking KIR3DL2-HLA-A3 interactions.

Provided are antibodies that bind the major (in terms of frequencies in human populations) KIR3DL2 alleles, yet without binding to the closely related KIR3DL1 polypeptide (e.g. allele *00101 comprising the amino acid sequence shown in SEQ ID NO: 169). In one embodiment, the antibodies bind to 1, 2, 3, 4 or 5 or more of the KIR3DL2 polypeptides (e.g., alleles *002, *003, *005, *007, and/or *008) of SEQ ID NOS: 1 and 159 to 168. Consequently, provided are antibodies having the advantageous functional properties described herein, and that can be administered for the treatment of disease substantially across the human population, e.g. without the need to conduct diagnostic tests to assess the KIR3DL2 allele expressed in an individual.

Also provided, through the study of antibodies' epitopes, are regions on KIR3DL2 (in the D0 domain and D2 domain) that can be targeted by antibodies to give rise to advantageous properties.

In one aspect, the antibodies furthermore have the additional advantage of binding to multiple alleles of human KIR3DL2 while maintaining KIR3DL2 specificity over KIR3DL1.

Provided are antibodies that have the advantage of blocking KIR3DL2's natural ligands and that are thus well-suited for treating or preventing inflammatory disorders, either as a depleting or non-depleting mAb format. Furthermore, different epitopes provide different ligand blocking specificity.

Also provided are antibodies, including non-internalizing antibodies, that do not block KIR3DL2 ligands (HLA-A3 and HLA-B27); these antibodies may be advantageous in ADCC-based approaches where it may be helpful to avoid competition with ligands.

In one embodiment, provided is an antibody that binds a KIR3DL2 polypeptide, wherein said antibody does not substantially bind to a KIR3DL1 polypeptide (e.g. wherein the KIR3DL1 polypeptide comprises an amino acid sequence of SEQ ID NO: 169), and wherein said antibody is not internalized into KIR3DL2-expressing cells.

In one embodiment, provided is an antibody that binds at least two KIR3DL2 polypeptides (alleles), and wherein said antibody does not substantially bind to a KIR3DL1 polypeptide (e.g. KIR3DL1 allele *00101 comprising the amino acid sequence shown in SEQ ID NO: 169).

In one embodiment, the antibodies bind to 1, 2, 3, 4 or 5 of the KIR3DL2 polypeptides (alleles *002, *003, *005, *007, and/or *008) of SEQ ID NOS: 1, 161, 163, 165 and/or 166.

In one embodiment, the antibodies bind to each of the KIR3DL2 polypeptides having the amino acid sequence shown in SEQ ID NOS: 1, 171 and 176 (alleles_*002, *001 and *007, respectively). In one embodiment, the antibodies bind to each of the KIR3DL2 polypeptides having the amino acid sequence shown in SEQ ID NOS: 171 and 178 (alleles_*001 and *009, respectively). In one embodiment, the antibodies bind to each of the KIR3DL2 polypeptides having the amino acid sequence shown in SEQ ID NOS: 171, 1, 176 and 178 (alleles_*001, *002, *007 and *009, respectively). In one embodiment, the antibodies bind to each of the KIR3DL2 polypeptides having the amino acid sequence shown in SEQ ID NOS: 171, 1, 172, 174 and 176 (alleles_*001, *002, *003, *005 and *007, respectively). In one embodiment, the antibodies bind to each of the KIR3DL2 polypeptides having the amino acid sequence shown in SEQ ID NOS: 171, 1, 176 and 177 (alleles_*001, *002, *007 and *008, respectively). In one embodiment, the antibodies bind to each of the KIR3DL2 polypeptides having the amino acid sequence shown in SEQ ID NOS: 171, 1, 172, 174, 176 and 177 (alleles_*001, *002, *003, *005, *007 and *008, respectively). In one embodiment of any of the foregoing, the antibodies further bind a KIR3DL2 polypeptide having the amino acid sequence shown in SEQ ID NO: 178 (allele *09). In one embodiment of any of the foregoing, the antibodies further bind a KIR3DL2 polypeptide having the amino acid sequence shown in SEQ ID NO: 173 (allele *004). In one embodiment of any of the foregoing, the antibodies further bind a KIR3DL2 polypeptide allele *010 (having the same extracellular domain of SEQ ID NO: 171 as *001). In one embodiment of any of the foregoing, the antibodies further bind a KIR3DL2 polypeptide allele *011 (having the same extracellular domain (of SEQ ID NO: 179) as *003). In one embodiment of any of the foregoing, the antibodies further bind a KIR3DL2 polypeptide allele *006. Optionally, in each case, the antibody binds to said KIR3DL2 polypeptide expressed on the surface of a cell (e.g. a reporter cell line, wherein KIR3DL2 is in native conformation). Optionally the antibody binds a conformational epitope.

Optionally, in each case, the antibody binds to said KIR3DL2 polypeptide expressed on the surface of a cell with binding affinity ($K_D$), optionally wherein binding affinity is bivalent, for a human KIR3DL2 polypeptide at less than $10^{-8}$ M, preferably less than $10^{-9}$ M, or preferably less than $10^{-10}$M. Preferably the antibody binds a conformational epitope on KIR3DL2.

In one embodiment, provided is an antibody that binds to an amino acid residue in the D0 or D2 domain of a KIR3DL2 polypeptide, and wherein said antibody does not substantially bind to a KIR3DL1 polypeptide.

Optionally, the antibody has binding affinity ($K_D$), optionally wherein binding affinity is bivalent, for a human KIR3DL2 polypeptide of less than (i.e., better affinity than) $10^{-8}$ M, preferably less than $10^{-9}$ M, or preferably less than $10^{-10}$M.

Optionally, the antibodies have an EC50 of no more than 5 μg/ml, optionally no more than 3 μg/ml, no more than 2 μg/ml, no more than 1 μg/ml or no more than 0.5 μg/ml for binding to cells made to express at their surface a particular KIR3DL2 allele (e.g. alleles_*001, *002, *003, *005, *007 and/or *008).

In one aspect provided are antibodies that bind the KIR3DL2 polypeptide in the ligand (HLA) binding region (e.g. HLA binding pocket) or at least partly on the HLA binding face of KIR3DL2 protein.

Preferably, in any of the embodiments herein, provided is an antibody binds to an amino acid residue within the D0 domain (residues 1 to 98 of SEQ ID NO: 1) and/or the D2 domain (residues 193 to 292 of SEQ ID NO: 1) of a KIR3DL2 polypeptide. Optionally, binding of the antibody to a KIR3DL2 polypeptide having a mutation at a residue within the D0 and/or D2 domain is substantially reduced, in comparison to binding to a wild-type KIR3DL2 polypeptide of SEQ ID NO: 1.

In one aspect, the antibodies bind an epitope comprising one, two, three, four, five or more of residues selected from the group consisting of: R13, P14, S15, H23, A25, Q27, I60 and G62 (with reference to SEQ ID NO: 1), and/or the antibodies have reduced binding to a KIR3DL2 polypeptide having a mutation at a residue selected from the group consisting of: R13, P14, S15, H23, A25, Q27, I60 and G62 (with reference to SEQ ID NO: 1).

The shorthand notation used for mutations herein is: wild type residue: position in polypeptide, with numbering of residues as indicated in SEQ ID NO: 1: mutant residue.

In one aspect provided are antibodies that bind an epitope comprising residues R13, A25 and/or Q27 of the KIR3DL2 polypeptide, and/or have reduced binding to a KIR3DL2 polypeptide having a mutation at residues R13, A25 and/or Q27 (with reference to SEQ ID NO: 1). For example, an antibody can have reduced binding to a KIR3DL2 polypeptide having the mutations R13W, A25T and/or Q27R. Optionally, the epitope additionally comprises one or more of residues I60 and/or G62 (with reference to SEQ ID NO: 1), and/or the antibodies have reduced binding to a KIR3DL2 polypeptide having a mutation at residues I60 and/or G62 (with reference to SEQ ID NO: 1, e.g. I60N, G62S). Optionally, the epitope additionally or alternatively comprises one or more of residues P14, S15 and/or H23 (with reference to SEQ ID NO: 1), and/or the antibodies have reduced binding to a KIR3DL2 polypeptide having a mutation at residues P14, S15 and/or H23 (with reference to SEQ ID NO: 1, e.g. P14S, S15A, H23S). Optionally, the epitope does not comprise residues R32 and/or G33 (with reference to SEQ ID NO: 1), and/or the antibodies do not have reduced binding to a KIR3DL2 polypeptide having a mutation at residues R32 and/or G33 (with reference to SEQ ID NO: 1, e.g., R32H and/or G33R). Optionally, the epitope does not comprises of residues F50 and/or R53 (with reference to SEQ ID NO: 1), and/or the antibodies do not have reduced binding to a KIR3DL2 polypeptide having a mutation at residues F50 and/or R53 (with reference to SEQ ID NO: 1, e.g., F50A, R53S). The antibody may (e.g. antibodies that block the KIR3DL2-HLA B27 and -HLA A3 interactions) or may not (e.g. non-internalizing antibodies) bind to residues Q56 and/or E57, and/or residues F9 and/or S11; thus, in one embodiment, optionally, the epitope does not comprise residues F9, S11, Q56 and/or E57 (with reference to SEQ ID NO: 1), and/or the antibodies do not have reduced binding to a KIR3DL2 polypeptide having a mutation at residues F9, S11, Q56 and/or E57 (with reference to SEQ ID NO: 1, e.g., F9S and S11A, Q56S and E57A); in another embodiment, optionally, the epitope comprises residues F9, S11, Q56 and/or E57 (with reference to SEQ ID NO: 1), and/or the antibodies have reduced binding to a KIR3DL2 polypeptide having a mutation at residues F9, S11, Q56 and/or E57 (with reference to SEQ ID NO: 1, e.g., F9S and S11A, Q56S and E57A). Optionally, the epitope does not comprise residues H29 and/or F34 (with reference to SEQ ID NO: 1), and/or the antibodies do not have reduced binding to a KIR3DL2 polypeptide having a mutation at residues H29 and/or F34 (with reference to SEQ ID NO: 1, e.g., H29S, F34A). Optionally, the epitope does not comprises one or more of residues F9 and/or S11 (with reference to SEQ ID NO: 1), and/or the antibodies do not have reduced binding to a KIR3DL2 polypeptide having a mutation at residues F9 and/or S11 (with reference to SEQ ID NO: 1, e.g., F9S, S11A).

In one aspect provided are antibodies that bind an epitope comprising residues I60 and/or G62 of the KIR3DL2 polypeptide of SEQ ID NO: 1, and/or have reduced binding to a KIR3DL2 polypeptide having a mutation at residues I60 and/or G62 (with reference to SEQ ID NO: 1). For example, an antibody can have reduced binding to a KIR3DL2 polypeptide having the mutations I60N and/or G62S. Optionally, the epitope additionally or alternatively comprises one or more of residues P14, S15 and/or H23 (with reference to SEQ ID NO: 1), and/or the antibodies have reduced binding to a KIR3DL2 polypeptide having a mutation at residues P14, S15 and/or H23 (with reference to SEQ ID NO: 1, e.g. P14S, S15A, H23S). Optionally, the antibodies do not bind residues R13, A25 and/or Q27 of the KIR3DL2 polypeptide, and/or do not have reduced binding to a KIR3DL2 polypeptide having a mutation at residues R13, A25 and/or Q27 (e.g., a KIR3DL2 polypeptide having the mutations R13W, A25T and/or Q27R).

In one aspect provided are antibodies that bind an epitope comprising residues P14, S15 and/or H23 of the KIR3DL2 polypeptide of SEQ ID NO: 1, and/or have reduced binding to a KIR3DL2 polypeptide having a mutation at residues P14, S15 and/or H23 (with reference to SEQ ID NO: 1, e.g. P14S, S15A, H23S).

In one aspect, provided are antibodies that have reduced binding to (1) a KIR3DL2 polypeptide having a mutation at residues I60 and/or G62 (with reference to SEQ ID NO: 1, e.g. I60N, G62S), and (2) a KIR3DL2 polypeptide having a mutation at residues P14, S15 and/or H23 (with reference to SEQ ID NO: 1, e.g. P14S, S15A, H23S).

In one aspect, provided are antibodies that bind an epitope comprising: (a) 1, 2 or 3 of residues R13, A25 and/or Q27 and (b) one or both of residues I60 and/or G62 of the KIR3DL2 polypeptide. In one aspect antibodies have reduced binding to a KIR3DL2 polypeptide having: (a) a mutation at 1, 2 or 3 of residues R13, A25 and/or Q27, and (b) a mutation at one or both of residues I60 and/or G62.

In one aspect, provided are antibodies that bind an epitope comprising residues R78 and/or L82 of the KIR3DL2 polypeptide of SEQ ID NO: 1, and/or have reduced binding to a KIR3DL2 polypeptide having a mutation at residues R78 and/or L82 (with reference to SEQ ID NO: 1). For example, an antibody can have reduced binding to a KIR3DL2 polypeptide having the mutations R78H and L82P. Optionally, the epitope additionally comprises, or excludes, one or more of residues K7, Y30, R31, P79, H80, S81, T83, G84, W85, S86 and/or A87 (with reference to SEQ ID NO: 1), and/or the antibodies have reduced binding to, or does not have reduced binding to, a KIR3DL2 polypeptide having a mutation at residues K7, Y30, R31, P79, H80, S81, T83, G84, W85, S86 and/or A87 (with reference to SEQ ID NO: 1). In one embodiment, the antibodies bind an epitope comprising 1, 2, 3, 4, 5, 6, 7 or more residues in the segment corresponding to residues 1 to 98 of the KIR3DL2 polypeptide (with reference to SEQ ID NO: 1), optionally further wherein the epitope comprises one or more (e.g. 1, 2, 3, 4, 5) of residues K7, Y30, R31, R78, P79, H80, S81, L82, T83, G84, W85, S86 and/or A87.

In one aspect, provided are antibodies that bind an epitope comprising residues W226 of the KIR3DL2 polypeptide of SEQ ID NO: 1, and/or have reduced binding to a KIR3DL2 polypeptide having a mutation at residues W226 (with reference to SEQ ID NO: 1). Optionally, the epitope additionally comprises one or more of residues I231 and/or R246 (with reference to SEQ ID NO: 1), and/or the antibodies have reduced binding to a KIR3DL2 polypeptide having a mutation at residues I231 and/or R246 (with reference to SEQ ID NO: 1, e.g., I231M, R246P). Optionally, the epitope additionally comprises residue E239 (with reference to SEQ ID NO: 1), and/or the antibodies have reduced binding to a KIR3DL2 polypeptide having a mutation at residue E239 (with reference to SEQ ID NO: 1, e.g., E239G).

In one aspect, provided are antibodies that bind an epitope comprising residues I231 and/or R246 of the KIR3DL2 polypeptide of SEQ ID NO: 1, and/or have reduced binding to a KIR3DL2 polypeptide having a mutation at residues I231 and/or R246 (with reference to SEQ ID NO: 1).

In one aspect, provided are antibodies that bind an epitope comprising residue W226 and one or both of residues I231 and/or R246 of the KIR3DL2 polypeptide.

In one aspect antibodies have reduced binding to a KIR3DL2 polypeptide having a mutation at residues W226 and a mutation at one or both of residues I231 and/or R246.

In any embodiment herein, the antibody optionally does not cause the internalization of KIR3DL2 polypeptides in KIR3DL2-expressing cells and/or is not internalized into KIR3DL2-expressing cells.

In one embodiment, provided is an antibody that binds a KIR3DL2 polypeptide, wherein said antibody detectably reduces (or eliminates) binding between the KIR3DL2 and an HLA natural ligand of KIR3DL2. In one embodiment, provided is an antibody that binds a KIR3DL2 polypeptide, wherein said antibody detectably reduces (or eliminates) binding between the KIR3DL2 and a first HLA natural ligand of KIR3DL2 but does not detectably reduce (or eliminate) binding between the KIR3DL2 and a second HLA natural ligand of KIR3DL2.

In one embodiment, the antibody optionally detectably reduces binding between the KIR3DL2 and an HLA class I-ligand of KIR3DL2 (e.g. HLA-B27, HLA-A3, HLA-B7, HLA-B35 and/or HLA-A2).

In one embodiment, the antibody optionally detectably reduces binding between the KIR3DL2 and HLA-B27 but does not detectably reduce binding between KIR3DL2 and HLA-A3.

In one embodiment, the antibody optionally detectably reduces binding between the KIR3DL2 and HLA-A3 but does not detectably reduce binding between KIR3DL2 and HLA-B27.

In one embodiment, the antibody optionally does not detectably reduce binding between the KIR3DL2 and HLA-B27, or between KIR3DL2 and HLA-A3.

In one embodiment, the antibody optionally antibody binds at least two KIR3DL2 polypeptides (alleles) having different amino acid sequences.

In one embodiment, the antibody optionally antibody does not substantially bind to a KIR3DL1 polypeptide.

In embodiments herein for ligand-blocking antibodies and/or for antibodies that bind an epitope comprising residues H32 and/or G33 of the KIR3DL2 polypeptide, the antibody may optionally cause the internalization of KIR3DL2 polypeptides in KIR3DL2-expressing cells and/or is internalized into KIR3DL2-expressing cells.

An anti-KIR3DL2 antibody can be useful for the treatment of cancers, inflammatory disorders and autoimmune disorders, e.g. in human subjects. This antibody can be used with or without coupling to a toxic or other agent, depending on the desired effect or use made of the antibodies. In one embodiment, the anti-KIR3DL2 antibody is a "naked antibody" and is not coupled to a toxic agent. In one embodiment, a naked or coupled antibody comprises a heavy chain comprising a Fc region (e.g. IgG1) that binds Fcγ receptors (e.g. CD16). Optionally wherein such antibody induces complement dependent cytotoxicity (CDC) and/or antibody dependent cellular cytotoxicity (ADCC) toward a cell that expresses KIR3DL2. Optionally, in one embodiment, when the antibody is used for the treatment of an inflammatory or autoimmune disorder (e.g. spondyloarthritis), the antibody comprises a human Fc region that does not substantially bind Fcγ receptors (e.g. CD16); in one embodiment the Fc region is a human IgG4 isotype or any isotype wherein the constant domain comprises an amino acid modification (e.g. substitution) that decreases or abolishes binding to one or more human Fcγ receptors.

Optionally, in any embodiment, the antibody (e.g. IgG4, IgG1, antibody fragment, etc.) further comprises a toxic agent (e.g. a chemotherapeutic agent) that is toxic to a cell upon internalization of the antibody-toxin conjugate. In one embodiment the antibody is conjugated to a radioactive agent.

The present disclosure further provides antibodies, antibody fragments, and derivatives that specifically bind human KIR3DL2. The disclosure provides such antibody compositions, as well their use in any of the methods disclosed herein of treating, preventing and diagnosing cancer, inflammatory disorders or autoimmune disorders.

In one embodiment, the antibodies have binding affinity ($K_D$) for a human KIR3DL2 polypeptide of less than $10^{-8}$ M, preferably less than $10^{-9}$ M, or preferably less than $10^{-10}$ M. Optionally, affinity refers to bivalent binding.

In one aspect of any of the embodiments herein, the antibody may have a heavy and/or light chain having one, two or three CDRs of the respective heavy and/or light chain of an antibody selected from the group consisting of antibody 10F6, 2B12, 18C6, 9E10, 10G5, 13H1, 5H1, 1E2, 1C3 and/or 20E9.

In one aspect of any of the embodiments herein, the antibody competes for binding to a KIR3DL2 polypeptide with any one or any combination of monoclonal antibodies 10F6, 2B12, 18C6, 9E10, 10G5, 13H1, 5H1, 1E2, 1C3 and/or 20E9. In one embodiment, an antibody competes for binding to a KIR3DL2 polypeptide.

In one aspect the disclosure provides a monoclonal antibody that specifically binds KIR3DL2 selected from the group consisting of:

(a) an antibody having (i) a heavy chain comprising CDR 1, 2 and 3 (HCDR1, HCDR2, HCDR3) comprising a sequence of SEQ ID NOS: 4, 5 or 6 (HCDR1), SEQ ID NOS: 7 or 8 (HCDR2) and SEQ ID NO: 9 (HCDR3), respectively, and (ii) a light chain comprising CDR 1, 2 and 3 (LCDR1, LCDR2, LCDR3) comprising a sequence of SEQ ID NO: 10, 11 or 12, respectively, wherein each CDR may optionally comprise 1, 2, 3 or 4 amino acid substitutions, deletions or insertions;

(b) an antibody having (i) a heavy chain comprising CDR 1, 2 and 3 (HCDR1, HCDR2, HCDR3) comprising a sequence of SEQ ID NOS: 15, 16 or 17 (HCDR1), SEQ ID NOS: 18 or 19 (HCDR2) and SEQ ID NO: 20 (HCDR3), respectively, and (ii) a light chain comprising CDR 1, 2 and 3 (LCDR1, LCDR2, LCDR3) comprising a sequence of SEQ ID NO: 10, 21 or 22, respectively, wherein each CDR may optionally comprise 1, 2, 3 or 4 amino acid substitutions, deletions or insertions;

(c) an antibody having (i) a heavy chain comprising CDR 1, 2 and 3 (HCDR1, HCDR2, HCDR3) comprising a sequence of SEQ ID NOS: 25, 26 or 27 (HCDR1), SEQ ID NOS: 28 or 29 (HCDR2) and SEQ ID NO: 30 (HCDR3), respectively, and (ii) a light chain comprising CDR 1, 2 and 3 (LCDR1, LCDR2, LCDR3) comprising a sequence of SEQ ID NO: 31, 32 or 33, respectively, wherein each CDR may optionally comprise 1, 2, 3 or 4 amino acid substitutions, deletions or insertions;

(d) an antibody having (i) a heavy chain comprising CDR 1, 2 and 3 (HCDR1, HCDR2, HCDR3) comprising a sequence of SEQ ID NOS: 36, 37 or 38 (HCDR1), SEQ ID NOS: 39 or 40 (HCDR2) and SEQ ID NO: 41 (HCDR3), respectively, and (ii) a light chain comprising CDR 1, 2 and 3 (LCDR1, LCDR2, LCDR3) comprising a sequence of SEQ ID NO: 42, 43 or 44, respectively, wherein each CDR may optionally comprise 1, 2, 3 or 4 amino acid substitutions, deletions or insertions;

(e) an antibody having (i) a heavy chain comprising CDR 1, 2 and 3 (HCDR1, HCDR2, HCDR3) comprising a sequence of SEQ ID NOS: 47, 48 or 49 (HCDR1), SEQ ID NOS: 50 or 51 (HCDR2) and SEQ ID NO: 52 (HCDR3), respectively, and (ii) a light chain comprising CDR 1, 2 and 3 (LCDR1, LCDR2, LCDR3) comprising a sequence of SEQ ID NO: 53, 54 or 55, respectively, wherein each CDR may optionally comprise 1, 2, 3 or 4 amino acid substitutions, deletions or insertions;

(f) an antibody having (i) a heavy chain comprising CDR 1, 2 and 3 (HCDR1, HCDR2, HCDR3) comprising a sequence of SEQ ID NOS: 58, 59 or 60 (HCDR1), SEQ ID NOS: 61 or 62 (HCDR2) and SEQ ID NO: 63 (HCDR3), respectively, and (ii) a light chain comprising CDR 1, 2 and 3 (LCDR1, LCDR2, LCDR3) comprising a sequence of SEQ ID NO: 64, 65 or 66, respectively, wherein each CDR may optionally comprise 1, 2, 3 or 4 amino acid substitutions, deletions or insertions;

(g) an antibody having (i) a heavy chain comprising CDRs 1, 2 and 3 (HCDR1, HCDR2, HCDR3) comprising a sequence of SEQ ID NO: 172, 173 or 174 (HCDR1), SEQ ID NO: 175 or 176 (HCDR2) and SEQ ID NO: 177 (HCDR3), respectively, and (ii) a light chain comprising CDR 1, 2 and 3 (LCDR1, LCDR2, LCDR3) comprising a sequence of SEQ ID NO: 178, 179 or 180, respectively, wherein each CDR may optionally comprise 1, 2, 3 or 4 amino acid substitutions, deletions or insertions; and (h) an antibody having (i) a heavy chain comprising CDRs 1, 2 and 3 (HCDR1, HCDR2, HCDR3) comprising a sequence of SEQ ID NO: 183, 184 or 185 (HCDR1), SEQ ID NO: 186 or 187 (HCDR2) and SEQ ID NO: 188 (HCDR3), respectively, and (ii) a light chain comprising CDR 1, 2 and 3 (LCDR1, LCDR2, LCDR3) comprising a sequence of SEQ ID NO: 189, 190 or 191, respectively, wherein each CDR may optionally comprise 1, 2, 3 or 4 amino acid substitutions, deletions or insertions.

In one aspect, provided is an antibody that specifically binds KIR3DL2, wherein the antibody has one or more (including any combination thereof, to the extent that such combination is not contradictory) of the following properties:

(a) has a Kd of less than $10^{-8}$ M, preferably less than $10^{-9}$ M, or preferably less than $10^{-10}$ M for binding to a KIR3DL2 polypeptide;

(b) binds to at least one residue in the segment corresponding to residues 1-98 or residues 193-292 of the KIR3DL2 polypeptide;

(c) competes for binding to a KIR3DL2 polypeptide with antibody 10F6, 2B12, 18C6, 9E10, 10G5, 13H1, 5H1, 1E2, 1C3 and/or 20E9;

(d) does or does not compete with a natural ligand of KIR3DL2 (e.g. HLA polypeptides HLA-A3, HLA-11 and/or HLA-B27) for binding to a KIR3DL2 polypeptide (e.g. in a polypeptide interaction assay);

(e) does not cause the internalization of KIR3DL2 polypeptides in KIR3DL2-expressing cells and/or is not internalized into KIR3DL2-expressing cells;

(f) does or does not inhibit KIR3DL2 signaling induced by a natural ligand of KIR3DL2 (e.g. HLA polypeptides HLA-A3, HLA-11 and/or HLA-B27);

(g) does not substantially bind to a KIR3DL1, KIR3DS1, KIR3DL3, KIR2DS1, KIR2DS2, KIR2DL3, KIR2DL1 and/or KIR2DS4 polypeptide;

(h) binds to 1, 2, 3, 4, 5 or 6 of the KIR3DL2 polypeptides (e.g., alleles *001, *002, *003, *005, *007 and/or *008) of SEQ ID NOS: 160, 1, 161, 163, 165 and/or 166);

(i) binds to an epitope comprising any one or more of amino acid residues R13, P14, S15, H23, A25, Q27, H32, G33, I60, G62, R78, L82, W226, I231 and/or R246 of a KIR3DL2 polypeptide; and (j) has reduced binding to a KIR3DL2 polypeptide having a mutation at one or more of residues R13, P14, S15, H23, A25, Q27, H32, G33, I60, G62, R78, L82, W226, I231 and/or R246 of a KIR3DL2 polypeptide.

In any of the embodiments herein, an antibody may be characterized by any one or more features of (a)-(j), above.

In one embodiment, the antibody is human-suitable. In one embodiment the antibody is chimeric, e.g. contains a non-murine, optionally a human, constant region. In one embodiment, the antibody is human or humanized. In another embodiment, the antibody is a mouse antibody.

In one aspect of any of the embodiments herein, the isotype of the antibody is IgG, optionally IgG1, IgG2, IgG3 or IgG4. In one embodiment the antibody comprises an Fc domain or is of an isotype that is bound by FcγR (e.g. FcγRIIIA), e.g. an antibody of IgG1 or IgG3 isotype.

In one aspect of any of the embodiments herein, the antibody is an antibody fragment selected from Fab, Fab', Fab'-SH, F(ab')2, Fv, diabodies, single-chain antibody fragment, or a multispecific antibody comprising multiple different antibody fragments. In one aspect of any of the embodiments herein, the antibody does not comprise an Fc domain or is of an isotype that is not substantially bound by FcγR. In one embodiment, the antibody is of an IgG4 or IgG2 isotype.

Optionally such antibodies are furthermore tetrameric (two heavy and two light chains) and are thus bivalent (e.g. IgG antibodies).

In certain embodiments, the antibodies further comprise a toxic agent. In one embodiment, the antibodies comprising a toxic agent are able to directly cause the death of cells expressing KIR3DL2. In one embodiment, the antibodies are capable of directly inducing (e.g. in the absence of immune effector cells) at least 20%, 30%, 40% or 50% cell death, e.g. in an in vitro assay, of KIR3DL2-expressing cells.

In one embodiment, the antibodies are able to induce CDC and/or ADCC of cells expressing KIR3DL2. In one embodiment, the antibodies are capable of inducing at least 20%, 30, 40 or 50% cell lysis, in a cytotoxicity assay, of KIR3DL2-expressing cells (e.g. of T cell lymphoma cells, cells from SS patients or SS cell lines).

In one embodiment, provided is a method of testing an anti-KIR3DL2 antibody, said method comprising bringing an antibody that binds a KIR3DL2 polypeptide into contact with a cell expressing a KIR3DL2 polypeptide and assessing whether the antibody is internalized into the KIR3DL2-expressing cells and/or whether the antibody induces and/or increases intracellular internalization of a KIR3DL2 polypeptide, and selecting an antibody if the antibody does not induce and/or does not increase intracellular internalization of a KIR3DL2 polypeptide.

In one embodiment, provided is a method of testing an anti-KIR3DL2 antibody, said method comprising bringing an antibody that binds a KIR3DL2 polypeptide into contact with a cell expressing a KIR3DL2 polypeptide and assessing whether the antibody induces and/or increases the number of KIR3DL2 polypeptides present at the cell surface, and selecting an antibody if the antibody induces and/or increases the number of KIR3DL2 polypeptides present at the cell surface. In one aspect, the step of assessing comprises incubating an antibody that binds a KIR3DL2 polypeptide with a cell expressing a KIR3DL2 polypeptide for a period of at least 1 hour, 3 hours, 6 hours, 12 hours or 24 hours, and assessing (e.g., by detecting cell surface KIR3DL2 with an affinity reagent, e.g. anti-KIR3DL2 antibody) whether the antibody induces and/or increases the number of KIR3DL2 polypeptides present at the cell surface. The assessment can be made, e.g., after at least 1 hour, 3 hours, 6 hours, 12 hours or 24 hours of incubation. In one embodiment, the assessment comprises bringing the cell into contact, after the incubation period with said (first) antibody, with a second antibody that binds KIR3DL2 which does not compete for binding to KIR3DL2 with the first antibody, and detecting said second antibody bound to cells.

In another embodiment, provided is a method of producing an antibody that binds a KIR3DL2 polypeptide in a mammalian subject, optionally for the treatment of a cancer, an inflammatory disorder or an autoimmune disorder, said method comprising the steps of: a) providing a plurality of antibodies, optionally immunizing a non-human mammal with an immunogen comprising a human KIR3DL2 polypeptide; b) determining whether each of the plurality of antibodies are capable of binding to 1, 2, 3, 4, 5, or more different KIR3DL2 polypeptides alleles (e.g. alleles *001, *002, *003, *005, *007, *008, *009 and/or *011), optionally in each case wherein the KIR3DL2 polypeptide is expressed on the surface of a cell, and c) selecting (e.g. for production, development, use in therapy, etc.) an antibody from said plurality that are capable of binding to 1, 2, 3, 4, 5, or more different KIR3DL2 polypeptides alleles (e.g. alleles *001, *002, *003, *005, *007, *008, *009 and/or *011), optionally in each case wherein the KIR3DL2 polypeptide is expressed on the surface of a cell. Optionally, the method further comprises determining whether each of the plurality of antibodies are capable of binding to a KIR3DL1 polypeptide, and selecting an antibody from said plurality that are capable of binding to said KIR3DL1 polypeptide.

In another embodiment, provided is a method of producing an antibody that binds a KIR3DL2 polypeptide in a mammalian subject, optionally for the treatment of a cancer, an inflammatory disorder or an autoimmune disorder, said method comprising the steps of: a) providing a plurality of antibodies, optionally immunizing a non-human mammal with an immunogen comprising a human KIR3DL2 polypeptide; and b) selecting (e.g. for production, development, use in therapy, etc.) an antibody from said plurality that:

(i) binds to the KIR3DL2 polypeptide but not to a KIR3DL1 polypeptide; and/or (ii) (a) binds to at least one residue in the segment corresponding to residues 99-192, of the mature KIR3DL2 polypeptide of SEQ ID NO: 1, and/or to any one or more (e.g. 2, 3, 4, 5 or more) of residues R13, P14, S15, H23, A25, Q27, H32, G33, I60, G62, R78, L82, W226, I231 and/or R246, and/or has reduced binding to a KIR3DL2 polypeptide having an amino acid substitution at said residue(s), or (b) binds to at least one residue in the segment corresponding to residues 1-98, of the mature KIR3DL2 polypeptide of SEQ ID NO: 1, and/or to any one or more (e.g. 2, 3, 4, 5 or more) of residues R13, P14, S15, H23, A25, Q27, H32, G33, I60, G62, R78, L82, W226, I231 and/or R246, and/or has reduced binding to a KIR3DL2 polypeptide having an amino acid substitution at said residue(s); and/or (iii) is not internalized into KIR3DL2-expressing cells and/or does not induce and/or increase intracellular internalization of a KIR3DL2 polypeptide.

In one aspect, provided are methods of inhibiting the biological activity of a KIR3DL2-expressing cell comprising bringing the cell into contact with anti-KIR3DL2 antibodies, in vitro, ex vivo or in vivo. Optionally said bringing into contact is in the presence of a ligand (e.g. HLA) of KIR3DL2, optionally a cell expressing a ligand (e.g. HLA) of KIR3DL2. Preferably the KIR3DL2-expressing cell is an immune cell, e.g. a T cell or an NK cell, a malignant T cell or NK cell, a CD4 Th17 cell (e.g., a proinflammatory CD4 T cells that express IL-23R and produces IL-17A) or a proinflammatory NK cell that expresses produces IL-17A. In one embodiment, provided are methods of inhibiting the biological activity of a KIR3DL2-expressing T or NK cell that produces IL-17A comprising bringing the cell into contact with anti-KIR3DL2 antibodies, in vitro, ex vivo or in vivo. Preferably the biological activity is activation, lytic activity, cytokine (e.g. IL-17A) production and/or cellular proliferation. Preferably the biological activity is ligand-induced (e.g. HLA-induced) signaling. In one aspect, provided are methods of inhibiting the biological activity of a KIR3DL2-expressing cell comprising brining the cell into contact with an anti-KIR3DL2 antibodies, in vitro, ex vivo or in vivo.

In one aspect, provided are methods of eliminating or depleting a KIR3DL2-expressing cell comprising bringing the cell into contact with anti-KIR3DL2 antibodies, in vitro, ex vivo or in vivo. The cell may be, e.g. a malignant T cell or NK cell, a T cell or an NK cell, a CD4 Th17 cell (e.g., a proinflammatory CD4 T cells that express IL-23R and produces IL-17A) or a proinflammatory NK cell that expresses produces IL-17A.

In one aspect, provided is a method of increasing the amount or number of KIR3DL2 polypeptides at the surface of a KIR3DL2-expressing cell, or a method of increasing the amount or number of KIR3DL2 polypeptides at the surface of a KIR3DL2-expressing cell available for binding by an anti-KIR3DL2 antibody, the method comprising bringing the cell into contact with an anti-KIR3DL2 antibody of the disclosure, in vitro, ex vivo or in vivo. The cell may be, e.g. a malignant T cell or NK cell, a T cell or an NK cell, a CD4 Th17 cell (e.g., a pro-inflammatory CD4 T cells that express IL-23R and produces IL-17A) or a pro-inflammatory NK cell that expresses produces IL-17A.

In one aspect, provided are methods of treatment using the anti-KIR3DL2 antibodies herein. The antibodies can be used as prophylactic or therapeutic treatment; in any of the embodiments herein, a therapeutically effective amount of the antibody can be interchanged with a prophylactically effective amount of an antibody. In one aspect, provided is a method of treating a patient with a cancer, e.g. a T cell lymphoma, a CD4+ or CD8+ CTCL, Sézary syndrome (SS), Mycosis fungoides (MF), a CD30+ T cell lymphoma, the method comprising administering to the patient a pharmaceutically effective amount of an antigen-binding compound described herein that specifically binds to a KIR3DL2 polypeptide. In another embodiment, provided is a method of treating a patient with an autoimmune or inflammatory disorder mediated at least in part by KIR3DL2-expressing T cells, the method comprising administering to the patient a pharmaceutically effective amount of an antigen-binding compound described herein that specifically binds to a KIR3DL2 polypeptide.

In one aspect, provided is a method of increasing the amount or number of KIR3DL2 polypeptides at the surface of a KIR3DL2-expressing cell (e.g. a CD4+ T cell, a malignant CD4+ T cell) in an individual, the method comprising administering an effective amount of an anti-KIR3DL2 antibody (e.g. an antibody of the disclosure) to the individual. In one embodiment, the effective amount is an amount of an anti-KIR3DL2 antibody that results in an increase in the amount or number of KIR3DL2 polypeptides at the surface of a KIR3DL2-expressing cell (e.g. a CD4+ T cell, a malignant CD4+ T cell) in an individual following administration of the antibody. In one embodiment, the effective amount results in an increase in the amount or number of KIR3DL2 polypeptides at the surface of a KIR3DL2-expressing cell 1 hour, 3 hours, 6 hours, 12 hours or 24 hours following administration of the effective amount. In one aspect, the individual has a cancer, e.g. a T cell lymphoma, a CD4+ or CD8+ CTCL, Sézary syndrome (SS), Mycosis fungoides (MF), a CD30+ T cell lymphoma, the method comprising administering to the patient a pharmaceutically effective amount of an antigen-binding compound described herein that specifically binds to a KIR3DL2 polypeptide.

The methods of treatment and the anti-KIR3DL2 antibody can be used to a treat an individual in combination with a second therapeutic agent, including immunomodulators (e.g. chemotherapeutic drugs, anti-inflammatory drugs, tumor vaccines, antibodies that bind to tumor-specific antigens on tumor cells, antibodies that induce ADCC toward tumors cells, antibodies that potentiate immune responses, disease-modifying anti-rheumatic drugs (DMARDs), etc.). In one embodiment, the second therapeutic agent is an anti-CD4 antibody or an anti-CD30 antibody.

The present disclosure further concerns a method for selecting subjects having a disease that responds to a treatment using an antibody that binds to a KIR3DL2 polypeptide of the disclosure, the method comprising determining whether disease-related cells in said subject express a KIR3DL2 receptor, the expression of a KIR3DL2 receptor being indicative of a responder subject. Optionally, the method further comprises administering to a responder subject an antibody (e.g. an anti-KIR3DL2 antibody of the invention) that binds to a KIR3DL2 polypeptide. In one embodiment, the method is used for selecting subjects having a cancer, and the disease-related cells are cancer cells. In one embodiment, the method is used for selecting subjects having an inflammatory or autoimmune disorder, and the disease-related cells are T cells.

The expression of a KIR3DL2 receptor in said disease-related cell can be determined using a KIR3DL2-specific ligand. Preferably, the ligand is an antibody, or a fragment or derivative thereof. In one aspect, the present invention provides compositions comprising, and methods of using monoclonal antibodies, including but not limited to antibody fragments, and derivatives that specifically bind human KIR3DL2.

In another aspect, provided is a method (e.g., a method of conducting a diagnostic assay, a responder assay, etc.), comprising assessing whether a patient has disease-related cells expressing a KIR3DL2 polypeptide, e.g. a KIR3DL2 polypeptide (one or more KIR3DL2 alleles) bound by an antibody described herein. Said method may comprise, for example, obtaining a biological sample from a patient comprising disease-related cells, bringing said disease-related cells into contact with such antibody and assessing whether the antibody binds to disease-related cells. A finding that KIR3DL2 is expressed by disease-related cells indicates that the patient has a condition characterized by KIR3DL2-expressing cells and/or is suitable for treatment with an anti-KIR3DL2 antibody described herein. The patient can further be treated with a treatment suitable for the particular disease characterized by KIR3DL2-expressing cells. Optionally the patient is treated with the anti-KIR3DL2 antibody. In one embodiment, the method is used for selecting subjects having a cancer, and the disease-related cells are cancer cells. In one embodiment, the method is used for selecting subjects having an inflammatory or autoimmune disorder, and the disease-related cells are T cells. In one embodiment, the antibody brought into contact with disease-related cells in order to assess whether the antibody binds to disease-related cells is an antibody described herein.

Also provided is a method of treating a patient, the method comprising:

a) determining whether the patient has pathogenic KIR3DL2-expressing cells, and b) if the patient is determined to patient have pathogenic KIR3DL2-expressing cells, administering an antigen-binding compound (e.g., antibody) of the disclosure.

Also provided is a method for the assessment of the development level of a CTCL (staging disease) permitting the evaluation of the proportion (e.g. percentage) of malignant CD4+ CTCL cells present within a certain body compartment of a patient. According to this method, cells from a biological sample collected from said body compartment are brought into contact with an anti-KIR3DL2 antibody of the disclosure and the proportion of CD4+ cells expressing a KIR3DL2 polypeptide at their surface is measured. The proportion of CD4+ CTCL cells that are actually present in said body compartment can be considered as substantially equal to said measured proportion, e.g., within a ±10% range around this measured proportion.

Also provided is a method for CTCL diagnosis, comprising bringing cells from a biological sample from an individual into contact with an anti-KIR3DL2 antibody of the disclosure and the proportion (e.g. percentage) of T cells expressing a KIR3DL2 polypeptide at their surface is measured, and comparing such proportion to the average proportion (e.g. percentage) of T cells expressing a KIR3DL2 polypeptide at their surface observed in non-CTCL humans (preferably in healthy humans), wherein a CTCL-positive diagnosis is made when said measured proportion is significantly higher than said average proportion.

Also provided is a method determining the KIR3DL2 polypeptide status of malignant cells (e.g. CD4+ T cells) from an individual having a cancer (e.g., a CD4+ lymphoma, a CTCL), comprising obtaining a biological sample comprising malignant cells from an individual having a cancer, incubating said malignant cells in the presence of an antibody that binds KIR3DL2 polypeptide for a period of at least 1 hour, 3 hours, 6 hours, 12 hours or 24 hours, and assessing whether the antibody induces and/or increases the number of KIR3DL2 polypeptides present at the cell surface. The assessment can be made, e.g., after at least 1 hour, 3 hours, 6 hours, 12 hours or 24 hours of incubation. Optionally the antibody is an antibody capable of causing an increase of the amount of KIR3DL2 polypeptides detectable at the cell surface of a KIR3DL2-expressing cell.

Also provided is a method of treating an individual having a malignancy (e.g., a CD4+ lymphoma, a CTCL), the method comprising:

(a) obtaining a biological sample comprising malignant cells from an individual having a cancer, incubating said malignant cells in the presence of an antibody that binds KIR3DL2 polypeptide for a period of at least 1 hour, 3 hours, 6 hours, 12 hours or 24 hours, and assessing whether the antibody induces and/or increases the number of KIR3DL2 polypeptides present at the cell surface; and (b) upon a determination that the antibody induces and/or increases the number of KIR3DL2 polypeptides present at the cell surface of malignant cells from an individual, administering to the individual an anti-NKG2A antibody according to the treatment methods described herein.

These and additional advantageous aspects and features of the invention may be further described elsewhere herein.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIG. 3 shows a view of each face of the KIR3DL2 polypeptide, including portions within the D0 domain, showing amino acid residues mutated indicated as "Mutant 6" which resulted in loss of binding by antibody 5H1, with "Mutant 3" that did not result in loss of binding shown. Also shown in shading are residues adjacent to residues adjacent to mutant 6 that may also be bound by the antibodies (K7, Y30, R31, P79, H80, S81, T83, G84, W85, S86 and/or A87).

FIG. 4 shows a view of the KIR3DL2 polypeptide, including portions within the D2 domain (D1/D2 junction), showing amino acid residues mutated indicated as "Mutant 14" to which antibodies 1C3 and 20E9 lost binding, and "Mutant 12" and "Mutant 17" which did not cause loss of binding by antibodies; also shown in shading are residues adjacent to residues (Q201, K202, P203, S204, S224, S225, S227, S228, N252, R253 and/or T254 adjacent to mutant 14).

FIG. 5 shows a view of the KIR3DL2 polypeptide, including portions within the D2 domain (D1/D2 junction), showing amino acid residues mutated indicated as "Mutant 15" to which antibody 20E9 lost binding; also shown in shading are residues adjacent to residues (D230, I231, R244, L245, R246, A247, V248, S275, R277 and/or P280) adjacent to mutant 14).

FIG. 6C shows that incubation at 37° C. with antibody 2B12 increases surface expression of KIR3DL2 (as detected by non-competing non-competing anti-KIR3DL2 (mAb2) or by 2B12 itself+secondary Ab), in a dose-dependent manner. This increase is already observed after 1 h at 37° C., and seems to reach its maximum after 24 h. Staining is optimal after 24 h (in terms of total staining and of detected Ab-bound receptors).

FIG. 7A shows ability of antibodies to mediate CDC; anti-KIR3DL2 mAbs that bind the D0 domain are in gray, those that bind the D1 domain are in black, showing that with the parental murine mAbs, the isotype of the mAb has the most prominent influence on CDC.

FIG. 7B shows that the internalization of KIR3DL2 upon binding totally abrogates the ability of mo19H12 to kill B221-KIR3DL2 with complement recruitment, whereas in temperature conditions that limit internalization, CDC activity of mo19H12 is clearly observed.

DETAILED DESCRIPTION OF THE INVENTION

Introduction

Figure 1:
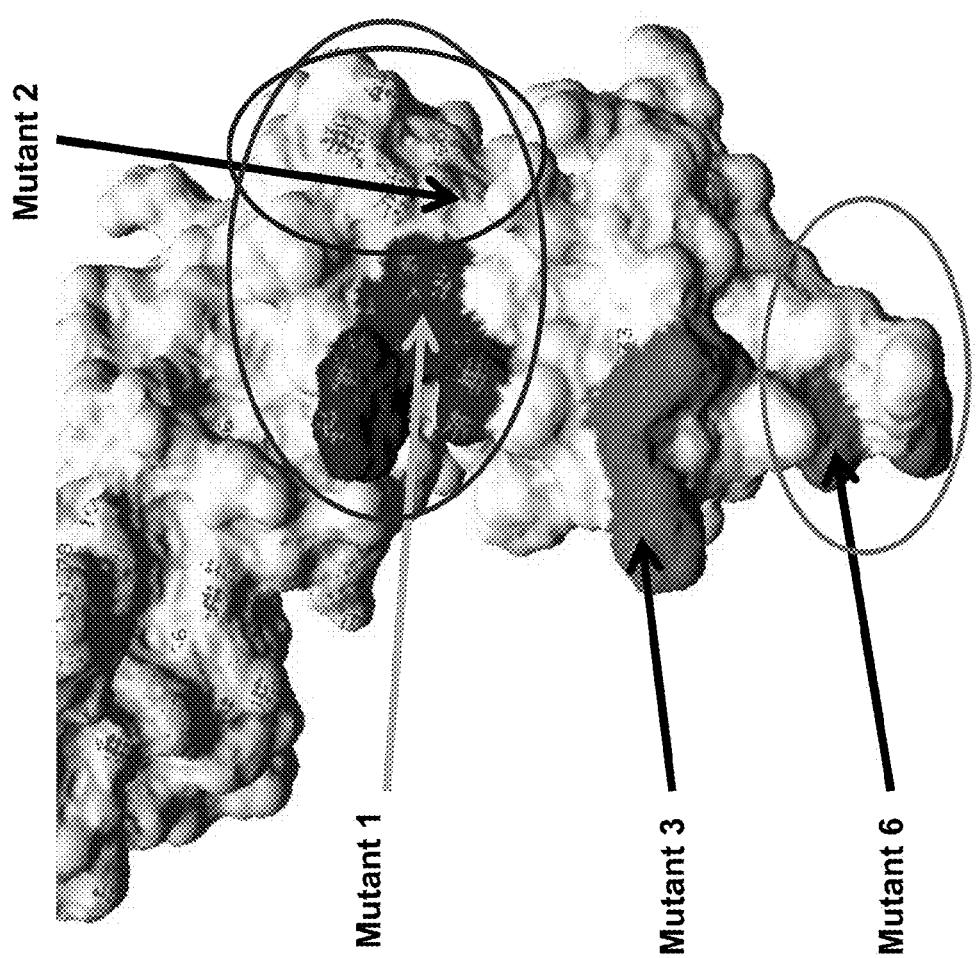
FIG. 1 shows a view of the KIR3DL2 polypeptide, including portions within the D0 domain, showing amino acid residues mutated indicated as "Mutant 1", "Mutant 2", "Mutant 3" and "Mutant 6" which resulted (in different combinations) in loss of binding by antibodies.

The antibodies of the disclosure are able to directly and specifically target KIR3DL2-expressing cells, notably CD4+, KIR3DL2+ T cells, without targeting other cells such as KIR3DL1+ cells (or KIR3DL2+ KIR3DL1+ cells, KIR3DS1+ cells; or KIR3DS1 KIR3DL2+ cells), and do not internalize into KIR3DL2+ cells. Also provided are antibodies that do or not inhibit binding of natural ligands of KIR3DL2 (or ligand-induced KIR3DL2 signaling). The disclosure provides a number of antibodies having such properties, and which compete with each other for binding to a region of KIR3DL2+ that includes domains 0 and 2 defined by amino acid residues 1-98 and residues 193-292, respectively, of the mature KIR3DL2 polypeptides of SEQ ID NO: 1.

KIR3DL2 (CD158k) is a disulphide-linked homodimer of three-Ig domain molecules of about 140 kD, described in Pende et al. (1996) J. Exp. Med. 184: 505-518, the disclosure of which is incorporated herein by reference. KIR3DL1 (CD158e1) is a monomeric molecule of about 70 kD, described in Colonna and Samaridis (1995) Science 268 (5209), 405-408; the HLA binding pocket has been described in Vivian et al. (2011) Nature 479: 401-405. Natural ligands of KIR3DL2 include, inter alia, HLA-A and HLA-B polypeptides, notably HLA-A3 and HLA-A11 (see Hansasuta et al. (2004) Eur. J. Immunol. 34: 1673-1679 and HLA-B27. HLA-B27 (see, e.g., Weiss et al. (1985) Immunobiology 170(5):367-380 for organization, sequence and expression of the HLA-B27 gene, and for HLA-B27 multimers and HLA-B27$_2$ homodimers see Allen et al. (1999) J. Immunol. 162: 5045-5048 and Kollnberger et al (2007) Eur. J. Immunol. 37: 1313-1322. The disclosures of all of the above references are incorporated herein by reference. As used herein, "KIR3D" refers to any KIR3D receptor (e.g. KIR3DL1, KIR3DL2, KIR3DS1) individually or collectively, and the term "KIR3D" may be substituted by the term "KIR3DL1, KIR3DL2 and/or KIR3DS1". Similarly, "KIR3DL" refers to any KIR3DL receptor (e.g. KIR3DL1, KIR3DL2) individually or collectively, and the term "KIR3DL" may be substituted by the term "KIR3DL1 and/or KIR3DL2". The terms "KIR3D", "KIR3DL", "KIR3DL", "KIR3DL2", "KIR3DS1" each furthermore include any variant, derivative, or isoform of the KIR3D gene or encoded protein(s) to which they refer. Several allelic variants have been reported for KIR3D polypeptides (e.g. KIR3DL2), each of these are encompassed by the respective terms. The amino acid sequence of the mature human KIR3DL2 (allele *002) is shown in SEQ ID NO: 1, corresponding to Genbank accession no. AAB52520 in which the 21 amino acid residue leader sequence has been omitted, and corresponding to IPD KIR database (published by the EMBL-EBI, European Bioinformatics Institute, United Kingdom) accession no. KIR00066. The cDNA of KIR3DL2 (allele *002) is shown in Genbank accession no. U30272. The precursor amino acid sequence (including leader sequence) of a human KIR3DL2 allele *002 is shown in SEQ ID NO: 159, corresponding to Genbank accession no. AAB52520. The amino acid sequence of a human KIR3DL2 allele *001 is shown in SEQ ID NO: 160, corresponding to IPD KIR database accession no. KIR00065. The amino acid sequence of a human KIR3DL2 allele *003 is shown in SEQ ID NO: 161, corresponding to Genbank accession no. AAB36593 and IPD KIR database accession no. KIR00067. The amino acid sequence of a human KIR3DL2 allele *004 is shown in SEQ ID NO: 162, corresponding to IPD KIR database accession no. KIR00068. The amino acid sequence of a human KIR3DL2 allele *005 is shown in SEQ ID NO: 163, corresponding to IPD KIR database accession no. KIR00069. The amino acid sequence of a human KIR3DL2 allele *006 (mature) is shown in SEQ ID NO: 164, corresponding to Genbank accession no. AAK30053 and IPD KIR database accession no. KIR00070. The amino acid sequence of a human KIR3DL2 allele *007 (mature) is shown in SEQ ID NO: 165, corresponding to Genbank accession no. AAK30052 and IPD KIR database accession no. KIR00071. The amino acid sequence of a human KIR3DL2 allele *008 is shown in SEQ ID NO: 166, corresponding to Genbank accession no. AAK30054 and IPD KIR database accession no. KIR00072. The amino acid sequence of a human KIR3DL2 allele *009 is shown in SEQ ID NO: 167, corresponding to IPD KIR database accession no. KIR00457. The amino acid sequence of a human KIR3DL2 allele *011 is shown in SEQ ID NO: 168, corresponding to IPD KIR database accession no. KIR00544. The cDNA encoding a KIR3DL1 (CD158e2) polypeptide (allele *00101) is shown in Genbank accession no. L41269; the encoded amino acid sequence is shown in SEQ ID NO: 169, corresponding to Genbank accession no. AAA69870. Where a leader sequence is present in a particular SEQ ID NO describing a KIR3DL2 polypeptide sequence (e.g. SEQ ID NOS: 1 and 159 to 168), any reference to amino acid residue positions herein will be to the mature KIR3DL polypeptide.

Provided are methods of using the antigen-binding compounds; for example, a method for inhibiting cell proliferation or activity, for delivering a molecule into a cell (e.g. a toxic molecule, a detectable marker, etc.), for targeting, identifying or purifying a cell, for depleting, killing or eliminating a cell, for reducing cell proliferation, the method comprising exposing a cell, such as a T cell which expresses a KIR3DL polypeptide, to an antigen-binding compound of the disclosure that binds a KIR3DL2 polypeptide. It will be appreciated that for the purposes of the present disclosure, "cell proliferation" can refer to any aspect of the growth or proliferation of cells, e.g., cell growth, cell division, or any aspect of the cell cycle. The cell may be in cell culture (in vitro) or in a mammal (in vivo), e.g. a mammal suffering from a KIR3DL2-expressing pathology. Also provided is a method for inducing the death of a cell or inhibiting the proliferation or activity of a cell which expresses a KIR3DL2 polypeptide, comprising exposing the cell to an antigen-binding compound that binds a KIR3DL2 polypeptide linked to a toxic agent, in an amount effective to induce death and/or inhibit the proliferation of the cell. Thus, provided is a method for treating a mammal suffering from a proliferative disease, and any condition characterized by a pathogenic expansion or activation of cells expressing of a KIR3DL2 polypeptide, the method comprising administering a pharmaceutically effective amount of an antigen-binding compound disclosed herein to the mammal. Examples of such conditions include Sézary Syndrome, Mycosis Fungoides, CTCL, and autoimmune or inflammatory conditions, e.g. arthritis, cardiovascular disease. Preferably such pathogenically expanded cells express KIR3DL2 but do not prominently express KIR3DL1 (e.g. no more than 20%, 40%, 50% or 60% of pathogenic cells express KIR3DL1, these conditions benefiting particularly from selective antibodies.

Several KIR3DL2-expressing disorders, particularly T and NK cell mediated disorders can be treated or diagnosed using the methods and compositions of the disclosure. The disorders may be for example CD4+ T cell malignancies such as CTCL, MF or SS, or autoimmune or inflammatory disorders where the elimination or inhibiting the activity and/or proliferation of T and/or NK cells would be useful. CD4+ T cells includes for example activated CD4+ T cells, Th17 T cells, CD4+ T cells expressing or not one or more other markers (e.g. CD2+, CD3+, CD5+, CD8-, CD28$^+$, CD28-, CD45RO+ and TCRαβ+). CD4+CD28- T cells, for example, are known to be capable of expressing KIR3DL2 and are present in high frequencies of clonally expanded cells in some autoimmune and inflammatory disorders but are rare in healthy individuals. These T cells can be cytotoxic, secrete large amounts of IFN-gamma, and proliferate upon stimulation with autologous adherent mononuclear cells.

The antibodies of the disclosure have the advantage of binding across different KIR3DL2 alleles permitting a broad use to treat, characterize and diagnose diseases. Cutaneous and circulating MF/SS cells have been reported to not express preferential alleles among nine KIR3DL2 alleles tested. Thirteen alleles have also been described to date. Whereas the p140-KIR3DL2 receptor is expressed on a minor subset of NK cells and on rare CD8+ T cells in healthy persons, it appears to be restricted to CTCL tumor CD4+ T cells in MF/SS patients. Other receptors that are usually observed at the surface of NK cells (such as p58.1, p58.2, p70KIRs, CD94/NKG2A) are not found at the surface of malignant CD4+ T cells (Bahler D. W. et al., (2008) Cytometry B Clin Cytom. 74(3):156-62). SS cells are also typically characterized, in addition to CD4+, by having a mature T lymphocyte phenotype, CD2+, CD3+, CD5+, CD8-, CD28+, CD45RO+ and TCRαβ+.

The methods and compositions of the disclosure can be used in the treatment of autoimmune and inflammatory conditions characterized by KIR3DL2 expression, by eliminating KIR3DL2-expressing cells and/or by inhibiting the biological activity KIR3DL2-expressing cells (i.e. by blocking KIR3DL2 signaling induced by its natural ligands). Inhibiting the biological activity KIR3DL2-expressing cells can comprise for example decreasing the proliferation of KIR3DL2-expressing cells, decreasing the reactivity or cytotoxicity of KIR3DL2-expressing cells toward target cells, decreasing activation, activation markers (e.g. CD107 expression) and/or cytokine production (e.g., IFNγ production) by a KIR3DL2-expressing cell, and/or decreasing the frequency in vivo of such activated, reactive, cytotoxic and/or activated KIR3DL2-expressing cells.

For example, it has been shown that several such disorders are mediated at least in part by CD4+ T cells, including particular CD4+CD28null T cells. Activation of CD4+ T cells is generally thought to be governed by interplay between stimulatory and inhibitory receptors, where a predominance of stimulatory signals favors autoimmune reactions. Chan et al. ((2005) Arthrit. Rheumatism 52(11): 3586-3595 report that increased number of peripheral blood and synovial fluid CD4+ T cells and NK cells express KIR3DL2 in spondyloarthritis. In patients with rheumatoid arthritis, expression of the critical costimulatory molecule, CD28, is frequently lost. Instead, a CD4$^+$ T cell population which lacks CD28 (CD4$^+$CD28$^-$ T cells) express killer immunoglobulin-like receptors (KIRs). CD4+CD28$^{null}$ T cells in particular have been reported to express KIR3D polypeptides. Compared with their CD28$^+$ counterparts, CD4+CD28- cells produce significantly higher levels of IFN-γ giving them the ability to function as proinflammatory cells. CD4$^+$CD28$^{null}$ T cell clones persist for years in circulation. These T cells are known to differ from CD28$^+$ T cells by being resistant to Fas-mediated apoptosis upon cross-linking of CD3. CD28$^{null}$ T cells progress through the cell cycle, and cells at all stages of the cell cycle are resistant to apoptosis, unlike their CD28$^+$ counterparts. Dysregulation of apoptotic pathways in CD4$^+$CD28$^{null}$ T cells has been shown to favor their clonal outgrowth and maintenance in vivo. Namekawa et al. ((2000) J. Immunol. 165:1138-1145 report that KIR, including KIR3DL2, was present on CD4+ CD28null T cells expanded in rheumatoid arthritis. Rheumatoid arthritis involves lymphocyte infiltrates, inflammatory mediators, and synovial hyperplasia resulting from aggressive proliferation of fibroblast-like synoviocytes and macrophages. Prognoses of joint erosions and disease severity correlate with high frequencies of clonally expanded CD4+CD28− T cells. Lamprecht et al. (2001) Thorax 56:751-757 report recruitment of CD4+CD28− T cells in Wegener's granulomatosis. Markovic-Plese et al. (2001) J Clin Invest. 108: 1185-1194 report the presence of CD4+ CD28− costimulation-independent T cells in the CNS, and their associate with multiple sclerosis. The methods and compositions can therefore be used in the treatment or prevention of Wegener's granulomatosis, multiple sclerosis or other central nervous system inflammatory or autoimmune disorders, arthritis, or other rheumatic disorders characterized by inflammation.

CD4+CD28− T cells have also been associated with cardiovascular disorders. Betjes et al. (2008) Kidney International 74, 760-767 report that the increased risk for atherosclerotic disease in patients with Cytomegalovirus (CMV) seropositivity is associated with age-dependent increase of CD4+CD28− T cells, which can comprise over half of the circulating CD4 T cells in individuals. Patients over 50 years of age were reported to have a 50-fold higher percentage of CD4+CD28− T cells compared to CMV seronegative patients and a 5-fold higher percentage when compared to seropositive healthy controls. Nakajima et al. ((2003) Circ. Res. 93:106-113) report de novo expression of KIR in acute coronary syndrome, where CD4+ T cells from patients with acute coronary syndrome (ACS) express multiple KIR whereas normal CD4+CD28null T cells from healthy donors do not express KIR. Yen et al. Journal of Experimental Medicine, Volume 193, Number 10, May 21, 2001 1159-1168 studied CD4+CD28$^{null}$ T cell clones established from patients with rheumatoid vasculitis for the expression of inhibitory and stimulatory KIR by RT-PCR. In patients with rheumatoid arthritis and a patient with ACS, the expression patterns favored the inhibitory KIR, including KIR3DL2, whereas expression of stimulatory receptors was highly restricted to KIR2DS2. The methods and compositions can therefore be used in the treatment or prevention of cardiovascular disorders, e.g. ACS, atherosclerotic disease, rheumatoid vasculitis, characterized by inflammation.

Bowness et al (2011) J. Immunol. 186: 2672-2680 report that KIR3DL2+CD4 T cells account for the majority of IL-23R expression by peripheral blood CD4 T cells, and that such KIR3DL2+ cells of the Th17 type produce more IL-17 in the presence of IL-23. Despite KIR3DL2+ cells comprising a mean of just 15% of CD4 T in the peripheral blood of SpA patients, this subset accounted for 70% of the observed increase in Th17 numbers in SpA patients compared with control subjects. TCR-stimulated peripheral blood KIR3DL2+CD4 T cell lines from SpA patients secreted 4-fold more IL-17 than KIR3DL2+ lines from controls or KIR3DL2− CD4 T cells.

Provided are methods for producing and using antibodies and other compounds suitable for the treatment of disorders (e.g. cancers, inflammatory and autoimmune disorders) where eliminating KIR3DL2-expressing cells would be useful. Antibodies, antibody derivatives, antibody fragments, and cell producing them are encompassed, as are methods of producing the same and methods of treating patients using the antibodies and compounds.

Since the present antibodies are specific for KIR3DL2, they can be used for a range of purposes, including purifying KIR3DL2 or KIR3DL2-expressing cells, modulating (e.g. activating or inhibiting) KIR3DL2 receptors in vitro, ex vivo, or in vivo, targeting KIR3DL2-expressing cells for destruction in vivo, or specifically labeling/binding KIR3DL2 in vivo, ex vivo, or in vitro, including for methods such as immunoblotting, IHC analysis, i.e. on frozen biopsies, FACS analysis, and immunoprecipitation.

Definitions

As used in the specification, "a" or "an" may mean one or more. As used in the claim(s), when used in conjunction with the word "comprising", the words "a" or "an" may mean one or more than one. As used herein "another" may mean at least a second or more.

Where "comprising" is used, this can preferably be replaced by "consisting essentially of", more preferably by "consisting of".

"Treatment of a proliferative disease" or "treatment of a tumor", or "treatment of cancer" or the like, with reference to anti-KIR3DL2 binding agent (e.g. antibody), includes, but is not limited to: (a) method of treatment of a proliferative disease, said method comprising the step of administering (for at least one treatment) an anti-KIR3DL2 binding agent, (e.g., in a pharmaceutically acceptable carrier material) to a warm-blooded animal, especially a human, in need of such treatment, in a dose that allows for the treatment of said disease (a therapeutically effective amount), e.g., in a dose (amount) as specified hereinabove and herein below; (b) the use of an anti-KIR3DL2 binding agent for the treatment of a proliferative disease, or an anti-KIR3DL2 binding agent, for use in said treatment (especially in a human); (c) the use of an anti-KIR3DL2 binding agent, for the manufacture of a pharmaceutical preparation for the treatment of a proliferative disease, a method of using an anti-KIR3DL2 binding agent for the manufacture of a pharmaceutical preparation for the treatment of a proliferative disease, comprising admixing an anti-KIR3DL2 binding agent with a pharmaceutically acceptable carrier, or a pharmaceutical preparation comprising an effective dose of an anti-KIR3DL2 binding agent that is appropriate for the treatment of a proliferative disease; or (d) any combination of a), b), and c), in accordance with the subject matter allowable for patenting in a country where this application is filed. In cases where a particular disease (e.g., inflammatory or autoimmune disease) or a specific tumor (e.g. CTCL) are mentioned instead of "proliferative disease", categories a) to e) are also encompassed, meaning that the respective disease can be filled in under a) to e) above instead of "proliferative disease", in accordance with the patentable subject matter.

The terms "cancer" and "tumor" as used herein are defined as a new growth of cells or tissue comprising uncontrolled and progressive multiplication. In a specific embodiment, upon a natural course the cancer is fatal. In specific embodiments, a cancer is invasive, metastatic, and/or anaplastic (loss of differentiation and of orientation to one another and to their axial framework).

"Autoimmune" disorders include any disorder, condition, or disease in which the immune system mounts a reaction against self cells or tissues, due to a breakdown in the ability to distinguish self from non-self or otherwise. Examples of autoimmune disorders include rheumatoid arthritis, rheumatoid vasculitis, systemic lupus erythematosus, multiple sclerosis, Wegener's granulomatosis, spondyloarthritis, and others. An "inflammatory disorder" includes any disorder characterized by an unwanted immune response. Autoimmune and inflammatory disorders can involve any component of the immune system, and can target any cell or tissue type in the body.

The term "biopsy" as used herein is defined as removal of a tissue from an organ (e.g., a joint) for the purpose of examination, such as to establish diagnosis. Examples of types of biopsies include by application of suction, such as through a needle attached to a syringe; by instrumental removal of a fragment of tissue; by removal with appropriate instruments through an endoscope; by surgical excision, such as of the whole lesion; and the like.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains, respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG and/or IgM are the preferred classes of antibodies employed herein, with IgG being particularly preferred, because they are the most common antibodies in the physiological situation and because they are most easily made in a laboratory setting. Preferably the antibody is a monoclonal antibody. Particularly preferred are humanized, chimeric, human, or otherwise-human-suitable antibodies. "Antibodies" also includes any fragment or derivative of any of the herein described antibodies.

The term "specifically binds to" means that an antibody can bind preferably in a competitive binding assay to the binding partner, e.g. KIR3DL2, as assessed using either recombinant forms of the proteins, epitopes therein, or native proteins present on the surface of isolated target cells. Competitive binding assays and other methods for determining specific binding are further described below and are well known in the art.

When an antibody is said to "compete with" a particular monoclonal antibody (e.g. 10F6, 2B12, 18C6, 9E10, 10G5, 13H1, 5H1, 1E2, 1C3 or 20E9), it means that the antibody competes with the monoclonal antibody in a binding assay using either recombinant KIR3DL2 molecules or surface expressed KIR3DL2 molecules. For example, if a test antibody reduces the binding of 10F6, 2B12, 18C6, 9E10, 10G5, 13H1, 5H1, 1E2, 1C3 or 20E9 to a KIR3DL2 polypeptide or KIR3DL2-expressing cell in a binding assay, the antibody is said to "compete" respectively with 10F6, 2B12, 18C6, 9E10, 10G5, 13H1, 5H1, 1E2, 1C3 or 20E9.

The term "affinity", as used herein, means the strength of the binding of an antibody to an epitope. The affinity of an antibody is given by the dissociation constant Kd, defined as [Ab]×[Ag]/[Ab-Ag], where [Ab-Ag] is the molar concentration of the antibody-antigen complex, [Ab] is the molar concentration of the unbound antibody and [Ag] is the molar concentration of the unbound antigen. The affinity constant $K_a$ is defined by 1/Kd. Examples of methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One standard method well known in the art for determining the affinity of mAbs is the use of surface plasmon resonance (SPR) screening (such as by analysis with a BIAcore™ SPR analytical device).

As used herein, a "determinant" designates a site of interaction or binding on a polypeptide.

The term "epitope" refers to an antigenic determinant, and is the area or region on an antigen to which an antibody binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

The term "intracellular internalization", or "internalization" when referring to a KIR3DL2 polypeptide and/or antibody that binds such, refers to the molecular, biochemical and cellular events associated with the process of translocating a molecule from the extracellular surface of a cell to the intracellular surface of a cell. The processes responsible for intracellular internalization of molecules are well-known and can involve, inter alia, the internalization of extracellular molecules (such as hormones, antibodies, and small organic molecules); membrane-associated molecules (such as cell-surface receptors); and complexes of membrane-associated molecules bound to extracellular molecules (for example, a ligand bound to a transmembrane receptor or an antibody bound to a membrane-associated molecule). Thus, "inducing and/or increasing intracellular internalization" comprises events wherein intracellular internalization is initiated and/or the rate and/or extent of intracellular internalization is increased.

The term "depleting", with respect to KIR3DL2-expressing cells means a process, method, or compound that can kill, eliminate, lyse or induce such killing, elimination or lysis, so as to negatively affect the number of KIR3DL2-expressing cells present in a sample or in a subject.

The term "agent" is used herein to denote a chemical compound, a mixture of chemical compounds, a biological macromolecule, or an extract made from biological materials. The term "therapeutic agent" refers to an agent that has biological activity.

The terms "toxic agent" and "cytotoxic agent" encompass any compound that can slow down, halt, or reverse the proliferation of cells, decrease their activity in any detectable way, or directly or indirectly kill them. Preferably, cytotoxic agents cause cell death primarily by interfering directly with the cell's functioning, and include, but are not limited to, alkylating agents, tumor necrosis factor inhibitors, intercalators, microtubule inhibitors, kinase inhibitors, proteasome inhibitors and topoisomerase inhibitors. A "toxic payload" as used herein refers to a sufficient amount of cytotoxic agent which, when delivered to a cell results in cell death. Delivery of a toxic payload may be accomplished by administration of a sufficient amount of immunoconjugate comprising an antibody or antigen binding fragment and a cytotoxic agent. Delivery of a toxic payload may also be accomplished by administration of a sufficient amount of an immunoconjugate comprising a cytotoxic agent, wherein the immunoconjugate comprises a secondary antibody or antigen binding fragment thereof which recognizes and binds an antibody or antigen binding fragment.

For the purposes herein, a "humanized" or "human" antibody refers to an antibody in which the constant and variable framework region of one or more human immunoglobulins is fused with the binding region, e.g. the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, Md.).

The term "antibody-dependent cell-mediated cytotoxicity" or "ADCC" is a term well understood in the art, and refers to a cell-mediated reaction in which non-specific cytotoxic cells that express Fc receptors (FcRs) recognize bound antibody on a target cell and subsequently cause lysis of the target cell. Non-specific cytotoxic cells that mediate ADCC include natural killer (NK) cells, macrophages, monocytes, neutrophils, and eosinophils.

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

The term "modification" when referring to a sequence of amino acids (e.g., "amino acid modification"), is meant an amino acid substitution, insertion, and/or deletion in a polypeptide sequence. By "modification" or "amino acid modification" is meant an amino acid substitution, insertion, and/or deletion in a polypeptide sequence. By "amino acid substitution" or "substitution" herein is meant the replacement of an amino acid at a given position in a protein sequence with another amino acid. For example, the substitution P14S refers to a variant of a parent polypeptide, in which the proline at position 14 is replaced with serine. A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or insertions at certain positions within the native amino acid sequence.

As used herein, "T cells" refers to a sub-population of lymphocytes that mature in the thymus, and which display, among other molecules T cell receptors on their surface. T cells can be identified by virtue of certain characteristics and biological properties, such as the expression of specific surface antigens including the TCR, CD4 or CD8, optionally CD4 and IL-23R, the ability of certain T cells to kill tumor or infected cells, the ability of certain T cells to activate other cells of the immune system, and the ability to release protein molecules called cytokines that stimulate or inhibit the immune response. Any of these characteristics and activities can be used to identify T cells, using methods well known in the art. As used herein, "active" or "activated" T cells designate biologically active T cells, more particularly T cells having the capacity of cytolysis or of stimulating an immune response by, e.g., secreting cytokines. Active cells can be detected in any of a number of well-known methods, including functional assays and expression-based assays such as the expression of cytokines such as TNF-alpha or IL-17A.

As used herein, the term antibody that "binds" a polypeptide or epitope designates an antibody that binds said determinant with specificity and/or affinity.

Antibodies and Epitopes

The antibodies disclosed are antibodies that bind human KIR3DL2. In an embodiment, the antibodies selectively bind KIR3DL2 (e.g. the 1, 2, 3, 4 or more most predominant KIR3DL2 alleles) and do not bind KIR3DL1 (e.g. the 1, 2, 3, 4 or more most predominant KIR3DL1 alleles). In one embodiment, the antibodies bind the D0 domain of KIR3DL2 corresponding to amino acid residues 1-98 of the KIR3DL2 polypeptide of SEQ ID NO: 1. In one embodiment, the antibodies bind the D2 domain of KIR3DL2, or to a region spanning both the D1 and D2 domains (at the border of the D1 and D2 domains), of the KIR3DL2 polypeptide of SEQ ID NO: 1. In one embodiment, the antibodies have an affinity for human KIR3DL2 characterized by a $K_D$ of less than $10^{-9}$ M, preferably less than $10^{-10}$M.

In another embodiment, the antibodies bind substantially the same epitope as antibody 10F6, 2B12, 18C6, 9E10, 10G5, 13H1, 5H1, 1E2, 1C3 or 20E9. In another embodiment, the antibodies at least partially overlaps, or includes at least one residue in the segment corresponding to residues 1-98 or residues 193-292 of the KIR3DL2 polypeptide of SEQ ID NO: 1 (or a subsequence thereof. In one embodiment, all key residues of the epitope are in a segment corresponding to residues 1-98. In one embodiment, the antibody binds a residue present in the D1 domain as well as a residue present in in the D2 domain; optionally one or more key residues is at the border of the D1 (residues 99-192) and D2 domains (residues 193-292). In one embodiment, the antibodies bind an epitope comprising 1, 2, 3, 4, 5, 6, 7 or more residues in the segment corresponding to residues 1-98, 99-292, 99-192, or 193-292 of the KIR3DL2 polypeptide of SEQ ID NO: 1. Preferably the residues bound by the antibody are present on the surface of the of the KIR3DL2 polypeptide.

In one embodiment, the antibodies bind an epitope comprising residues R13, A25, and/or Q27. Optionally, the antibodies bind an epitope comprising residues R13, A25, and/or Q27, as well residues I60 and/or G62. Optionally, the antibodies do not bind residues H32 and/or H33. Optionally, the antibodies further bind residues Q56 and/or E57.

In one embodiment, the antibodies bind an epitope comprising residues I60 and/or G62. Optionally, the antibodies bind an epitope comprising one or more of residues I60 and/or G62, but not residues R13, A25, and/or Q27.

In one embodiment, the antibodies bind an epitope comprising one or more of residues I60 and/or G62 as well as one or more of residues P14, S15 and/or H23. Optionally, the antibodies bind an epitope comprising 1, 2, 3, 4, 5, 6 or 7 of residues G21, G22, H23, E57, S58, F59, P63 and/or H68.

Optionally, the antibodies bind an epitope comprising one or more of residues R78 and/or L82. Optionally, the antibodies bind an epitope comprising 1, 2, 3, 4, 5, 6 or 7 of residues K7, Y30, R31, P79, H80, S81, T83, G84, W85, S86 and/or A87.

Optionally, the antibodies bind an epitope comprising residue W226. Optionally, the antibodies bind an epitope comprising 1, 2, 3, 4, 5, 6 or 7 of residues Q201, K202, P203, S204, S224, S225, S227, S228, N252, R253 and/or T254.

Optionally, the antibodies bind an epitope comprising one or more of residues I231 and/or R246. Optionally, the antibodies bind an epitope comprising residues I231 and/or R246 as well as to an epitope comprising residue W226.

Optionally, the antibodies bind an epitope comprising 1, 2, 3, 4, 5, 6 or 7 of residues D230, I231, R244, L245, R246, A247, V248, S275, R277 and/or P280.

Optionally, the antibodies bind an epitope comprising residue E239. Optionally, the antibodies further bind one or more of residues I231 and/or R246. Optionally, the antibodies further bind residue W226.

The Examples section herein describes the construction of a series of mutant human KIR3DL2 polypeptides. Binding of anti-KIR3DL2 antibody to cells transfected with the KIR3DL2 mutants was measured and compared to the ability of anti-KIR3DL2 antibody to bind wild-type KIR3DL2 polypeptide (SEQ ID NO:1). A reduction in binding between an anti-KIR3DL2 antibody and a mutant KIR3DL2 polypeptide as used herein means that there is a reduction in binding affinity (e.g., as measured by known methods such FACS testing of cells expressing a particular mutant, or by Biacore testing of binding to mutant polypeptides) and/or a reduction in the total binding capacity of the anti-KIR3DL2 antibody (e.g., as evidenced by a decrease in Bmax in a plot of anti-KIR3DL2 antibody concentration versus polypeptide concentration). A significant reduction in binding indicates that the mutated residue is directly involved in binding to the anti-KIR3DL2 antibody or is in close proximity to the binding protein when the anti-KIR3DL2 antibody is bound to KIR3DL2. An antibody epitope will thus preferably include such residue and may include additional residues adjacent to such residue.

In some embodiments, a significant reduction in binding means that the binding affinity and/or capacity between an anti-KIR3DL2 antibody and a mutant KIR3DL2 polypeptide is reduced by greater than 40%, greater than 50%, greater than 55%, greater than 60%, greater than 65%, greater than 70%, greater than 75%, greater than 80%, greater than 85%, greater than 90% or greater than 95% relative to binding between the antibody and a wild type KIR3DL2 polypeptide (e.g., the polypeptide shown in SEQ ID NO:1). In certain embodiments, binding is reduced below detectable limits. In some embodiments, a significant reduction in binding is evidenced when binding of an anti-KIR3DL2 antibody to a mutant KIR3DL2 polypeptide is less than 50% (e.g., less than 45%, 40%, 35%, 30%, 25%, 20%, 15% or 10%) of the binding observed between the anti-KIR3DL2 antibody and a wild-type KIR3DL2 polypeptide (e.g., the extracellular domain shown in SEQ ID NO: 1). Such binding measurements can be made using a variety of binding assays known in the art. A specific example of one such assay is described in the Example section.

In some embodiments, anti-KIR3DL2 antibodies are provided that exhibit significantly lower binding for a mutant KIR3DL2 polypeptide in which a residue in a wild-type KIR3DL2 polypeptide (e.g., SEQ ID NO:1) is substituted. In the shorthand notation used here, the format is: Wild type residue: Position in polypeptide: Mutant residue, with the numbering of the residues as indicated in SEQ ID NO: 1.

In some embodiments, an anti-KIR3DL2 antibody binds a wild-type KIR3DL2 polypeptide but has decreased binding to a mutant KIR3DL2 polypeptide having any one or more of the following mutations (with reference to SEQ ID NO: 1):

R13W, A25T and/or G25R;

I60N and/or G62S;

P14S, S15A and/or H23S;

one or more of R13W, A25T and/or G25R, and one or more of I60N and/or G62S;

one or more of P14S, S15A and/or H23S, and one or more of I60N and/or G62S;

one or more of R13W, A25T and/or G25R, one or more of I60N and/or G62S; and one or more of P14S, S15A and/or H23S;

one or more of P14S, S15A and/or H23S, and one or more of I60N and/or G62S;

R78H and/or L82P;

W226A;

I231M and/or R246P;

one or more of I231M and/or R246P, and additionally W226A; or one or more of I231M and/or R246P, but wherein the antibody does not have decreased binding to a mutant have a mutation in W226A.

Preferably binding to the particular mutant(s) of KIR3DL2 is significantly reduced compared to binding to the wild-type KIR3DL2.

Producing Anti-KIR3DL2 Antibodies

The antibodies may be produced by a variety of techniques known in the art. Typically, they are produced by immunization of a non-human animal, preferably a mouse, with an immunogen comprising a KIR3DL2 polypeptide, preferably a human KIR3DL2 polypeptide. The KIR3DL2 polypeptide may comprise the full length sequence of a human KIR3DL2 polypeptide, or a fragment or derivative thereof, typically an immunogenic fragment, i.e., a portion of the polypeptide comprising an epitope exposed on the surface of cells expressing a KIR3DL2 polypeptide, preferably the epitope recognized by the 10F6, 2B12, 18C6, 9E10, 10G5, 13H1, 5H1, 1E2, 1C3 or 20E9 antibody. Such fragments typically contain at least about 7 consecutive amino acids of the mature polypeptide sequence, even more preferably at least about 10 consecutive amino acids thereof. Fragments typically are essentially derived from the extracellular domain of the receptor. In one embodiment, the immunogen comprises a wild-type human KIR3DL2 polypeptide in a lipid membrane, typically at the surface of a cell. In a specific embodiment, the immunogen comprises intact cells, particularly intact human cells, optionally treated or lysed. In another embodiment, the polypeptide is a recombinant KIR3DL2 polypeptide. In a specific embodiment, the immunogen comprises intact SS or MF cells, particularly intact human malignant CD4+ T cells, or CD4+CD28− T cells, optionally treated or lysed. In another embodiment, the polypeptide is a recombinant dimeric KIR3DL2 polypeptide.

The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, N.Y. (1988), the entire disclosure of which is herein incorporated by reference). The immunogen is suspended or dissolved in a buffer, optionally with an adjuvant, such as complete or incomplete Freund's adjuvant. Methods for determining the amount of immunogen, types of buffers and amounts of adjuvant are well known to those of skill in the art. These parameters may be different for different immunogens, but are easily elucidated.

Similarly, the location and frequency of immunization sufficient to stimulate the production of antibodies is also well known in the art. In a typical immunization protocol, the non-human animals are injected intraperitoneally with antigen on day 1 and again about a week later. This is followed by recall injections of the antigen around day 20, optionally with an adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be used as long as they result in the production of B cells expressing an antibody directed to the antigen used in immunization.

For polyclonal antibody preparation, serum is obtained from an immunized non-human animal and the antibodies present therein isolated by well-known techniques. The serum may be affinity purified using any of the immunogens set forth above linked to a solid support so as to obtain antibodies that react with KIR3DL2 polypeptides.

In an alternate embodiment, lymphocytes from a non-immunized non-human mammal are isolated, grown in vitro, and then exposed to the immunogen in cell culture. The lymphocytes are then harvested and the fusion step described below is carried out.

For monoclonal antibodies, the next step is the isolation of splenocytes from the immunized non-human mammal and the subsequent fusion of those splenocytes with an immortalized cell in order to form an antibody-producing hybridoma. The isolation of splenocytes from a non-human mammal is well-known in the art and typically involves removing the spleen from an anesthetized non-human mammal, cutting it into small pieces and squeezing the splenocytes from the splenic capsule through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the lymphocytes can be fused to an immortal cell line. This is typically a mouse myeloma cell line, although many other immortal cell lines useful for creating hybridomas are known in the art. Murine myeloma lines include, but are not limited to, those derived from MOPC-21 and MPC-11 mouse tumors available from the Salk Institute Cell Distribution Center, San Diego, U.S.A, X63 Ag8653 and SP-2 cells available from the American Type Culture Collection, Rockville, Md. U.S.A The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Hybridomas are typically grown on a feeder layer of macrophages. The macrophages are preferably from littermates of the non-human mammal used to isolate splenocytes and are typically primed with incomplete Freund's adjuvant or the like several days before plating the hybridomas. Fusion methods are described in Goding, "Monoclonal Antibodies: Principles and Practice," pp. 59-103 (Academic Press, 1986), the disclosure of which is herein incorporated by reference.

The cells are allowed to grow in the selection media for sufficient time for colony formation and antibody production. This is usually between about 7 and about 14 days.

The hybridoma colonies are then assayed for the production of antibodies that specifically bind to KIR3DL2 polypeptide gene products, optionally the epitope specifically recognized by antibody 10F6, 2B12, 18C6, 9E10, 10G5, 13H1, 5H1, 1E2, 1C3 or 20E9. The assay is typically a colorimetric ELISA-type assay, although any assay may be employed that can be adapted to the wells that the hybridomas are grown in. Other assays include radioimmunoassays or fluorescence activated cell sorting. The wells positive for the desired antibody production are examined to determine if one or more distinct colonies are present. If more than one colony is present, the cells may be re-cloned and grown to ensure that only a single cell has given rise to the colony producing the desired antibody.

Hybridomas that are confirmed to produce a suitable monoclonal antibody can be grown up in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

Positive wells with a single apparent colony are typically re-cloned and re-assayed to insure only one monoclonal antibody is being detected and produced.

Antibodies may also be produced by selection of combinatorial libraries of immunoglobulins, as disclosed for instance in (Ward et al. Nature, 341 (1989) p. 544, the entire disclosure of which is herein incorporated by reference).

The identification of one or more antibodies that bind(s) to KIR3DL2, particularly substantially or essentially the same epitope as monoclonal antibody 10F6, 2B12, 18C6, 9E10, 10G5, 13H1, 5H1, 1E2, 1C3 or 20E9, can be readily determined using any one of a variety of immunological screening assays in which antibody competition can be assessed. Many such assays are routinely practiced and are well known in the art (see, e. g., U.S. Pat. No. 5,660,827, which is specifically incorporated herein by reference). It will be understood that actually determining the epitope to which an antibody described herein binds is not in any way required to identify an antibody that binds to the same or substantially the same epitope as the monoclonal antibody described herein.

For example, where the test antibodies to be examined are obtained from different source animals, or are even of a different Ig isotype, a simple competition assay may be employed in which the control (10F6, for example for purposes of illustration, or any other antibody such as 2B12, 18C6, 9E10, 10G5, 13H1, 5H1, 1E2, 1C3 or 20E9) and test antibodies are admixed (or pre-adsorbed) and applied to a sample containing KIR3DL2 polypeptides. Protocols based upon western blotting and the use of BIACORE analysis are suitable for use in such competition studies.

In certain embodiments, one pre-mixes the control antibodies (10F6, for example, although any other of antibodies) with varying amounts of the test antibodies (e.g., about 1:10 or about 1:100) for a period of time prior to applying to the KIR3DL2 antigen sample. In other embodiments, the control and varying amounts of test antibodies can simply be admixed during exposure to the KIR3DL2 antigen sample. As long as one can distinguish bound from free antibodies (e. g., by using separation or washing techniques to eliminate unbound antibodies) and (10F6 from the test antibodies (e. g., by using species-specific or isotype-specific secondary antibodies or by specifically labeling 10F6 with a detectable label) one can determine if the test antibodies reduce the binding of 10F6 to the antigens, indicating that the test antibody recognizes substantially the same epitope as 10F6. The binding of the (labeled) control antibodies in the absence of a completely irrelevant antibody can serve as the control high value. The control low value can be obtained by incubating the labeled (10F6) antibodies with unlabelled antibodies of exactly the same type (10F6), where competition would occur and reduce binding of the labeled antibodies. In a test assay, a significant reduction in labeled antibody reactivity in the presence of a test antibody is indicative of a test antibody that recognizes substantially the same epitope, i.e., one that "cross-reacts" or competes with the labeled (10F6) antibody. Any test antibody that reduces the binding of 10F6 to KIR3DL2 antigens by at least about 50%, such as at least about 60%, or more preferably at least about 80% or 90% (e. g., about 65-100%), at any ratio of 10F6:test antibody between about 1:10 and about 1:100 is considered to be an antibody that binds to substantially the same epitope or determinant as 10F6. Preferably, such test antibody will reduce the binding of 10F6 to the KIR3DL2 antigen by at least about 90% (e.g., about 95%).

Competition can also be assessed by, for example, a flow cytometry test. In such a test, cells bearing a given KIR3DL2 polypeptide can be incubated first with 10F6, for example, and then with the test antibody labeled with a fluorochrome or biotin. The antibody is said to compete with 10F6 if the binding obtained upon preincubation with a saturating amount of 10F6 is about 80%, preferably about 50%, about 40% or less (e.g., about 30%, 20% or 10%) of the binding (as measured by mean of fluorescence) obtained by the antibody without preincubation with 10F6. Alternatively, an antibody is said to compete with 10F6 if the binding obtained with a labeled 10F6 antibody (by a fluorochrome or biotin) on cells preincubated with a saturating amount of test antibody is about 80%, preferably about 50%, about 40%, or less (e. g., about 30%, 20% or 10%) of the binding obtained without preincubation with the test antibody.

A simple competition assay in which a test antibody is pre-adsorbed and applied at saturating concentration to a surface onto which a KIR3DL2 antigen is immobilized may also be employed. The surface in the simple competition assay is preferably a BIACORE chip (or other media suitable for surface plasmon resonance analysis). The control antibody (e.g., 10F6) is then brought into contact with the surface at a KIR3DL2-saturating concentration and the KIR3DL2 and surface binding of the control antibody is measured. This binding of the control antibody is compared with the binding of the control antibody to the KIR3DL2-containing surface in the absence of test antibody. In a test assay, a significant reduction in binding of the KIR3DL2-containing surface by the control antibody in the presence of a test antibody indicates that the test antibody recognizes substantially the same epitope as the control antibody such that the test antibody "cross-reacts" with the control antibody. Any test antibody that reduces the binding of control (such as 10F6) antibody to a KIR3DL2 antigen by at least about 30% or more, preferably about 40%, can be considered to be an antibody that binds to substantially the same epitope or determinant as a control (e.g., 10F6). Preferably, such a test antibody will reduce the binding of the control antibody (e.g., 10F6) to the KIR3DL2 antigen by at least about 50% (e. g., at least about 60%, at least about 70%, or more). It will be appreciated that the order of control and test antibodies can be reversed: that is, the control antibody can be first bound to the surface and the test antibody is brought into contact with the surface thereafter in a competition assay. Preferably, the antibody having higher affinity for the KIR3DL2 antigen is bound to the surface first, as it will be expected that the decrease in binding seen for the second antibody (assuming the antibodies are cross-reacting) will be of greater magnitude. Further examples of such assays are provided in, e.g., Saunal (1995) J. Immunol. Methods 183: 33-41, the disclosure of which is incorporated herein by reference.

Preferably, monoclonal antibodies that recognize a KIR3DL2 epitope will react with an epitope that is present on a substantial percentage of or even all relevant cells, e.g., malignant CD4+ T cells, cells from a SS or MF patient, but will not significantly react with other cells, i.e., cells that do not express KIR3DL2. In one aspect, the anti-KIR3DL2 antibodies bind KIR3DL2 but do not bind KIR3DL1 and/or KIR3DS1.

In some embodiments, the antibodies will bind to KIR3DL2-expressing cells from an individual or individuals with a disease characterized by expression of KIR3DL2-positive cells, i.e. an individual that is a candidate for treatment with one of the herein-described methods using an anti-KIR3DL2 antibody. Accordingly, once an antibody that specifically recognizes KIR3DL2 on cells is obtained, it can be tested for its ability to bind to KIR3DL2-positive cells (e.g. malignant CD4+ T cells) taken from a patient with a disorder such as SS or MF. In particular, prior to treating a patient with one of the present antibodies, it will be beneficial to test the ability of the antibody to bind malignant cells taken from the patient, e.g. in a blood sample, to maximize the likelihood that the therapy will be beneficial in the patient.

In one embodiment, the antibodies are validated in an immunoassay to test their ability to bind to KIR3DL2-expressing cells, e.g. malignant CD4+ T cells, pro-inflammatory CD4+ cells. For example, peripheral blood lymphocytes (PBLs) are taken from a plurality of patients, and CD4+ T cells are enriched from the PBLs, e.g., by flow cytometry using relevant antibodies (for malignant CD4+ cells see, e.g., Bagot et al. (2001) Blood 97:1388-1391, the disclosure of which is incorporated herein by reference), or CD4+CD28− cell fractions are isolated by magnetic separation on a MACS column (Miltenyi Biotec). The ability of a given antibody to bind to the cells is then assessed using standard methods well known to those in the art. Antibodies that are found to bind to a substantial proportion (e.g., 20%, 30%, 40%, 50%, 60%, 70%, 80% or more) of cells known to express KIR3DL2, e.g. T cells, from a significant percentage of individuals or patients (e.g., 5%, 10%, 20%, 30%, 40%, 50% or more) are suitable for use herein, both for diagnostic purposes to determine the presence or level of malignant T cells in a patient or for use in the herein-described therapeutic methods, e.g., for use to increase or decrease malignant T cell number or activity. To assess the binding of the antibodies to the cells, the antibodies can either be directly or indirectly labeled. When indirectly labeled, a secondary, labeled antibody is typically added. The binding of the antibodies to the cells can then be detected using, e.g., cytofluorometric analysis (e.g. FAC-Scan). Such methods are well known to those of skill in the art.

Determination of whether an antibody binds within an epitope region can be carried out in ways known to the person skilled in the art. As one example of such mapping/characterization methods, an epitope region for an anti-KIR3DL2 antibody may be determined by epitope "footprinting" using chemical modification of the exposed amines/carboxyls in the KIR3DL2 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e. g., Ehring H, Analytical Biochemistry, Vol. 267 (2) pp. 252-259 (1999) Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectra of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectrum of the complex compared to the spectrum of the free antigen, and the amino acids involved in the binding can be identified that way. See, e. g., Ernst Schering Res Found Workshop. 2004; (44): 149-67; Huang et al. Journal of Molecular Biology, Vol. 281 (1) pp. 61-67 (1998); and Saito and Patterson, Methods. 1996 June; 9 (3): 516-24.

Epitope mapping/characterization also can be performed using mass spectrometry methods. See, e.g., Downward, J Mass Spectrom. 2000 April; 35 (4): 493-503 and Kiselar and Downard, Anal Chem. 1999 May 1; 71 (9): 1792-801. Protease digestion techniques also can be useful in the context of epitope mapping and identification. Antigenic determinant-relevant regions/sequences can be determined by protease digestion, e.g. by using trypsin in a ratio of about 1:50 to KIR3DL2 or o/n digestion at and pH 7-8, followed by mass spectrometry (MS) analysis for peptide identification. The peptides protected from trypsin cleavage by the anti-KIR3DL2 binder can subsequently be identified by comparison of samples subjected to trypsin digestion and samples incubated with antibody and then subjected to digestion by e.g. trypsin (thereby revealing a footprint for the binder). Other enzymes like chymotrypsin, pepsin, etc., also or alternatively can be used in similar epitope characterization methods. Moreover, enzymatic digestion can provide a quick method for analyzing whether a potential antigenic determinant sequence is within a region of the KIR3DL2 polypeptide that is not surface exposed and, accordingly, most likely not relevant in terms of immunogenicity/antigenicity. See, e. g., Manca, Ann Ist Super Sanita. 1991; 27: 15-9 for a discussion of similar techniques.

Site-directed mutagenesis is another technique useful for elucidation of a binding epitope. For example, in "alanine-scanning", each residue within a protein segment is re-placed with an alanine residue, and the consequences for binding affinity measured. If the mutation leads to a significant reduction in binding affinity, it is most likely involved in binding. Monoclonal antibodies specific for structural epitopes (i.e., antibodies which do not bind the unfolded protein) can be used to verify that the alanine-replacement does not influence over-all fold of the protein. See, e.g., Clackson and Wells, Science 1995; 267:383-386; and Wells, Proc Natl Acad Sci USA 1996; 93:1-6.

Electron microscopy can also be used for epitope "footprinting". For example, Wang et al., Nature 1992; 355:275-278 used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include surface plasmon resonance (SPR, BIACORE) and reflectometric interference spectroscopy (RifS). See, e.g., Fägerstam et al., Journal Of Molecular Recognition 1990; 3:208-14; Nice et al., J. Chromatogr. 1993; 646:159-168; Leipert et al., Angew. Chem. Int. Ed. 1998; 37:3308-3311; Kröger et al., Biosensors and Bioelectronics 2002; 17:937-944.

It should also be noted that an antibody binding the same or substantially the same epitope as an antibody described herein can be identified in one or more of the exemplary competition assays described herein.

Optionally, cellular uptake or localization is assessed in order to select an antibody that is readily taken up into the cell and/or into the cellular compartment where it KIR3DL2 is present. Cellular uptake or localization will generally be measured in the cells in which the antibody is sought or believed to exert its activity. Cellular uptake or localization can be assessed by standard methods, such as by confocal staining using an antibody marked with a detectable moiety (e.g. a fluorescent moiety).

Upon immunization and production of antibodies in a vertebrate or cell, particular selection steps may be performed to isolate antibodies as claimed. In this regard, in a specific embodiment, provided are methods of producing such antibodies, comprising: (a) immunizing a non-human mammal with an immunogen comprising a KIR3DL2 polypeptide; and (b) preparing antibodies from said immunized animal; and (c) selecting antibodies from step (b) that are capable of binding KIR3DL2.

Typically, an anti-KIR3DL2 antibody herein has an affinity for a KIR3DL2 polypeptide in the range of about $10^4$ to about $10^{11}$ M$^{-1}$ (e.g., about $10^8$ to about $10^{10}$ M$^{-1}$). For example, an antibody can have an average disassociation constant ($K_d$) of less than $1\times10^{-9}$ M with respect to KIR3DL2, as determined by, e.g., surface plasmon resonance (SPR) screening (such as by analysis with a BIAcore™ SPR analytical device). In a more particular exemplary aspect, an antibody can have a $K_d$ of about $1\times10^{-8}$ M to about $1\times10^{-10}$ M, or about $1\times10^{-9}$ M to about $1\times10^{-11}$ M, for KIR3DL2.

Antibodies can be characterized for example by a mean $K_d$ of no more than about (i.e. better affinity than) 100, 60, 10, 5, or 1 nanomolar, preferably sub-nanomolar or optionally no more than about 500, 200, 100 or 10 picomolar. $K_d$ can be determined for example for example by immobilizing recombinantly produced human KIR3DL2 proteins on a chip surface, followed by application of the antibody to be tested in solution. In one embodiment, the method further comprises a step (d), selecting antibodies from (b) that are capable of competing for binding to KIR3DL2 with antibody 10F6, 2B12, 18C6, 9E10, 10G5, 13H1, 5H1, 1E2, 1C3 or 20E9.

In one aspect of any of the embodiments, the antibodies prepared according to the present methods are monoclonal antibodies. In another aspect, the non-human animal used to produce antibodies according to the methods of the invention is a mammal, such as a rodent, bovine, porcine, fowl, horse, rabbit, goat, or sheep. The antibodies encompass 10F6, 2B12, 18C6, 9E10, 10G5, 13H1, 5H1, 1E2, 1C3 or 20E9. Additionally, antibodies of can optionally be specified to be antibodies other than any of antibodies Q241 and Q66 (Pende, et al. (1996) J Exp Med 184:505-518), clone 5.133 (Miltenyi Biotec), "AZ158" (Parolini, S., et al. (2002) In Leucocyte typing VII. D. Mason, editor. Oxford University Press, Oxford. 415-417 and WO2010/081890 (e.g. antibodies having the heavy and light chain variable region of SEQ ID NOS: 8 and 10 of WO2010/081890), or derivatives of the foregoing, e.g. that comprise the antigen binding region in whole or in part.

According to an alternate embodiment, the DNA encoding an antibody that binds an epitope present on KIR3DL2 polypeptides is isolated from the hybridoma and placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

DNA encoding the monoclonal antibodies, e.g., antibody 10F6, 2B12, 18C6, 9E10, 10G5, 13H1, 5H1, 1E2, 1C3 or 20E9, can be readily isolated and sequenced using conventional procedures (e. g., by using oligonucleotide probes that are capable of binding specifically to genes encoding the heavy and light chains of murine antibodies). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. As described elsewhere in the present specification, such DNA sequences can be modified for any of a large number of purposes, e.g., for humanizing antibodies, producing fragments or derivatives, or for modifying the sequence of the antibody, e.g., in the antigen binding site in order to optimize the binding specificity of the antibody.

Recombinant expression in bacteria of DNA encoding the antibody is well known in the art (see, for example, Skerra et al., Curr. Opinion in Immunol., 5, pp. 256 (1993); and Pluckthun, Immunol. 130, p. 151 (1992).

Assessing Activity

Once an antigen-binding compound is obtained it will generally be assessed for its ability to internalize into KIR3DL2-expressing target cells or cause KIR3DL2 internalization into KIR3DL2-expressing target cells, to increase the number of KIR3DL2 polypeptides at the surface of a cell, to induce ADCC or CDC towards, to inhibit the pro-inflammatory activity and/or proliferation of and/or cause the elimination of KIR3DL2-expressing target cells. Assessing the antigen-binding compound's ability to internalize or to induce ADCC, CDC or generally lead to the elimination or inhibition of activity of KIR3DL2-expressing target cells, can be carried out at any suitable stage of the method, e.g. as in the examples are provided herein. This assessment can be useful at one or more of the various steps involved in the identification, production and/or development of an antibody (or other compound) destined for therapeutic use. For example, activity may be assessed in the context of a screening method to identify candidate antigen-binding compounds, or in methods where an antigen-binding compound is selected and made human suitable (e.g. made chimeric or humanized in the case of an antibody), where a cell expressing the antigen-binding compound (e.g. a host cell expressing a recombinant antigen-binding compound) has been obtained and is assessed for its ability to produce functional antibodies (or other compounds), and/or where a quantity of antigen-binding compound has been produced and is to be assessed for activity (e.g. to test batches or lots of product). Generally the antigen-binding compound will be known to specifically bind to a KIR3DL2 polypeptide. The step may involve testing a plurality (e.g., a very large number using high throughput screening methods or a smaller number) of antigen-binding compounds.

As used herein, an anti-KIR3DL2 antibody that is not "internalized" or that does not "internalize" is one that is not substantially taken up by (i.e., enters) the cell upon binding to KIR3DL2 on a mammalian cell (i.e. cell surface KIR3DL2). The non-internalizing antibody will of course include antibody fragments, human or humanized antibody and antibody conjugate.

Whether an anti-KIR3DL2 antibody internalizes upon binding KIR3DL2 on a mammalian cell, or whether a KIR3DL2 polypeptide undergoes intracellular internalization (e.g. upon being bound by an antibody) can be determined by various assays including those described in the experimental examples herein. For example, to test internalization in vivo, the test antibody is labeled and introduced into an animal known to have KIR3DL2 expressed on the surface of certain cells. The antibody can be radiolabeled or labeled with fluorescent or gold particles, for instance. Animals suitable for this assay include a mammal such as a nude mouse that contains a human KIR3DL2-expressing tumor transplant or xenograft, or a mouse into which cells transfected with human KIR3DL2 have been introduced, or a transgenic mouse expressing the human KIR3DL2 transgene. Appropriate controls include animals that did not receive the test antibody or that received an unrelated antibody, and animals that received an antibody to another antigen on the cells of interest, which antibody is known to be internalized upon binding to the antigen. The antibody can be administered to the animal, e.g., by intravenous injection. At suitable time intervals, tissue sections of the animal can be prepared using known methods or as described in the experimental examples below, and analyzed by light microscopy or electron microscopy, for internalization as well as the location of the internalized antibody in the cell. For internalization in vitro, the cells can be incubated in tissue culture dishes in the presence or absence of the relevant antibodies added to the culture media and processed for microscopic analysis at desired time points. The presence of an internalized, labeled antibody in the cells can be directly visualized by microscopy or by autoradiography if radiolabeled antibody is used. Optionally, in microscopy, co-localization with a known polypeptide or other cellular component can be assessed; for example co-localization with endosomal/lysosomal marker LAMP-1 (CD107a) can provide information about the subcellular localization of the internalized antibody. Alternatively, in a quantitative biochemical assay, a population of cells comprising KIR3DL2-expressing cells are contacted in vitro or in vivo with a radiolabeled test antibody and the cells (if contacted in vivo, cells are then isolated after a suitable amount of time) are treated with a protease or subjected to an acid wash to remove uninternalized antibody on the cell surface. The cells are ground up and the amount of protease resistant, radioactive counts per minute (cpm) associated with each batch of cells is measured by passing the homogenate through a scintillation counter. Based on the known specific activity of the radiolabeled antibody, the number of antibody molecules internalized per cell can be deduced from the scintillation counts of the ground-up cells. Cells are "contacted" with antibody in vitro preferably in solution form such as by adding the cells to the cell culture media in the culture dish or flask and mixing the antibody well with the media to ensure uniform exposure of the cells to the antibody.

Testing whether an antibody is capable of increasing the number of KIR3DL2 polypeptides at the surface of a cell can be carried out by incubating the test antibody with a KIR3DL2-expressing cell (e.g. a T cell lymphoma) and detecting KIR3DL2 polypeptides at the surface of the cell after the incubation period. KIR3DL2 polypeptides can be carried out using a suitable affinity regent, e.g. one or more antibodies. Exemplary assays are shown in Example 4. For example, an antibody may induce an increase of at least 20%, 50%, 75% or 100% of the number of KIR3DL2 polypeptides detectable at the surface of cells after incubation (e.g. for at least 1, 3, 6, 12, 24 or 48 hours) in the presence of test antibody, compared to a control antibody (e.g. an antibody not binding to KIR3DL2, a different anti-KIR3DL2 antibody). Optionally, the number of KIR3DL2 polypeptides detectable at the surface of cells after incubation is the number detectable using the test antibody. Optionally, the number of KIR3DL2 polypeptides detectable at the surface of cells after incubation is the number detectable using a second anti-KIR3DL2 antibody that does not compete with the test antibody for binding to KIR3DL2.

Testing CDC and ADCC can be carried out can be determined by various assays including those described in the experimental examples herein (see Examples 4 and 5). Testing ADCC typically involves assessing cell-mediated cytotoxicity in which a KIR3DL2-expressing target cell (e.g. a Cou-L cell, Sézary Syndrome cell or other KIR3DL2-expressing cell) with bound anti-KIR3DL2 antibody is recognized by an effector cell bearing Fc receptors, without the involvement of complement. A cell which does not express a KIR3DL2 antigen can optionally be used as a control. Activation of NK cell cytotoxicity is assessed by measuring an increase in cytokine production (e.g. IFN-γ production) or cytotoxicity markers (e.g. CD107 mobilization). Preferably the antibody will induce an increase in cytokine production, expression of cytotoxicity markers, or target cell lysis of at least 20%, 50%, 80%, 100%, 200% or 500% in the presence of target cells, compared to a control antibody (e.g. an antibody not binding to KIR3DL2, a KIR3DL2 antibody having murine constant regions). In another example, lysis of target cells is detected, e.g. in a chromium release assay, preferably the antibody will induce lysis of at least 10%, 20%, 30%, 40% or 50% of target cells. Where an antigen-binding compound is tested for both its ability to (a) induce both ADCC and (b) internalize into KIR3DL2-expressing cells and/or induce KIR3DL2 internalization, the assays of (a) and (b) can be carried out in any order. However, greater the extent and speed of internalization will generally be expected to be associated with a decrease of the extent of CDC and ADCC activity.

Antibody 10F6

The amino acid sequence of the heavy chain variable region of antibody 10F6 is listed as SEQ ID NO: 2, the amino acid sequence of the light chain variable region is listed as SEQ ID NO: 3. In a specific embodiment, provided is an antibody that binds essentially the same epitope or determinant as monoclonal antibodies 10F6; optionally the antibody comprises an antigen binding region of antibody 10F6. In any of the embodiments herein, antibody 10F6 can be characterized by its amino acid sequence and/or nucleic acid sequence encoding it. In one embodiment, the monoclonal antibody comprises the Fab or F(ab')$_2$ portion of 10F6. Also provided is a monoclonal antibody that comprises the heavy chain variable region of 10F6. According to one embodiment, the monoclonal antibody comprises the three CDRs of the heavy chain variable region of 10F6 Also provided is a monoclonal antibody that further comprises the variable light chain variable region of 10F6 or one, two or three of the CDRs of the light chain variable region of 10F6. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 10F6 are fused to an immunoglobulin constant region of the human IgG type, optionally a human constant region, optionally a human IgG1 or IgG3 isotype.

In another aspect, provided is a purified polypeptide which encodes an antibody, wherein the antibody comprises: a HCDR1 region comprising an amino acid sequence GYTFTIAGMQ as set forth in SEQ ID NO: 6, or a sequence of at least 4, 5, 6, 7, 8, 9 or 10 contiguous amino acids thereof (e.g. IAGMQ (SEQ ID NO: 4), GYTFTI (SEQ ID NO: 5)), wherein one or more of these amino acids may be substituted by a different amino acid; a HCDR2 region comprising an amino acid sequence WINTHSGVPKYAEDFKG as set forth in SEQ ID NO: 7, or a sequence of at least 4, 5, 6, 7, 8, 9 or 10 contiguous amino acids thereof (e.g. WINTHSGVPK (SEQ ID NO: 8)), wherein one or more of these amino acids may be substituted by a different amino acid; a HCDR3 region comprising an amino acid sequence GGDEGVMDY as set forth in SEQ ID NO: 9, or a sequence of at least 4, 5, 6, 7, 8, 9 or 10 contiguous amino acids thereof, wherein one or more of these amino acids may be substituted by a different amino acid; a LCDR1 region comprising an amino acid sequence KASQDVSTAVA as set forth in SEQ ID NO: 10, or a sequence of at least 4, 5, 6, 7, 8, 9 or 10 contiguous amino acids thereof, wherein one or more of these amino acids may be substituted by a different amino acid; a LCDR2 region comprising an amino acid sequence WASTRHT as set forth in SEQ ID NO: 11, or a sequence of at least 4, 5, 6, 7, 8, 9 or 10 contiguous amino acids thereof, wherein one or more of these amino acids may be substituted by a different amino acid; a LCDR3 region comprising an amino acid sequence QQHYNTPWT as set forth in SEQ ID NO: 12, or a sequence of at least 4, 5, 6, 7, 8, 9 or 10 contiguous amino acids thereof, wherein one or more of these amino acids may be deleted or substituted by a different amino acid.

In another aspect, provided is an antibody that binds human KIR3DL2, comprising:

(a) the heavy chain variable region of SEQ ID NO: 2, optionally wherein one, two, three or more residues may be substituted by a different amino acid; and/or (b) the light chain variable region of SEQ ID NO: 3, optionally wherein one, two, three or more residues may be substituted by a different amino acid; and/or (c) the heavy chain variable region of SEQ ID NO: 2, wherein one or more of these amino acids may be substituted by a different amino acid; and the light chain variable region of SEQ ID NO: 3, optionally wherein one, two, three or more residues may be substituted by a different amino acid; and/or (d) the heavy chain CDR 1, 2 and 3 (HCDR1, HCDR2, HCDR3) amino acid sequences as shown in SEQ ID NOS: 4-6, 7-8 and 9, respectively, optionally wherein one, two, three or more residues of any CDR may be substituted by a different amino acid; and/or (e) the light chain CDR 1, 2 and 3 (LCDR1, LCDR2, LCDR3) amino acid sequences as shown in SEQ ID NOS: 10, 11 and 12, optionally wherein one, two, three or more residues of any CDR may be substituted by a different amino acid; and/or (f) the heavy chain CDR 1, 2 and 3 (HCDR1, HCDR2, HCDR3) amino acid sequences as shown in SEQ ID NOS: 4, 7 and 9, respectively, optionally wherein one, two, three or more residues of any CDR may be substituted by a different amino acid; and the light chain CDRs 1, 2 and 3 (LCDR1, LCDR2, LCDR3) amino acid sequences as shown in SEQ ID NOS: 10, 11 and 12, optionally wherein one, two, three or more residues of any CDR may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, provided is an antibody that competes for KIR3DL2 binding with a monoclonal antibody of (a) to (f), above.

Antibody 2B12

The amino acid sequence of the heavy chain variable region of antibody 2B12 is listed in SEQ ID NO: 13, the amino acid sequence of the light chain variable region is listed as SEQ ID NO: 14. In one embodiment, provided is an antibody that binds essentially the same epitope or determinant as monoclonal antibodies 2B12; optionally the antibody comprises an antigen binding region of antibody 2B12. In any of the embodiments herein, antibody 2B12 can be characterized by its amino acid sequence and/or nucleic acid sequence encoding it. In one embodiment, the monoclonal antibody comprises the Fab or F(ab')$_2$ portion of 2B12. Also provided is a monoclonal antibody that comprises the heavy chain variable region of 2B12. According to one embodiment, the monoclonal antibody comprises the three CDRs of the heavy chain variable region of 2B12. Also provided is a monoclonal antibody that further comprises the variable light chain variable region of 2B12 or one, two or three of the CDRs of the light chain variable region of 2B12. Optionally any one or more of said light or heavy chain CDRs may contain one, two, three, four or five amino acid modifications (e.g. substitutions, insertions or deletions). Optionally, provided is an antibody where any of the light and/or heavy chain variable regions comprising part or all of an antigen binding region of antibody 2B12 are fused to an immunoglobulin constant region of the IgG type, optionally a human constant region, optionally an IgG1 or IgG4 isotype.

In another aspect, provided is a purified polypeptide which encodes an antibody, wherein the antibody comprises: a HCDR1 region comprising an amino acid sequence GYTFITAGMQ as set forth in SEQ ID NO: 17, or a sequence of at least 4, 5, 6, 7, 8, 9 or 10 contiguous amino acids thereof (e.g., TAGMQ (SEQ ID NO: 15), GYTFFT (SEQ ID NO:

16)), wherein one or more of these amino acids may be substituted by a different amino acid; a HCDR2 region comprising an amino acid sequence WINSHSGVPKYAE-DFK as set forth in SEQ ID NO: 18, or a sequence of at least 4, 5, 6, 7, 8, 9 or 10 contiguous amino acids thereof (e.g. WINSHSGVP (SEQ ID NO: 19)), wherein one or more of these amino acids may be substituted by a different amino acid; a HCDR3 region comprising an amino acid sequence GGDEGVMDYW as set forth in SEQ ID NO: 20, or a sequence of at least 4, 5, 6, 7, 8, 9 or 10 contiguous amino acids thereof, wherein one or more of these amino acids may be substituted by a different amino acid; a LCDR1 region comprising an amino acid sequence KASQDVSTAVA as set forth in SEQ ID NO: 10, or a sequence of at least 4, 5, 6, 7, 8, 9 or 10 contiguous amino acids thereof, wherein one or more of these amino acids may be substituted by a different amino acid; a LCDR2 region comprising an amino acid sequence WTSTRHT as set forth in SEQ ID NO: 21, or a sequence of at least 4, 5, 6, 7, 8, 9 or 10 contiguous amino acids thereof, wherein one or more of these amino acids may be substituted by a different amino acid; and/or a LCDR3 region comprising an amino acid sequence QQHYSTPWT as set forth in SEQ ID NO: 22, or a sequence of at least 4, 5, 6, 7, 8, 9 or 10 contiguous amino acids thereof, wherein one or more of these amino acids may be deleted or substituted by a different amino acid, or where the sequence may comprise an insertion of one or more amino acids.

In another aspect, provided is an antibody that binds human KIR3DL2, comprising:

(a) the heavy chain variable region of SEQ ID NO: 13, optionally wherein one, two, three or more of amino acid residues may be substituted by a different amino acid; and/or (b) the light chain variable region of SEQ ID NO: 14, optionally wherein one, two, three or more of amino acid residues may be substituted by a different amino acid; and/or (c) the heavy chain variable region of SEQ ID NO: 13, optionally wherein one, two, three or more of amino acid residues may be substituted by a different amino acid; and the light chain variable region of SEQ ID NO: 14, optionally wherein one or more of amino acid residues may be substituted by a different amino acid; and/or (d) the heavy chain CDR 1, 2 and 3 (HCDR1, HCDR2, HCDR3) amino acid sequences as shown in SEQ ID NOS: 15-17, 18-19 and 20, respectively, optionally wherein one, two, three or more residues of any CDR may be substituted by a different amino acid; and/or (e) the light chain CDR 1, 2 and 3 (LCDR1, LCDR2, LCDR3) amino acid sequences as shown in SEQ ID NOS: 10, 21 and 22, respectively, optionally wherein one, two, three or more residues of any CDR may be substituted by a different amino acid; and/or (f) the heavy chain CDR 1, 2 and 3 (HCDR1, HCDR2, HCDR3) amino acid sequences as shown in SEQ ID NOS: 15, 18 and 20, respectively, optionally wherein one, two, three or more residues of any CDR may be substituted by a different amino acid; and the light chain CDR 1, 2 and 3 (LCDR1, LCDR2, LCDR3) amino acid sequences as shown in SEQ ID NOS: 10, 21 and 22, optionally wherein one, two, three or more residues of any CDR may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, provided is an antibody that competes for KIR3DL2 binding with a monoclonal antibody of (a) to (f), above.

Antibody 10G5

The amino acid sequence of the heavy chain variable region of antibody 10G5 is listed as SEQ ID NO: 23, the amino acid sequence of the light chain variable region is listed as SEQ ID NO: 24. In a specific embodiment, provided is an antibody that binds essentially the same epitope or determinant as monoclonal antibodies 10G5; optionally the antibody comprises an antigen binding region of antibody 10G5. In any of the embodiments herein, antibody 10G5 can be characterized by its amino acid sequence and/or nucleic acid sequence encoding it. In one embodiment, the monoclonal antibody comprises the Fab or F(ab')$_2$ portion of 10G5. Also provided is a monoclonal antibody that comprises the heavy chain variable region of 10G5. According to one embodiment, the monoclonal antibody comprises the three CDRs of the heavy chain variable region of 10G5 Also provided is a monoclonal antibody that further comprises the variable light chain variable region of 10G5 or one, two or three of the CDRs of the light chain variable region of 10G5. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 10G5 are fused to an immunoglobulin constant region of the human IgG type, optionally a human constant region, optionally a human IgG1 or IgG3 isotype.

In another aspect, provided is a purified polypeptide which encodes an antibody, wherein the antibody comprises: a HCDR1 region comprising an amino acid sequence GYT-FTSYTMH as set forth in SEQ ID NO: 27, or a sequence of at least 4, 5, 6, 7, 8, 9 or 10 contiguous amino acids thereof (e.g. SYTMH (SEQ ID NO: 25), GYTFTS (SEQ ID NO: 26)), wherein one or more of these amino acids may be substituted by a different amino acid; a HCDR2 region comprising an amino acid sequence YINPSSGYTENNRKF as set forth in SEQ ID NO: 28, or a sequence of at least 4, 5, 6, 7, 8, 9 or 10 contiguous amino acids thereof (e.g. YINPSSGY (SEQ ID NO: 29)), wherein one or more of these amino acids may be substituted by a different amino acid; a HCDR3 region comprising an amino acid sequence RLGKGLLPPFDY as set forth in SEQ ID NO: 30, or a sequence of at least 4, 5, 6, 7, 8, 9 or 10 contiguous amino acids thereof, wherein one or more of these amino acids may be substituted by a different amino acid; a LCDR1 region comprising an amino acid sequence RASENIYSNLA as set forth in SEQ ID NO: 31, or a sequence of at least 4, 5, 6, 7, 8, 9 or 10 contiguous amino acids thereof, wherein one or more of these amino acids may be substituted by a different amino acid; a LCDR2 region comprising an amino acid sequence AATNLAD as set forth in SEQ ID NO: 32, or a sequence of at least 4, 5, 6, 7, 8, 9 or 10 contiguous amino acids thereof, wherein one or more of these amino acids may be substituted by a different amino acid; a LCDR3 region comprising an amino acid sequence QHFWGTPYT as set forth in SEQ ID NO: 33, or a sequence of at least 4, 5, 6, 7, 8, 9 or 10 contiguous amino acids thereof, wherein one or more of these amino acids may be deleted or substituted by a different amino acid.

In another aspect, provided is an antibody that binds human KIR3DL2, comprising:

(a) the heavy chain variable region of SEQ ID NO: 23, optionally wherein one, two, three or more residues may be substituted by a different amino acid; and/or (b) the light chain variable region of SEQ ID NO: 24, optionally wherein one, two, three or more residues may be substituted by a different amino acid; and/or (c) the heavy chain variable region of SEQ ID NO: 23, optionally wherein one or more residues may be substituted by a different amino acid; and the light chain variable region of SEQ ID NO: 24 wherein one, two, three or more residues may be substituted by a different amino acid; and/or (d) the heavy chain CDR 1, 2 and 3 (HCDR1, HCDR2, HCDR3) amino acid sequences as shown in SEQ ID NO: 25-27, 28-29 and 30, respectively, optionally wherein one, two, three or more residues of any CDR may be substituted by a different amino acid; and/or (e) the light chain CDR 1, 2 and 3 (LCDR1, LCDR2, LCDR3) amino acid sequences as shown in SEQ ID NOS: 31, 32, and 33, optionally wherein one, two, three or more residues of any CDR may be substituted by a different amino acid; and/or (f) the heavy chain CDR 1, 2 and 3 (HCDR1, HCDR2, HCDR3) amino acid sequences as shown in SEQ ID NOS: 25, 28 and 30, respectively, optionally wherein one or more residues of any CDR may be substituted by a different amino acid; and the light chain CDRs 1, 2 and 3 (LCDR1, LCDR2, LCDR3) amino acid sequences as shown in SEQ ID NOS: 31, 32, and 33, optionally wherein one, two, three or more residues of any CDR may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, provided is an antibody that competes for KIR3DL2 binding with a monoclonal antibody of (a) to (f), above.

Antibody 13H1

The amino acid sequence of the heavy chain variable region of antibody 13H1 is listed as SEQ ID NO: 34, the amino acid sequence of the light chain variable region is listed as SEQ ID NO: 35. In a specific embodiment, provided is an antibody that binds essentially the same epitope or determinant as monoclonal antibodies 13H1; optionally the antibody comprises an antigen binding region of antibody 13H1. In any of the embodiments herein, antibody 13H1 can be characterized by its amino acid sequence and/or nucleic acid sequence encoding it. In one embodiment, the monoclonal antibody comprises the Fab or F(ab')₂ portion of 13H1. Also provided is a monoclonal antibody that comprises the heavy chain variable region of 13H1. According to one embodiment, the monoclonal antibody comprises the three CDRs of the heavy chain variable region of 13H1. Also provided is a monoclonal antibody that further comprises the variable light chain variable region of 13H1 or one, two or three of the CDRs of the light chain variable region of 13H1. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 13H1 are fused to an immunoglobulin constant region of the human IgG type, optionally a human constant region, optionally a human IgG1 or IgG3 isotype.

In another aspect, provided is a purified polypeptide which encodes an antibody, wherein the antibody comprises: a HCDR1 region comprising an amino acid sequence HYSFIGY™ as set forth in SEQ ID NO: 38, or a sequence of at least 4, 5, 6, 7, 8, 9 or 10 contiguous amino acids thereof (e.g. GYTMN (SEQ ID NO: 36), HYSFIG (SEQ ID NO: 37)), wherein one or more of these amino acids may be substituted by a different amino acid; a HCDR2 region comprising an amino acid sequence LINPYNGDTTYNQK-FKG as set forth in SEQ ID NO: 39, or a sequence of at least 4, 5, 6, 7, 8, 9 or 10 contiguous amino acids thereof (e.g. LINPYNGDTIT (SEQ ID NO: 40)), wherein one or more of these amino acids may be substituted by a different amino acid; a HCDR3 region comprising an amino acid sequence ENWGYPYAMDY as set forth in SEQ ID NO: 41, or a sequence of at least 4, 5, 6, 7, 8, 9 or 10 contiguous amino acids thereof, wherein one or more of these amino acids may be substituted by a different amino acid; a LCDR1 region comprising an amino acid sequence RASESVDNFGISFMN as set forth in SEQ ID NO: 42, or a sequence of at least 4, 5, 6, 7, 8, 9 or 10 contiguous amino acids thereof, wherein one or more of these amino acids may be substituted by a different amino acid; a LCDR2 region comprising an amino acid sequence AASNQGS as set forth in SEQ ID NO: 43, or a sequence of at least 4, 5, 6, 7, 8, 9 or 10 contiguous amino acids thereof, wherein one or more of these amino acids may be substituted by a different amino acid; a LCDR3 region comprising an amino acid sequence QQSKEVPYT as set forth in SEQ ID NO: 44, or a sequence of at least 4, 5, 6, 7, 8, 9 or 10 contiguous amino acids thereof, wherein one or more of these amino acids may be deleted or substituted by a different amino acid.

In another aspect, provided is an antibody that binds human KIR3DL2, comprising:

(a) the heavy chain variable region of SEQ ID NO: 34, optionally wherein one, two, three or more amino acid residues may be substituted by a different amino acid; and/or (b) the light chain variable region of SEQ ID NO: 35, optionally wherein one, two, three or more amino acid residues may be substituted by a different amino acid; and/or (c) the heavy chain variable region of SEQ ID NO: 34, optionally wherein one or more amino acid residues may be substituted by a different amino acid; and the light chain variable region of SEQ ID NO: 35, wherein one, two, three or more of these amino acids may be substituted by a different amino acid; and/or (d) the heavy chain CDR 1, 2 and 3 (HCDR1, HCDR2, HCDR3) amino acid sequences as shown in SEQ ID NOS: 36-38, 39-40 and 41, respectively, optionally wherein one, two, three or more amino acid residues of any CDR may be substituted by a different amino acid; and/or (e) the light chain CDR 1, 2 and 3 (LCDR1, LCDR2, LCDR3) amino acid sequences as shown in SEQ ID NOS: 42, 43 and 44, optionally wherein one, two, three or more amino acid residues of any CDR may be substituted by a different amino acid; and/or (f) the heavy chain CDR 1, 2 and 3 (HCDR1, HCDR2, HCDR3) amino acid sequences as shown in SEQ ID NOS: 36, 39 and 41, respectively, optionally wherein one or more amino acid residues of any CDR may be substituted by a different amino acid; and the light chain CDRs 1, 2 and 3 (LCDR1, LCDR2, LCDR3) amino acid sequences as shown in SEQ ID NOS: 42, 43 and 44, optionally wherein one, two, three or more amino acid residues of any CDR may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, provided is an antibody that competes for KIR3DL2 binding with a monoclonal antibody of (a) to (f), above.

Antibody 1E2

The amino acid sequence of the heavy chain variable region of antibody 1E2 is listed as SEQ ID NO: 45, the amino acid sequence of the light chain variable region is listed as SEQ ID NO: 46. In a specific embodiment, provided is an antibody that binds essentially the same epitope or determinant as monoclonal antibodies 1E2; optionally the antibody comprises an antigen binding region of antibody 1E2. In any of the embodiments herein, antibody 1E2 can be characterized by its amino acid sequence and/or nucleic acid sequence encoding it. In one embodiment, the monoclonal antibody comprises the Fab or F(ab')$_2$ portion of 1E2. Also provided is a monoclonal antibody that comprises the heavy chain variable region of 1E2. According to one embodiment, the monoclonal antibody comprises the three CDRs of the heavy chain variable region of 1E2 Also provided is a monoclonal antibody that further comprises the variable light chain variable region of 1E2 or one, two or three of the CDRs of the light chain variable region of 1E2. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 1E2 are fused to an immunoglobulin constant region of the human IgG type, optionally a human constant region, optionally a human IgG1 or IgG3 isotype.

In another aspect, provided is a purified polypeptide which encodes an antibody, wherein the antibody comprises: a HCDR1 region comprising an amino acid sequence GYT-FTDYAMN as set forth in SEQ ID NO: 49, or a sequence of at least 4, 5, 6, 7, 8, 9 or 10 contiguous amino acids thereof (e.g. DYAMN (SEQ ID NO: 47), GYTFTD (SEQ ID NO: 48)), wherein one or more of these amino acids may be substituted by a different amino acid; a HCDR2 region comprising an amino acid sequence VISTYYGDANYN-QKFKG as set forth in SEQ ID NO: 50, or a sequence of at least 4, 5, 6, 7, 8, 9 or 10 contiguous amino acids thereof (e.g. VISTYYGDAN (SEQ ID NO: 51)), wherein one or more of these amino acids may be substituted by a different amino acid; a HCDR3 region comprising an amino acid sequence IYYDYDGSY as set forth in SEQ ID NO: 52, or a sequence of at least 4, 5, 6, 7, 8, 9 or 10 contiguous amino acids thereof, wherein one or more of these amino acids may be substituted by a different amino acid; a LCDR1 region comprising an amino acid sequence RSSQSLVHSNGN-TYLH as set forth in SEQ ID NO: 53, or a sequence of at least 4, 5, 6, 7, 8, 9 or 10 contiguous amino acids thereof, wherein one or more of these amino acids may be substituted by a different amino acid; a LCDR2 region comprising an amino acid sequence KVSNRFS as set forth in SEQ ID NO: 54, or a sequence of at least 4, 5, 6, 7, 8, 9 or 10 contiguous amino acids thereof, wherein one or more of these amino acids may be substituted by a different amino acid; a LCDR3 region comprising an amino acid sequence SQSTHVPPYT as set forth in SEQ ID NO: 55, or a sequence of at least 4, 5, 6, 7, 8, 9 or 10 contiguous amino acids thereof, wherein one or more of these amino acids may be deleted or substituted by a different amino acid.

In another aspect, provided is an antibody that binds human KIR3DL2, comprising:

(a) the heavy chain variable region of SEQ ID NO: 42, optionally wherein one, two, three or more amino acid residues may be substituted by a different amino acid; and/or (b) the light chain variable region of SEQ ID NO: 43, optionally wherein one, two, three or more amino acid residues may be substituted by a different amino acid; and/or (c) the heavy chain variable region of SEQ ID NO: 42, optionally wherein one or more amino acid residues may be substituted by a different amino acid; and the light chain variable region of SEQ ID NO: 43, optionally wherein one, two, three or more of these amino acids may be substituted by a different amino acid; and/or (d) the heavy chain CDR 1, 2 and 3 (HCDR1, HCDR2, HCDR3) amino acid sequences as shown in SEQ ID NOS: 47-49, 50-51 and 52, respectively, optionally wherein one, two, three or more amino acid residues of any CDR may be substituted by a different amino acid; and/or (e) the light chain CDR 1, 2 and 3 (LCDR1, LCDR2, LCDR3) amino acid sequences as shown in SEQ ID NOS: 53, 54 and 55, optionally wherein one, two, three amino acid residues of any CDR may be substituted by a different amino acid; and/or (f) the heavy chain CDR 1, 2 and 3 (HCDR1, HCDR2, HCDR3) amino acid sequences as shown in SEQ ID NOS: 47, 50 and 52, optionally wherein one or more amino acid residues of any CDR may be substituted by a different amino acid; and the light chain CDRs 1, 2 and 3 (LCDR1, LCDR2, LCDR3) amino acid sequences as shown in SEQ ID NOS: 53, 54 and 55, optionally wherein one, two, three or more amino acid residues of any CDR may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, provided is an antibody that competes for KIR3DL2 binding with a monoclonal antibody of (a) to (f), above.

Antibody 9E10

The amino acid sequence of the heavy chain variable region of 9E10 is listed as SEQ ID NO: 56, the amino acid sequence of the light chain variable regions (two alternative light chains available) of 9E10 are listed as SEQ ID NOS: 57 and 67. In a specific embodiment, provided is an antibody that binds essentially the same epitope or determinant as monoclonal antibodies 9E10; optionally the antibody comprises an antigen binding region of antibody 9E10. In any of the embodiments herein, antibody 9E10 can be characterized by its amino acid sequence and/or nucleic acid sequence encoding it. In one embodiment, the monoclonal antibody comprises the Fab or F(ab')2 portion of 9E10. Also provided is a monoclonal antibody that comprises the heavy chain variable region of 9E10. According to one embodiment, the monoclonal antibody comprises the three CDRs of the heavy chain variable region of 9E10. Also provided is a monoclonal antibody that further comprises the variable light chain variable region of 9E10 or one, two or three of the CDRs of the light chain variable region of 9E10. Optionally any one or more of said light or heavy chain CDRs may contain one, two, three, four or five amino acid modifications (e.g. substitutions, insertions or deletions). Optionally, provided is an antibody where any of the light and/or heavy chain variable regions comprising part or all of an antigen binding region of antibody 9E10 are fused to an immunoglobulin constant region of the IgG type, optionally a human constant region, optionally a human IgG or IgG4 isotype.

In another aspect, provided is a purified polypeptide which encodes an antibody, wherein the antibody comprises: a HCDR1 region comprising an amino acid sequence GYTFTSYTMH as set forth in SEQ ID NO: 60, or a sequence of at least 4, 5, 6, 7, 8, 9 or 10 contiguous amino acids thereof (e.g., SYTMH (SEQ ID NO: 58), GYTFTS (SEQ ID NO: 59)), wherein one or more of these amino acids may be substituted by a different amino acid; a HCDR2 region comprising an amino acid sequence YINPSSGYTDYNQKFKD as set forth in SEQ ID NO: 61, or a sequence of at least 4, 5, 6, 7, 8, 9 or 10 contiguous amino acids thereof (e.g. YINPSSGYTD (SEQ ID NO: 62)), wherein one or more of these amino acids may be substituted by a different amino acid; a HCDR3 region comprising an amino acid sequence LGKGLLPPFDY as set forth in SEQ ID NO: 63, or a sequence of at least 4, 5, 6, 7, 8, 9 or 10 contiguous amino acids thereof, wherein one or more of these amino acids may be substituted by a different amino acid; a LCDR1 region comprising an amino acid sequence KSNQNLLWSGNQRYCLV as set forth in SEQ ID NO: 64, or a sequence of at least 4, 5, 6, 7, 8, 9 or 10 contiguous amino acids thereof, wherein one or more of these amino acids may be substituted by a different amino acid; a LCDR2 region comprising an amino acid sequence WTSDRYS as set forth in SEQ ID NO: 65, or a sequence of at least 4, 5, 6, 7, 8, 9 or 10 contiguous amino acids thereof, wherein one or more of these amino acids may be substituted by a different amino acid; a LCDR3 region comprising an amino acid sequence QQHLHIPYT as set forth in SEQ ID NO: 66, or a sequence of at least 4, 5, 6, 7, 8, 9 or 10 contiguous amino acids thereof, wherein one or more of these amino acids may be deleted or substituted by a different amino acid, or where the sequence may comprise an insertion of one or more amino acids.

In another aspect, provided is an antibody that binds human KIR3DL2, comprising:

(a) the heavy chain variable region of SEQ ID NO: 56, optionally wherein one, two, three or amino acid residues may be substituted by a different amino acid; and/or (b) the light chain variable region of SEQ ID NOS: 57 or 67, optionally wherein one, two, three or more amino acid residues may be substituted by a different amino acid; and/or (c) the heavy chain variable region of SEQ ID NO: 56, optionally wherein one, two, three or more amino acid residues may be substituted by a different amino acid; and the light chain variable region of SEQ ID NOS: 57 or 67, optionally wherein one, two, three or more amino acid residues may be substituted by a different amino acid; and/or (d) the heavy chain CDR 1 and 2 (HCDR1, HCDR2) amino acid sequences as shown in SEQ ID NOS: 58, 59 or 60, 61-62 and 63, optionally wherein one, two, three or more residues of any CDR may be substituted by a different amino acid; and/or (e) the light chain CDR 1, 2 and 3 (LCDR1, LCDR2, LCDR3) amino acid sequences as shown in SEQ ID NOS: 64, 65 and 66, optionally wherein one, two, three or more residues of any CDR may be substituted by a different amino acid; and/or (f) the heavy chain CDR 1, 2 and 3 (HCDR1, HCDR2, HCDR3) amino acid sequences as shown in SEQ ID NOS: 58, 61 and 63, optionally wherein one, two, three residues of any CDR may be substituted by a different amino acid; and the light chain CDR 1, 2 and 3 (LCDR1, LCDR2, LCDR3) amino acid sequences as shown in SEQ ID NOS: 64, 65 and 66, optionally wherein one, two, three or more residues of any CDR may be substituted by a different amino acid.

In another embodiment, provided is antibody 1C3 (anti-D2 domain), its variable region and CDRs. In one embodiment, provided is an antibody having respectively a VH and VL region of SEQ ID NOS: 170 and 171 (1C3). In one embodiment, provided is an antibody having a heavy chain comprising CDRs 1, 2 and 3 (HCDR1, HCDR2, HCDR3) comprising a sequence of SEQ ID NO: 172, 173 or 174 (HCDR1), SEQ ID NO: 175 or 176 (HCDR2) and SEQ ID NO: 177 (HCDR3), respectively, wherein each CDR may optionally comprise 1, 2, 3 or 4 amino acid substitutions, deletions or insertions. In one embodiment, provided is an antibody having (i) a heavy chain comprising CDRs 1, 2 and 3 (HCDR1, HCDR2, HCDR3) comprising a sequence of SEQ ID NO: 172, 173 or 174 (HCDR1), SEQ ID NO: 175 or 176 (HCDR2) and SEQ ID NO: 177 (HCDR3), respectively, and (ii) a light chain comprising CDR 1, 2 and 3 (LCDR1, LCDR2, LCDR3) comprising a sequence of SEQ ID NO: 178, 179 or 180, respectively, wherein each CDR may optionally comprise 1, 2, 3 or 4 amino acid substitutions, deletions or insertions.

In another embodiment, provided is antibody 20E9 (anti-D2 domain), its variable region and CDRs. In one embodiment, provided is an antibody having respectively a VH and VL region of SEQ ID NOS: 181 and 182 (20E9). In one embodiment, provided is an antibody having a heavy chain comprising CDRs 1, 2 and 3 (HCDR1, HCDR2, HCDR3) comprising a sequence of SEQ ID NO: 183, 184 or 185 (HCDR1), SEQ ID NO: 186 or 187 (HCDR2) and SEQ ID NO: 188 (HCDR3), respectively, wherein each CDR may optionally comprise 1, 2, 3 or 4 amino acid substitutions, deletions or insertions. In one embodiment, provided is an antibody having (i) a heavy chain comprising CDRs 1, 2 and 3 (HCDR1, HCDR2, HCDR3) comprising a sequence of SEQ ID NO: 183, 184 or 185 (HCDR1), SEQ ID NO: 186 or 187 (HCDR2) and SEQ ID NO: 188 (HCDR3), respectively, and (ii) a light chain comprising CDR 1, 2 and 3 (LCDR1, LCDR2, LCDR3) comprising a sequence of SEQ ID NO: 189, 190 or 191, respectively, wherein each CDR may optionally comprise 1, 2, 3 or 4 amino acid substitutions, deletions or insertions.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, provided is an antibody that competes for KIR3DL2 binding with a monoclonal antibody above.

In any of the antibodies, the specified variable region and CDR sequences may comprise one, two, three, four, five or more conservative sequence modifications. Conservative sequence modifications refers to amino acid modifications that do not significantly affect or alter the binding characteristics of the antibody containing the amino acid sequence.

Such conservative modifications include amino acid substitutions, additions and deletions. Modifications can be introduced into an antibody by standard techniques known in the art, such as site-directed mutagenesis and PCR-mediated mutagenesis. Conservative amino acid substitutions are typically those in which an amino acid residue is replaced with an amino acid residue having a side chain with similar physicochemical properties. Specified variable region and CDR sequences may comprise one, two, three, four or more amino acid insertions, deletions or substitutions. Where substitutions are made, substitutions can optionally be conservative modifications. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g. threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for retained function (i.e., the properties set forth herein) using the assays described herein.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

The sequences of the CDRs of antibodies, according to AbM (Oxford Molecular's AbM antibody modelling software definition), Kabat and Chothia definitions systems, have been summarized in Table 1 for heavy chain CDRs, and in Table 2 below for light chain CDRs (light chain CDRs are the same for each of AbM, Kabat and Chothia definitions). The amino acids sequences described herein are numbered according to Abm, Kabat and Chothia numbering systems. While any suitable numbering system may be used to designated CDR regions, in the absence of any other indication, Abm numbering can be used. Such numbering has been established using the following indications: CDR-L1: Start: approx. residue 24, residue before: always a Cys, residue after: always a Trp (typically Trp-Tyr-Gln, but also, Trp-Leu-Gln, Trp-Phe-Gln, Trp-Tyr-Leu), length: 10 to 17 residues; CDR-L2: Start: always 16 residues after the end of L1, Residues before: generally Ile-Tyr (but also, Val-Tyr, Ile-Lys, Ile-Phe), Length: always 7 residues; CDR-L3, Start: always 33 residues after end of L2, Residue before: always Cys, Residues after: always Phe-Gly-Xaa-Gly, Length: 7 to 11 residues; CDR-H1, Start: approx. residue 26 (always 4 after a Cys) (Chothia/AbM definition, the Kabat definition starts 5 residues later), Residues before: always Cys-Xaa-Xaa-Xaa, Residues after: always a Trp (typically Trp-Val, but also, Trp-Ile, Trp-Ala), Length: 10 to 12 residues (AbM definition, Chothia definition excludes the last 4 residues); CDR-H2, Start: always 15 residues after the end of Kabat/AbM definition of CDR-H1, Residues before: typically Leu-Glu-Trp-Ile-Gly (SEQ ID NO: 192) (but a number of variations, Residues after Lys/Arg-Leu/IleNal/Phe/Thr/Ala-Thr/Ser/Ile/Ala), Length: Kabat definition 16 to 19 residues; AbM (and Chothia) definition ends 7 residues earlier; CDR-H3, Start: always 33 residues after end of CDR-H2 (always 2 after a Cys), Residues before: always Cys-Xaa-Xaa (typically Cys-Ala-Arg), Residues after: always Trp-Gly-Xaa-Gly, Length: 3 to 25 residues.

In one embodiment, the antibodies are of the human or mouse IgG1 isotype. In another embodiment, the antibodies are of the human IgG1 isotype In an embodiment, the antibodies are antibody fragments that retain their binding and/or functional properties. In one embodiment, the antibody is an antibody having the Kabat, Chotia or AbM heavy and light chain CDR1, CDR2 and CDR3 of any of the antibodies as shown in Table 1 below.

TABLE 1

| mAb | CDR definition | HCDR1 SEQ ID | Sequence | HCDR2 SEQ ID | Sequence | HCDR3 SEQ ID | Sequence |
|---|---|---|---|---|---|---|---|
| 10F6 | Kabat | 4 | IAGMQ | 7 | WINTHSGVPKYAEDFKG | 9 | GGDEGVMDY |
|  | Chotia | 5 | GYTFTI | 8 | WINTHSGVPK | 9 | GGDEGVMDY |
|  | AbM | 6 | GYTFTIAGMQ | 8 | WINTHSGVPK | 9 | GGDEGVMDY |
| 2B12 | Kabat | 15 | TAGMQ | 18 | WINSHSGVPKYAEDFK | 20 | GGDEGVMDYW |
|  | Chotia | 16 | GYTFTT | 19 | WINSHSGVP | 20 | GGDEGVMDYW |
|  | AbM | 17 | GYTFTTAGMQ | 19 | WINSHSGVP | 20 | GGDEGVMDYW |

TABLE 1 -continued

| mAb | CDR definition | HCDR1 SEQ ID | Sequence | HCDR2 SEQ ID | Sequence | HCDR3 SEQ ID | Sequence |
|---|---|---|---|---|---|---|---|
| 10G5 | Kabat | 25 | SYTMH | 28 | YINPSSGYTENNRKF | 30 | RLGKGLLPPFDY |
|  | Chotia | 26 | GYTFTS | 29 | YINPSSGY | 30 | RLGKGLLPPFDY |
|  | AbM | 27 | GYTFTSYTMH | 29 | YINPSSGY | 30 | RLGKGLLPPFDY |
| 13H1 | Kabat | 36 | GYTMN | 39 | LINPYNGDTTYNQKFKG | 41 | ENWGYPYAMDY |
|  | Chotia | 37 | HYSFIG | 40 | LINPYNGDTT | 41 | ENWGYPYAMDY |
|  | AbM | 38 | HYSFIGYTMN | 40 | LINPYNGDTT | 41 | ENWGYPYAMDY |
| 1E2 | Kabat | 47 | DYAMN | 50 | VISTYYGDANYNQKFKG | 52 | IYYDYDGSY |
|  | Chotia | 48 | GYTFTD | 51 | VISTYYGDAN | 52 | IYYDYDGSY |
|  | AbM | 49 | GYTFTDYAMN | 51 | VISTYYGDAN | 52 | IYYDYDGSY |
| 9E10 | Kabat | 58 | SYTMH | 61 | YINPSSGYTDYNQKFKD | 63 | LGKGLLPPFDY |
|  | Chotia | 59 | GYTFTS | 62 | YINPSSGYTD | 63 | LGKGLLPPFDY |
|  | AbM | 60 | GYTFTSYTMH | 62 | YINPSSGYTD | 63 | LGKGLLPPFDY |
| 1C3 | Kabat | 172 | SYWMQ | 175 | AIYPGDGDTRYTQKFKG | 177 | RYDGYYHFDY |
|  | Chotia | 173 | GYTFTS | 176 | AIYPGDGDTR | 177 | RYDGYYHFDY |
|  | AbM | 174 | GYTFTSYWMQ | 176 | AIYPGDGDTR | 177 | RYDGYYHFDY |
| 20E9 | Kabat | 183 | TYWMQ | 186 | AIYPGDGDTRYTQKFKG | 188 | RGDYGNYGMDY |
|  | Chotia | 184 | GFTFTT | 187 | AIYPGDGDTR | 188 | RGDYGNYGMDY |
|  | AbM | 185 | GFTFTTYWMQ | 187 | AIYPGDGDTR | 188 | RGDYGNYGMDY |

TABLE 2

| mAb | LCDR1 SEQ ID | Sequence | LCDR2 SEQ ID | Sequence | LCDR3 SEQ ID | Sequence |
|---|---|---|---|---|---|---|
| 10F6 | 10 | KASQDVSTAVA | 11 | WASTRHT | 12 | QQHYNTPWT |
| 2B12 | 10 | KASQDVSTAVA | 21 | WTSTRHT | 22 | QQHYSTPWT |
| 10G5 | 31 | RASENIYSNLA | 32 | AATNLAD | 33 | QHFWGTPYT |
| 13H1 | 42 | RASESVDNFGISFMN | 43 | AASNQGS | 44 | QQSKEVPYT |
| 1E2 | 53 | RSSQSLVHSNGNTYLH | 54 | KVSNRFS | 55 | SQSTHVPPYT |
| 9E10 | 64 | KSNQNLLWSGNQRYCLV | 65 | WTSDRYS | 66 | QQHLHIPYT |
| 1C3 | 178 | KSSQSLLWSVNQKNYLS | 179 | GASIRES | 180 | QHNHGSFLPLT |
| 20E9 | 189 | RSSQSIVHSNGNTYLE | 190 | KVSNHFS | 191 | FQGSHVPPT |

The sequences of the variable chains of the antibodies are listed in Table 3 below, with the CDRs underlined. In any embodiment herein, a VL or VH sequence can be specified or numbered so as to contain or lack a signal peptide or any part thereof.

TABLE 3

| Antibody portion | SEQ ID NO: | |
|---|---|---|
| 10F6 VH | 2 | Q I Q L V Q S G P E L K K P G E T V R I S C K A S <u>G Y T F T I A G M Q</u> W V Q K M P G K G L K W I G <u>W I N T H S G V P K Y A E D F K G</u> R F A F S L E T S A N I A Y L Q I S N L K N E D T A T Y F C A R <u>G G D E G V M D Y</u> W G Q G T S V T V S |
| 10F6 VL | 3 | D I V M T Q S H K F M S T S V G D R V S I T C <u>K A S Q D V S T A V A</u> W Y H Q K P G Q S P K L L I Y <u>W A S T R H T</u> G V P D R F S G S G S G T D Y T L T I S A L Q A E D L A L Y Y C <u>Q Q H Y N T P W T</u> F G G G T K L E I K |
| 2B12 VH | 13 | Q I Q L V Q S G P E L K K P G E T V R I S C K A S <u>G Y T F T T A G M Q</u> W V Q K T P G K G L K W I G <u>W I N S H S G V P K Y A E D F K G</u> R F A F S L E T S A S T A Y L Q I S T L K N E D T A T Y F C A R <u>G G D E G V M D Y</u> W G Q G T S V T V S |

TABLE 3 -continued

| Antibody portion | SEQ ID NO: | |
|---|---|---|
| 2B12 VL | 14 | D I V M T Q S H K F M S T S L G D R V S F T C <u>K A S Q</u> <u>D V S T A V A W</u> Y Q Q K P G Q S P K L L I Y <u>W T S T R</u> <u>H T</u> G V P D R F T G S G S G T D Y T L T I S S V Q A E D L A L Y Y C <u>Q Q H Y S T P W T</u> F G G G T K L E I K |
| 10G5 VH | 23 | Q V Q L Q Q S A A E L A R P G A S V K M S C K A S <u>G Y</u> <u>T F T S Y T M H</u> W V K Q R P G Q G L E W I G <u>Y I N P S</u> <u>S G Y T E N N R K F</u> K D K T T L T A D K S S S T A Y M Q L S S L T S E D S A V Y Y C A R <u>R L G K G L L P P F D</u> <u>Y</u> W G Q G T T L T V S S A K T T P P S V Y P L A P G S A A Q T |
| 10G5 VL | 24 | D I Q M T Q S P A S L S V S V G E T V T I T C <u>R A S E</u> <u>N I Y S N L A</u> W Y Q Q K Q G K S P Q L L V Y <u>A A T N L</u> <u>A D</u> G V P S R F S G S G S G T Q Y S L K I N S L Q S E D F G S Y Y C <u>Q H F W G T P Y T</u> F G G G T K L E I K |
| 13H1 VH | 34 | E V Q L Q Q S G P E L V K P G A S M K I S C K A S <u>H Y</u> <u>S F I G Y T M N</u> W V K Q R H G K N L E W I G <u>L I N P Y</u> <u>N G D T T Y N Q K F K G</u> K A S L T V D K S S S T A Y M E I L S L T S E D S A V Y Y C A R <u>E N W G Y P Y A M</u> <u>Y</u> W G Q G T S V T V S |
| 13H1 VL | 35 | D I V L T Q S P A S L A V S L G Q R A T I S C <u>R A S E</u> <u>S V D N F G I S F M N</u> W F Q Q K P G Q P P K L L I Y <u>A</u> <u>A S N Q G</u> S G V P A R F S G S R S G T D F S L N I H P M E E D D T A M Y F C <u>Q Q S K E V P Y T</u> F G G G T K L E I K |
| 1E2 VH | 45 | Q V Q L Q Q S G A E L V R P G V S V K I S C K G S <u>G Y</u> <u>T F T D Y A M N</u> W V K Q S H A K S L E W I G <u>V I S T Y</u> <u>Y G D A N Y N Q K F K G</u> K A T M T V D K S S S T A Y M E L A R L T S E D S A I Y Y C A L <u>I Y Y D Y D G S Y</u> W G Q G T T L T V S |
| 1E2 VL | 46 | D V V M T Q T P L S L P V S L G D Q A S I S C <u>R S S Q</u> <u>S L V H S N G N T Y L H</u> W Y L Q K P G Q S P K L L I Y <u>K V S N R F S</u> G V P D R F S G S G S G T D F T L K I S R V E A E D L G V Y F C <u>S Q S T H V P P Y T</u> F G G G T K L E I K |
| 9E10 VH | 56 | Q V Q L Q Q S A A E L A R P G A S V K M S C K A S <u>G Y</u> <u>T F T S Y T M H</u> W V K Q R P G Q G L E W I G <u>Y I N P S</u> <u>S G Y T D Y N Q K F K D</u> K T T L T A D R S S S T A Y M Q L S S L T S E D S A V Y Y C A R <u>L G K G L L P P F D</u> <u>Y</u> W G Q G S T L T V S S |
| 9E10 VL1 | 57 | E I V L T Q S I P S L T V S A G E R V T I S C <u>K S N Q</u> <u>N L L W S G N Q R Y C L V</u> W H Q W K P G Q T P T P L I <u>T W T S D R Y S</u> G V P D R F I G S G S V T D F T L T I S S V Q A E D V A V Y F C <u>Q Q H L H I P Y T</u> F G G G T K L E I K |
| 9E10 VL2 | 67 | D I Q M T Q S P A S L S V S V G E T V T I T C <u>R A S E</u> <u>N I Y S N L A</u> W Y Q Q K Q G K S P Q L L V Y <u>A A T N L</u> <u>A D</u> G V P S R F S G S G S G T Q Y S L K I N S L Q S E D F G S Y Y C <u>Q H F W G T P Y T</u> F G G G T K L E I K |
| 1C3 VH | 170 | Q V Q L Q Q S G A E L A R P G A S V K L S C K A S G Y T F T S Y W M Q W V K Q R P G Q G L E W I G A I Y P G D G D T R Y T Q K F K G K A T L T A D K S S S T A Y M Q L S S L A S E D S A V Y Y C A R R Y D G Y Y H F D Y W G Q G T T L T V S |
| 1C3 VL | 171 | D I V M T Q S P S S L A V T A G E K V T M S C K S S Q S L L W S V N Q K N Y L S W Y Q Q K R Q P P K L L I Y G A S I R E S W V P D R F T G S G S G T D F T L T I S N V H A E D L A V Y Y C Q H N H G S F L P L T F G S G T K L E I K |
| 20E9 VH | 181 | Q V Q L Q Q S G A E V A R P G A S V K L S C K S S G F T F T T Y W M Q W V K Q R P G Q G L E W I G A I Y P G D G D T R Y T Q K F K G K A T L T A D K S S I T A Y M Q L S S L A S E D S A V Y Y C A R R G D Y G N Y G M D Y W G Q G T S V T V S S |

TABLE 3 -continued

| Antibody portion | SEQ ID NO: | |
|---|---|---|
| 20E9 VL | 182 | D V L M T Q T P L S L P V S L G D Q A S I S C R S S Q S I V H S N G N T Y L E W Y L Q K P G Q S P K L L I Y K V S N H F S G V P D R F S G S G S G T D F T L K I S R V E A E D L G V Y Y C F Q G S H V P P T F G G G T K L E I K |

Fragments and Derivatives

Fragments and derivatives of antibodies (which are encompassed by the term "antibody" or "antibodies" as used in this application, unless otherwise stated or clearly contradicted by context), preferably a 10F6, 2B12, 18C6, 9E10, 10G5, 13H1, 5H1, 1E2, 1C3 or 20E9-like antibody, can be produced by techniques that are known in the art. "Fragments" comprise a portion of the intact antibody, generally the antigen binding site or variable region. Examples of antibody fragments include Fab, Fab', Fab'-SH, F (ab') 2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments. Included, inter alia, are a nanobody, domain antibody, single domain antibody or a "dAb".

Fragments of the present antibodies can be obtained using standard methods. For instance, Fab or F (ab') 2 fragments may be produced by protease digestion of the isolated antibodies, according to conventional techniques. It will be appreciated that immunoreactive fragments can be modified using known methods, for example to slow clearance in vivo and obtain a more desirable pharmacokinetic profile the fragment may be modified with polyethylene glycol (PEG). Methods for coupling and site-specifically conjugating PEG to a Fab' fragment are described in, for example, Leong et al, 16 (3): 106-119 (2001) and Delgado et al, Br. J. Cancer 73 (2): 175-182 (1996), the disclosures of which are incorporated herein by reference.

Alternatively, the DNA of a hybridoma producing an antibody, preferably a 10F6, 2B12, 18C6, 9E10, 10G5, 13H1, 5H1, 1E2, 1C3 or 20E9-like antibody, may be modified so as to encode a fragment. The modified DNA is then inserted into an expression vector and used to transform or transfect an appropriate cell, which then expresses the desired fragment.

In certain embodiments, the DNA of a hybridoma producing an antibody, preferably a 10F6, 2B12, 18C6, 9E10, 10G5, 13H1, 5H1, 1E2, 1C3 or 20E9-like antibody, can be modified prior to insertion into an expression vector, for example, by substituting the coding sequence for human heavy- and light-chain constant domains in place of the homologous non-human sequences (e.g., Morrison et al., PNAS pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody.

Thus, according to another embodiment, the antibody, preferably a 10F6, 2B12, 18C6, 9E10, 10G5, 13H1, 5H1, 1E2, 1C3 or 20E9-like antibody, is humanized. "Humanized" forms of antibodies are specific chimeric immunoglobulins, immunoglobulin chains or fragments thereof (such as Fv, Fab, Fab', F (ab') 2, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody.

In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature, 321, pp. 522 (1986); Reichmann et al, Nature, 332, pp. 323 (1988); Presta, Curr. Op. Struct. Biol., 2, pp. 593 (1992); Verhoeyen et Science, 239, pp. 1534; and U.S. Pat. No. 4,816,567, the entire disclosures of which are herein incorporated by reference.)

The choice of human variable domains, both light and heavy, to be used in making the humanized antibodies is very important to reduce antigenicity. According to the so-called "best-fit" method, the sequence of the variable domain of an antibody is screened against the entire library of known human variable-domain sequences. The human sequence which is closest to that of the mouse is then accepted as the human framework (FR) for the humanized antibody (Sims et al., J. Immunol. 151, pp. 2296 (1993); Chothia and Lesk, J. Mol. 196, 1987, pp. 901). Another method uses a particular framework from the consensus sequence of all human antibodies of a particular subgroup of light or heavy chains. The same framework can be used for several different humanized antibodies (Carter et al., PNAS 89, pp. 4285 (1992); Presta et al., J. Immunol., 151, p. 2623 (1993)).

It is further important that antibodies be humanized with retention of high affinity for KIR3DL2 receptors and other favorable biological properties. To achieve this goal, according to an exemplary method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen (s), is achieved. In general, the CDR residues are directly and most substantially involved in influencing antigen binding.

Another method of making "humanized" monoclonal antibodies is to use a murine host according that has had its immunoglobulin genes replaced by functional human immunoglobulin genes (see, e.g., U.S. Pat. No. 6,162,963, which is herein incorporated in its entirety by reference).

Human antibodies may also be produced according to various other techniques, such as by using, for immunization, other transgenic animals that have been engineered to express a human antibody repertoire (Jakobovitz et al., Nature 362 (1993) 255), or by selection of antibody repertoires using phage display methods. Such techniques are known to the skilled person and can be implemented starting from monoclonal antibodies as disclosed herein.

The antibodies, optionally a 10F6, 2B12, 18C6, 9E10, 10G5, 13H1, 5H1, 1E2, 1C3 or 20E9-like antibody, may also be derivatized to "chimeric" antibodies (immunoglobulins) in which a portion of the heavy/light chain(s) is identical with or homologous to corresponding sequences in the original antibody, while the remainder of the chain (s) is identical with or homologous to corresponding sequences in antibodies derived from another species or belonging to another antibody class or subclass, as well as fragments of such antibodies, so long as they exhibit the desired biological activity and binding specificity (Cabilly et al., supra; Morrison et al., Proc. Natl. Acad. Sci. U.S.A, pp. 6851 (1984)).

Various forms of the humanized antibody or affinity-matured antibody are contemplated. For example, the humanized antibody or affinity-matured antibody may be an antibody fragment, such as a Fab. Alternatively, the humanized antibody or affinity-matured antibody may be a full-length or intact antibody, such as a full-length or intact IgG or IgG4 antibody. In one embodiment, the humanized antibody is a full-length IgG4 antibody or a fragment thereof. To produce such antibodies, humanized VH and VL regions, or variant versions thereof, can be cloned into expression vectors encoding full-length or truncated constant regions from a human antibody according to standard recombinant methods (see, e.g., Sambrook et al., Molecular Cloning: A Laboratory Manual, $2^{nd}$ Ed., Cold Spring Harbor Laboratory, Cold Spring Harbor, N.Y., 1989). The result is a transfected cell line that expresses and secretes the humanized antibody molecule of interest, comprising the selected VH and VL regions and constant regions. cDNA sequences encoding the constant regions of human antibodies are known.

The constant region may further be modified according to known methods. For example, in an IgG4 constant region, residue S241 may be mutated to a proline (P) residue to allow complete disulphide bridge formation at the hinge (see, e.g., Angal et al., Mol Immunol. 1993; 30:105-8).

Modified Constant Regions

In view of the ability of the anti-KIR3DL2 antibodies (particularly the non-internalizing antibodies) to induce ADCC and CDC, the antibodies can also be made with modifications that increase their ability to bind Fc receptors which can affect effector functions such as antibody-dependent cytotoxicity, mast cell degranulation, and phagocytosis, as well as immunomodulatory signals such as regulation of lymphocyte proliferation and antibody secretion. Typical modifications include modified human IgG1 constant regions comprising at least one amino acid modification (e.g. substitution, deletions, insertions), and/or altered types of glycosylation, e.g., hypofucosylation. Such modifications can affect interaction with Fc receptors: FcγRI (CD64), FcγRII (CD32), and FcγRIII (CD 16). FcγRI (CD64), FcγRIIA (CD32A) and FcγRIII (CD 16) are activating (i.e., immune system enhancing) receptors while FcγRIIB (CD32B) is an inhibiting (i.e., immune system dampening) receptor. A modification may, for example, increase binding of the Fc domain to FcγRIIIa on effector (e.g. NK) cells.

Anti-KIR3DL2 antibodies preferably comprise an Fc domain (or portion thereof) of human IgG1 or IgG3 isotype, optionally modified. Residues 230-341 (Kabat EU) are the Fc CH2 region. Residues 342-447 (Kabat EU) are the Fc CH3 region. Anti-KIR3DL2 antibodies may comprise a variant Fc region having one or more amino acid modifications (e.g., substitutions, deletions, insertions) in one or more portions, which modifications increase the affinity and avidity of the variant Fc region for an FcγR (including activating and inhibitory FcγRs). In some embodiments, said one or more amino acid modifications increase the affinity of the variant Fc region for FcγRIIIA and/or FcγRIIA. In another embodiment, the variant Fc region further specifically binds FcγRIIB with a lower affinity than does the Fc region of the comparable parent antibody (e.g., an antibody having the same amino acid sequence as the antibody except for the one or more amino acid modifications in the Fc region). For example, the one or both of the histidine residues at amino acid positions 310 and 435 may be substituted, for example by lysine, alanine, glycine, valine, leucine, isoleucine, proline, methionine, tryptophan, phenylalanine, serine or threonine (see, e.g. PCT publication no. WO 2007/080277); such substituted constant regions provide decreased binding to the inhibitory FcγRIIB without decreasing binding to the activatory FcγRIIIA. In some embodiments, such modifications increase the affinity of the variant Fc region for FcγRIIIA and/or FcγRIIA and also enhance the affinity of the variant Fc region for FcγRIIB relative to the parent antibody. In other embodiments, said one or more amino acid modifications increase the affinity of the variant Fc region for FcγRIIIA and/or FcγRIIA but do not alter the affinity of the variant Fc regions for FcγRIIB relative to the Fc region of the parent antibody. In another embodiment, said one or more amino acid modifications enhance the affinity of the variant Fc region for FcγRIIIA and FcγRIIA but reduce the affinity for FcγRIIB relative to the parent antibody. Increased affinity and/or avidity results in detectable binding to the FcγR or FcγR-related activity in cells that express low levels of the FcγR when binding activity of the parent molecule (without the modified Fc region) cannot be detected in the cells.

The affinities and binding properties of the antibodies for an FcγR can be determined using in vitro assays (biochemical or immunological based assays) known in the art for determining antibody-antigen or Fc-FcγR interactions, i.e., specific binding of an antigen to an antibody or specific binding of an Fc region to an FcγR, respectively, including but not limited to ELISA assay, surface plasmon resonance assay, immunoprecipitation assays.

In some embodiments, the antibodies comprising a variant Fc region comprise at least one amino acid modification (for example, possessing 1, 2, 3, 4, 5, 6, 7, 8, 9, or more amino acid modifications) in the CH3 domain of the Fc region. In other embodiments, the antibodies comprising a variant Fc region comprise at least one amino acid modification (for example, possessing 1, 2, 3, 4, 5, 6, 7, 8, 9, or more amino acid modifications) in the CH2 domain of the Fc region, which is defined as extending from amino acids 231-341. In some embodiments, antibodies comprise at least two amino acid modifications (for example, possessing 2, 3, 4, 5, 6, 7, 8, 9, or more amino acid modifications), wherein at least one such modification is in the CH3 region and at least one such modification is in the CH2 region. Encompasses also are amino acid modification in the hinge region. In one embodiment, encompassed are amino acid modification in the CH1 domain of the Fc region, which is defined as extending from amino acids 216-230.

Any combination of Fc modifications can be made, for example any combination of different modifications disclosed in U.S. Pat. Nos. 7,632,497; 7,521,542; 7,425,619; 7,416,727; 7,371,826; 7,355,008; 7,335,742; 7,332,581; 7,183,387; 7,122,637; 6,821,505 and 6,737,056; in PCT Publications Nos. WO2011/109400; WO 2008/105886; WO 2008/002933; WO 2007/021841; WO 2007/106707; WO 06/088494; WO 05/115452; WO 05/110474; WO 04/1032269; WO 00/42072; WO 06/088494; WO 07/024249; WO 05/047327; WO 04/099249 and WO 04/063351; and in Presta, L. G. et al. (2002) Biochem. Soc. Trans. 30(4):487-490; Shields, R. L. et al. (2002) J. Biol. Chem. 26; 277(30):26733-26740 and Shields, R. L. et al. (2001) J. Biol. Chem. 276(9):6591-6604).

Anti-KIR3DL2 antibodies may comprise a variant Fc region, wherein the variant Fc region comprises at least one amino acid modification (for example, possessing 1, 2, 3, 4, 5, 6, 7, 8, 9, or more amino acid modifications) relative to a wild-type Fc region, such that the molecule has an enhanced effector function relative to a molecule comprising a wild-type Fc region, optionally wherein the variant Fc region comprises a substitution at any one or more of positions 221, 239, 243, 247, 255, 256, 258, 267, 268, 269, 270, 272, 276, 278, 280, 283, 285, 286, 289, 290, 292, 293, 294, 295, 296, 298, 300, 301, 303, 305, 307, 308, 309, 310, 311, 312, 316, 320, 322, 326, 329, 330, 332, 331, 332, 333, 334, 335, 337, 338, 339, 340, 359, 360, 370, 373, 376, 378, 392, 396, 399, 402, 404, 416, 419, 421, 430, 434, 435, 437, 438 and/or 439. In one embodiment, anti-KIR3DL2 antibodies may comprise a variant Fc region, wherein the variant Fc region comprises at least one amino acid modification (for example, possessing 1, 2, 3, 4, 5, 6, 7, 8, 9, or more amino acid modifications) relative to a wild-type Fc region, such that the molecule has an enhanced effector function relative to a molecule comprising a wild-type Fc region, optionally wherein the variant Fc region comprises a substitution at any one or more of positions 329, 298, 330, 332, 333 and/or 334 (e.g. S239D, S298A, A330L, I332E, E333A and/or K334A substitutions).

In one embodiment, antibodies having variant or wild-type Fc regions may have altered glycosylation patterns that increase Fc receptor binding ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. See, for example, Shields, R. L. et al. (2002) J. Biol. Chem. 277:26733-26740; Umana et al. (1999) Nat. Biotech. 17:176-1, as well as, European Patent No: EP 1,176,195; PCT Publications WO 06/133148; WO 03/035835; WO 99/54342, each of which is incorporated herein by reference in its entirety.

Generally, such antibodies with altered glycosylation are "glyco-optimized" such that the antibody has a particular N-glycan structure that produces certain desirable properties, including but not limited to, enhanced ADCC and effector cell receptor binding activity when compared to non-modified antibodies or antibodies having a naturally occurring constant region and produced by murine myeloma NSO and Chinese Hamster Ovary (CHO) cells (Chu and Robinson, Current Opinion Biotechnol. 2001, 12: 180-7), HEK293T-expressed antibodies as produced herein in the Examples section, or other mammalian host cell lines commonly used to produce recombinant therapeutic antibodies.

Monoclonal antibodies produced in mammalian host cells contain an N-linked glycosylation site at Asn297 of each heavy chain. Glycans on antibodies are typically complex biatennary structures with very low or no bisecting N-acetylglucosamine (bisecting GlcNAc) and high levels of core fucosylation. Glycan temini contain very low or no terminal sialic acid and variable amounts of galactose. For a review of effects of glycosylation on antibody function, see, e.g., Wright & Morrison, Trend Biotechnol. 15:26-31(1997). Considerable work shows that changes to the sugar composition of the antibody glycan structure can alter Fc effector functions. The important carbohydrate structures contributing to antibody activity are believed to be the fucose residues attached via alpha-1,6 linkage to the innermost N-acetylglucosamine (GlacNAc) residues of the Fc region N-linked oligosaccharides (Shields et al., 2002). Antibodies having lowered fucose content on N-linked glycans (hypofucosylated N-linked glycans) can therefore be produced.

FcγR binding requires the presence of oligosaccharides covalently attached at the conserved Asn297 in the Fc region of human IgG1, IgG2 or IgG3 type. Non-fucosylated oligosaccharides structures have recently been associated with dramatically increased in vitro ADCC activity. "Asn 297" refers to the amino acid asparagine located at about position 297 in the Fc region; based on minor sequence variations of antibodies, Asn297 can also be located some amino acids (usually not more than ±3 amino acids) upstream or downstream.

Historically, antibodies produced in CHO cells contain about 2 to 6% in the population that are nonfucosylated. YB2/0 (rat myeloma) and Lec13 cell line (a lectin mutant of CHO line which has a deficient GDP-mannose 4,6-dehydratase leading to the deficiency of GDP-fucose or GDP sugar intermediates that are the substrate of alpha6-fucosyltransferase have been reported to produce antibodies with 78 to 98% non-fucosylated species. In other examples, RNA interference (RNAi) or knock-out techniques can be employed to engineer cells to either decrease the FUT8 mRNA transcript levels or knock out gene expression entirely, and such antibodies have been reported to contain up to 70% non-fucosylated glycan.

An antibody binding to KIR3DL2 may be glycosylated with a sugar chain at Asn297, said antibody showing increased binding affinity via its Fc portion to FcγRIII. In one embodiment of the invention, an antibody will comprise a constant region comprising at least one amino acid alteration in the Fc region that improves antibody binding to FcγRIIIa and/or ADCC.

In one aspect, the antibodies are hypofucosylated in their constant region. Such antibodies may comprise an amino acid alteration or may not comprise an amino acid alteration but be produced or treated under conditions so as to yield such hypofucosylation. In one aspect, an antibody composition comprises a chimeric, human or humanized antibody described herein, wherein at least 20, 30, 40, 50, 60, 75, 85, 90, 95% or substantially all of the antibody species in the composition have a constant region comprising a core carbohydrate structure (e.g. complex, hybrid and high mannose structures) which lacks fucose. In one embodiment, provided is an antibody composition which is free of antibodies comprising a core carbohydrate structure having fucose. The core carbohydrate will preferably be a sugar chain at Asn297.

In one embodiment, provided is an antibody composition, e.g. a composition comprising antibodies which bind to KIR3DL2, are glycosylated with a sugar chain at Asn297, wherein the antibodies are partially fucosylated. Partially fucosylated antibodies are characterized in that the proportion of anti-KIR3DL2 antibodies in the composition that lack fucose within the sugar chain at Asn297 is between 20% and 90/%, preferably between 20% and 80%, preferably between 20% and 50%, 55%, 60%, 70% or 75%, between 35% and 50%, 55%, 60%, 70% or 75%, or between 45% and 50%, 55%, 60%, 70% or 75%. Preferably the antibody is of human IgG1 or IgG3 type.

The sugar chain show can further show any characteristics (e.g. presence and proportion of complex, hybrid and high mannose structures), including the characteristics of N-linked glycans attached to Asn297 of an antibody from a human cell, or of an antibody recombinantly expressed in a rodent cell, murine cell (e.g. CHO cell) or in an avian cell.

In one embodiment, the antibody is expressed in a cell that is lacking in a fucosyltransferase enzyme such that the cell line produces proteins lacking fucose in their core carbohydrates. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their core carbohydrates. These cell lines were created by the targeted disruption of the FUT8 gene in CHO/DG44 cells using two replacement vectors (see U.S. Patent Publication No. 20040110704 by Yamane et al.; and Yamane-Ohnuki et al. (2004) Biotechnol Bioeng 87:614-22, the disclosures of which are incorporated herein by reference). Other examples have included use of antisense suppression, double-stranded RNA (dsRNA) interference, hairpin RNA (hpRNA) interference or intron-containing hairpin RNA (ihpRNA) interference to functionally disrupt the FUT8 gene. In one embodiment, the antibody is expressed in a cell line with a functionally disrupted FUT8 gene, which encodes a fucosyl transferase, such that antibodies expressed in such a cell line exhibit hypofucosylation by reducing or eliminating the alpha 1,6 bond-related enzyme.

In one embodiment, the antibody is expressed in cell lines engineered to express glycoprotem-modifying glycosyl transferases (e.g., beta(1,4)-N-acetylglucosaminyl-transferase III (GnTHI)) such that antibodies expressed in the engineered cell lines exhibit increased bisecting GlcNac structures which results in increased ADCC activity of the antibodies (PCT Publication WO 99/54342 by Umana et al.; and Umana et al. (1999) Nat. Biotech. 17:176-180, the disclosures of which are incorporated herein by reference).

In another embodiment, the antibody is expressed and the fucosyl residue(s) is cleaved using a fucosidase enzyme. For example, the fucosidase alpha-L-fucosidase removes fucosyl residues from antibodies (Tarentino, et al. (1975) Biochem. 14:5516-5523). In other examples, a cell line producing an antibody can be treated with a glycosylation inhibitor; Zhou et al. Biotech. and Bioengin. 99: 652-665 (2008) described treatment of CHO cells with the alpha-mannosidase I inhibitor, kifunensine, resulting in the production of antibodies with non-fucosylated oligomannose-type N-glucans.

In one embodiment, the antibody is expressed in a cell line which naturally has a low enzyme activity for adding fucosyl to the N-acetylglucosamine that binds to the Fc region of the antibody or does not have the enzyme activity, for example the rat myeloma cell line YB2/0 (ATCC CRL 1662). Other example of cell lines include a variant CHO cell line, Led 3 cells, with reduced ability to attach fucosyl to Asn(297)-linked carbohydrates, also resulting in hypofucosylation of antibodies expressed in that host cell (WO 03/035835 (Presta et al); and Shields, R X. et al. (2002) J. Biol. Chem. 277:26733-26740, the disclosures of which are incorporated herein by reference). In another embodiment, the antibody is expressed in an avian cell, preferably a EBx® cell (Vivalis, France) which naturally yields antibodies with low fucose content e.g. WO2008/142124. Hypofucosylated glycans can also be produced in cell lines of plant origin, e.g. WO 07/084926A2 (Biolex Inc.), WO 08/006554 (Greenovation Biotech GMBH), the disclosures of which are incorporated herein by reference.

Uses in Diagnostics and Therapy

In certain embodiments, the present antibodies are used to purify or identify KIR3DL2 positive cells from a biological sample. Biological samples can be obtained from a patient, e.g. for diagnostic or ex vivo therapeutic purposes, or from individuals or non-human primates to obtain a source of such cells for research purposes.

KIR3DL2 positive cells can be purified or identified using the present antibodies with any of a number of standard methods. For example, peripheral blood cells can be sorted using a FACS scanner using labeled antibodies specific for KIR3DL2, and optionally to other cell surface molecules typically present on cells, e.g., CD4, CD8 or CD30 for T cell; CD4 CD2+, CD3+, CD5+, CD8-, CD28+, CD45RO+ and/or TCRαβ+ for malignant cells in Sézary Syndrome; CD4+(optionally CD4+ and CD28−) in inflammatory, autoimmune or cardiovascular diseases.

In addition, the antibodies can be conjugated or covalently linked to a solid support and used to purify or identify KIR3DL2 positive cells or any cells expressing KIR3DL2 from a biological sample, e.g., from a blood sample or mucosal tissue biopsy from a patient or other individual. Specifically, the biological sample is placed into contact with the antibodies under conditions that allow cells within the sample to bind to the antibody, and then the cells are eluted from the solid-support-bound antibody.

Regardless of the method used to isolate, purify or identify the KIR3DL2 positive cells, the ability to do so is useful for numerous purposes, e.g. to diagnose a disorder characterized by a pathogenic expansion of KIR3DL2-expressing cells, by assessing the number or activity or other characteristics of KIR3DL2 positive cells obtained from a patient, or to evaluate the ability of the antibodies, or fragments or derivatives thereof, to modulate the activity or behavior of the cells of a patient prior, e.g., to one of the herein-described treatments using the antibodies. Further, purified KIR3DL2 positive cells are useful in a research context, e.g., to better characterize the cells and their various properties and behaviors, as well as to identify compounds or methods that can be used to modulate their behavior, activity, or proliferation. The antibodies can also be useful in diagnostic methods, for example in methods of detecting KIR polypeptides on cells, e.g. disease cells from a patient.

The present disclosure also provides pharmaceutical compositions that comprise an antibody which specifically binds to KIR3DL2 polypeptides on the surface of cells. The antibody preferably inhibits the growth or activity (e.g. cytokine production) of the cells and/or leads to the elimination of the KIR3DL2 positive cells, preferably via induction of CDC and/or ADCC. The composition further comprises a pharmaceutically acceptable carrier.

The disclosure further provides a method of inhibiting the growth or activity of, and/or depleting, KIR3DL2-positive cells, in a patient in need thereof, comprising the step of administering to said patient a composition described herein. Such treatment methods can be used for a number of disorders, including, but not limited to CTCL, SS and MF, inflammatory, autoimmune and cardiovascular disorders.

Regardless of the form of CD4+ CTCL, there are malignant CD4+ T cells which express KIR3DL2 at their surface. KIR3DL2 thus covers the range of CD4+ CTCL, and notably the Sézary Syndrome ("SS"), transformed Mycosis Fungoides ("transformed MF"), Lymphomatoide Papulosis ("LP"), and CD30+ lymphomas.

A diagnosis (e.g. a CTCL diagnosis) may be based on the analysis of the presence of KIR3DL2 at the surface of CD4+ cells collected from the suspected body area (e.g. sample of skin erythroderma when transformed MF is suspected, or sample of peripheral blood when a more aggressive CTCL form, such as SS, is suspected). It can typically be concluded that a CD4+ T cell is tumoral as soon as there are KIR3DL2 polypeptides detected at the surface of these CD4+ T cells. The percentage of CD4+ KIR3DL2+ T cells can measured in a sample of peripheral blood collected from a patient for whom a SS is suspected, and such percentage will substantially correspond to the percentage of malignant SS cells that are actually present in the peripheral blood of this patient (generally within a ±10% range or even a ±5% range for KIR3DL2+, CD4+ cells. KIR3DL2 and the anti-KIR3DL2 antibodies described herein therefore can be used in the staging of disease, particularly SS.

Insofar as KIR3DL2 is a universal marker for CTCL, the antibodies can be used in combination with other treatments or diagnostic markers for CTCL. For example, CD30 of which presence at the surface of malignant CD4+ T cells indicates that the patient has a particular form of CD4+ CTCL which is referred to in the art as CD30+ lymphoma. CD30 is therefore a CTCL marker for a particular form of CTCL (CD30+ lymphomas), however CD30 does not cover every form of CD4+ CTCL since for CD4+ CTCL such as SS, transformed MF, or LP, there does not necessarily exist a malignant CD4+ T cell which would express CD30 at its surface. CD30 can therefore be used in addition to KIR3DL2 as a marker in CTCL diagnosis and therapy. Furthermore, a finding that a patient has CD4+ CTCL which expresses CD30 can indicate that the patient is suitable for treatment with an anti-KIR3DL2 antibody and an anti-CD30 antibody; optionally the patient can then be treated anti-KIR3DL2 antibody and an anti-CD30 antibody.

In some embodiments, prior to the administration of the anti-KIR3DL2 antibody or composition, the presence of CD2, CD3, CD4, CD5, CD8, CD28, CD30, CD45RO and/or TCRaI3 will be assessed on cells (e.g. pathogenic cells) from a patient. A patient whose cells express (or do not express, in accordance with the particular disorder and cells sought to be targeted) a marker can then be treated with an anti-KIR3DL2 antibody or composition. In some embodiments, prior to the administration of the anti-KIR3DL2 antibody or composition, the presence of KIR3DL2 on cells of the patient will be assessed, e.g., to determine the relative level and activity of KIR3DL2-positive cells in the patient as well as to confirm the binding efficacy of the antibodies to the cells of the patient. A patient whose cells express KIR3DL2 can then be treated with an anti-KIR3DL2 antibody or composition. This can be accomplished by obtaining a sample of PBLs or cells from the site of the disorder, and testing e.g., using immunoassays, to determine the relative prominence of markers such as CD4, CD8, CD30 or KIR3DL2 on the cells.

In one embodiment, where it is sought to inhibit the activity or growth of, or deplete, a patient's KIR3DL2-positive cells, the ability of the anti-KIR3DL2 antibody to inhibit proliferation of or deplete a patient's KIR3DL2-positive cells is assessed. If the KIR3DL2-positive cells are depleted by the anti-KIR3DL2 antibody or composition, the patient is determined to be responsive to therapy with an anti-KIR3DL2 antibody or composition, and optionally the patient is treated with an anti-KIR3DL2 antibody or composition.

In some embodiments, the method may comprise the additional step of administering to said patient an appropriate additional (second) therapeutic agent selected from an immunomodulatory agent, an immunosuppressive agent, a hormonal agent, a chemotherapeutic agent, a second antibody (e.g. a depleting antibody) that binds to a polypeptide present on a KIR3DL2-expessing cell. Such additional agents can be administered to said patient as a single dosage form together with said antibody, or as a separate dosage form. The dosage of the antibody (or antibody and the dosage of the additional therapeutic agent collectively) are sufficient to detectably induce, promote, and/or enhance a therapeutic response in the patient. Where administered separately, the antibody, fragment, or derivative and the additional therapeutic agent are desirably administered under conditions (e.g., with respect to timing, number of doses, etc.) that result in a detectable combined therapeutic benefit to the patient.

Mycosis fungoides and the more aggressive Sézary syndrome represent the most common forms of CTCL. The clinical course of MF/SS is usually indolent, with pruritic erythematous areas slowly developing over long periods. Eventually, however, the erythematous patches become progressively infiltrated, developing into plaques and finally to ulcerating tumors. The prognosis of MF/SS is based on the extent of disease at presentation. Patients with stage I disease have a median survival of 20 years or more, in comparison with a median survival of approximately 3 to 4 years for patients with stage III/IV disease.

The compositions described herein can be used for treatment in combination with any agent known to be useful in the treatment of the particular T cell malignancy. Various treatments for CTCL are in use, including corticosteroids, nitrogen mustard, carmustine, topical tacrolimus (Protopic), imiquimod (Aldara®; 3M Inc.), topical retinoids, and rexinoids (bexarotene; Targretin®; Ligand Pharmaceuticals, San Diego, Calif.)), as well as ultraviolet light therapy (Psoralen+UVA (PUVA), narrowband UVB, and UVB), Photodynamic therapy (PDT) and body irradiation. Treatments also include histone deacetylase inhibitors such as vorinostat (suberoylanilide hydroxamic acid, Zolinza) and Romidepsin (depsipeptide, FK-228, Istodax), a cyclic peptide that selectively inhibits histone deacetylase isotypes 1, 2, 4 and 6. Chemotherapy or combination chemotherapy are also used. Examples include gemcitabine, antifolate analogues such as Pralatrexate (Folotyn). Further therapies include IMiDs (immunomodulatory drugs), analogs derived from thalidomide that have a wide range of effects, including both immune and non-immune related effects. Representatives of the IMiD class include CC-5013 (lenalidomide; Revlimid), CC-4047 (Actimid), and ENMD-0995. Further treatments include proteosome inhibitors such as bortezomib (Velcade), a reversible 26S proteasome inhibitor. Stem cell transplantation is also used.

Although there is no current standard of care for MF/SS, there is a general tendency to rely on topical interventions for early disease delaying systemic and more toxic therapy until the development of extensive symptoms. Psoralen and ultraviolet A radiation (PUVA), combined or not with low doses of interferon-α, is effective in early-stage MF/SS, inducing complete remission (CR) in most patients. Local radiotherapy or total-skin electron-beam irradiation (TSEB) has been used with success to control advanced skin disease. Extra corporeal photopheresis may also be used successfully but is not generally available. Once the disease becomes refractory to topical therapy, interferon-α, the rexinoid bexarotene (Targretin®, Ligand Pharmaceuticals, San Diego, Calif.), a synthetic retinoid analog targeting the retinoid X receptor, single-agent chemotherapy or combination chemotherapy may be given. Treatments, particularly skin-directed therapies, include, e.g., corticosteroids, nitrogen mustard, carmustine, topical tacrolimus (Protopic) and imiquimod (Aldara®; 3M Inc.). The duration of response is however often less than 1 year, and ultimately all patients have relapses and the disease becomes refractory. The recombinant IL2-diphteria toxin denileukin diftitox (DAB389IL-2, ONTAK®, Ligand Pharmaceuticals, San Diego, Calif.) is active in patients with stage Ib to stage IV CTCL refractory to previous treatments (overall objective response in 30% of 71 patients with a median duration response of 7 months) and appears to have a beneficial effect in symptoms relief and quality of life. More recently, denileukin diftitox have been tested in a Phase I trial in combination with bexarotene, since it induces CD25 up regulation in vitro. The combination was well tolerated and induced objective response in 67% of 14 patients. The most significant adverse events were those already reported with bexarotene alone (hypertriglyceridemia and suppression of thyroid function due to decreased TSH production) and grade 3 or 4 lymphopenia but resolving within one month of cessation of therapy. The time to treatment failure was not reported in this study. In other studies, anti-CD4 antibodies that deplete CD4 expressing cells have been developed. Examples include the fully human IgG anti-CD4 antibody zanolimumab (HuMax-CD4; Genmab A/S and TenX BioPharma Inc.), and the chimeric monoclonal anti-CD4 (cM-T412, Centocor, Malvern, Pa.) was administered to 8 patients with MF and induced objective response in 7 of them but with a median response duration of only 5 months. Uvadex® (methoxsalen, Therakos Inc. Exton, Pa.) in extra corporal photopheresis, has also shown signs of efficacy. The humanized monoclonal antibody alemtuzumab (hu-IgG, anti-CD52 mAb, Campath®, Millennium Pharmaceuticals, Inc. and ILEX Oncology, Inc., marketed and distributed in the US by Berlex Laboratories, Inc., Montville, N.J.) is indicated for the treatment of B-cell chronic lymphocytic leukemia (B-CLL) in patients who have been treated with alkylating agents and who have failed fludarabine therapy. It has been tested in patients with advanced MF/SS (stage III or IV disease) and led to objective responses in at least half of cases (55% of 22 patients). Its side effect profile consists mainly of immunosuppression and infusion reactions. An independent retrospective study described also significant cardiac toxicity in 4 out of 8 patients. With long lasting remissions observed (median time to treatment failure 12 months, range 5 to 32+ months), alemtuzumab therapy appears to be the treatment with the more favorable median response duration compared to all treatments reported to date. Other agents that may be useful include anti-CCR4 (C—C chemokine receptor 4; CD194) antibodies. One example is mogamulizumab (KW-0761; AMG-761; trade name Poteligeo, Kyowa Hakko Kirin Ltd., Japan and Amgen, USA), and humanized anti-CCR4 antibody. Other agents that may be useful include anti-CD30 antibodies. One example is SGN-35 is an antibody-drug conjugate (ADC) containing the potent antimitotic drug, monomethylauristatin E (MMAE), linked to the anti-CD30 monoclonal antibody, cAC10 (Okeley et al. (2010) Clin. Cancer Res. 16(3): 888-897); another examples is the human anti-CD30 immunoglobulin (Ig) G1κ monoclonal antibody MDX-060 (Medarex Inc. and Bristol Myers Squibb; Ansell et al. (2007) J. Clin. Oncol. 25: 2767-2769). Each of these treatments can be used in combination with the antibodies of the disclosure.

The antibodies produced using the present methods are particularly effective at treating autoimmune and inflammatory disorders, as well as cardiovascular disorders most particularly acute coronary syndrome, arthritis, rheumatoid arthritis, rheumatoid vasculitis, systemic lupus erythematosus, multiple sclerosis, Wegener's granulomatosis, and spondyloarthritis. In general, the present methods can be used to treat any disorder caused at least in part by the presence or activity of KIR3DL-expressing cells, e.g., NK cells or T cells, proinflammatory T or NK cells producing IL-17A, T cells such as Th17 cells or CD4$^+$CD28$^-$ cells expressing KIR3DL2, and which can therefore be effectively treated by selectively killing or inhibiting the proliferation or activation of KIR3DL2-expressing cells.

In some embodiments, prior to the administration of the anti-KIR3DL2 antibody, the expression of KIR3DL2 on cells underlying the particular disorder will be assessed. This can be accomplished by obtaining a sample of PBLs or cells from the site of the disorder (e.g., from the synovium in RA patients), and testing e.g., using immunoassays, to determine the relative prominence of markers such as CD4, CD28, etc., as well as KIR3DL2 on the cells. Other methods can also be used to detect expression of KIR3DL2 and other genes, such as RNA-based methods, e.g., RT-PCR or Northern blotting.

The treatment may involve multiple rounds of antibody or compound administration. For example, following an initial round of administration, the level and/or activity of KIR3DL-expressing T or NK cells (e.g., CD4$^+$CD28$^-$ T cells, malignant CD4+ T cells), in the patient will generally be re-measured, and, if still elevated, an additional round of administration can be performed. In this way, multiple rounds of receptor detection and antibody or compound administration can be performed, e.g., until the disorder is brought under control.

When used for the treatment of autoimmune or inflammatory disorders, the anti-KIR3DL2 antibodies of the disclosure can be used for treatment in combination with any agent known to be useful in the treatment of the particular inflammatory disorder, autoimmune disorder, or cardiovascular disorder. Anti-KIR3DL2 antibodies can be combined for example with steroidal anti-inflammatory agents, non-steroidal anti-inflammatory agents, anti-metabolites and other agents used in treating cardiovascular, inflammatory or autoimmune diseases. In some embodiments, anti-inflammatory agents comprise steroidal anti-inflammatory agents, which include glucocorticosteroids and mineralocorticosteroids. These may be administered by any methods suitable for treating the inflammatory disorders, including, among others, oral, intravenous, intramuscular, dermal, or nasal routes. In some embodiments, the anti-inflammatory agents comprise non-steroidal anti-inflammatory agents. These agents generally act by inhibiting the action of cyclooxygenase and lipoxygenase enzymes, or receptors for mediators generated by these enzymes. The non-steroidal anti-inflammatory compounds include non-selective COX inhibitors, selective COX inhibitors, as well as FLAP antagonists and 5-lipoxygenase antagonists. In some embodiments, the anti-inflammatory agents can comprise anti-metabolites that affect proliferation of cells involved in the immune response. Suitable anti-metabolites include folate analogs, such as methotrexate; inosine monophosphate dehydrogenase (IMPDH) inhibitors, such as mycophenolate mofetil; and azathiopurine. Compounds of this group generally affect production of the substrates necessary for DNA replication, thereby inhibiting the proliferation of cells involved or activated in response to an inflammatory reaction. In some embodiments, the anti-inflammatory agent is an agent that blocks the action of TNF-alpha, the major cytokine implicated in inflammatory disorders. In some embodiments, the anti-TNF is an antibody that blocks the action of TNFalpha. An exemplary anti-TNF antibody is infliximab (Remicade®). In other embodiments, the anti-TNFalpha agent is a receptor construct that binds TNFalpha and prevents its interaction with TNF receptors on present on cells, e.g. entanercept (Enbrel®). In other embodiments, the anti-inflammatory agent is any other agent (e.g. an antibody agent) having immunosuppressive properties and useful in the treatment of the disorder being treated with the KIR3DL2 antibody described herein.

Pharmaceutical Formulations

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. The antibodies described herein may be employed in a method of modulating, e.g. inhibiting, the activity of KIR3DL2-expressing cells in a patient. This method comprises the step of contacting said composition with said patient. Such method will be useful for both prophylaxis and therapeutic purposes.

For use in administration to a patient, the composition will be formulated for administration to the patient. The compositions described herein may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques. The antibody can be present in a single dose in an amount, for example, of between about 25 mg and 500 mg.

Sterile injectable forms of the compositions described herein may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The compositions described herein may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added.

Alternatively, the compositions described herein may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The compositions described herein may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds described herein include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The present antibodies can be included in kits. The kits may optionally further contain any number of antibodies and/or other compounds, e.g., 1, 2, 3, 4, or any other number of therapeutic antibodies and/or compounds. It will be appreciated that this description of the contents of the kits is not limiting in any way. For example, the kit may contain other types of therapeutic compounds. Preferably, the kits also include instructions for using the antibodies, e.g., detailing the herein-described methods.

Dosage Forms

Therapeutic formulations of the antibodies are prepared for storage by mixing the antibodies having the desired degree of purity with optional pharmaceutically acceptable carriers, excipients, or stabilizers in the form of lyophilized formulations or aqueous solutions. For general information concerning formulations, see, e.g., Gilman et al. (eds.), The Pharmacological Bases of Therapeutics, 8 Ed. (Pergamon Press, 1990); Gennaro (ed.), Remington's Pharmaceutical Sciences, 18 Edition (Mack Publishing Co., Easton, Pa., 1990); Avis et al. (eds.), Pharmaceutical Dosage Forms: Parenteral Medications (Dekker, New York, 1993); Lieberman et al. (eds.), Pharmaceutical Dosage Forms: Tablets (Dekker, New York, 1990); Lieberman et al. (eds.) Pharmaceutical Dosage Forms: Disperse Systems (Dekker, New York, 1990); and Walters (ed.), Dermatological and Transdermal Formulations (Drugs and the Pharmaceutical Sciences), Vol. 119 (Dekker, New York, 2002).

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low-molecular-weight (less than about 10 residues) polypeptides; proteins such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as ethylenediaminetetraacetic acid (EDTA); sugars such as sucrose, mannitol, trehalose, or sorbitol; salt-forming counter-ions such as sodium; metal complexes (e.g., Zn-protein complexes); and/or non-ionic surfactants such as TWEEN™, PLURONICS™, or PEG.

Exemplary antibody formulations are described for instance in WO 1998/56418, which describes a liquid multidose formulation for an anti-CD20 antibody, comprising 40 mg/mL rituximab, 25 mM acetate, 150 mM trehalose, 0.9% benzyl alcohol, and 0.02% polysorbate20™ at pH 5.0 that has a minimum shelf life of two years storage at 2-8° C. Another anti-CD20 formulation of interest comprises 10 mg/mL rituximab in 9.0 mg/mL sodium chloride, 7.35 mg/mL sodium citrate dihydrate, 0.7 mg/mL polysorbate80™, and Sterile Water for Injection, pH 6.5.

Lyophilized formulations adapted for subcutaneous administration are described, for example, in U.S. Pat. No. 6,267,958 (Andya et al.). Such lyophilized formulations may be reconstituted with a suitable diluent to a high protein concentration and the reconstituted formulation may be administered subcutaneously to the mammal to be treated herein.

The formulation herein may also contain more than one active compound (a second medicament as noted above), preferably those with complementary activities that do not adversely affect each other. The type and effective amounts of such medicaments depend, for example, on the amount and type of B-cell antagonist present in the formulation, and clinical parameters of the subjects. Exemplary second medicaments are noted above.

The active ingredients may also be entrapped in microcapsules prepared, e.g., by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's Pharmaceutical Sciences, supra, for example.

Sustained-release formulations may be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid.

The formulations to be used for in vivo administration must be sterile. This is readily accomplished by filtration through sterile filtration membranes. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Further aspects and advantages will be disclosed in the following experimental section, which should be regarded as illustrative and not limiting the scope of this application.

EXAMPLES

Example 1—Generation of Anti-KIR3DL2 Antibodies

Materials and Methods
Primary and Secondary Flow Cytometry Screenings

Anti-KIR3DL2 mAbs were primarily screened in flow cytometry for binding to KIR3DL2-expressing Sézary cell lines (HUT78 and COU-L) and to KIR3DL2-transfected tumor cell lines (HEK-293T). Flow cytometry devices include: FACSarray (BD Biosciences, primary screen), FACSCanto II No. 1 and No. 2 (BD Biosciences) (secondary screens) and FC500 (Beckman Coulter) (secondary screens). The KIR3DL2+ and other tumor cell lines used included:

HUT-78 (KIR3DL2 positive Sézary cell line) grown in complete IMDM;

HEK-293T (human kidney cancer)/KIR3DL2 and HEK-293T/KIR3DL2 Domain 0-eGFP cell lines (grown in complete DMEM);
COU-L (KIR3DL2 positive Sézary cell line) (grown in complete RPMI complemented with 10% human serum AB);
HEK-293T/KIR3DL1 and HEK-293T/KIR3DL1-eGFP cell lines (grown in complete DMEM);
B221 (B-lymphoblastoid, CD20 positive human cell line)/KIR3DL2 cell line (grown in complete RPMI containing FCS serum); and
RAJI (Burkitt's lymphoma CD20 positive human cell line)/KIR3DL2 cell line (grown in complete RPMI containing FCS serum).

Whereas none of the Sézary cell lines used grow after IV or SC transfer to immune compromised mice, KIR3DL2-transfected B221 or RAJI cells grow as disseminated (IV) or solid (SC) tumors after injection to mice.

Based on the information available in Gardiner et al, *Journal of Immunology* 2001 (Vol 166, p2992-3001), the KIR3DL2 gene alleles present in the tumor cell lines used were determined. We established that the Sézary cell line COU-L is heterozygous for alleles 3DL2*003 and 3DL2*008 and HUT-78 is heterozygous for alleles 3DL2*002 and 3DL2*007. All 4 alleles 3DL2*003, 3DL2*008, 3DL2*002 and 3DL2*007 encode KIR3DL2 protein variants bearing differences in their extracellular domains. Of note, the recombinant KIR3DL2-Fc fusion protein that was used to immunize mice is encoded by different KIR3DL2 gene alleles 3DL2*006 and 3DL2*007 (clone 1.1, both alleles encoding the same extracellular domain protein sequence).

KIR3DL2 Domains 0, 1 and 2 Cell Lines

HEK293T/17 cells were cultured in DMEM (Gibco) supplemented with sodium pyruvate (1 mM), penicillin (100 U/ml), streptomycin (100 µg/ml) and 10% heat inactivated FCS (PAN biotech). Lipofectamine 2000 reagent, Trizol, SuperScript II reverse Transcriptase, pcDNA3.1 vector and anti-V5-FITC antibodies were purchased from Invitrogen. Goat anti-mouse (H+L)-PE was purchased from Beckman Coulter. PBMC ($5 \times 10^6$ cells) from *Homo Sapiens* were re-suspended into 1 ml of Trizol reagent. RNA extraction was performed by adding 200 µl chloroform. After centrifugation (15 min, 13,000 rpm), RNA was precipitated from aqueous phase with 500 µl isopropanol. After incubation (10 min, RT) and centrifugation (10 min, 13,000), RNA was washed with 70% ethanol and re-centrifugated (5 min, 13,000 rpm). RNA was re-suspended in $H_2O$ Rnase free water. cDNA was obtained using SuperScript II reverse Transcriptase using 2 µg of specific RNA and following manufacturer instructions. Human KIR3DL2 (accession number U30272, KIR3DL2 allele *002) domain 0, domain 1 and domain 2 sequences are shown in Table 4.

*Homo Sapiens* KIR3DL2 (accession number U30272) domain 0, domain 1 and domain 2 sequences were amplified by PCR reaction from cDNA using 5' AA GCT AGC GGT AAG CCT ATC CCT AAC CCT CTC CTC GGT CTC GAT TCT ACG CTC ATG GGT GGT CAG GAC AAA C (SEQ ID NO: 71) (forward) and 3' AA GGA TCC CTC TCC TGA TTT CAG CAG GGT (SEQ ID NO: 72) (reverse); 5' AA GCT AGC GGT AAG CCT ATC CCT AAC CCT CTC CTC GGT CTC GAT TCT ACG ACA GTC ATC CTG CAA TGT TGG (SEQ ID NO: 73) (forward) and 3' AA GGA TCC CTC TCC TGC CTG AAC CGT GGG (SEQ ID NO: 74) (reverse); 5' AA GCT AGC GGT AAG CCT ATC CCT AAC CCT CTC CTC GGT CTC GAT TCT ACG AAC GTG ACC TTG TCC TGT AGC (SEQ ID NO: 75) (forward) and 3' AA GGA TCC ATG CAG GTG TCT GCA GAT ACC (SEQ ID NO: 76) (reverse) oligonucleotides, respectively. After TA-cloning and sequencing, sequences were cloned into pcDNA3.1 vector between NheI and BamHI restriction sites. These constructs were inserted between the CD33 peptide leader and the CD24 GPI anchor (CD24 GPI anchor DNA and amino acid sequences are shown in SEQ ID NOS: 77 and 78, respectively) synthesized by MWG Biotech (inserted between BamHI and HindIII restriction sites).

HEK-293T/17 cells were seeded 24 hours prior to transfection into 6 wells plates ($5.10^5$ cells/well) in DMEM without antibiotics. Transfections were performed using 5 plg of the different pcDNA3.1/KIR3DL2 domain 0, pcDNA3.1/KIR3DL2 domain 1 or pcDNA3.1/KIR3DL2 domain 2 constructs using Lipofectamine 2000 according to manufacturer instructions. To ensure DNA purity for transfection, Maxi-prep endotoxin free kit from Qiagen was used. The Lipofectamine/DNA ratio used was fixed at 2/1. Cells were harvested 48 hours after transfection for flow cytometry experiments.

Immunization

Mice were immunized with recombinant KIR3DL2-Fc fusion protein (allele *006). Supernatant (SN) of the growing hybridomas were tested by flow cytometry on HUT78, COU-L and HEK-293T/KIR3DL2 Domain 0-eGFP. Potentially interesting hybridomas selected from the initial screening were cloned by limiting dilution techniques in 96-wells plates. The secondary screen involved selection of hybridomas of interest by testing supernatants of the subclones by flow cytometry on HUT78, COU-L, HEK-293T/KIR3DL1 Domain 0-eGFP and HEK-293T/KIR3DL2 Domain 0-eGFP. Positive subclones were injected into mice to produce ascitis and antibodies of interest were purified before being tested in a Biacore assay using rec KIR3DL2 chips, followed by various assays formats based on binding to human KIR3DL2-expressing cells. Among the clones

TABLE 4

| Ig-like domain of KIR3DL2 | SEQ ID NO: | Amino acid sequence |
|---|---|---|
| Domain 0 | 68 | PLMGGQDKPF LSARPSTVVP RGGHVALQCH YRRGFNNFML YKEDRSHVPI FHGRIFQESF IMGPVTPAHA GTYRCRGSRP HSLTGWSAPS NPLVIMVTGN HRKPSLLAHP GPLLKSG |
| Domain 1 | 69 | TVILQCWSDV MFEHFFLHRE GISEDPSRLV GQIHDGVSKA NFSIGPLMPV LAGTYRCYGS VPHSPYQLSA PSDPLDIVIT GLYEKPSLSA QPGPTVQAGE |
| Domain 2 | 70 | NVTLSCSSWS SYDIYHLSRE GEAHERRLRA VPKVNRTFQA DFPLGPATHG GTYRCFGSFR ALPCVWSNSS DPLLVSVTGN PSSSWPSPTE PSSKSGICRH LH | selected were supernatants for antibodies 10F6, 2B12, 18C6, 9E10, 10G5, 13H1, 4B5, 5H1, 1E2, 1C3 and 20E9. Based on the screen that permitted selection among D0 or D½ domain binding, antibodies 10F6, 2B12, 18C6, 9E10, 10G5, 13H1, 4B5, 5H1 and 1E2 bind to KIR3DL2 present on extracellular domain 0 (D0) while 1C3 and 20E9 bind to an epitope present on domain ½ (D2).

Sequences of the variable domains of heavy (VH) and light (VL) chain of selected antibodies were amplified by PCR from the cDNA of each antibody. Sequences amplified were run on agarose gel then purified using the Qiagen Gel Extraction kit. VH and VL sequences were then sub-cloned into the Lonza expression vectors (Double-Gene Vectors) using the InFusion system (Clontech) according to the manufacturer's instructions. After sequencing, vectors containing the VH and VL sequences were prepared as Maxiprep using the Promega PureYield™ Plasmid Maxiprep System. Vectors were then used for HEK-293T cell transfection using Invitrogen's Lipofectamine 2000 according to the manufacturer instructions.

Example 2—Antibodies that do not Induce KIR3DL2 Internalization

Briefly, either no antibody or 20 µg/mL of an anti-KIR3DL2 domain 0 antibody, or antibody 10F6, 2B12, 18C6, 9E10, 10G5, 13H1, 4B5, 5H1, 1E2, 1C3 or 20E9 were incubated with fresh Sézary Syndrome cells from 5 different human donors, for 24 h at 37° C. Cells were then washed, fixed and permeabilized using IntraPrep permeabilization reagent from Beckman Coulter. Presence of KIR3DL2-bound 10F6, 2B12, 18C6, 9E10, 10G5, 13H1, 4B5, 5H1, 1E2, 1C3 or 20E9 Ab is revealed with a goat anti-mouse Ab, labelled with GAM-PE. Table 6 shows an example of an anti-KIR3DL2 domain 0 antibody 13H1, after 24 h incubation, respectively. Table 5 shows a strong decrease in fluorescence for 13H1 in each of the different donors, confirming that the binding of this antibody down-modulates the expression of KIR3DL2 on SS cells. Similar results were obtained for anti-D0 antibody 4B5 as well as a range of anti-D1 antibodies. Conversely, the anti-KIR3DL2 domain 0 or domain 2 antibodies 10F6, 2B12, 18C6, 9E10, 10G5, 5H1, 1C3 and 20E9 did not result in a decrease in fluorescence indicating that this antibody did not down-modulate the expression of KIR3DL2 on SS cells. Table 6 shows an representative example for antibody 10G5.

TABLE 5

| Patient | KIR3DL2 mfi after 24h incubation without mAb | KIR3DL2 mfi after 24h incubation with 10 µg/ml mAb |
| --- | --- | --- |
| KLU | 1426 | 592 |
| HAE | 2676 | 871 |
| STA | 1095 | 544 |
| CER | 475 | 197 |

TABLE 6

| Patient | KIR3DL2 mfi after 24h incubation without mAb | KIR3DL2 mfi after 24h incubation with 10 µg/ml mAb |
| --- | --- | --- |
| KLU | 2237 | 4015 |
| HAE | 3587 | 4909 |
| STA | 1558 | 2786 |
| CER | 462 | 733 |

Example 3—Antibodies that do not Internalize into Sézary Syndrome Cell Line

Internalization of antibodies 10F6, 2B12, 18C6, 9E10, 10G5, 13H1, 4B5, 5H1, 1E2, 1C3 and 20E9, as well as antibody AZ158 (an anti-domain 0 mAb) and other anti-D1 antibodies were assessed by fluoro-microscopy using the HUT78 SS cell line.

Materials and Methods:

Hut-78 cells were incubated during 1H at 4° C. with 10 µg/ml of the different antibodies. After this incubation cells were either fixed (t=0H) or incubated for 2H at 37° C. Cells incubated for 2H were then fixed and stained. Antibodies were stained using goat anti-mouse antibodies coupled to Alexa594 (Invitrogen, A11032). LAMP-1 compartments were stained using rabbit anti-LAMP-1 antibodies (Abcam, ab24170) revealed by goat anti-rabbit polyclonal antibodies coupled to FITC (Abcam ab6717). Pictures were acquired using an Apotome device (Zeiss) and analyzed using the Axiovision software.

Results:

Anti-KIR3DL2 mAbs were visible in red while LAMP-1 compartments were visible in green. At the time of addition of antibodies, KIR3DL2 staining in red was visible at the cell surface while green LAMP-1 were visible intracellularly in green. However, at 2 hours following the addition of antibodies, each of antibodies AZ158, 13H1 and 4B5, and anti-D1 antibodies caused red staining to be colocalized with green staining, along with a decrease in red staining at the cell surface, indicating that AZ158, 13H1 and 4B5, and anti-D1 antibodies were rapidly internalized. Antibodies 10F6, 2B12, 18C6, 9E10, 10G5, 5H1, 1E2, 1C3 and 20E9, however was not internalized, and at 2 hours following the addition of antibody, red staining remained entirely on the cell surface.

Example 4—Antibodies that Increase the Number of Available Cell Surface KIR3DL2 Receptors Part 1: Impact of Staining Conditions on 2B12 Labelling of KIR3DL2-Expressing Cells This study aimed to evaluate the impact of staining conditions on 2B12 labelling of KIR3DL2-expressing cells, gated on total cells, at 4° C. or 37° C., and with incubation times of 2 hours, 4 hours or 24 hours. Briefly, 100,000 HUT78 cells per well were incubated with a dose range of 2B12 antibody starting from 0.0005 µg/ml to 30 µg/ml (serial dilution 1/3 in complete medium). The protocol used was as follows: incubation 2H; 4H and overnight at 4° C. and 37°; staining in RPMI 10% with or without PFA fixation; 2 washes in SB (150 µl/w); addition of anti-human-Fc PE for 30 min at 4° C.; 2 washes in SB (100 µl/w); and detection using FACS CANTO II.

Figure 6A:
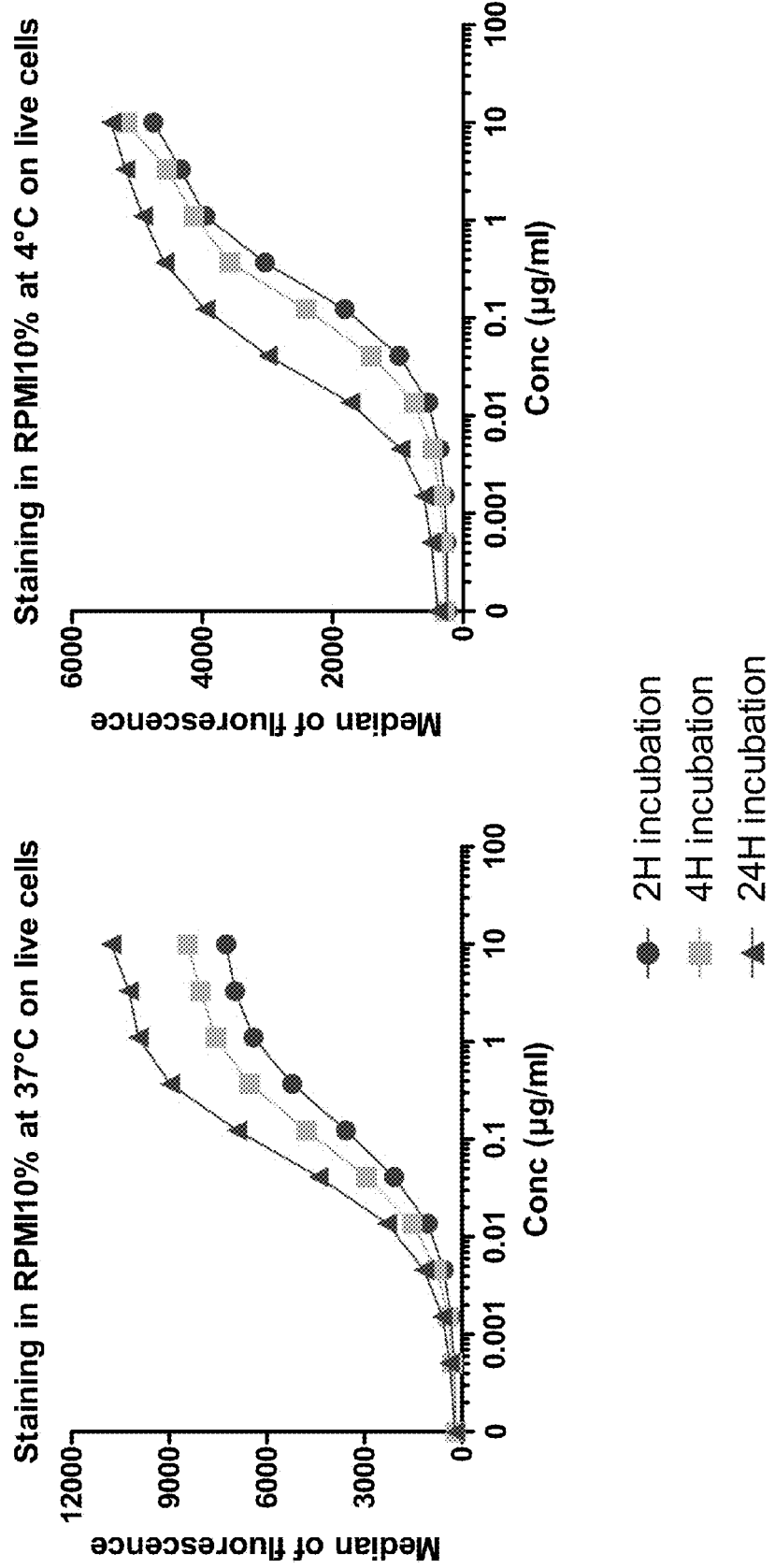
FIG. 6A shows while incubation at 4° C. which inhibits receptor internalization/cycling was expected to result in an at least equal level of cell-surface KIR3DL2, staining with antibody 2B12 (human IgG1) was higher at 37° C. than at 4° C. Furthermore, higher median fluorescence was observed with increasing duration of incubation, the greatest KIR3DL2 expression was observed after 24 hours of incubation.

Results are shown in FIG. 6A. While incubation at 4° C. which inhibits receptor internalization/cycling was expected to result in an at least equal level of available cell-surface KIR3DL2, staining with antibody 2B12 (human IgG1) was higher at 37° C. than at 4° C. Furthermore, higher median fluorescence was observed with increasing duration of incubation, the greatest KIR3DL2 expression was observed after 24 hours of incubation.

Part 2: Total, Free and 2B12-Bound KIR3DL2 Detection on HUT78 Tumor Cells after Overnight Incubation This study aimed to evaluate the impact of a 20 hour incubation with antibody 2B12 on cell surface KIR3DL2 level by observing the amount of bound 2B12 (human IgG1), free (non-antibody bound) cell surface KIR3DL2 polypeptide, and total cell surface KIR3DL2 polypeptide. Briefly, HUT78 (100,000 cells/well) were incubated for 20 h at 37° C. with a dose range of 2B12 antibody starting from (decreasing) 8.88 µg/ml, 1/3 serial dilution, 11 concentrations. Dose ranges were made in duplicate in order to perform the following 2 staining conditions:
1. Total KIR3DL2+bound KIR3DL2 (GaH IgG Fc-PE+ mAb2-APC (a non-competing anti-KIR3LD2 mAb) (10 µg/ml)
2. Free KIR3DL2: 2B12-PE (10 µg/ml)

Figure 6B:
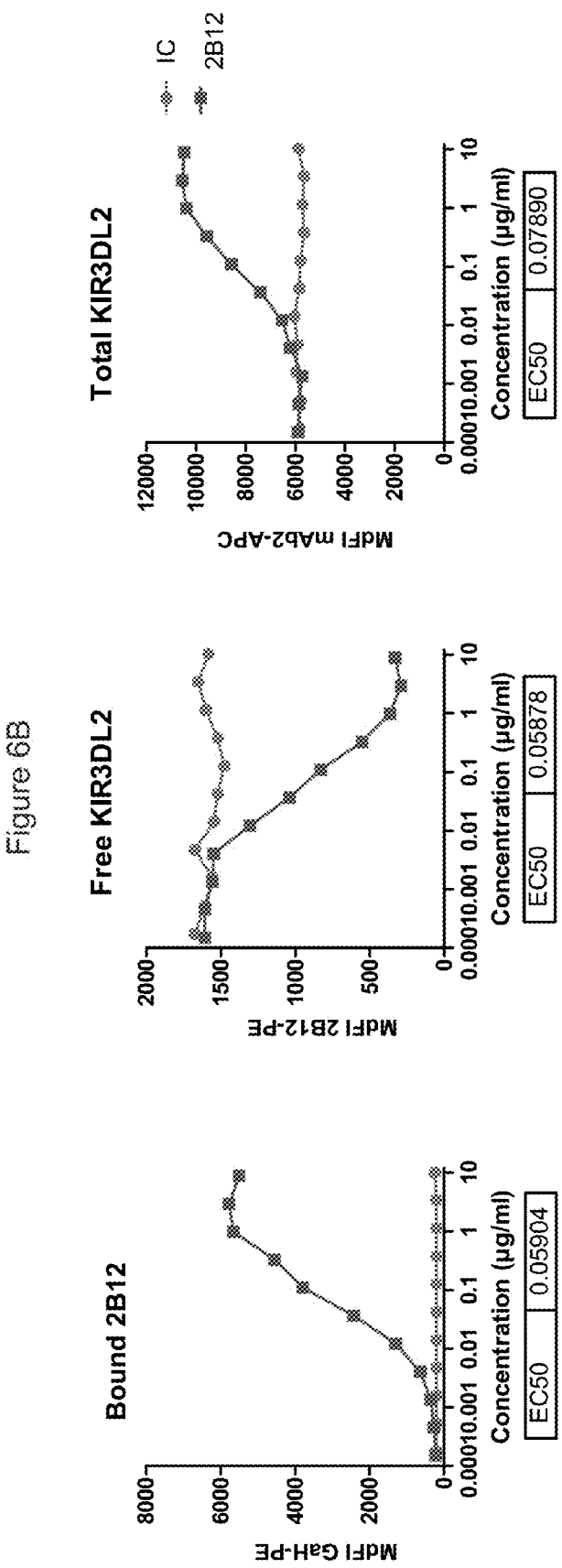
FIG. 6B shows the effect of antibody 2B12 (dark line/ squares) and isotype control (light line/circles) of KIR3DL2 levels. It can be seen that free receptors and 2B12-bound KIR3DL2 receptors read-outs were correlated, with similar $EC_{50}$. The rightmost panel shows that a 20 hour incubation with 2B12 increases total KIR3DL2 receptor level at cell surface as detected by non-competing anti-KIR3DL2 (mAb2) linked to APC.

Staining was performed at 4° C. in staining buffer for 1 h and analyzed with a FACS Canto II HTS. Results are shown in FIG. 6B. The dark line/squares represents antibody 2B12 while the light line/circles represents isotype control. It can be seen that free KIR3DL2 receptors can be detected when incubating cells with 10 µg/ml of 2B12-PE and detecting free receptors with non-competing anti-KIR3DL2 antibody. It can be seen that 2B12-bound KIR3DL2 receptors can be detected by incubating cells with goat anti-human IgG Fc-PE secondary Ab. Both read-outs were correlated, with similar $EC_{50}$. The rightmost panel shows that a 20 hour incubation with 2B12 increases KIR3DL2 receptor level at cell surface as detected by the non-competing anti-KIR3DL2 antibody mAb2-APC. Antibody 2B12 may be causing conformational change upon binding, receptor stabilization/accumulation at cell surface and/or internalization/recycling blockade.

Part 3: Total, Free and 2B12-Bound KIR3DL2 Detection on HUT78 Tumor Cells after 1, 24 or 48 Hours This study aimed to evaluate the dynamics of KIR3DL2 receptor expression by observing by observing the amount of total, free and 2B12-bound KIR3DL2 after different periods of incubation with antibody 2B12. Briefly, HUT78 cells (50,000 cells/well) were incubated for 1 h, 24 h or 48 h at 37° C. in complete medium with 2B12 (human IgG1), dose range starting from 10 µg/ml (decreasing), 1/3 serial dilution, 11 concentrations, or with isotype control (IC), dose range starting (decreasing) from 10 µg/ml, 1/3 serial dilution, 11 concentrations. Dose ranges were made in triplicate in order to perform 3 staining conditions:
Bound KIR3DL2 (30 min at 4° C.): GaH IgG Fc-PE,
Free KIR3DL2+total KIR3DL2 (1 h at 4° C.): 2B12-PE (10 µg/ml)+mAb2-APC (non-competing anti-KIR3DL2) (10 µg/ml),
Total KIR3DL2 (1 h+30 min at 4° C.): 2B12 (10 µg/ml)+ GaH IgG Fc-PE.

Staining was performed at 4° C. in staining buffer, and analysis conducted with HTFC Intellicyt.

Results are shown in FIG. 6C. In these culture conditions (96 well-plates, 50,000 HUT78/well at T0), KIR3DL2 detection at cell surface decreases in the absence of any Ab (as detected by mAb2-APC, 2B12-PE or 2B12+GaH-PE, points on the Y-axis).

Incubation with 2B12 at 37° C. increases surface expression of KIR3DL2 (as detected by non-competing mAb2 or by 2B12 itself+secondary Ab), in a dose-dependent manner. Isotype control did not give rise to any change in KIR3DL2. This increase is already observed after 1 h at 37° C., and seems to reach its maximum after 24 h. Staining is optimal after 24 h (in terms of total staining and of detected Ab-bound receptors).

Example 5—Antibodies are Able to Kill KIR3DL2 Expressing Targets Via Complement-Dependent Mechanism (CDC)

Briefly, 50 µl of 20 µg/ml antibodies (2× concentrated) diluted were provided in standard medium a White clear bottom P96 wells (Ref 655098—Greiner), to which were added 50 µl of a cell suspension at 2 million per ml (100,000 cells per well) in standard medium, and incubated for 30 min at 4° C. 5 µl per well of freshly reconstituted complement (Ref CL3441—Cedarlan) was added, followed by incubation 1H at 37° C. 100 µl per well of Cell Titer Glo (Ref G7572—Promega) was added followed by incubation 10 min at room temperature protect from light. Results were read using a luminometer (VICTOR).

Using complement purified from rabbit blood, the ability of our anti-KIR3DL2 mAbs to recruit complement and lyse KIR3DL2-transfected B221 cells was addressed in vitro.

FIG. 7A shows ability of antibodies to mediate CDC; anti-KIR3DL2 mAbs that bind the D0 domain are in gray, those that bind the D1 domain are in black. With the parental murine mAbs, the isotype of the mAb has the most prominent influence on the result of this assay as IgG2b murine mAbs bind complement more efficiently than any other isotype (mouse IgG1 do not bind complement at all).

To address the impact on complement-mediated target cell death of KIR3DL2 internalization upon binding with anti-KIR3DL2 mAbs, we used mo19H12, an anti-KIR3DL2 antibody that induces rapid internalization of KIR3DL2 into HUT78 Sézary cell line and B221-KIR3DL2. Before incubation with complement, we pre-incubated the target B221-KIR3DL2 targets with mo19H12 either at 4° C. (internalization is blocked) or 37° C. (that allows optimal internalization). Then, complement was added, incubated and CDC measured as above.

In this experiment, the internalization of KIR3DL2 upon binding totally abrogates the ability of mo19H12 to kill B221-KIR3DL2 with complement recruitment, whereas in temperature conditions that limit internalization, CDC activity of mo19H12 is clearly observed (FIG. 7B). Anti-CD20 rituximab is used as a control that mediates CDC against CD20+ targets but does not induce CD20 internalization.

Figure 8:
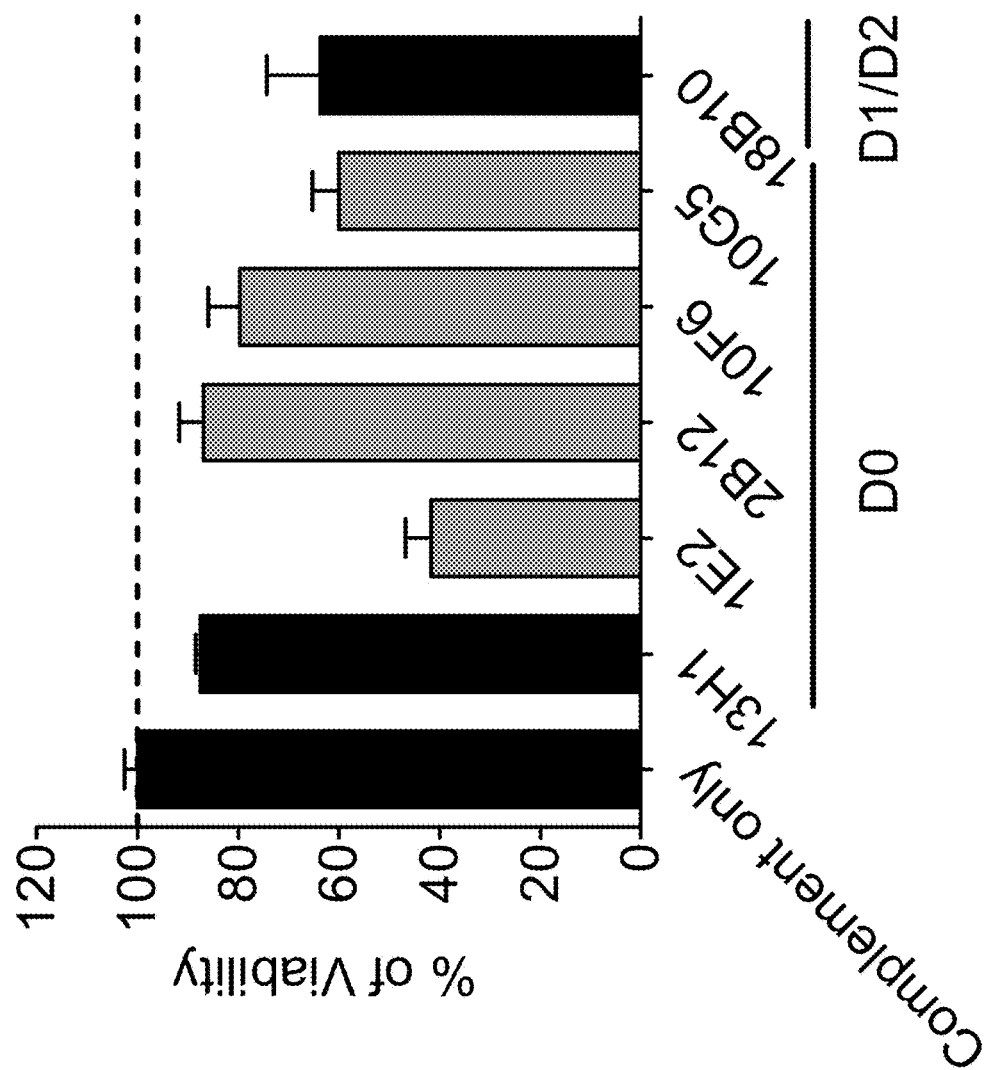
FIG. 8 shows the ability of chimeric anti-KIR3DL2 mAbs to mediate CDC against B221-KIR3DL2 in vitro.

Selected mAbs were chimerized into human IgG1 to render them able of mediating effector functions (ADCC and CDC). FIG. 8 shows the ability of chimeric anti-KIR3DL2 mAbs to mediate CDC against B221-KIR3DL2 in vitro.

Certain mAb clones like 1E2 and 10G5 have, after chimerization, acquired the ability to kill KIR3DL2 positive targets through a CDC mechanism. In this experiment, for anti-D0 mAbs, potent internalization (such as that induced by 13H1, in black), might prevent optimal efficacy as observed for 1E2 and 10G5 in particular.

Example 6—Antibodies are Able to Kill KIR3DL2 Expressing Targets Via Antibody Dependent Cellular Cytotoxicity (ADCC)

Cell lysis through an ADCC mechanism was monitored in a radioactivity-based $^{51}$Cr release experiment (the level of radioactivity released from the preloaded target cells being proportional to their death). One million target cells were loaded with $^{51}$Cr for 1 hour at 37° C. and washed 3 times. 3,000 cells were seeded per well (U-shaped bottom 96-well plates) and test mAbs are added at 10 or g/ml final concentration (or increasing concentrations if dose-response relationship is studied). Effector cells were added at a defined effector:target ratio (in general 10:1) and the mixture was incubated at 37° C. for 4 h. Supernatant is analyzed on a Lumaplate apparatus. When chimeric huIgG1 mAbs are used, effector cells were allogeneic human NK cells purified from PBMCs taken from a healthy volunteer donor.

Figure 9:
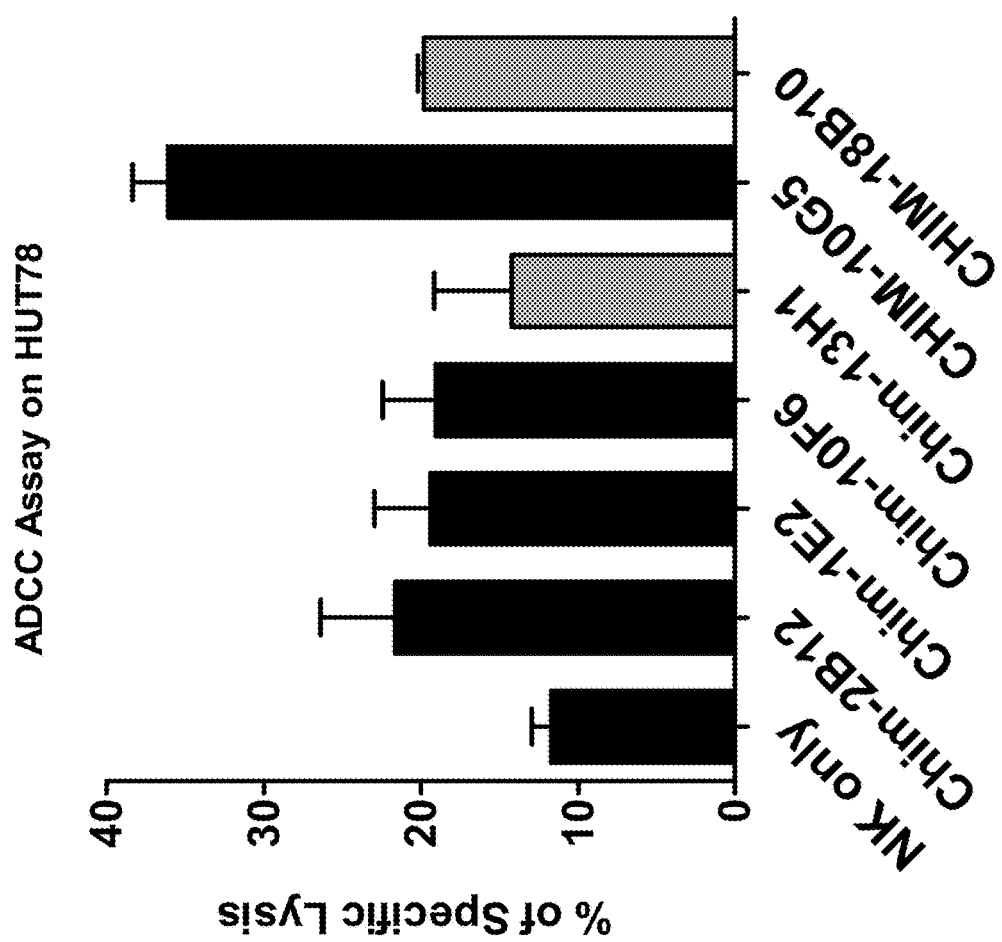
FIG. 9 shows the ability of a series of anti-KIR3DL2 mAbs, tested at the same final concentration (10 µg/ml), to kill the prototypical Sézary cell line HUT78 through an ADCC-mediated mechanism.

For optimal assessment, ADCC experiments were performed generally using chimerized huIgG1 mAbs generated from various parental murine anti-KIR3DL2 mAbs. FIG. 9 shows the ability of a series of anti-KIR3DL2 mAbs, tested at the same final concentration (10 µg/ml), to kill the prototypical Szary cell line HUT78 through an ADCC-mediated mechanism.

Figure 10:
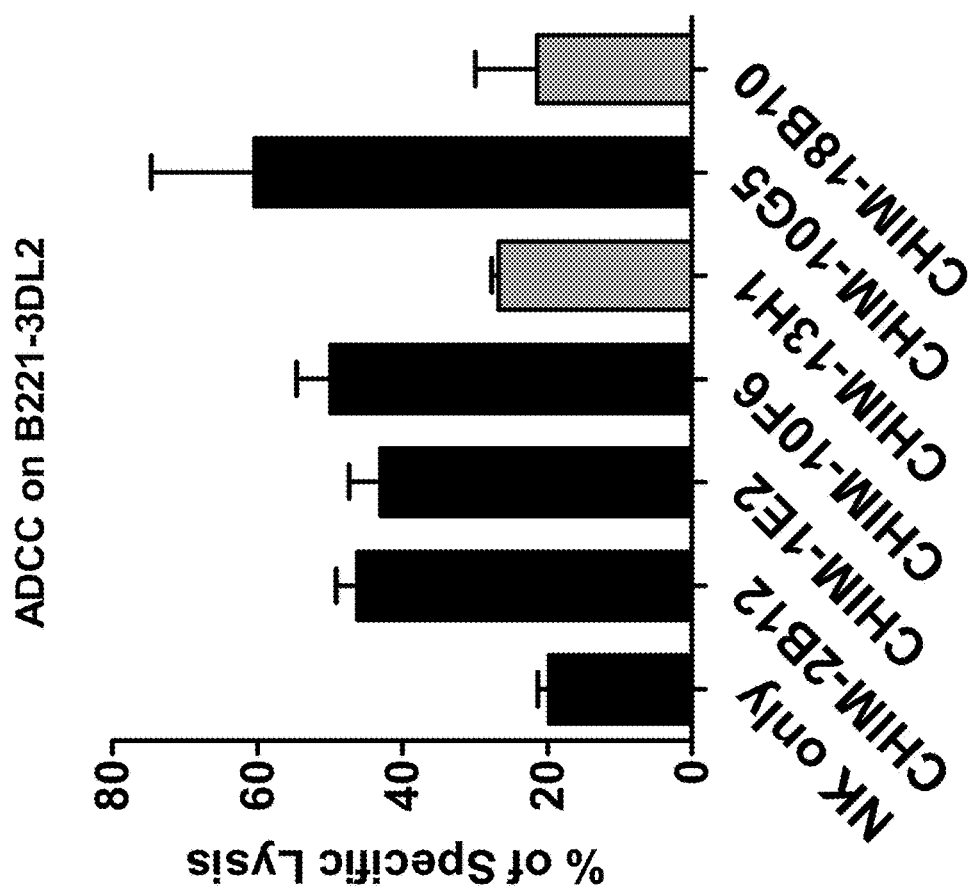
FIG. 10 shows the ability of anti-KIR3DL2 mAbs to ADCC-mediated killing of KIR3DL2-transfected B221 cells. The mAbs shown in gray induce internalization of the receptor and seem to be less efficient than the 4 other mAbs that do not induce KIR3DL2 internalization.

FIG. 10 shows a similar experiment in which target cells used are KIR3DL2-transfected B221 which are overall more sensitive to ADCC-mediated killing by anti-KIR3DL2 mAbs. The mAbs shown in gray induce internalization of the receptor and seem to be less efficient than the 4 other mAbs that do not induce KIR3DL2 internalization.

Figure 11:
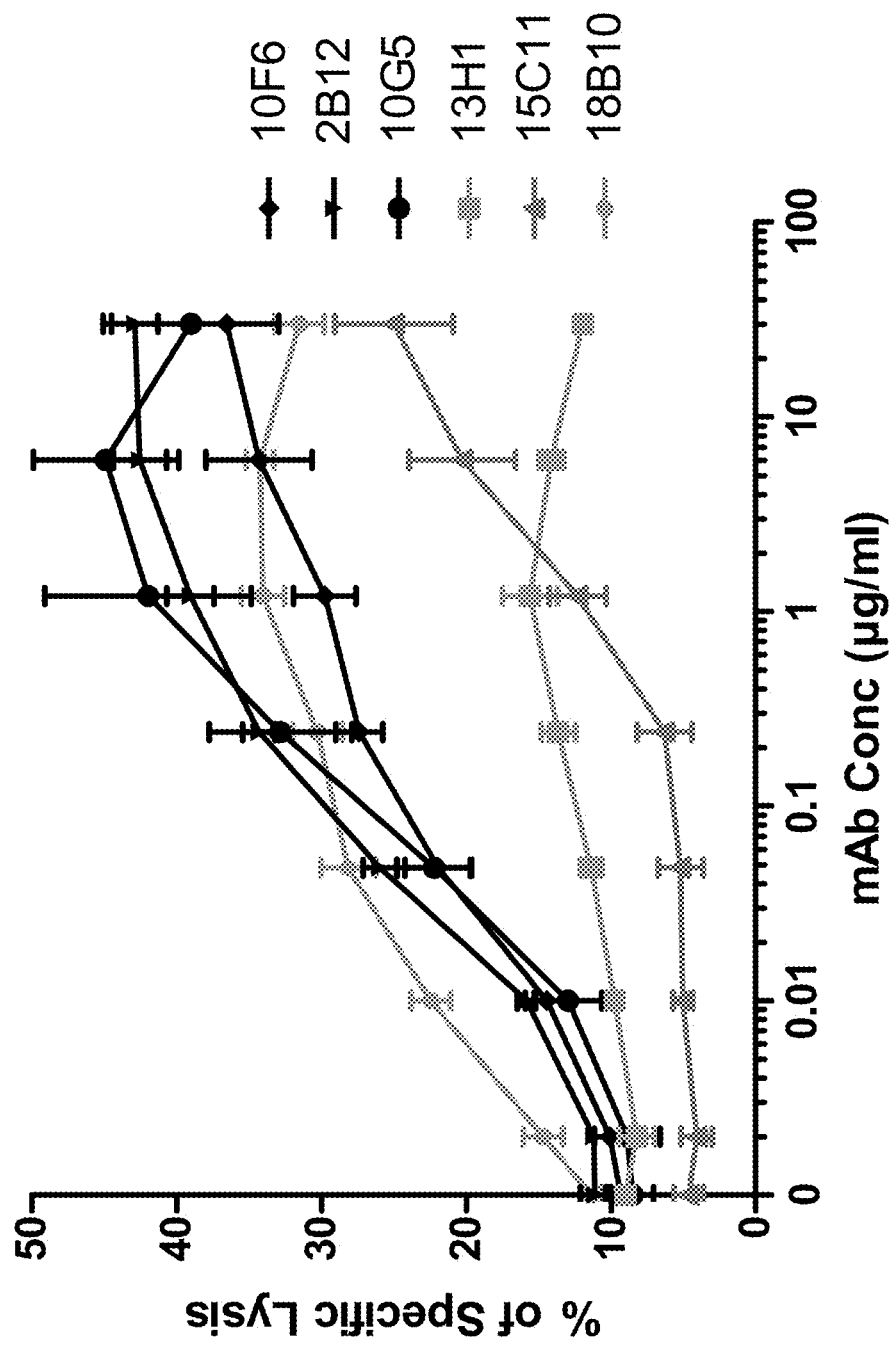
FIG. 11 shows a comparison of antibodies in a dose-ranging experiment the ability of chimerized huIgG1 anti-KIR3DL2 mAbs to mediate ADCC against KIR3DL2-expressing B221 targets.

FIG. 11 shows a comparison of antibodies in a dose-ranging experiment the ability of chimerized huIgG1 anti-KIR3DL2 mAbs to mediate ADCC against KIR3DL2-expressing B221 targets, the efficacy profile of mAbs that do not induce internalization of the target (10F6, 2B12 and 10G5) is better than that of mAbs inducing KIR3DL2 internalization (13H1 and anti-D0 mAbs 15C11 and 18B10).

Example 7—Activity in Mouse Xenograft Models of KIR3DL2 Expressing Human Tumors

Materials & Methods
Immune compromised mice used for B221-KIR3DL2 and RAJI-KIR3DL2 models were NOD-SCID purchased from Charles River Laboratories. In the following models, 5 million human tumor cells (in 100 µl PBS as vehicle) were engrafted IV on Day 0 (D0), i.e. 1 day before treatment initiation (D1). From D1, mice were treated IV with different doses of mAbs (doses were adapted to mouse body weight) diluted in PBS, 2 injections per week for the duration of the whole experiment.

Control groups included, depending on the experiment:
PBS/placebo-treated mice as a control of normal/unaffected tumor growth;
mice injected with the same dose of isotype control-matched mAbs directed against an irrelevant antigen.

Mice were weighed and observed for clinical signs every 2 to 5 days depending on the model. Percent of body weight changes were calculated as compared to body weight at D0 before tumor engraftment or to the highest body weight reached during the experiment. Mouse deaths or important weight losses were recorded and used to draw survival Kaplan-Meier curves and calculate improvement in survival as compared to control groups of mice.

Figure 12:
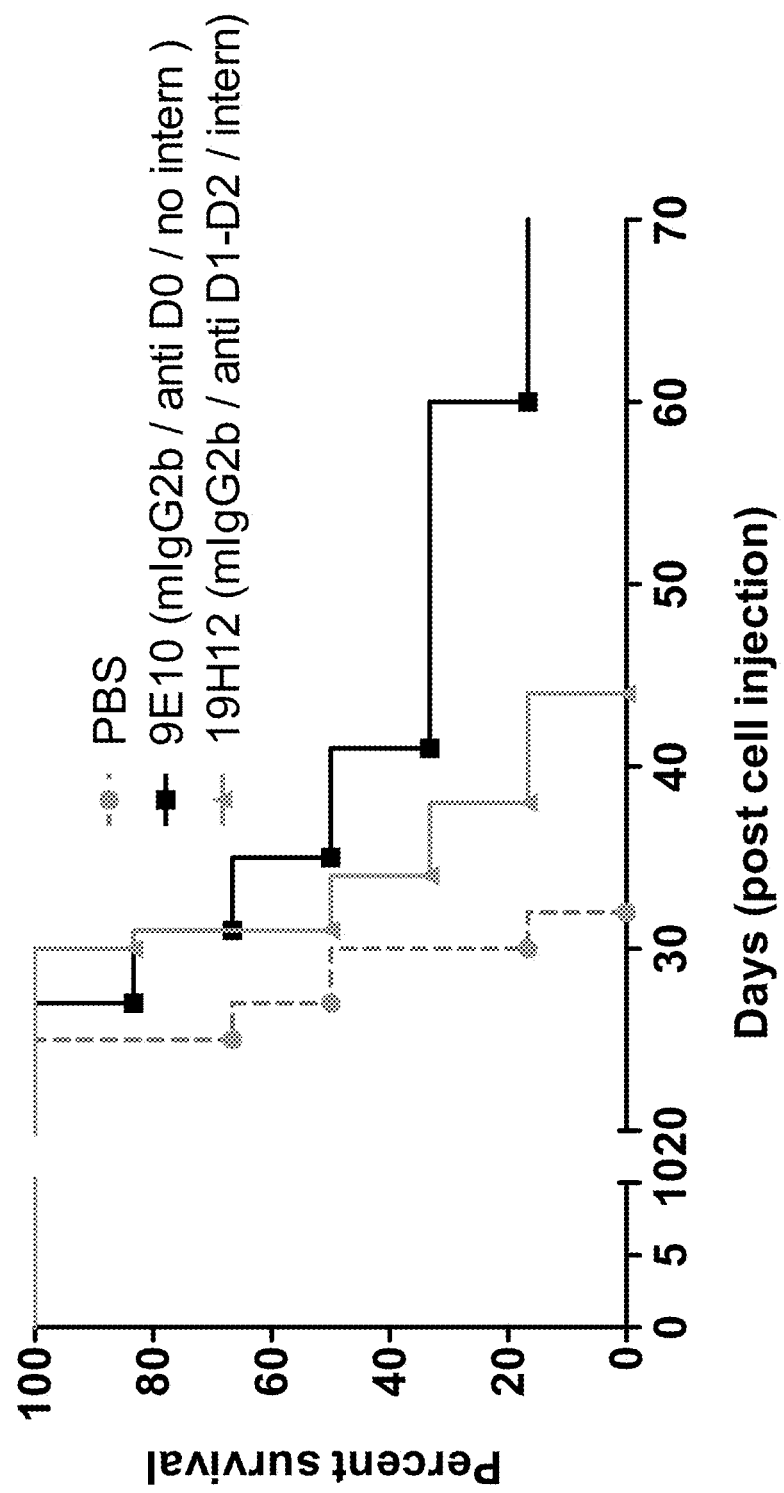
FIG. 12 shows the results of an experiment (n=6 NOD-SCID mice per group) in which the efficacy of 3 IgG2b isotype murine anti-KIR3DL2 9E10 and 19H12 was tested against SC B221-KIR3DL2 xenografts. Non-internalizing anti-D0 antibody 9E10 showed increased survival compared to both PBS and internalizing anti-D1 antibody 19H12.

Results
FIG. 12 shows the results of an experiment (n=6 NOD-SCID mice per group) in which the efficacy of 3 IgG2b isotype murine anti-KIR3DL2 9E10 and 19H12 (both given at 300 Gg/mouse, twice a week) was tested against SC B221-KIR3DL2 xenografts. Non-internalizing anti-D0 antibody 9E10 showed increased survival compared to both PBS and internalizing anti-D1/D2 antibody 19H12.

Figure 13:
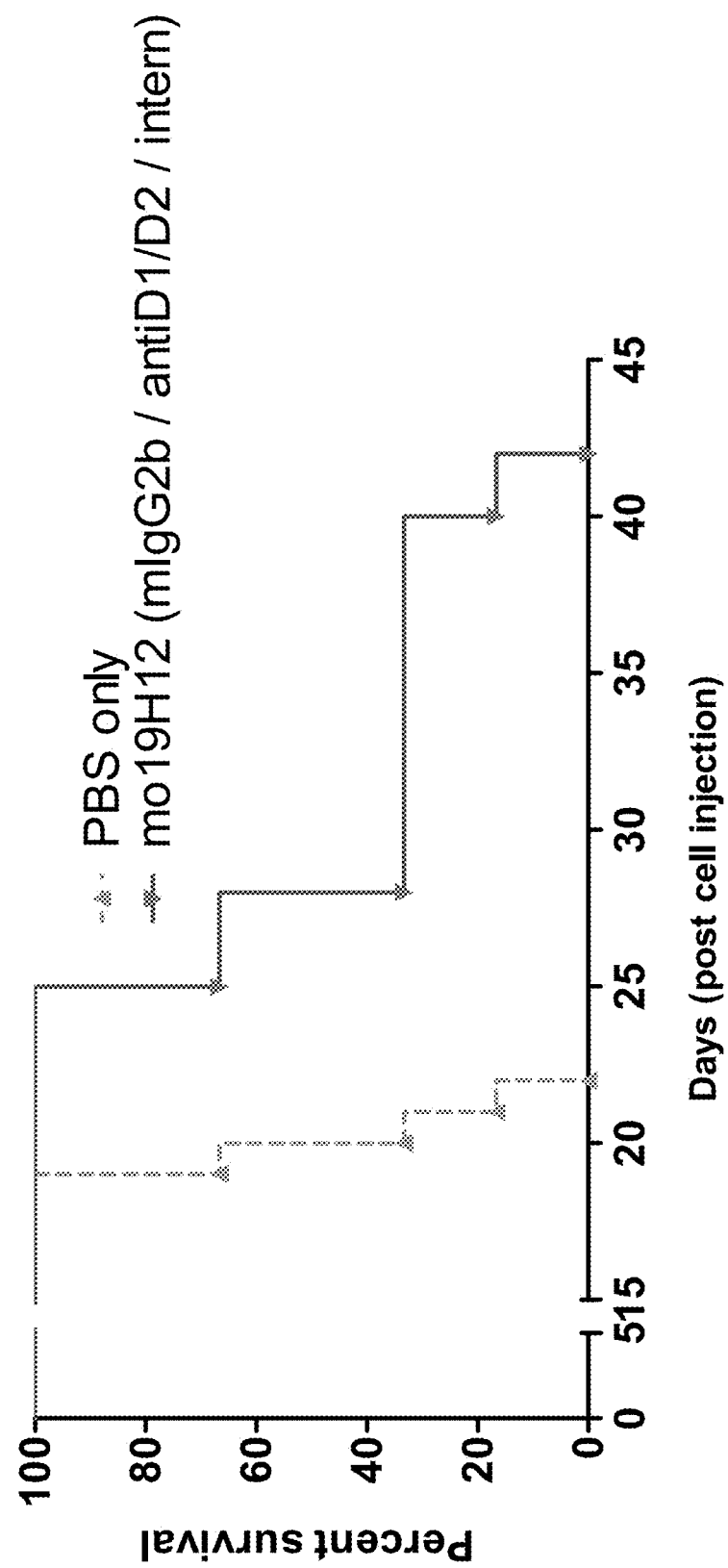
FIG. 13 shows the results of another experiment (n=6 NOD-SCID mice per group) in which the efficacy of murine anti-KIR3DL2 19H12 was tested against SC RAJI-KIR3DL2 xenografts. In vitro, KIR3DL2-transfected RAJI cells showed less internalization upon mAb binding than B221-KIR3DL2 or Sézary cell lines. In the RAJI-KIR3DL2 xenograft model, mo19H12 mAb was more efficient than in the B221-KIR3DL2 model. This is due to less potent internalization of the target in vivo.

FIG. 13 shows the results of another experiment (n=6 NOD-SCID mice per group) in which the efficacy of murine anti-KIR3DL2 19H12 (given at 300 Gg/mouse, twice a week) was tested against SC RAJI-KIR3DL2 xenografts. In vitro, KIR3DL2-transfected RAJI cells showed less internalization upon mAb binding than B221-KIR3DL2 or Sézary cell lines. In the RAJI-KIR3DL2 xenograft model, mo19H12 mAb was more efficient than in the B221-KIR3DL2 model. This is due to less potent internalization of the target in vivo.

Example 8—Ligand Blockade

Materials & Methods
Antibody Inhibition of Tetramer Staining
B27 dimer and HLA-A3 tetramer preparation and FACS staining have been described previously (Kollnberger, et al. (2007) *Eur J Immunol* 37:1313-1322). HLA-A3 tetramers were prepared with For antibody inhibition experiments Baf3 cells transduced with KIR3DL2 were stained with 5 µg antibody or IgG1/IgG2a isotype control (Biolegend UK Ltd) at 4° C. for 20 minutes before staining with tetramer at room temperature for 20 minutes. Stained cells were then washed and fixed as described previously before FACS analysis on a BD Fortessa FACS machine. FACS analysis was performed using Flowjo software (Tree star Inc US).

Antibody Inhibition of Jurkat KIR3DL2 CD3e Reporter Cells

Jurkat reporter cells transduced to express KIR3DL2CD3e fusion protein have been previously described (Payeli, et al. (2012) *Arthritis Rheum.*). For antibody inhibition experiments reporter cells 100,000/well in RPM1640 (Sigma, supplemented with 10% FCS and penicillin and streptomycin) were first stained at 4° C. with 10 µg antibody or isotype control antibody for 20 minutes. Subsequently reporter cells were stimulated with 200,000 parental LCL.LBL.721.221 cells (hereafter referred to as 221 cells) or 221 cells transfected with HLA-B27 or control HLA-class 1 in a final volume of 200 µl. Supernatants were harvested after overnight stimulation for IL-2 assay by ELISA (Ebiosciences UK Ltd) performed according to the manufacturer's instructions.

Figure 14:
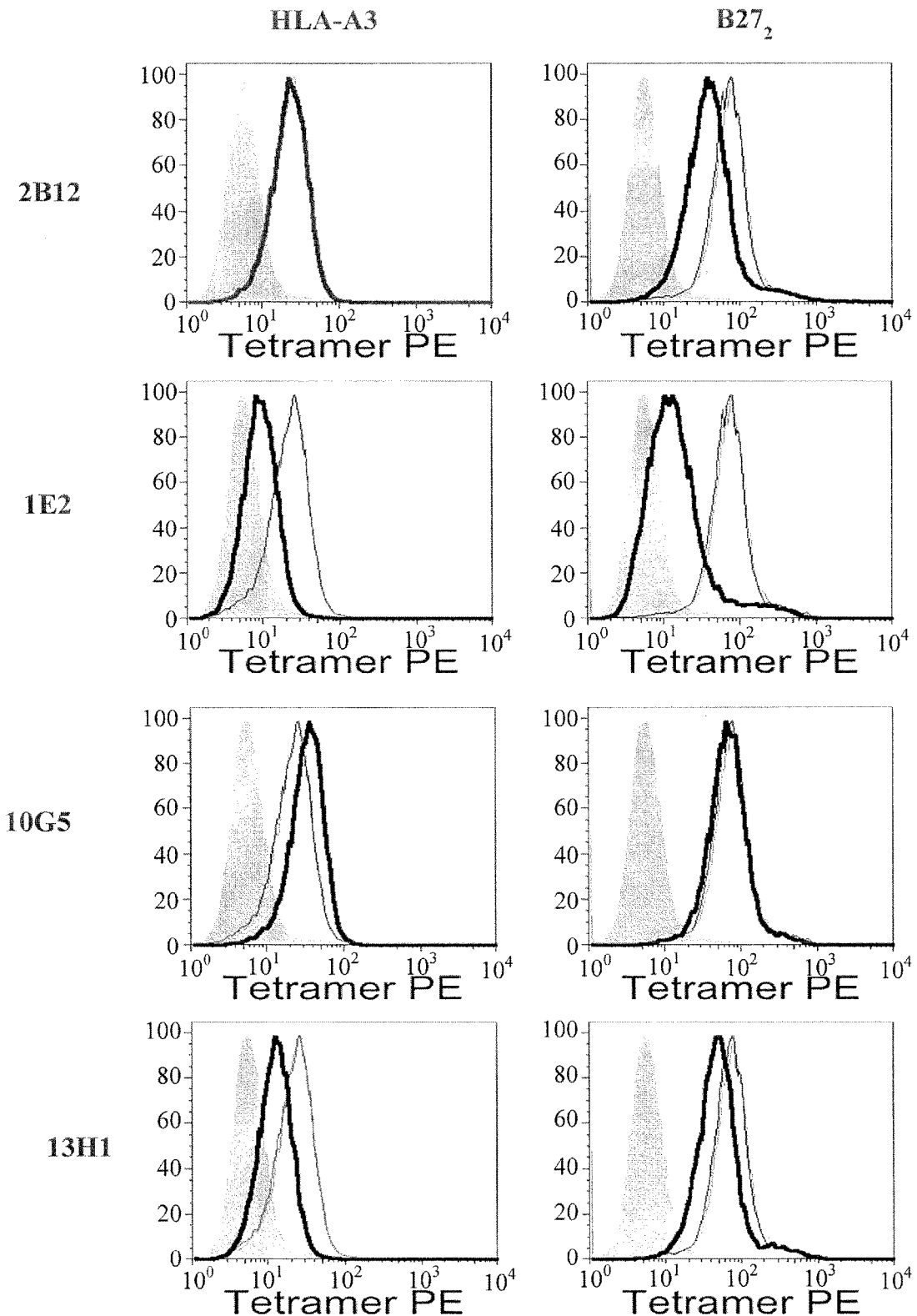
FIG. 14 shows KIR3DL2 D0 domain antibodies inhibit HLA-A3 and B27 heavy chain dimer (B27$_2$) binding. Representative FACS staining showing the effect of anti KIR3DL2 D0 antibodies on HLA-A3 and B27$_2$ tetramer binding to KIR3DL2 transduced Baf3 cells. (Representative of 1 of three independent experiments).
Figure 16A:
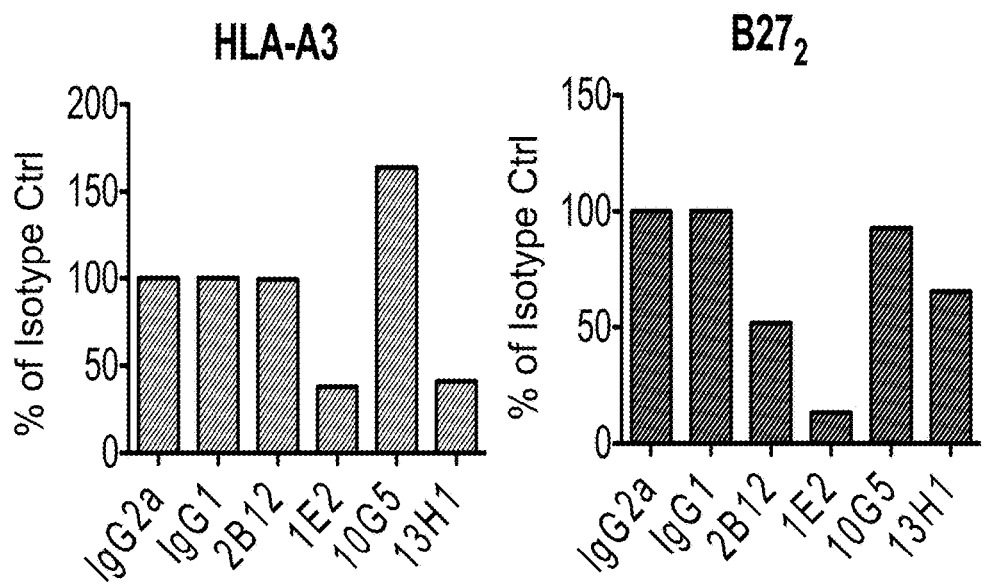
FIG. 16A shows KIR3DL2 D0 domain antibodies inhibit HLA-A3 and B27 heavy chain dimer tetramer binding.

Results
D0 Domain-Specific Antibodies Inhibit HL4-A3 and B27dimer (B27$_2$) Tetramer Staining of KIR3DL2 Transduced Cells First we studied the ability of D0 and D1/D2 domain-specific anti-KIR3DL2 antibodies to inhibit HLA-A3 and B27 dimer tetramer staining of KIR3DL2. The D0-domain specific anti-KIR3DL2 antibodies 1E2 and 13H1 consistently inhibited HLA-A3 and B27 heavy chain (B27$_2$) staining of KIR3DL2 transduced Baf3 cells (FIGS. 14 and 16A). 2B12 inhibited B27$_2$ while demonstrating negligible effects on HLA-A3 tetramer staining of KIR3DL2. By contrast 10G5 did not inhibit staining of KIR3DL2 with either HLA-A3 or B27$_2$ tetramers.

The D2 Domain Specific Antibody 1C3 Inhibits HLA-A3 but not B27 Dimer (B27$_2$) Tetramer Staining of KIR3DL2

Figure 15:
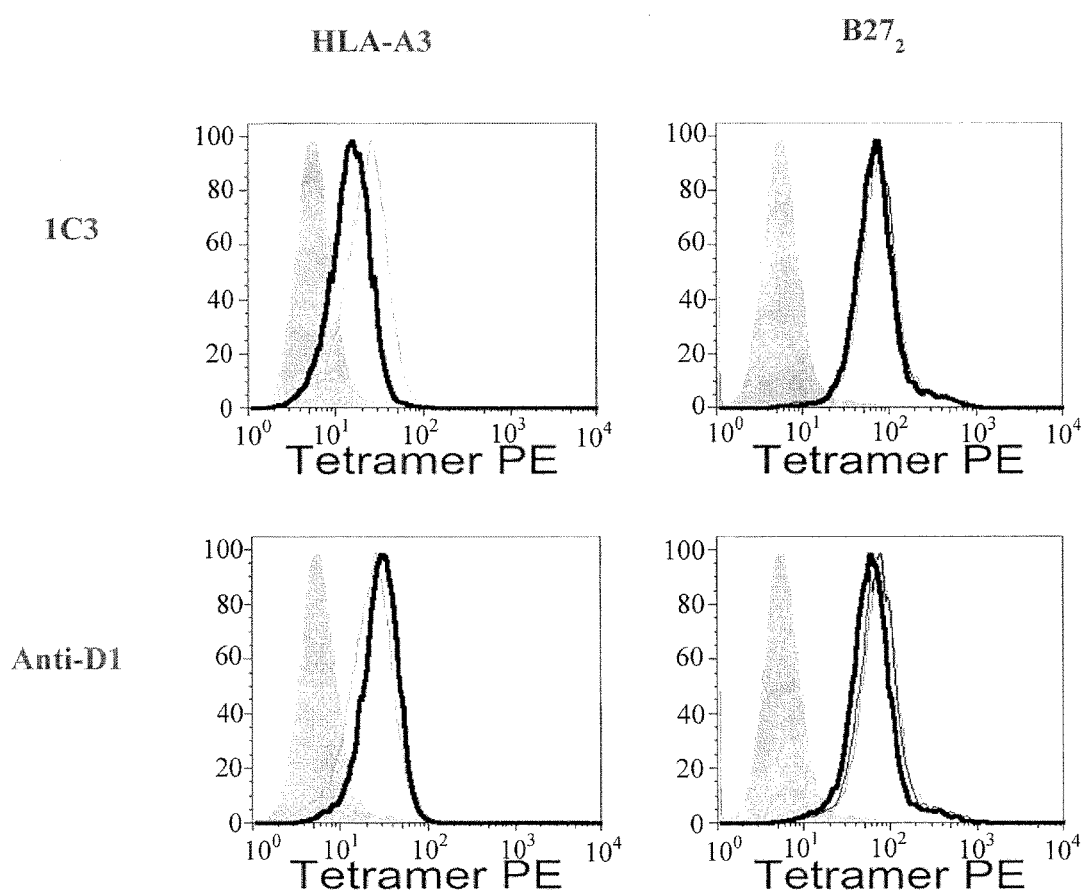
FIG. 15 shows KIR3DL2 anti-D1 and anti-D2 (1C3 antibody) domain antibodies inhibit HLA-A3 but not B27 heavy chain dimer (B27$_2$) binding. Representative FACS staining showing the effect of anti KIR3DL2 D1/D2 antibodies on HLA-A3 and B27$_2$ tetramer binding to KIR3DL2 transduced Baf3 cells. (Representative of 1 of three independent experiments).
Figure 16B:
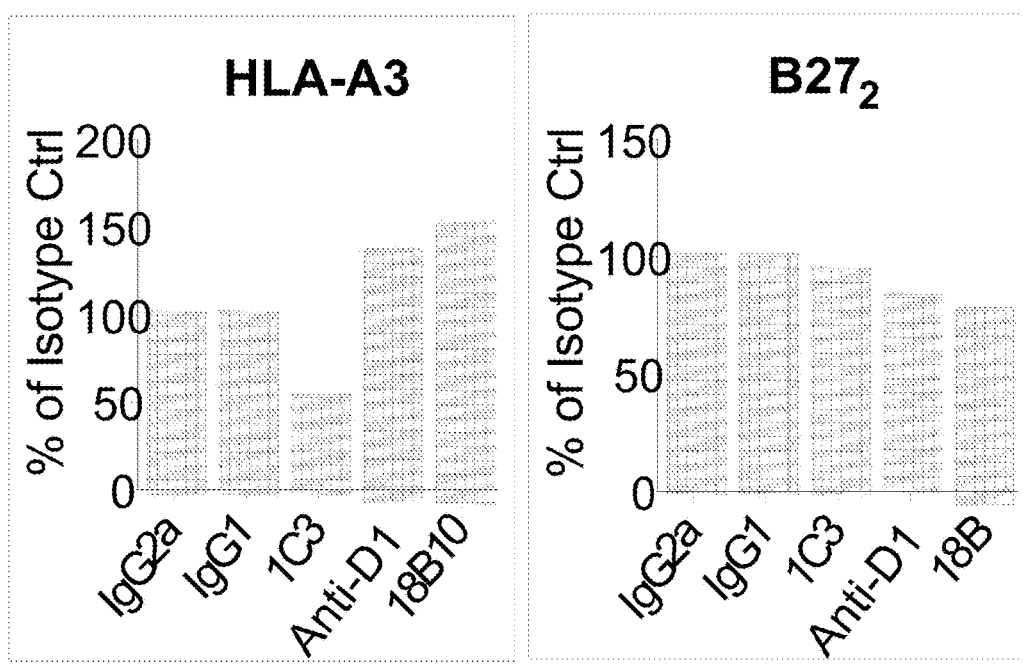
FIG. 16B. Anti-D2 (1C3) domain mAb inhibits HLA-A3 tetramer but not B27 heavy chain dimer (B27$_2$) binding. Results are expressed as % of the tetramer stain in the presence of isotype control MAb.

The D2 specific antibody 1C3 consistently inhibited HLA-A3 tetramer staining of KIR3DL2 transduced cells (FIGS. 15 and 16B). By contrast 1C3 MAb did not affect B27$_2$ staining of KIR3DL2 Baf3 cells and D1 specific antibodies did not significantly affect neither HLA-A3 nor B27$_2$ tetramer staining of KIR3DL2 (FIGS. 15 and 16B).

D0 Domain but not D1/D2 Specific Anti-KIR3DL2 MAbs Inhibit KIR3DL2 Reporter Cell Interactions with HLA-Class 1.

Figure 17:
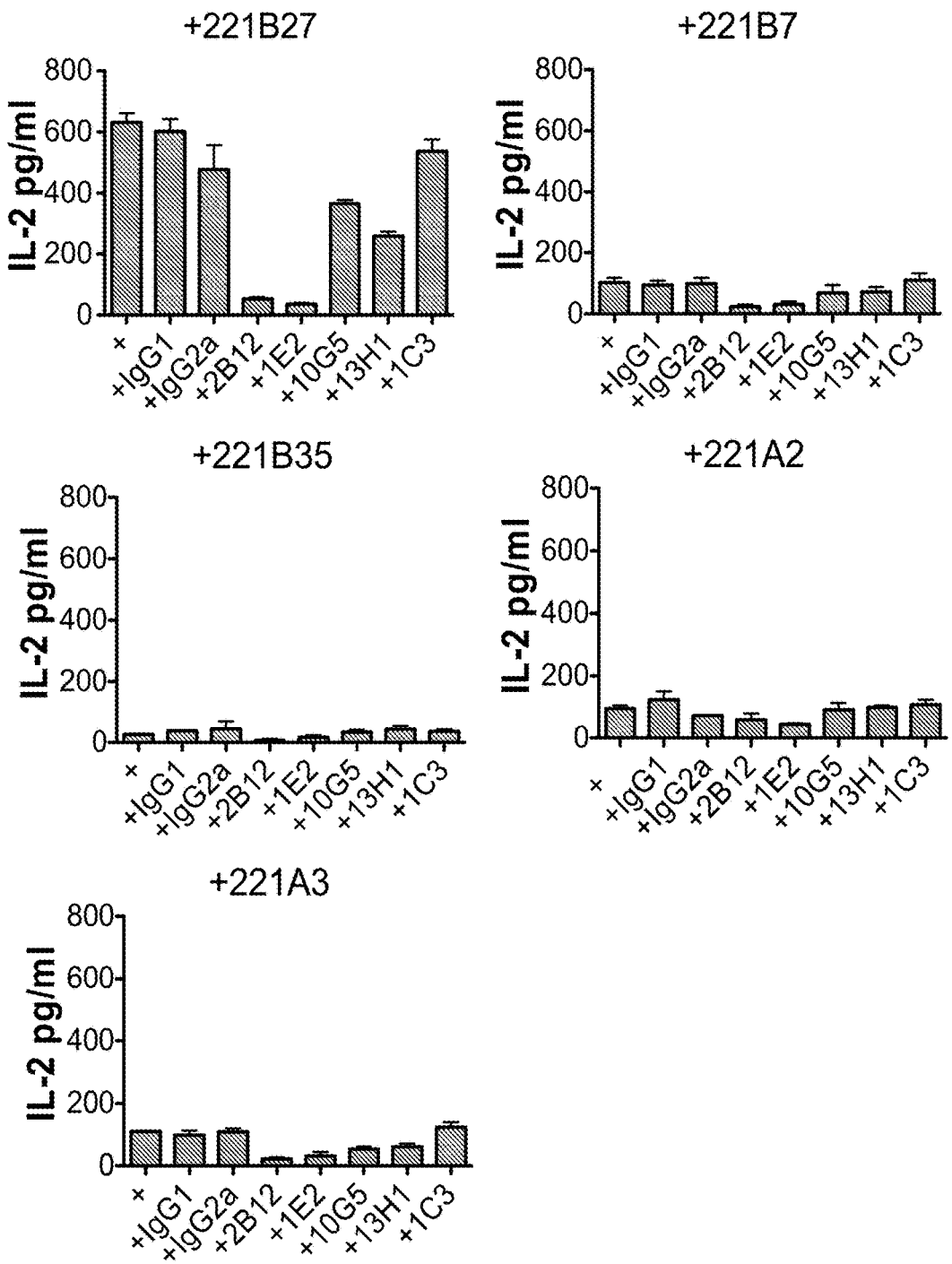
FIG. 17 shows KIR3DL2 D0 domain antibodies but not D1/D2 domain antibodies inhibit IL-2 secretion by KIR3DL2 CD3e reporter cell stimulated with HLA-B27 expressing B cell lines (221B27). D0 antibodies inhibit IL-2 production by reporter cells stimulated with B cell lines expressing control HLA-class 1 to a smaller extent compared with cells stimulated with HLA-B27. Representative ELISAs for IL-2 production from one of three independent experiments.
Figure 18:
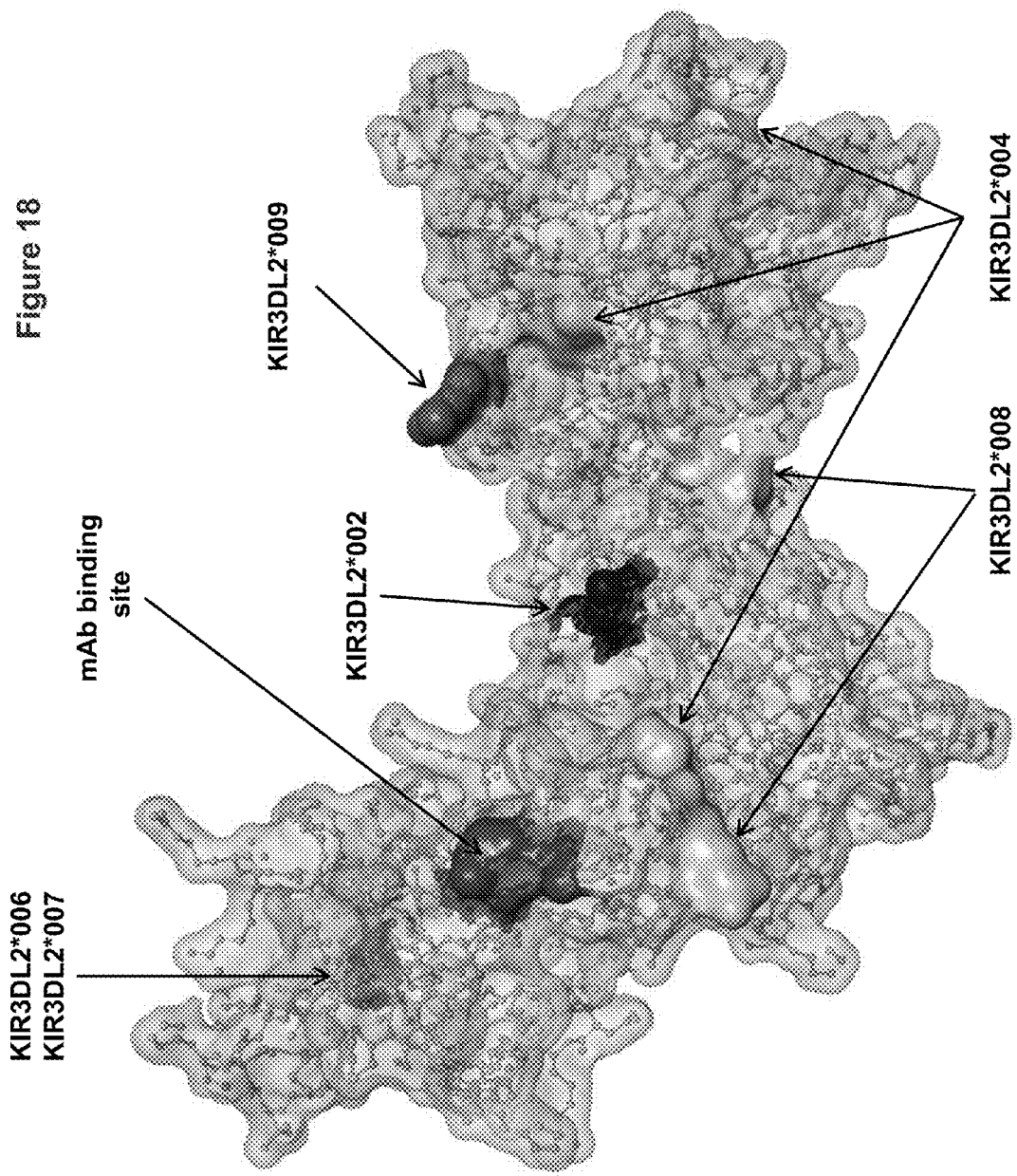
FIG. 18 shows a view of the KIR3DL2 polypeptide allele *001, including the antibody binding site corresponding to mutant 2 having substitutions I60N and G62S within the D0 domain (e.g., binding site for antibodies 2B12, 10F6, 18C10, 10G5 and 13H1). Shown in the figure also are amino acid differences between KIR3DL2 allele *001 and alleles *002, *004, *006/*007, *008 and *009.
Figure 19:
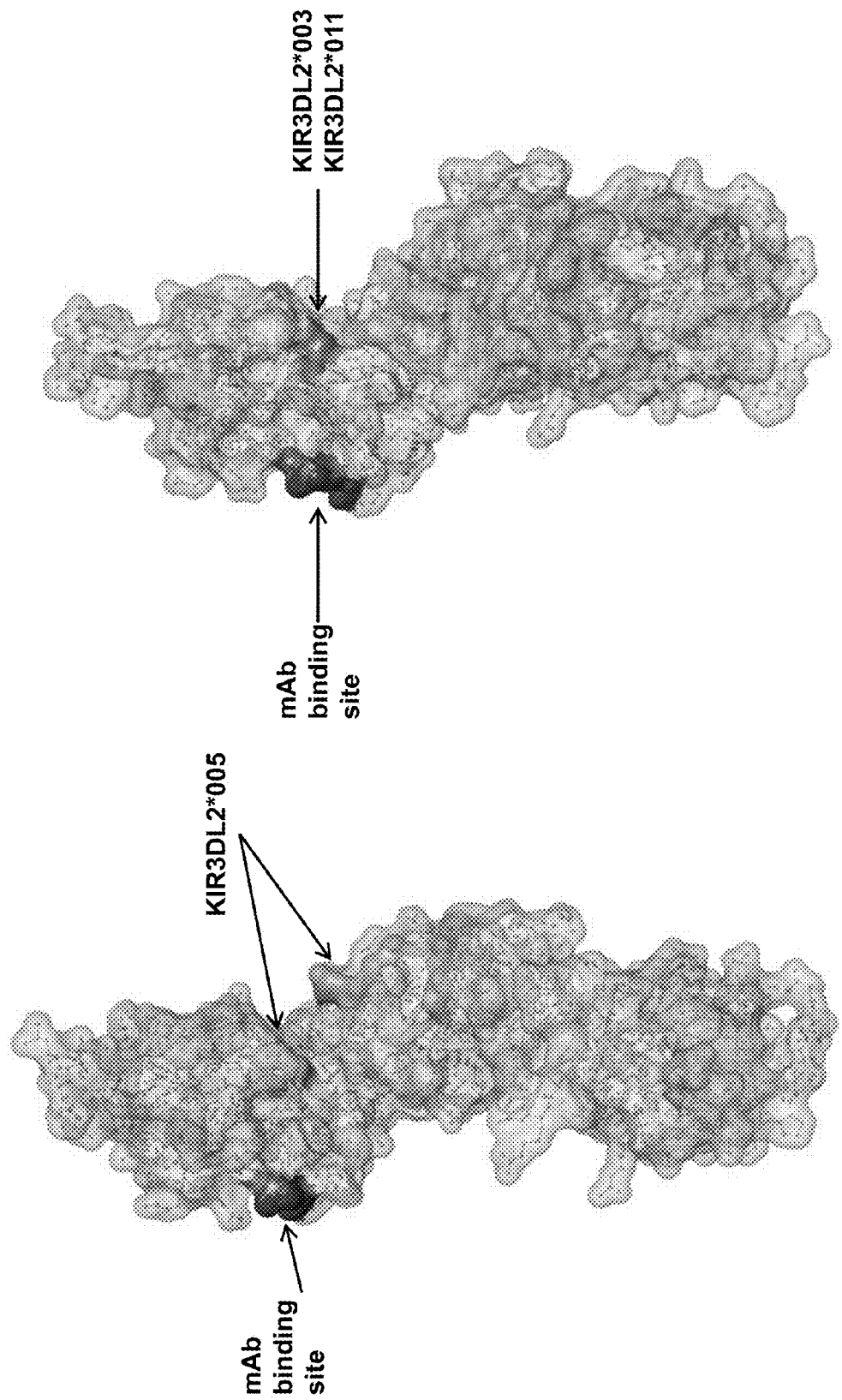
FIG. 19 shows an alternative view of the KIR3DL2 polypeptide allele *001, including the antibody binding site corresponding to mutant 2 having substitutions I60N and G62S within the D0 domain. Shown in the figure also are amino acid differences between KIR3DL2 allele *001 and alleles *005 and *003/*011.
Figure 20:
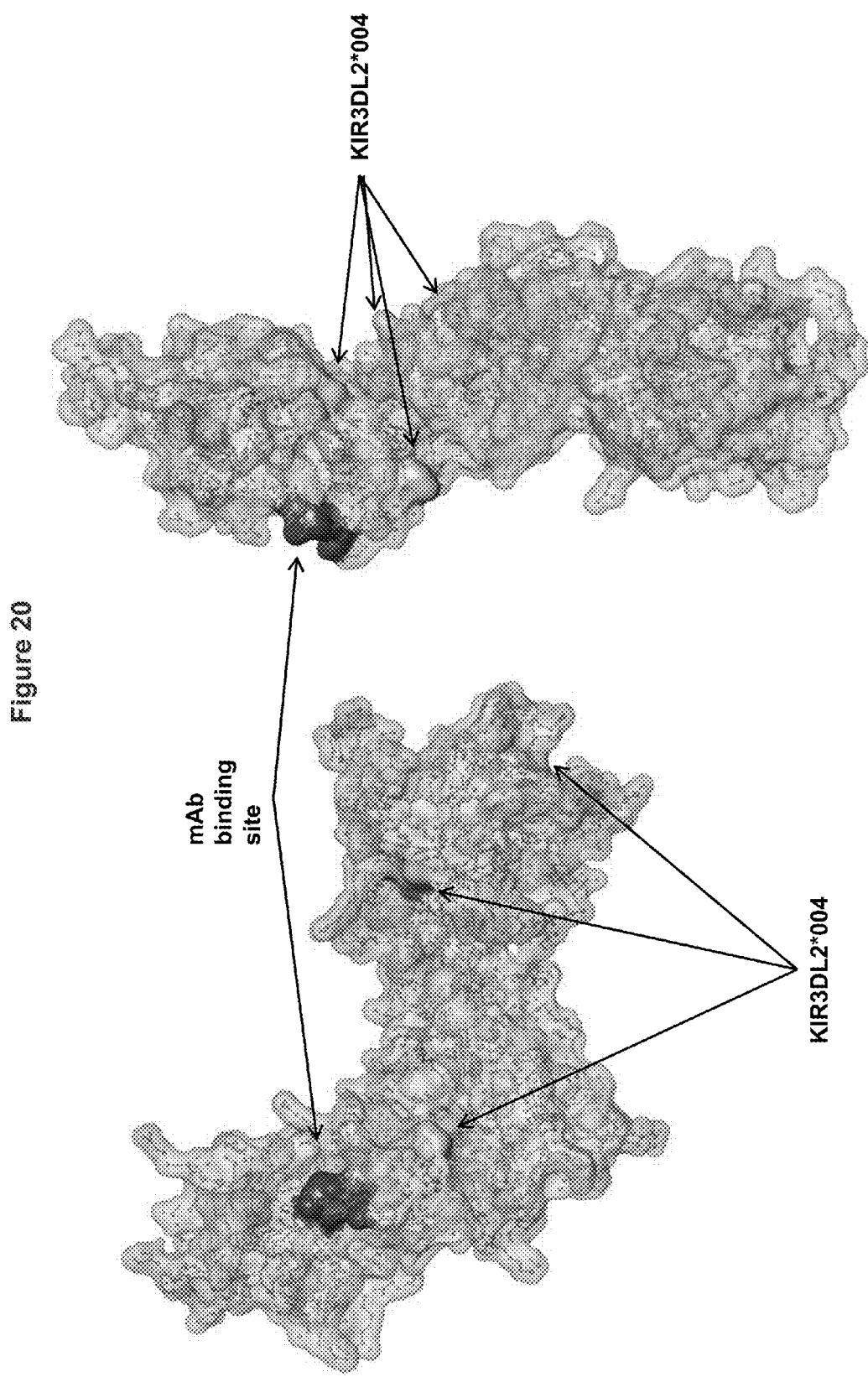
FIG. 20 shows two alternative (front and back) views of the KIR3DL2 polypeptide allele *001, including the antibody binding site corresponding to mutant 2 having substitutions I60N and G62S within the D0 domain. Shown in the figure also are amino acid differences between KIR3DL2 allele *001 and allele *004.

We next determined the effect of KIR3DL2 specific antibodies on KIR3DL2 recognition of HLA-B27 and other HLA-class 1 by studying the effect of antibodies on IL-2 production KIR3DL2CD3e transduced Jurkat reporter cells stimulated with 221 transfectants. In agreement with our previous findings 221 cells expressing HLA-B27 consistently stimulated 6 fold greater IL-2 production by KIR3DL2 reporter cells compared to stimulation with cells expressing control HLA class 1 (FIG. 17).

D0 domain-specific antibodies 2B12, 1E2, 10G5 and 13H1 all inhibited IL-2 production by KIR3DL2 reporter cells stimulated with HLA-B27 transfected cells to some degree (FIG. 4) with 2B12 and 1E2 demonstrating the greatest inhibitory effect. By contrast the D2 specific antibody 1C3 had no significant effect on reporter cell recognition of HLA-B27.

D0 domain-specific antibodies also inhibited IL-2 production by KIR3DL2 reporter cells stimulated with 221 cells transfected with HLA-B7, HLA-B35 and HLA-A2 and HLA-A3, although effects were less pronounced than those observed when cells were stimulated with HLA-B27. By contrast the D2 specific antibody 1C3 had no significant effect on IL-2 production by KIR3DL2 reporter cells stimulated with 221 cells transfected with HLA-B7, HLA-B35 and HLA-A2 and HLA-A3.

Summary

Here we show that monoclonal antibodies against the D0 domain of KIR3DL2 (2B12, 1E2, 13H1) inhibit binding to β2m-free B27 heavy chain dimers (B27$_2$) and β2m-associated ligands such as HLA-A3. By contrast antibodies against the D2 domain of KIR3DL2 (1C3) only inhibit interactions with HLA-A3 and have little effect on B27$_2$ tetramer binding.

Although KIR3DL2 reporter T cells produce IL-2 when stimulated with HLA-B27, HLA-B7, HLA-B35, HLA-A2 and HLA-A3 transfected LBL.721.221 B cells, reporter cells consistently produce 6 fold higher IL-2 in response to HLA-B27. KIR3DL2 interactions with B cells expressing HLA-B27 and other HLA-class 1 are consistently inhibited with the D0 domain specific antibodies 2B12 and 1E2 and to a lesser extent 13H1. This suggests that the D0 domain of KIR3DL2 may have some affinity for common shared features of different HLA-class 1. The KIR3DL2 D0 domain may bind at least in part to a region in HLA-B27 which is shared between different HLA class 1. The increased avidity of KIR3DL2 for HLA-B27 may result from dimerization of B27 heavy chains.

It has been reported that the three immunoglobulin-like domains D0, D1 and D2 of KIR3DL2 are involved in binding ligand. The results from the antibody inhibition studies suggest that the dominant contact of KIR3DL2 with HLA-class 1 is via the D0 domain. Notably the D2 antibody 1C3 only inhibited HLA-A3 binding to KIR3DL2 and not B27 dimer. We therefore propose that the D0 domain contacts residues are conserved between different HLA-class 1 and the D1 and D2 domains contact polymorphic regions and peptide in the peptide MHC complex. The antibodies identified can be used for therapeutic, diagnostic and other research applications depending on the particular application, to selectively block different ligands, or to block multiple ligands, or to not compete with ligands for binding to KIR3DL2.

Example 9—Epitope Mapping

KIR3DL2 mutants were developed to identify KIR3DL2-specific antibodies that had desired binding properties. Antibodies will advantageously have binding to most or all of the major KIR3DL2 alleles in the population (in terms of allele frequency) while not binding to the major KIR3DL1 alleles (e.g. allele *00101).

Mutations were generated that corresponded to residues that differ between KIR3DL1 and KIR3DL2. A first set of mutations were generated in which the amino acid in KIR3DL1 were substituted into KIR3DL2. However, many of these mutated proteins failed to express at the cell surface, suggesting that incorporating the KIR3DL1 deeply impacted the folding of the entire KIR3DL2 molecule. In particular, mutants in clusters D21, D22, D23, D26 and D27 shown below in Table 7A did not express at the cell surface.

TABLE 7A

| Cluster | Residues in KIR3DL1 | Residues in KIR3DL2 |
|---|---|---|
| D21 | V196;P199;D285;P286 | I196;L199;N285;S286 |
| D22 | K212;S218 | T212;N218 |
| D23 | R226 | W226 |
| D26 | R249 | P249 |
| D27 | H278; S279; E282; Y281 | A278; L279; V282; C281 |

Further mutants were redesigned and tested, with the final set of mutations shown in Table 7B below. Antibodies were tested for binding KIR3DL2 to various KIR3DL2 mutants. KIR3DL2 mutants were generated by PCR (see Table 7B below). All the Mx-R primers were used with the following 5' primer ACCCAAGCTGGCTAGCATGTCGCTCACG-GTCGTCAGCATG (SEQ ID NO: 79). All the Mx-F primers were used with the following 3' primer AGCACAGTG-GCGGCCGCCTAGAAAA CCCCCTCAAGACC (SEQ ID NO: 80). The sequences amplified were run on agarose gel then purified using the Qiagen Gel Extraction kit.

To create mutants 12 and 21, it was necessary to do a third PCR. Primers used for these PCR were: M12a-F primer (5'-GCCACAGGTGCATATGAGAAACCTCTCTCTCA-GCC-3') (SEQ ID NO: 81) with the M12b-R primer (5'-TGGGTCACTrGCGGCTGACCACACGCAGGGCA-GGG-3') (SEQ ID NO: 82) and M21a-F primer (5'-CGTGCCCTGCCCTACGTGTGGTCAAACTCAAGTG-AC-3') (SEQ ID NO: 83) with the M21b-R primer (5'-ATG CAGGTGTCTGGGGATACCAGATITGGAGCTGGTrC-3') (SEQ ID NO: 84).

The two or three PCR products generated for each mutant were then ligated into a pcDNA3.1 vector, digested with the restriction enzyme NheI and NotI, with the InFusion system (Clontech) according to the manufacturer's instructions.

After sequencing, the vectors containing the mutated sequences were prepared as Maxiprep using the Promega PureYield™ Plasmid Maxiprep System. Vectors were then used for HEK-293T cell transfection using Invitrogen's Lipofectamine 2000 according to the manufacturer instructions.

TABLE 7B

| Mutants | Reverse primers | Forward primers |
|---|---|---|
| Number 1 R13W + A25T + Q27R | M1-R 5'-ccgaagagtcacgtgtcctcctcga ggcaccacagtgctgggccaggcaga-3' (SEQ ID NO: 85) | M1-F 5'-cacgtgactcttcggtgtcactatcgtcg tggg-3' (SEQ ID NO: 86) |
| Number 2 160N + G62S | M2-R 5'-cacagggctcatgttgaagctctcc tggaatattc-3' (SEQ ID NO: 87) | M2-F 5'-aacatgagccctgtgaccccagcacat g-3' (SEQ ID NO: 88) |

TABLE 7B-continued

| Mutants | Reverse primers | Forward primers |
|---|---|---|
| Number 3<br>R32H +<br>G33R | M3-R<br>5'-attgttaaacctatgacgatagtga<br>cactgaagag-3'<br>(SEQ ID NO: 89) | M3-F<br>5'-cataggtttaacaatttcatgctgta<br>c-3' (SEQ ID NO: 90) |
| Number 4<br>S45I +<br>V45I | M4-R<br>5'-gatgggaatgtggattctgtcttct<br>ttgtacagcatg-3'<br>(SEQ ID NO: 91) | M4-F<br>5'-atccacattcccatcttccacggcagaat<br>attc-3' (SEQ ID NO: 92) |
| Number 5<br>P66T | M5-R<br>5'-atgtgctgtggtcacagggcccatg<br>atgaag-3'<br>(SEQ ID NO: 93) | M5-F<br>5'-gtgaccacagcacatgcagggaccta<br>cag-3' (SEQ ID NO: 94) |
| Number 6<br>R78H +<br>L82P | M6-R<br>5'-gggggagtgtgggtgtgaaccccga<br>catctgtag-3'<br>(SEQ ID NO: 95) | M6-F<br>5'-cacccacactcccccactgggtggtcggc<br>ac-3' (SEQ ID NO: 96) |
| Number 7<br>L113V +<br>T118R | M7-R<br>5'-ttgcaggatgactctctctcctgat<br>ttcaccagggg-3'<br>(SEQ ID NO: 97) | M7-F<br>5'-agagtcatcctgcaatgttggtcagatgt<br>c-3' (SEQ ID NO: 98) |
| Number 8<br>V127I | M8-R<br>5'-ctcaaacatgatatctgaccaacat<br>tgcaggatgac-3'<br>(SEQ ID NO: 98) | M8-F<br>5'-gatatcatgtttgagcacttctttctgca<br>c-3' (SEQ ID NO: 100) |
| Number 9<br>L164M +<br>P166L +<br>V167A | M9-R<br>5'-aagggcaagcatcatgggaccgatg<br>gagaagttggccttg-3'<br>(SEQ ID NO: 101) | M9-F<br>5'-atgatgcttgcccttgcaggaacctacag<br>atgttatgg-3' (SEQ ID NO: 102) |
| Number 10<br>R136K +<br>E141K | M10-R<br>5'-tagagatcccatctttgtgcagaaa<br>gaagtgctcaaacat-3'<br>(SEQ ID NO: 103) | M10-F<br>5'-aagatgggatctctaaggacccctcacgc<br>ctcgttgg-3' (SEQ ID NO: 104) |
| Number 11<br>P179T +<br>S181T | M11-R<br>5'-gggggtgtgagtaacagaaccataa<br>catctgtagg-3'<br>(SEQ ID NO: 105) | M11-F<br>5'-gttactcacaccccctatcagttgtcagc<br>tc-3' (SEQ ID NO: 106) |
| Number 12<br>I196A +<br>L199A +<br>N285A +<br>S286A | M12a-R<br>5'-atatgcacctgtggccacgatgtcc<br>aggggtcactgg-3'<br>(SEQ ID NO: 107) | M12b-F<br>5'-gccgcaagtgacccactgcttgtttctgt<br>c-3' (SEQ ID NO: 108) |
| Number 13<br>T212A +<br>N218A | M13-R<br>5'-ggcctctcctgcctgaaccgcgggg<br>cccggctgggctgag-3'<br>(SEQ ID NO: 109) | M13-F<br>5'-caggcaggagaggccgtgaccttgtcctg<br>tagctcc-3' (SEQ ID NO: 110) |
| Number 14<br>W226A | M14-R<br>5'-ataggagctcgcggagctacaggac<br>aaggtcac-3'<br>(SEQ ID NO: 111) | M14-F<br>5'-tccgcgagctcctatgacatctaccatct<br>gtcc-3' (SEQ ID NO: 112) |
| Number 15<br>I231M +<br>R246P | M15-R<br>5'-atgggcctcccccttccctggacaga<br>tggtacatgtcatagga-3'<br>(SEQ ID NO: 113) | M15-F<br>5'-gaaggggaggcccatgaacgtaggctccc<br>tgcagtg-3' (SEQ ID NO: 114) |
| Number 16<br>E239G | M16-R<br>5'-atgtgctccaccttccctggacaga<br>tggtagatgtc-3'<br>(SEQ ID NO: 115) | M16-F<br>5'-gaaggtggagcacatgaacgtaggctccg<br>tgcagtg-3' (SEQ ID NO: 116) |
| Number 17<br>P249A | M17-R<br>5'-tctgttgaccttggccactgcacgg<br>agcctacgttc-3'<br>(SEQ ID NO: 117) | M17-F<br>5'-gccaaggtcaacagaacattccaggcaga<br>c-3' (SEQ ID NO: 118) |

TABLE 7B-continued

| Mutants | Reverse primers | Forward primers |
| --- | --- | --- |
| Number 18<br>A278H +<br>L279A +<br>C281A +<br>V282A | M18-R<br>5'-cgcggcgggcgcgtgacggaaagag<br>ccgaagcatctg-3'<br>(SEQ ID NO: 119) | M18-F<br>5'-cacgcgcccgccgcgtggtcaaactcaag<br>tgaccc-3' (SEQ ID NO: 120) |
| Number 19<br>A278H +<br>L279S +<br>V282E | M19-R<br>5'-ctcgcagggcgagtgacggaaagag<br>ccgaagcatctgtag-3'<br>(SEQ ID NO: 121) | M19-F<br>5'-cactcgccctgcgagtggtcaaactcaag<br>tgaccc-3' (SEQ ID NO: 122) |
| Number 21<br>C281Y +<br>C315P | M21a-R<br>5'-gtagggcagggcacggaaagagccg<br>aagca-3'<br>(SEQ ID NO: 123) | M21b-F<br>5'-cccagacacctgcatgttctgattg-3'<br>(SEQ ID NO: 124) |
| Number 22<br>(5 + 11)<br>P66T+<br>P179T;<br>S181T | M22a-R<br>5'-tgt ggt cac agg gcc cat<br>gat gaa gct ctc ctg gaa<br>tat tc-3'<br>(SEQ ID NO: 125) | M22a-F<br>5'-ggc cct gtg acc Aca gca<br>cat gca ggg acc tac aga-3'<br>(SEQ ID NO: 126) |
| Number 22<br>(5 + 11) | M22b-R<br>5'-gtc act ggg agc tga caa<br>ctg ata ggg ggT gtg agT aac-3'<br>(SEQ ID NO: 127) | M22b-F<br>5'-tca gct ccc agt gac ccc<br>ctg gac atc gtg atc aca gg-3'<br>(SEQ ID NO: 128) |
| Number 23<br>(8 + 11)<br>V127I +<br>P179T +<br>S181T | M23a-R<br>5'-gaT atc tga cca aca ttg<br>cag gat gac tgt ctc tcc-3'<br>(SEQ ID NO: 129) | M23a-F<br>5'-tgt tgg tca gat Atc atg<br>ttt gag cac ttc ttt ctg-3'<br>(SEQ ID NO: 130) |
| Number 23<br>(8 + 11)<br>V127I +<br>P179T +<br>S181T | Same primers as M22b-R | Same primers as M22b-F |
| Number 24<br>(11A1)<br>V178A +<br>H180S | M24-R<br>5'-gga gGA agg aGc aga acc<br>ata aca tct gta ggt tcc-3'<br>(SEQ ID NO: 131) | M24-F<br>5'-tct gCt cct TCc Tcc ccc<br>tat cag ttg tca gct ccc-3'<br>(SEQ ID NO: 132) |
| Number 26<br>(11A3)<br>Q184A +<br>H100S +<br>N99S | M26a-R<br>5'-gat cac cag ggg gtt<br>gct ggg agc cga cca ccc-3'<br>(SEQ ID NO: 133) | M26a-F<br>5'-aac ccc ctg gtg atc atg<br>gtc aca gga aGc TCc AGA AAA<br>CCT TCC-3'<br>(SEQ ID NO: 134) |
| Number 26<br>(11A3)<br>Q184A +<br>H100S +<br>N99S | M26b-R<br>5'-gtc cag ggg gtc act ccc<br>agct ga caa cGC ata ggg gga<br>gtg agg-3'<br>(SEQ ID NO: 135) | M26b-F<br>5'-agt gac ccc ctg gac atc<br>gtg atc aca ggt c-3'<br>(SEQ ID NO: 136) |
| Number 27<br>(11A4)<br>E130S +<br>H131S +<br>R145S | M27-R<br>5'-aga gat ccc atc tct gtg<br>cag aaa gaa gGA cGA aaa c-3'<br>(SEQ ID NO: 137) | M27-F<br>5'-aga gat ggg atc tct Gag<br>gac ccc tca Agc ctc-3'<br>(SEQ ID NO: 138) |
| Number 28<br>(11A5)<br>V147A +<br>Q149S | M28-R<br>5'-atg gat cGA tcc aGc gag<br>gcg tga ggg gtc ctc-3'<br>(SEQ ID NO: 139) | M28-F<br>5'-gCt gga TCg atc cat gat<br>ggg gtc tcc aag gcc-3'<br>(SEQ ID NO: 140) |
| Number 29<br>(11A6)<br>I150A +<br>M128A | M29-R<br>5'-ctc aga gat ccc atc tct<br>gtg cag aaa gaa gtg ctc aaa<br>cGC gac-3'<br>(SEQ ID NO: 141) | M29-F<br>5'-gat ggg atc tct Gag gac<br>ccc tca cgc ctc gtt gga cag<br>GCc cat g-3'<br>(SEQ ID NO: 142) |

TABLE 7B-continued

| Mutants | Reverse primers | Forward primers |
|---|---|---|
| Number 30<br>(1 + 2)<br>R13W +<br>A25T +<br>Q27R +<br>I60N +<br>G62S | M30a-R<br>5'-tcc tcc tcg agg cac cac<br>agt ct ggg ccA ggc ag-3'<br>(SEQ ID NO: 143) | M30a-F<br>5'-gtg cct cga Gga gga cac<br>gtg Act ctt cGg tgt cac tat<br>cg-3'<br>(SEQ ID NO: 144) |
| Number 30<br>(1 + 2)<br>R13W +<br>A25T +<br>Q27R +<br>I60N +<br>G62S | M30b-R<br>5'-tgg ggt cac agg gcT cat<br>gTt gaa gct ctc ctg g-3'<br>(SEQ ID NO: 145) | M30b-F<br>5'-Agc cct gtg acc cca gca<br>cat gca ggg acc tac aga tgt<br>cg-3'<br>(SEQ ID NO: 146) |
| Number 31<br>(D0-HLA1)<br>F9S + S11A | M31-R<br>5'-ggc agC cag gGa ggg ttt<br>gtc ctg acc acc cat g-3'<br>(SEQ ID NO: 147) | M31-F<br>5'-ccc tCc ctg Gct gcc cgg<br>ccc agc act gtg gtg cc-3'<br>(SEQ ID NO: 148) |
| Number 32<br>(D0-HLA2)<br>H29S +<br>F34A | M32-R<br>5'-ccc acg acg ata gGA aca<br>ctg aag agc cac gtg tcc-3'<br>(SEQ ID NO: 149) | M32-F<br>5'-TCc tat cgt cgt ggg GCt<br>aac aat ttc atg ctg tac-3'<br>(SEQ ID NO: 150) |
| Number 33<br>(1 + 2<br>A1)<br>F50A +<br>R53S | M33-R<br>5'-tat Gct gcc gtg gGC gat<br>ggg aac gtg gct tct g-3'<br>(SEQ ID NO: 151) | M33-F<br>5'-GCc cac ggc agC ata ttc<br>cag gag agc ttc atc-3'<br>(SEQ ID NO: 152) |
| Number 34<br>(1 + 2<br>A2)<br>Q56S +<br>E57A | M34-R<br>5'-gaa gct cGc cGA gaa tat<br>tct gcc gtg gaa gat gg-3'<br>(SEQ ID NO: 153) | M34-F<br>5'-ttc TCg gCg agc ttc atc<br>Atg ggc cct gtg acc-3'<br>(SEQ ID NO: 154) |
| Number 35<br>(1 + 2<br>A3)<br>P14S +<br>S15A +<br>H23S | M35-R<br>5'-tcc tcg agg cac cac agt<br>gGC ggA ccg ggc aga cag-3'<br>(SEQ ID NO: 155) | M35-F<br>5'-gtg gtg cct cga Gga gga<br>TCc gtg gct ctt cag tgt c-3'<br>(SEQ ID NO: 156) |
| Number 37<br>(1 + 2<br>A5)<br>S140Q | M37-R<br>5'-gtc ctc TTG gat ccc atc<br>tct gtg cag aaa g-3'<br>(SEQ ID NO: 157) | M37-F<br>5'-ggg atc CAA Gag gac ccc<br>tca cgc ctc gtt gg-3'<br>(SEQ ID NO: 158) |

Each antibody was tested for binding to wild-type KIR3DL2 and to each of the D0, D1 and D2 domain mutants. Antibodies did not show any loss of binding to unmutated wild type KIR3DL2 (WTaKIR3DL2) but lost binding to one or more mutants, thereby identifying several epitopes.

A summary is shown in Tables 7C and 7D ("+" indicates no significant loss of binding, "+/−" indicates a decrease in binding (or partial loss of binding) and "−" indicates substantially complete loss of binding). Most non-internalizing D0 antibodies lost substantially all binding to mutant 2 (four antibodies: 10F6, 2B12, 18C6, 10G5). All of these antibodies also had at least partial loss of binding to mutant 2A3. One non-internalizing D0 antibody showed loss of binding to only mutant 1 (9E10). One non-internalizing D0 antibody (1E2) lost binding only to mutant 2A3. One antibody (5H1) lost binding to mutant 6.

Natural ligand blocking and internalizing antibody 13H1 additionally showed decreased binding to mutant 2A2 and MD0/HLA1, in addition to mutants 1 and 2.

As to the antibodies that bound domain D2 of KIR3DL2 (both non-internalizing) antibodies 1C3 and 20E9 lost binding to mutant 14, as well as partial loss of binding to mutant 15 and mutant 16.

Antibodies 10F6, 2B12, 18C6 and 10G5 had loss of binding to mutant 2 having I60N and G62S substitutions and decrease in binding to mutant 2A3 having P14S, S15A and H23S substitutions, but did not lose binding to any other mutants. The principal epitope of these antibodies therefore includes residues I60 and/or G62 (and the epitope optionally further includes one or more of P14, S15, and H23). Residues 60 and 62 are within the D0 domain of KIR3DL2.

Antibody 13H1 had loss of binding to both mutant 1 having R13W, A25T and Q27R and to mutant 2 having I60N and G62S substitutions. 13H1 also had decreased binding to mutant 2A2 (Q56S, E57A) and mutant MD0/HLA1 (F9S, S11A). The epitope of 13H1 therefore includes residues F9, S11, Q56 and/or E57. These residues are within the D0 domain.

Antibody 9E10 had decreased binding to mutant 1 having R13W, A25T and Q27R substitutions, but not to any other mutants. The epitope of 9E10 and 10G5 therefore includes residues R13, A25 and/or Q27.

Figure 2:
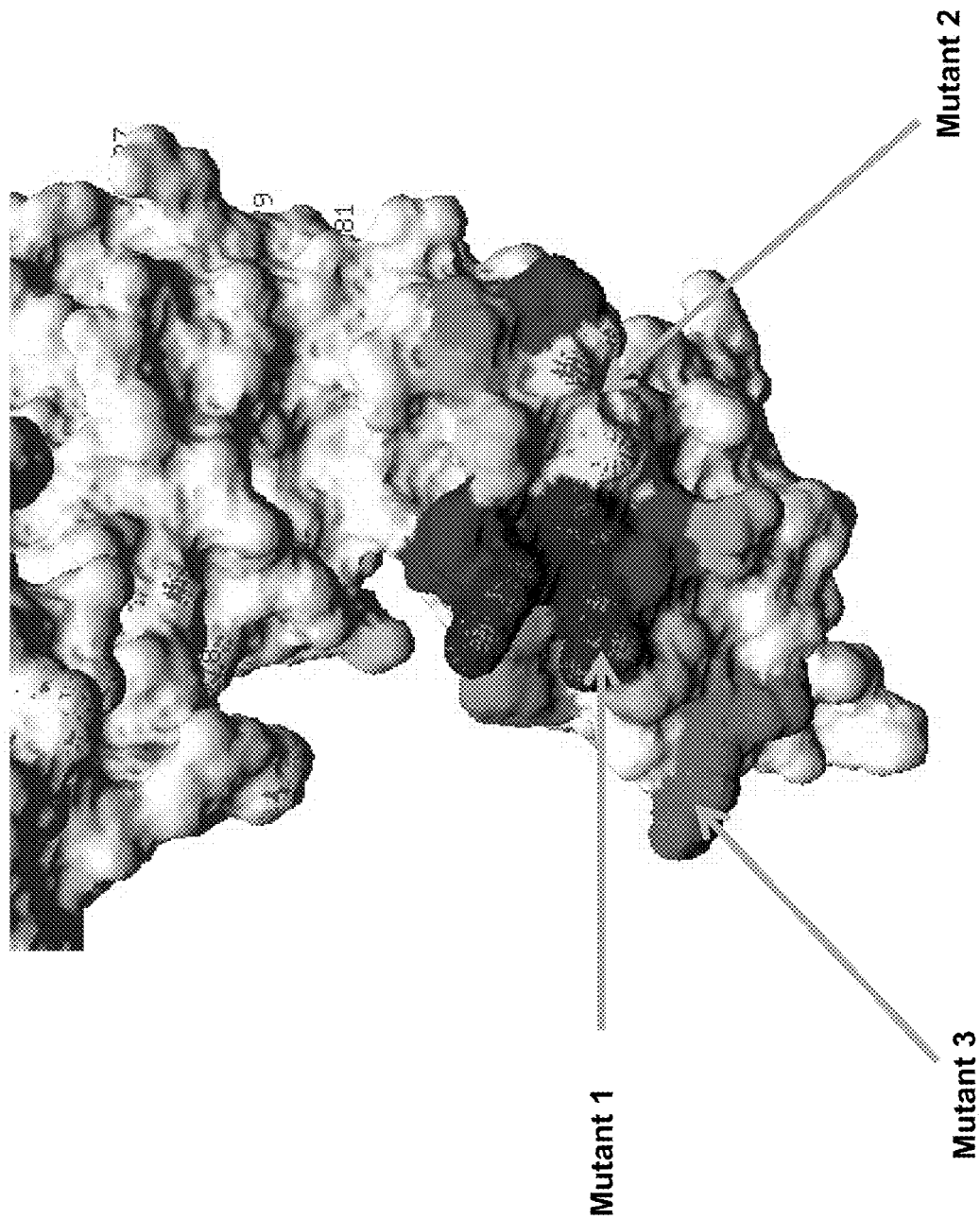
FIG. 2 shows a view of the KIR3DL2 polypeptide, including portions within the D0 domain, showing amino acid residues mutated indicated as "Mutant 1", "Mutant 2" and "Mutant 3", mutants 1, 2 and 6 resulting (in different combinations) in loss of binding by antibodies 10F6, 2B12, 18C6, 9E10, 10G5 and 13H1, with shading of residues adjacent to residues (F9, S11, P14, F34 and/or S140 adjacent to mutant 2, and G21, G22, H23, E57, S58, F59, P63 and/or H68 adjacent to mutant 1).

FIG. 1 shows a view of the KIR3DL2 polypeptide, including portions within the D0 domain, showing amino acid residues mutated indicated as "Mutant 1", "Mutant 2", "Mutant 3" and "Mutant 6" which resulted (in different combinations) in loss of binding by antibodies. FIG. 2 shows a view of the KIR3DL2 polypeptide, including portions within the D0 domain, showing amino acid residues mutated indicated as "Mutant 1", "Mutant 2" and "Mutant 3" which resulted (in different combinations) in loss of binding by antibodies, with shading of residues adjacent to residues (F9, S11, P14, F34 and/or S140 adjacent to mutant 2, and G21, G22, H23, E57, S58, F59, P63 and/or H68 adjacent to mutant 1).

Antibody 5H1 had loss of binding to mutant 6 having R78H and L82P substitutions, but did not lose binding to any other mutants. The principal epitope of 5H1 therefore includes residues R78 and/or L82. Residues R78 and L82 are within the D0 domain of KIR3DL2. Surface-exposed residues adjacent to these mutated residues can also contribute to the epitopes of the antibodies. FIG. 3 shows a view of each face of the KIR3DL2 polypeptide, including portions within the D0 domain, showing amino acid residues mutated indicated as "Mutant 6" which resulted (in different combinations) in loss of binding by antibodies, with "Mutant 3" that did not result in loss of binding shown. Also shown in shading are residues adjacent to residues adjacent to mutant 6 that may also be bound by the antibodies (K7, Y30, R31, P79, H80, S81, T83, G84, W85, S86 and/or A87).

Antibodies 1C3 and 20E9 had loss of binding to mutant 14 having a W226A substitution. The antibodies additionally had decreased binding to mutant 15 having I231M and R246P substitutions and to mutant 16 having an E239G substitution. The principal epitope of 1C3 therefore includes residues W226. The principal epitope of 20E9 may include residues I231M and/or R246P, and/or may additionally include E239. Residues W226, 1231 and R246 are in the region of the junction of the D1 and D2 domains of KIR3DL2. Surface-exposed residues adjacent to the mutated residues can also contribute to the epitopes of the antibodies, including for example residues Q201, K202, P203, S204, S224, S225, S227, S228, N252, R253 and/or T254 (reference to SEQ ID NO: 1) located at the surface of KIR3DL2 in the region of the W226 epitope but outside of the region of the KIR3DL2 mutations which did not result in loss of binding of the antibodies (e.g. mutants 12 and 17). Surface-exposed residues adjacent to the mutated residues I231 and R246 can also contribute to the epitopes of the antibodies, including for example residues D230, I231, R244, L245, R246, A247, V248, S275, R277 and/or P280 (reference to SEQ ID NO: 1) located at the surface of KIR3DL2 in the region of the I231/R246 epitope but outside of the region of the KIR3DL2 mutations which did not result in loss of binding of the antibodies (e.g. mutants 12 and 17).

FIG. 4 shows a view of the KIR3DL2 polypeptide, including portions within the D2 domain (D1/D2 junction), showing amino acid residues mutated indicated as "Mutant 14" to which antibodies lost binding, and "Mutant 12" and "Mutant 17" which did not cause loss of binding by antibodies; also shown in shading are residues adjacent to residues (Q201, K202, P203, S204, S224, S225, S227, S228, N252, R253 and/or T254 adjacent to mutant 14) that may also be bound.

FIG. 5 shows a view of the KIR3DL2 polypeptide, including portions within the D2 domain (D1/D2 junction), showing amino acid residues mutated indicated as "Mutant 15" to which antibodies lost binding; also shown in shading are residues adjacent to residues (D230, I231, R244, L245, R246, A247, V248, S275, R277 and/or P280) adjacent to mutant 14) that may also be bound.

FIGS. 18, 19 and 20 show views of the KIR3DL2 polypeptide, allele *001, with the binding site of mutant 2 shown, and showing amino acid differences seen in different KIR3DL2 alleles having highest frequency (studies of populations in the United States). It can be seen that the antibody binding site is at a site that is conserved across KIR3DL2 alleles, which is consistent with the ability of the antibody to bind cells from all individuals tested.

Table 7C

Domain 0 mutants

| | | KIR3DL2 D0 Antibodies | | | | | | | |
|---|---|---|---|---|---|---|---|---|---|
| Mutants | Mutations | 1E2 | 10F6 | 2B12 | 18C6 | 9E10 | 10G5 | 13H1 | 5H1 |
| M1 | R13W; A25T; Q27R | + | + | + | + | +/− | +/− | − | + |
| M2 | I60N; G62S | + | − | − | − | + | +/− | − | + |
| M3 | R32H; G33R | + | + | + | + | + | + | + | + |
| M4 | S45I; V47I | + | + | + | + | + | + | + | + |
| M5 | P66T | + | + | + | + | + | + | + | + |
| M6 | R78H; L82P | + | + | + | + | + | + | + | − |
| M1 + 2A1 | F50A; R53S | + | + | + | + | + | + | + | |
| M1 + 2A2 | Q56S; E57A | + | + | + | + | + | + | +/− | |
| M1 + 2A3 | P14S; S15A; H23S | − | +/− | +/− | − | + | +/− | + | |
| M1 + 2A5 | S140Q | + | + | + | + | + | + | + | |
| M1 + 2 | R13W; A25T; Q27R; I60N; G62S | + | − | − | − | + | +/− | − | |
| MD0/HLA1 | F9S; S11A | + | + | + | + | + | + | +/− | |
| MD0/HLA2 | H29S; F34A | + | + | + | + | + | + | | |

TABLE 7D

Domain 2 mutants

| | | KIR3DL2 D2 Antibodies | |
|---|---|---|---|
| Mutants | Mutations | 1C3 | 20E9 |
| M12 | I196A;L199A;N285A;S286A | + | + |
| M13 | T212A;N218A | + | + |
| M14 | W226A | − | − |
| M15 | I231M;R246P | +/− | +/− |
| M16 | E239G | +/− | +/− |
| M17 | P249A | + | + |
| M18 | A278H;L279A;C281A;V282A | + | + |
| M19 | A278H;L279S;V282E | + | + |
| M21 | C281Y;C315P | + | + |

All headings and sub-headings are used herein for convenience only and should not be construed as limiting the invention in any way. Any combination of the above-described elements in all possible variations thereof is encompassed by the invention unless otherwise indicated herein or otherwise clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e. g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as reference to an element or elements is intended to provide support for a similar aspect or embodiment of the invention that "consists of," "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

All publications and patent applications cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

We claim:

1. A monoclonal antibody that binds a KIR3DL2 polypeptide comprising SEQ ID NO: 1, wherein said antibody does not substantially bind to a KIR3DL1 polypeptide comprising SEQ ID NO: 169, and wherein said antibody is not internalized into KIR3DL2-expressing cells, wherein said antibody has (i) a heavy chain comprising CDRs 1, 2 and 3 (HCDR1, HCDR2, HCDR3), according to the Kabat definition, of the heavy chain variable region sequence of SEQ ID NO: 13, and (ii) a light chain comprising CDRs 1, 2 and 3 (LCDR1, LCDR2, LCDR3), according to the Kabat definition, of the light chain variable region sequence of SEQ ID NO: 14.

2. The antibody of claim 1, wherein said antibody comprises a human IgG heavy chain constant region.

3. The antibody of claim 1, wherein said antibody is a chimeric, human or humanized antibody.

4. The antibody of claim 1, wherein said antibody comprises a modified human heavy chain constant region with at least one amino acid substitution, wherein the binding affinity of said modified constant region to an FcγIIIA receptor is increased, compared to a constant region not having said amino acid substitution.

5. The antibody of claim 1, wherein the antibody causes an increase of the amount of KIR3DL2 polypeptides detectable at the cell surface of a KIR3DL2-expressing cell.

6. The antibody of claim 1, wherein said KIR3DL2-expressing cell is a CD4+ T cell lymphoma.

7. An antibody that competes for binding to a KIR3DL2 polypeptide with an antibody having respectively a VH and VL region of SEQ ID NOS: 13 and 14 (2B12), wherein the antibody that competes for binding to said KIR3DL2 polypeptide has (i) a heavy chain comprising CDRs 1, 2 and 3 (HCDR1, HCDR2, HCDR3), according to the Kabat definition, of the heavy chain variable region sequence of SEQ ID NO: 13, and (ii) a light chain comprising CDRs 1, 2 and 3 (LCDR1, LCDR2, LCDR3), according to the Kabat definition, of the light chain variable region sequence of SEQ ID NO: 14.

8. The antibody of claim 7, wherein the antibody causes an increase of the amount of KIR3DL2 polypeptides detectable at the cell surface of a KIR3DL2-expressing cell.

9. The antibody of claim 7, wherein said KIR3DL2-expressing cell is a CD4+ T cell lymphoma.

10. A pharmaceutical composition comprising the antibody of claim 1 and a pharmaceutically acceptable carrier.

* * * * *

UNITED STATES PATENT AND TRADEMARK OFFICE
CERTIFICATE OF CORRECTION

PATENT NO. : 10,577,419 B2
APPLICATION NO. : 14/662349
DATED : March 3, 2020
INVENTOR(S) : Laurent Gauthier et al.

It is certified that error appears in the above-identified patent and that said Letters Patent is hereby corrected as shown below:

In the Specification

Column 1,
Line 50, "MM that" should read --ITIM that--.
Line 52, "mM recruits" should read --ITIM recruits--.
Line 66, "IFN-7" should read --IFN-γ--.

Column 2,
Line 53, "(Aubum" should read --(Auburn--.

Column 18,
Line 38, ""KIR3DL"," should read --"KIR3DL1",--.

Column 40,
Lines 64-65, "GYTFITAGMQ" should read --GYTFTTAGMQ--.
Line 67, "GYTFFT" should read --GYTFTT--.

Column 44,
Line 16, "LINPYNGDTIT" should read --LINPYNGDTT--.

Column 50,
Lines 39-40, "Lys/Arg-Leu/IleNal/Phe/Thr/Ala-Thr/Ser/Ile/Ala)," should read
--Lys/Arg-Leu/Ile/Val/Phe/Thr/Ala-Thr/Ser/Ile/Ala),--.

Column 64,
Line 6, "TCRaI3" should read --TCRαβ--.
Line 66, "(Protopic)," should read --(Protopic®),--.

Signed and Sealed this
Twenty-fifth Day of August, 2020

Andrei Iancu
*Director of the United States Patent and Trademark Office*

CERTIFICATE OF CORRECTION (continued)
U.S. Pat. No. 10,577,419 B2

Column 65,
Line 6, "Zolinza)" should read --Zolinza®)--.
Line 7, "Istodax)," should read --Istodax®),--.
Line 11, "(Folotyn)." should read --(Folotyn®).--.
Line 15, "Revlimid)," should read --Revlimid®),--.
Line 17, "(Velcade)," should read --(Velcade®),--.
Line 37, "(Protopic)" should read --(Protopic®)--.

Column 72,
Lines 26-27, "5 plg" should read --5 µg--.

Column 76,
Line 58, "10 or g/ml" should read --10 or 20 µg/ml--.

Column 77,
Line 48, "300 Gg/mouse," should read --300 µg/mouse,--.
Line 54, "300 Gg/mouse," should read --300 µg/mouse,--.

Column 78,
Line 10, "CD3e" should read --CD3ε--.
Line 13, "KIR3DL2CD3e" should read --KIR3DL2CD3ε--.
Line 55, "KIR3DL2CD3e" should read --KIR3DL2CD3ε--.

Column 80,
Lines 35-36, "(5'-GCCACAGGTGCATATGAGAAACCTCTCTCTCAGCC-3')" should read
--(5'-GCCACAGGTGCATATGAGAAACCTTCTCTCTCAGCC-3')--.
Lines 36-38, "(5'-TGGGTCACTrGCGGCTGACCACACGCAGGGCAGGG-3')" should read
--(5'-TGGGTCACTTGCGGCTGACCACACGCAGGGCAGGG-3')--.
Lines 40-42, "(5'-ATGCAGGTGTCTGGGGATACCAGATITGGAGCTGGTrC-3')" should
read --(5'-ATGCAGGTGTCTGGGGATACCAGATTTGGAGCTTGGTTC-3')--.

Column 83,
Line 38, "5'-gga gGA agg aGc aga acc" should read --5'-gga gGA agg aGc aga acc--.

SEQUENCE LISTING

```
<160> NUMBER OF SEQ ID NOS: 192

<210> SEQ ID NO 1
<211> LENGTH: 434
<212> TYPE: PRT
<213> ORGANISM: homo sapiens

<400> SEQUENCE: 1

Leu Met Gly Gly Gln Asp Lys Pro Phe Leu Ser Ala Arg Pro Ser Thr
1               5                   10                  15

Val Val Pro Arg Gly Gly His Val Ala Leu Gln Cys His Tyr Arg Arg
                20                  25                  30

Gly Phe Asn Asn Phe Met Leu Tyr Lys Glu Asp Arg Ser His Val Pro
            35                  40                  45

Ile Phe His Gly Arg Ile Phe Gln Glu Ser Phe Ile Met Gly Pro Val
        50                  55                  60

Thr Pro Ala His Ala Gly Thr Tyr Arg Cys Arg Gly Ser Arg Pro His
65                  70                  75                  80

Ser Leu Thr Gly Trp Ser Ala Pro Ser Asn Pro Leu Val Ile Met Val
                85                  90                  95

Thr Gly Asn His Arg Lys Pro Ser Leu Leu Ala His Pro Gly Pro Leu
                100                 105                 110

Leu Lys Ser Gly Glu Thr Val Ile Leu Gln Cys Trp Ser Asp Val Met
            115                 120                 125

Phe Glu His Phe Phe Leu His Arg Glu Gly Ile Ser Glu Asp Pro Ser
        130                 135                 140

Arg Leu Val Gly Gln Ile His Asp Gly Val Ser Lys Ala Asn Phe Ser
145                 150                 155                 160

Ile Gly Pro Leu Met Pro Val Leu Ala Gly Thr Tyr Arg Cys Tyr Gly
                165                 170                 175

Ser Val Pro His Ser Pro Tyr Gln Leu Ser Ala Pro Ser Asp Pro Leu
                180                 185                 190
```

```
Asp Ile Val Ile Thr Gly Leu Tyr Glu Lys Pro Ser Leu Ser Ala Gln
            195                 200                 205

Pro Gly Pro Thr Val Gln Ala Gly Glu Asn Val Thr Leu Ser Cys Ser
210                 215                 220

Ser Trp Ser Ser Tyr Asp Ile Tyr His Leu Ser Arg Glu Gly Glu Ala
225                 230                 235                 240

His Glu Arg Arg Leu Arg Ala Val Pro Lys Val Asn Arg Thr Phe Gln
                245                 250                 255

Ala Asp Phe Pro Leu Gly Pro Ala Thr His Gly Gly Thr Tyr Arg Cys
                260                 265                 270

Phe Gly Ser Phe Arg Ala Leu Pro Cys Val Trp Ser Asn Ser Ser Asp
                275                 280                 285

Pro Leu Leu Val Ser Val Thr Gly Asn Pro Ser Ser Ser Trp Pro Ser
290                 295                 300

Pro Thr Glu Pro Ser Ser Lys Ser Gly Ile Cys Arg His Leu His Val
305                 310                 315                 320

Leu Ile Gly Thr Ser Val Val Ile Phe Leu Phe Ile Leu Leu Leu Phe
                325                 330                 335

Phe Leu Leu Tyr Arg Trp Cys Ser Asn Lys Lys Asn Ala Ala Val Met
                340                 345                 350

Asp Gln Glu Pro Ala Gly Asp Arg Thr Val Asn Arg Gln Asp Ser Asp
                355                 360                 365

Glu Gln Asp Pro Gln Glu Val Thr Tyr Ala Gln Leu Asp His Cys Val
                370                 375                 380

Phe Ile Gln Arg Lys Ile Ser Arg Pro Ser Gln Arg Pro Lys Thr Pro
385                 390                 395                 400

Leu Thr Asp Thr Ser Val Tyr Thr Glu Leu Pro Asn Ala Glu Pro Arg
                405                 410                 415

Ser Lys Val Val Ser Cys Pro Arg Ala Pro Gln Ser Gly Leu Glu Gly
                420                 425                 430

Val Phe

<210> SEQ ID NO 2
<211> LENGTH: 117
<212> TYPE: PRT
<213> ORGANISM: mus musculus

<400> SEQUENCE: 2

Gln Ile Gln Leu Val Gln Ser Gly Pro Glu Leu Lys Lys Pro Gly Glu
1               5                   10                  15

Thr Val Arg Ile Ser Cys Lys Ala Ser Gly Tyr Thr Phe Thr Ile Ala
                20                  25                  30

Gly Met Gln Trp Val Gln Lys Met Pro Gly Lys Gly Leu Lys Trp Ile
                35                  40                  45

Gly Trp Ile Asn Thr His Ser Gly Val Pro Lys Tyr Ala Glu Asp Phe
            50                  55                  60

Lys Gly Arg Phe Ala Phe Ser Leu Glu Thr Ser Ala Asn Ile Ala Tyr
65              70                  75                  80

Leu Gln Ile Ser Asn Leu Lys Asn Glu Asp Thr Ala Thr Tyr Phe Cys
                85                  90                  95

Ala Arg Gly Gly Asp Glu Gly Val Met Asp Tyr Trp Gly Gln Gly Thr
                100                 105                 110

Ser Val Thr Val Ser
            115
```

<210> SEQ ID NO 3
<211> LENGTH: 107
<212> TYPE: PRT
<213> ORGANISM: mus musculus

<400> SEQUENCE: 3

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr His Gln Lys Pro Gly Gln Ser Pro Lys Leu Leu Ile
        35                  40                  45

Tyr Trp Ala Ser Thr Arg His Thr Gly Val Pro Asp Arg Phe Ser Gly
50                  55                  60

Ser Gly Ser Gly Thr Asp Tyr Thr Leu Thr Ile Ser Ala Leu Gln Ala
65                  70                  75                  80

Glu Asp Leu Ala Leu Tyr Tyr Cys Gln Gln His Tyr Asn Thr Pro Trp
                85                  90                  95

Thr Phe Gly Gly Gly Thr Lys Leu Glu Ile Lys
            100                 105

<210> SEQ ID NO 4
<211> LENGTH: 5
<212> TYPE: PRT
<213> ORGANISM: Mus musculus

<400> SEQUENCE: 4

Ile Ala Gly Met Gln
1               5

<210> SEQ ID NO 5
<211> LENGTH: 6
<212> TYPE: PRT
<213> ORGANISM: Mus musculus

<400> SEQUENCE: 5

Gly Tyr Thr Phe Thr Ile
1               5

<210> SEQ ID NO 6
<211> LENGTH: 10
<212> TYPE: PRT
<213> ORGANISM: Mus musculus

<400> SEQUENCE: 6

Gly Tyr Thr Phe Thr Ile Ala Gly Met Gln
1               5                   10

<210> SEQ ID NO 7
<211> LENGTH: 17
<212> TYPE: PRT
<213> ORGANISM: Mus musculus

<400> SEQUENCE: 7

Trp Ile Asn Thr His Ser Gly Val Pro Lys Tyr Ala Glu Asp Phe Lys
1               5                   10                  15

Gly

<210> SEQ ID NO 8
<211> LENGTH: 10

```
<212> TYPE: PRT
<213> ORGANISM: Mus musculus

<400> SEQUENCE: 8

Trp Ile Asn Thr His Ser Gly Val Pro Lys
1               5                   10

<210> SEQ ID NO 9
<211> LENGTH: 9
<212> TYPE: PRT
<213> ORGANISM: Mus musculus

<400> SEQUENCE: 9

Gly Gly Asp Glu Gly Val Met Asp Tyr
1               5

<210> SEQ ID NO 10
<211> LENGTH: 11
<212> TYPE: PRT
<213> ORGANISM: Mus musculus

<400> SEQUENCE: 10

Lys Ala Ser Gln Asp Val Ser Thr Ala Val Ala
1               5                   10

<210> SEQ ID NO 11
<211> LENGTH: 7
<212> TYPE: PRT
<213> ORGANISM: Mus musculus

<400> SEQUENCE: 11

Trp Ala Ser Thr Arg His Thr
1               5

<210> SEQ ID NO 12
<211> LENGTH: 9
<212> TYPE: PRT
<213> ORGANISM: Mus musculus

<400> SEQUENCE: 12

Gln Gln His Tyr Asn Thr Pro Trp Thr
1               5

<210> SEQ ID NO 13
<211> LENGTH: 117
<212> TYPE: PRT
<213> ORGANISM: Mus musculus

<400> SEQUENCE: 13

Gln Ile Gln Leu Val Gln Ser Gly Pro Glu Leu Lys Lys Pro Gly Glu
1               5                   10                  15

Thr Val Arg Ile Ser Cys Lys Ala Ser Gly Tyr Thr Phe Thr Thr Ala
                20                  25                  30

Gly Met Gln Trp Val Gln Lys Thr Pro Gly Lys Gly Leu Lys Trp Ile
            35                  40                  45

Gly Trp Ile Asn Ser His Ser Gly Val Pro Lys Tyr Ala Glu Asp Phe
        50                  55                  60

Lys Gly Arg Phe Ala Phe Ser Leu Glu Thr Ser Ala Ser Thr Ala Tyr
65                  70                  75                  80

Leu Gln Ile Ser Thr Leu Lys Asn Glu Asp Thr Ala Thr Tyr Phe Cys
                85                  90                  95

Ala Arg Gly Gly Asp Glu Gly Val Met Asp Tyr Trp Gly Gln Gly Thr
```

Ser Val Thr Val Ser
        115

<210> SEQ ID NO 14
<211> LENGTH: 107
<212> TYPE: PRT
<213> ORGANISM: Mus musculus

<400> SEQUENCE: 14

Asp Ile Val Met Thr Gln Ser His Lys Phe Met Ser Thr Ser Leu Gly
1               5                   10                  15

Asp Arg Val Ser Phe Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Thr Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 15
<211> LENGTH: 5
<212> TYPE: PRT
<213> ORGANISM: Mus musculus

<400> SEQUENCE: 15

Thr Ala Gly Met Gln
1               5

<210> SEQ ID NO 16
<211> LENGTH: 6
<212> TYPE: PRT
<213> ORGANISM: Mus musculus

<400> SEQUENCE: 16

Gly Tyr Thr Phe Thr Thr
1               5

<210> SEQ ID NO 17
<211> LENGTH: 10
<212> TYPE: PRT
<213> ORGANISM: Mus musculus

<400> SEQUENCE: 17

Gly Tyr Thr Phe Thr Thr Ala Gly Met Gln
1               5                   10

<210> SEQ ID NO 18
<211> LENGTH: 16
<212> TYPE: PRT
<213> ORGANISM: Mus musculus

<400> SEQUENCE: 18

Trp Ile Asn Ser His Ser Gly Val Pro Lys Tyr Ala Glu Asp Phe Lys
1               5                   10                  15

```
<210> SEQ ID NO 19
<211> LENGTH: 9
<212> TYPE: PRT
<213> ORGANISM: Mus musculus

<400> SEQUENCE: 19

Trp Ile Asn Ser His Ser Gly Val Pro
1               5

<210> SEQ ID NO 20
<211> LENGTH: 10
<212> TYPE: PRT
<213> ORGANISM: Mus musculus

<400> SEQUENCE: 20

Gly Gly Asp Glu Gly Val Met Asp Tyr Trp
1               5                   10

<210> SEQ ID NO 21
<211> LENGTH: 7
<212> TYPE: PRT
<213> ORGANISM: Mus musculus

<400> SEQUENCE: 21

Trp Thr Ser Thr Arg His Thr
1               5

<210> SEQ ID NO 22
<211> LENGTH: 9
<212> TYPE: PRT
<213> ORGANISM: Mus musculus

<400> SEQUENCE: 22

Gln Gln His Tyr Ser Thr Pro Trp Thr
1               5

<210> SEQ ID NO 23
<211> LENGTH: 139
<212> TYPE: PRT
<213> ORGANISM: Mus musculus

<400> SEQUENCE: 23

Gln Val Gln Leu Gln Gln Ser Ala Ala Glu Leu Ala Arg Pro Gly Ala
1               5                   10                  15

Ser Val Lys Met Ser Cys Lys Ala Ser Gly Tyr Thr Phe Thr Ser Tyr
                20                  25                  30

Thr Met His Trp Val Lys Gln Arg Pro Gly Gln Gly Leu Glu Trp Ile
            35                  40                  45

Gly Tyr Ile Asn Pro Ser Ser Gly Tyr Thr Glu Asn Asn Arg Lys Phe
        50                  55                  60

Lys Asp Lys Thr Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Leu Gly Lys Gly Leu Leu Pro Pro Phe Asp Tyr Trp Gly Gln
            100                 105                 110

Gly Thr Thr Leu Thr Val Ser Ser Ala Lys Thr Thr Pro Pro Ser Val
        115                 120                 125

Tyr Pro Leu Ala Pro Gly Ser Ala Ala Gln Thr
    130                 135
```

<210> SEQ ID NO 24
<211> LENGTH: 107
<212> TYPE: PRT
<213> ORGANISM: Mus musculus

<400> SEQUENCE: 24

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Tyr
                85                  90                  95

Thr Phe Gly Gly Gly Thr Lys Leu Glu Ile Lys
            100                 105
```

<210> SEQ ID NO 25
<211> LENGTH: 5
<212> TYPE: PRT
<213> ORGANISM: Mus musculus

<400> SEQUENCE: 25

```
Ser Tyr Thr Met His
1               5
```

<210> SEQ ID NO 26
<211> LENGTH: 6
<212> TYPE: PRT
<213> ORGANISM: Mus musculus

<400> SEQUENCE: 26

```
Gly Tyr Thr Phe Thr Ser
1               5
```

<210> SEQ ID NO 27
<211> LENGTH: 10
<212> TYPE: PRT
<213> ORGANISM: Mus musculus

<400> SEQUENCE: 27

```
Gly Tyr Thr Phe Thr Ser Tyr Thr Met His
1               5                   10
```

<210> SEQ ID NO 28
<211> LENGTH: 15
<212> TYPE: PRT
<213> ORGANISM: Mus musculus

<400> SEQUENCE: 28

```
Tyr Ile Asn Pro Ser Ser Gly Tyr Thr Glu Asn Asn Arg Lys Phe
1               5                   10                  15
```

<210> SEQ ID NO 29
<211> LENGTH: 8
<212> TYPE: PRT
<213> ORGANISM: Mus musculus

<400> SEQUENCE: 29

```
Tyr Ile Asn Pro Ser Ser Gly Tyr
1               5
```

<210> SEQ ID NO 30
<211> LENGTH: 12
<212> TYPE: PRT
<213> ORGANISM: Mus musculus

<400> SEQUENCE: 30

```
Arg Leu Gly Lys Gly Leu Leu Pro Pro Phe Asp Tyr
1               5                   10
```

<210> SEQ ID NO 31
<211> LENGTH: 11
<212> TYPE: PRT
<213> ORGANISM: Mus musculus

<400> SEQUENCE: 31

```
Arg Ala Ser Glu Asn Ile Tyr Ser Asn Leu Ala
1               5                   10
```

<210> SEQ ID NO 32
<211> LENGTH: 7
<212> TYPE: PRT
<213> ORGANISM: Mus musculus

<400> SEQUENCE: 32

```
Ala Ala Thr Asn Leu Ala Asp
1               5
```

<210> SEQ ID NO 33
<211> LENGTH: 9
<212> TYPE: PRT
<213> ORGANISM: Mus musculus

<400> SEQUENCE: 33

```
Gln His Phe Trp Gly Thr Pro Tyr Thr
1               5
```

<210> SEQ ID NO 34
<211> LENGTH: 119
<212> TYPE: PRT
<213> ORGANISM: Mus musculus

<400> SEQUENCE: 34

```
Glu Val Gln Leu Gln Gln Ser Gly Pro Glu Leu Val Lys Pro Gly Ala
1               5                   10                  15

Ser Met Lys Ile Ser Cys Lys Ala Ser His Tyr Ser Phe Ile Gly Tyr
            20                  25                  30

Thr Met Asn Trp Val Lys Gln Arg His Gly Lys Asn Leu Glu Trp Ile
        35                  40                  45

Gly Leu Ile Asn Pro Tyr Asn Gly Asp Thr Thr Tyr Asn Gln Lys Phe
    50                  55                  60

Lys Gly Lys Ala Ser Leu Thr Val Asp Lys Ser Ser Ser Thr Ala Tyr
65                  70                  75                  80

Met Glu Ile Leu Ser Leu Thr Ser Glu Asp Ser Ala Val Tyr Tyr Cys
                85                  90                  95

Ala Arg Glu Asn Trp Gly Tyr Pro Tyr Ala Met Asp Tyr Trp Gly Gln
            100                 105                 110

Gly Thr Ser Val Thr Val Ser
            115
```

<210> SEQ ID NO 35
<211> LENGTH: 111
<212> TYPE: PRT
<213> ORGANISM: mus musculus

<400> SEQUENCE: 35

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Phe
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Arg Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Tyr Thr Phe Gly Gly Gly Thr Lys Leu Glu Ile Lys
            100                 105                 110

<210> SEQ ID NO 36
<211> LENGTH: 5
<212> TYPE: PRT
<213> ORGANISM: Mus musculus

<400> SEQUENCE: 36

Gly Tyr Thr Met Asn
1               5

<210> SEQ ID NO 37
<211> LENGTH: 6
<212> TYPE: PRT
<213> ORGANISM: mus musculus

<400> SEQUENCE: 37

His Tyr Ser Phe Ile Gly
1               5

<210> SEQ ID NO 38
<211> LENGTH: 10
<212> TYPE: PRT
<213> ORGANISM: mus musculus

<400> SEQUENCE: 38

His Tyr Ser Phe Ile Gly Tyr Thr Met Asn
1               5                   10

<210> SEQ ID NO 39
<211> LENGTH: 17
<212> TYPE: PRT
<213> ORGANISM: mus musculus

<400> SEQUENCE: 39

Leu Ile Asn Pro Tyr Asn Gly Asp Thr Thr Tyr Asn Gln Lys Phe Lys
1               5                   10                  15

Gly

<210> SEQ ID NO 40
<211> LENGTH: 10

```
<212> TYPE: PRT
<213> ORGANISM: mus musculus

<400> SEQUENCE: 40

Leu Ile Asn Pro Tyr Asn Gly Asp Thr Thr
1               5                   10

<210> SEQ ID NO 41
<211> LENGTH: 11
<212> TYPE: PRT
<213> ORGANISM: mus musculus

<400> SEQUENCE: 41

Glu Asn Trp Gly Tyr Pro Tyr Ala Met Asp Tyr
1               5                   10

<210> SEQ ID NO 42
<211> LENGTH: 15
<212> TYPE: PRT
<213> ORGANISM: mus musculus

<400> SEQUENCE: 42

Arg Ala Ser Glu Ser Val Asp Asn Phe Gly Ile Ser Phe Met Asn
1               5                   10                  15

<210> SEQ ID NO 43
<211> LENGTH: 7
<212> TYPE: PRT
<213> ORGANISM: mus musculus

<400> SEQUENCE: 43

Ala Ala Ser Asn Gln Gly Ser
1               5

<210> SEQ ID NO 44
<211> LENGTH: 9
<212> TYPE: PRT
<213> ORGANISM: mus musculus

<400> SEQUENCE: 44

Gln Gln Ser Lys Glu Val Pro Tyr Thr
1               5

<210> SEQ ID NO 45
<211> LENGTH: 117
<212> TYPE: PRT
<213> ORGANISM: Mus musculus

<400> SEQUENCE: 45

Gln Val Gln Leu Gln Gln Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met Asn Trp Val Lys Gln Ser His Ala Lys Ser Leu Glu Trp Ile
        35                  40                  45

Gly Val Ile Ser Thr Tyr Tyr Gly Asp Ala Asn Tyr Asn Gln Lys Phe
    50                  55                  60

Lys Gly Lys Ala Thr Met Thr Val Asp Lys Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Leu Ile Tyr Tyr Asp Tyr Asp Gly Ser Tyr Trp Gly Gln Gly Thr
```

```
                    100                 105                 110
Thr Leu Thr Val Ser
        115

<210> SEQ ID NO 46
<211> LENGTH: 113
<212> TYPE: PRT
<213> ORGANISM: Mus musculus

<400> SEQUENCE: 46

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Tyr Thr Phe Gly Gly Gly Thr Lys Leu Glu Ile
            100                 105                 110

Lys

<210> SEQ ID NO 47
<211> LENGTH: 5
<212> TYPE: PRT
<213> ORGANISM: Mus musculus

<400> SEQUENCE: 47

Asp Tyr Ala Met Asn
1               5

<210> SEQ ID NO 48
<211> LENGTH: 6
<212> TYPE: PRT
<213> ORGANISM: Mus musculus

<400> SEQUENCE: 48

Gly Tyr Thr Phe Thr Asp
1               5

<210> SEQ ID NO 49
<211> LENGTH: 10
<212> TYPE: PRT
<213> ORGANISM: Mus musculus

<400> SEQUENCE: 49

Gly Tyr Thr Phe Thr Asp Tyr Ala Met Asn
1               5                   10

<210> SEQ ID NO 50
<211> LENGTH: 17
<212> TYPE: PRT
<213> ORGANISM: Mus musculus

<400> SEQUENCE: 50

Val Ile Ser Thr Tyr Tyr Gly Asp Ala Asn Tyr Asn Gln Lys Phe Lys
1               5                   10                  15
```

Gly

<210> SEQ ID NO 51
<211> LENGTH: 10
<212> TYPE: PRT
<213> ORGANISM: Mus musculus

<400> SEQUENCE: 51

Val Ile Ser Thr Tyr Tyr Gly Asp Ala Asn
1               5                   10

<210> SEQ ID NO 52
<211> LENGTH: 9
<212> TYPE: PRT
<213> ORGANISM: Mus musculus

<400> SEQUENCE: 52

Ile Tyr Tyr Asp Tyr Asp Gly Ser Tyr
1               5

<210> SEQ ID NO 53
<211> LENGTH: 16
<212> TYPE: PRT
<213> ORGANISM: Mus musculus

<400> SEQUENCE: 53

Arg Ser Ser Gln Ser Leu Val His Ser Asn Gly Asn Thr Tyr Leu His
1               5                   10                  15

<210> SEQ ID NO 54
<211> LENGTH: 7
<212> TYPE: PRT
<213> ORGANISM: Mus musculus

<400> SEQUENCE: 54

Lys Val Ser Asn Arg Phe Ser
1               5

<210> SEQ ID NO 55
<211> LENGTH: 10
<212> TYPE: PRT
<213> ORGANISM: Mus musculus

<400> SEQUENCE: 55

Ser Gln Ser Thr His Val Pro Pro Tyr Thr
1               5                   10

<210> SEQ ID NO 56
<211> LENGTH: 120
<212> TYPE: PRT
<213> ORGANISM: Mus musculus

<400> SEQUENCE: 56

Gln Val Gln Leu Gln Gln Ser Ala Ala Glu Leu Ala Arg Pro Gly Ala
1               5                   10                  15

Ser Val Lys Met Ser Cys Lys Ala Ser Gly Tyr Thr Phe Thr Ser Tyr
                20                  25                  30

Thr Met His Trp Val Lys Gln Arg Pro Gly Gln Gly Leu Glu Trp Ile
            35                  40                  45

Gly Tyr Ile Asn Pro Ser Ser Gly Tyr Thr Asp Tyr Asn Gln Lys Phe
        50                  55                  60

Lys Asp Lys Thr Thr Leu Thr Ala Asp Arg Ser Ser Ser Thr Ala Tyr

```
                65                  70                  75                  80
Met Gln Leu Ser Ser Leu Thr Ser Glu Asp Ser Ala Val Tyr Tyr Cys
                    85                  90                  95

Ala Arg Leu Gly Lys Gly Leu Leu Pro Pro Phe Asp Tyr Trp Gly Gln
                100                 105                 110

Gly Ser Thr Leu Thr Val Ser Ser
                115                 120

<210> SEQ ID NO 57
<211> LENGTH: 113
<212> TYPE: PRT
<213> ORGANISM: Mus musculus

<400> SEQUENCE: 57

Glu Ile Val Leu Thr Gln Ser Ile Pro Ser Leu Thr Val Ser Ala Gly
1               5                   10                  15

Glu Arg Val Thr Ile Ser Cys Lys Ser Asn Gln Asn Leu Leu Trp Ser
                20                  25                  30

Gly Asn Gln Arg Tyr Cys Leu Val Trp His Gln Trp Lys Pro Gly Gln
            35                  40                  45

Thr Pro Thr Pro Leu Ile Thr Trp Thr Ser Asp Arg Tyr Ser Gly Val
        50                  55                  60

Pro Asp Arg Phe Ile Gly Ser Gly Ser Val Thr Asp Phe Thr Leu Thr
65                  70                  75                  80

Ile Ser Ser Val Gln Ala Glu Asp Val Ala Val Tyr Phe Cys Gln Gln
                85                  90                  95

His Leu His Ile Pro Tyr Thr Phe Gly Gly Thr Lys Leu Glu Ile
                100                 105                 110

Lys

<210> SEQ ID NO 58
<211> LENGTH: 5
<212> TYPE: PRT
<213> ORGANISM: Mus musculus

<400> SEQUENCE: 58

Ser Tyr Thr Met His
1               5

<210> SEQ ID NO 59
<211> LENGTH: 6
<212> TYPE: PRT
<213> ORGANISM: Mus musculus

<400> SEQUENCE: 59

Gly Tyr Thr Phe Thr Ser
1               5

<210> SEQ ID NO 60
<211> LENGTH: 10
<212> TYPE: PRT
<213> ORGANISM: Mus musculus

<400> SEQUENCE: 60

Gly Tyr Thr Phe Thr Ser Tyr Thr Met His
1               5                   10

<210> SEQ ID NO 61
<211> LENGTH: 17
<212> TYPE: PRT
```

```
<213> ORGANISM: Mus musculus

<400> SEQUENCE: 61

Tyr Ile Asn Pro Ser Ser Gly Tyr Thr Asp Tyr Asn Gln Lys Phe Lys
1               5                   10                  15

Asp

<210> SEQ ID NO 62
<211> LENGTH: 10
<212> TYPE: PRT
<213> ORGANISM: Mus musculus

<400> SEQUENCE: 62

Tyr Ile Asn Pro Ser Ser Gly Tyr Thr Asp
1               5                   10

<210> SEQ ID NO 63
<211> LENGTH: 11
<212> TYPE: PRT
<213> ORGANISM: Mus musculus

<400> SEQUENCE: 63

Leu Gly Lys Gly Leu Leu Pro Pro Phe Asp Tyr
1               5                   10

<210> SEQ ID NO 64
<211> LENGTH: 17
<212> TYPE: PRT
<213> ORGANISM: Mus musculus

<400> SEQUENCE: 64

Lys Ser Asn Gln Asn Leu Leu Trp Ser Gly Asn Gln Arg Tyr Cys Leu
1               5                   10                  15

Val

<210> SEQ ID NO 65
<211> LENGTH: 7
<212> TYPE: PRT
<213> ORGANISM: Mus musculus

<400> SEQUENCE: 65

Trp Thr Ser Asp Arg Tyr Ser
1               5

<210> SEQ ID NO 66
<211> LENGTH: 9
<212> TYPE: PRT
<213> ORGANISM: Mus musculus

<400> SEQUENCE: 66

Gln Gln His Leu His Ile Pro Tyr Thr
1               5

<210> SEQ ID NO 67
<211> LENGTH: 107
<212> TYPE: PRT
<213> ORGANISM: Mus musculus

<400> SEQUENCE: 67

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
                20                  25                  30
```

-continued

```
Leu Ala Trp Tyr Gln Gln Lys Gln Gly Lys Ser Pro Gln Leu Leu Val
        35                  40                  45
Tyr Ala Ala Thr Asn Leu Ala Asp Gly Val Pro Ser Arg Phe Ser Gly
    50                  55                  60
Ser Gly Ser Gly Thr Gln Tyr Ser Leu Lys Ile Asn Ser Leu Gln Ser
65                  70                  75                  80
Glu Asp Phe Gly Ser Tyr Tyr Cys Gln His Phe Trp Gly Thr Pro Tyr
                85                  90                  95
Thr Phe Gly Gly Gly Thr Lys Leu Glu Ile Lys
            100                 105

<210> SEQ ID NO 68
<211> LENGTH: 117
<212> TYPE: PRT
<213> ORGANISM: homo sapiens

<400> SEQUENCE: 68

Pro Leu Met Gly Gly Gln Asp Lys Pro Phe Leu Ser Ala Arg Pro Ser
1               5                   10                  15
Thr Val Val Pro Arg Gly Gly His Val Ala Leu Gln Cys His Tyr Arg
            20                  25                  30
Arg Gly Phe Asn Asn Phe Met Leu Tyr Lys Glu Asp Arg Ser His Val
        35                  40                  45
Pro Ile Phe His Gly Arg Ile Phe Gln Glu Ser Phe Ile Met Gly Pro
    50                  55                  60
Val Thr Pro Ala His Ala Gly Thr Tyr Arg Cys Arg Gly Ser Arg Pro
65                  70                  75                  80
His Ser Leu Thr Gly Trp Ser Ala Pro Ser Asn Pro Leu Val Ile Met
                85                  90                  95
Val Thr Gly Asn His Arg Lys Pro Ser Leu Leu Ala His Pro Gly Pro
            100                 105                 110
Leu Leu Lys Ser Gly
        115

<210> SEQ ID NO 69
<211> LENGTH: 100
<212> TYPE: PRT
<213> ORGANISM: homo sapiens

<400> SEQUENCE: 69

Thr Val Ile Leu Gln Cys Trp Ser Asp Val Met Phe Glu His Phe Phe
1               5                   10                  15
Leu His Arg Glu Gly Ile Ser Glu Asp Pro Ser Arg Leu Val Gly Gln
            20                  25                  30
Ile His Asp Gly Val Ser Lys Ala Asn Phe Ser Ile Gly Pro Leu Met
        35                  40                  45
Pro Val Leu Ala Gly Thr Tyr Arg Cys Tyr Gly Ser Val Pro His Ser
    50                  55                  60
Pro Tyr Gln Leu Ser Ala Pro Ser Asp Pro Leu Asp Ile Val Ile Thr
65                  70                  75                  80
Gly Leu Tyr Glu Lys Pro Ser Leu Ser Ala Gln Pro Gly Pro Thr Val
                85                  90                  95
Gln Ala Gly Glu
            100

<210> SEQ ID NO 70
```

```
<211> LENGTH: 102
<212> TYPE: PRT
<213> ORGANISM: Homo sapiens

<400> SEQUENCE: 70

Asn Val Thr Leu Ser Cys Ser Ser Trp Ser Ser Tyr Asp Ile Tyr His
1               5                   10                  15

Leu Ser Arg Glu Gly Glu Ala His Glu Arg Arg Leu Arg Ala Val Pro
            20                  25                  30

Lys Val Asn Arg Thr Phe Gln Ala Asp Phe Pro Leu Gly Pro Ala Thr
        35                  40                  45

His Gly Gly Thr Tyr Arg Cys Phe Gly Ser Phe Arg Ala Leu Pro Cys
50                  55                  60

Val Trp Ser Asn Ser Ser Asp Pro Leu Leu Val Ser Val Thr Gly Asn
65                  70                  75                  80

Pro Ser Ser Ser Trp Pro Ser Pro Thr Glu Pro Ser Ser Lys Ser Gly
                85                  90                  95

Ile Cys Arg His Leu His
            100

<210> SEQ ID NO 71
<211> LENGTH: 72
<212> TYPE: DNA
<213> ORGANISM: Homo sapiens

<400> SEQUENCE: 71
aagctagcgg taagcctatc cctaaccctc tcctcggtct cgattctacg ctcatgggtg      60
gtcaggacaa ac                                                         72

<210> SEQ ID NO 72
<211> LENGTH: 29
<212> TYPE: DNA
<213> ORGANISM: Homo sapiens

<400> SEQUENCE: 72
tgggacgact ttagtcctct ccctaggaa                                       29

<210> SEQ ID NO 73
<211> LENGTH: 71
<212> TYPE: DNA
<213> ORGANISM: Homo sapiens

<400> SEQUENCE: 73
aagctagcgg taagcctatc cctaaccctc tcctcggtct cgattctacg acagtcatcc      60
tgcaatgttg g                                                          71

<210> SEQ ID NO 74
<211> LENGTH: 29
<212> TYPE: DNA
<213> ORGANISM: Homo sapiens

<400> SEQUENCE: 74
gggtgccaag tccgtcctct ccctaggaa                                       29

<210> SEQ ID NO 75
<211> LENGTH: 71
<212> TYPE: DNA
<213> ORGANISM: Homo sapiens

<400> SEQUENCE: 75
```

```
aagctagcgg taagcctatc cctaaccctc tcctcggtct cgattctacg aacgtgacct    60
tgtcctgtag c                                                        71
```

<210> SEQ ID NO 76
<211> LENGTH: 29
<212> TYPE: DNA
<213> ORGANISM: Homo sapiens

<400> SEQUENCE: 76

```
ccatagacgt ctgtggacgt acctaggaa                                     29
```

<210> SEQ ID NO 77
<211> LENGTH: 90
<212> TYPE: DNA
<213> ORGANISM: Homo sapiens

<400> SEQUENCE: 77

```
actaatgcca ccaccaaggc ggctggtggt gccctgcagt caacagccag tctcttcgtg    60
gtctcactct ctcttctgca tctctactct                                    90
```

<210> SEQ ID NO 78
<211> LENGTH: 30
<212> TYPE: PRT
<213> ORGANISM: Homo sapiens

<400> SEQUENCE: 78

Thr Asn Ala Thr Thr Lys Ala Ala Gly Gly Ala Leu Gln Ser Thr Ala
1               5                   10                  15

Ser Leu Phe Val Val Ser Leu Ser Leu Leu His Leu Tyr Ser
            20                  25                  30

<210> SEQ ID NO 79
<211> LENGTH: 40
<212> TYPE: DNA
<213> ORGANISM: Homo sapiens

<400> SEQUENCE: 79

```
acccaagctg gctagcatgt cgctcacggt cgtcagcatg                         40
```

<210> SEQ ID NO 80
<211> LENGTH: 38
<212> TYPE: DNA
<213> ORGANISM: Homo sapiens

<400> SEQUENCE: 80

```
agcacagtgg cggccgccta gaaaaccccc tcaagacc                           38
```

<210> SEQ ID NO 81
<211> LENGTH: 36
<212> TYPE: DNA
<213> ORGANISM: Homo sapiens

<400> SEQUENCE: 81

```
gccacaggtg catatgagaa accttctctc tcagcc                             36
```

<210> SEQ ID NO 82
<211> LENGTH: 35
<212> TYPE: DNA
<213> ORGANISM: Homo sapiens

<400> SEQUENCE: 82

```
tgggtcactt gcggctgacc acacgcaggg caggg                              35
```

<210> SEQ ID NO 83
<211> LENGTH: 36
<212> TYPE: DNA
<213> ORGANISM: Homo sapiens

<400> SEQUENCE: 83
cgtgccctgc cctacgtgtg gtcaaactca agtgac                       36

<210> SEQ ID NO 84
<211> LENGTH: 39
<212> TYPE: DNA
<213> ORGANISM: Homo sapiens

<400> SEQUENCE: 84
atgcaggtgt ctggggatac cagatttgga gcttggttc                    39

<210> SEQ ID NO 85
<211> LENGTH: 51
<212> TYPE: DNA
<213> ORGANISM: Homo sapiens

<400> SEQUENCE: 85
ccgaagagtc acgtgtcctc ctcgaggcac cacagtgctg ggccaggcag a      51

<210> SEQ ID NO 86
<211> LENGTH: 33
<212> TYPE: DNA
<213> ORGANISM: Homo sapiens

<400> SEQUENCE: 86
cacgtgactc ttcggtgtca ctatcgtcgt ggg                          33

<210> SEQ ID NO 87
<211> LENGTH: 35
<212> TYPE: DNA
<213> ORGANISM: Homo sapiens

<400> SEQUENCE: 87
cacagggctc atgttgaagc tctcctggaa tattc                        35

<210> SEQ ID NO 88
<211> LENGTH: 28
<212> TYPE: DNA
<213> ORGANISM: Homo sapiens

<400> SEQUENCE: 88
aacatgagcc ctgtgacccc agcacatg                                28

<210> SEQ ID NO 89
<211> LENGTH: 35
<212> TYPE: DNA
<213> ORGANISM: Homo sapiens

<400> SEQUENCE: 89
attgttaaac ctatgacgat agtgacactg aagag                        35

<210> SEQ ID NO 90
<211> LENGTH: 27
<212> TYPE: DNA
<213> ORGANISM: Homo sapiens

<400> SEQUENCE: 90
cataggttta acaatttcat gctgtac                                               27

<210> SEQ ID NO 91
<211> LENGTH: 37
<212> TYPE: DNA
<213> ORGANISM: Homo sapiens

<400> SEQUENCE: 91
gatgggaatg tggattctgt cttctttgta cagcatg                                    37

<210> SEQ ID NO 92
<211> LENGTH: 33
<212> TYPE: DNA
<213> ORGANISM: Homo sapiens

<400> SEQUENCE: 92
atccacattc ccatcttcca cggcagaata ttc                                        33

<210> SEQ ID NO 93
<211> LENGTH: 31
<212> TYPE: DNA
<213> ORGANISM: Homo sapiens

<400> SEQUENCE: 93
atgtgctgtg gtcacagggc ccatgatgaa g                                          31

<210> SEQ ID NO 94
<211> LENGTH: 29
<212> TYPE: DNA
<213> ORGANISM: Homo sapiens

<400> SEQUENCE: 94
gtgaccacag cacatgcagg gacctacag                                             29

<210> SEQ ID NO 95
<211> LENGTH: 34
<212> TYPE: DNA
<213> ORGANISM: Homo sapiens

<400> SEQUENCE: 95
gggggagtgt gggtgtgaac cccgacatct gtag                                       34

<210> SEQ ID NO 96
<211> LENGTH: 31
<212> TYPE: DNA
<213> ORGANISM: Homo sapiens

<400> SEQUENCE: 96
cacccacact cccccactgg gtggtcggca c                                          31

<210> SEQ ID NO 97
<211> LENGTH: 36
<212> TYPE: DNA
<213> ORGANISM: Homo sapiens

<400> SEQUENCE: 97
ttgcaggatg actctctctc ctgatttcac cagggg                                     36

<210> SEQ ID NO 98
<211> LENGTH: 30
<212> TYPE: DNA
<213> ORGANISM: Homo sapiens

<400> SEQUENCE: 98
agagtcatcc tgcaatgttg gtcagatgtc                                              30

<210> SEQ ID NO 99
<211> LENGTH: 36
<212> TYPE: DNA
<213> ORGANISM: Homo sapiens

<400> SEQUENCE: 99
ctcaaacatg atatctgacc aacattgcag gatgac                                        36

<210> SEQ ID NO 100
<211> LENGTH: 30
<212> TYPE: DNA
<213> ORGANISM: Homo sapiens

<400> SEQUENCE: 100
gatatcatgt ttgagcactt ctttctgcac                                              30

<210> SEQ ID NO 101
<211> LENGTH: 40
<212> TYPE: DNA
<213> ORGANISM: Homo sapiens

<400> SEQUENCE: 101
aagggcaagc atcatgggac cgatggagaa gttggccttg                                    40

<210> SEQ ID NO 102
<211> LENGTH: 38
<212> TYPE: DNA
<213> ORGANISM: Homo sapiens

<400> SEQUENCE: 102
atgatgcttg cccttgcagg aacctacaga tgttatgg                                      38

<210> SEQ ID NO 103
<211> LENGTH: 40
<212> TYPE: DNA
<213> ORGANISM: Homo sapiens

<400> SEQUENCE: 103
tagagatccc atctttgtgc agaaagaagt gctcaaacat                                    40

<210> SEQ ID NO 104
<211> LENGTH: 37
<212> TYPE: DNA
<213> ORGANISM: Homo sapiens

<400> SEQUENCE: 104
aagatgggat ctctaaggac ccctcacgcc tcgttgg                                       37

<210> SEQ ID NO 105
<211> LENGTH: 35
<212> TYPE: DNA
<213> ORGANISM: Homo sapiens

<400> SEQUENCE: 105
gggggtgtga gtaacagaac cataacatct gtagg                                         35

<210> SEQ ID NO 106
<211> LENGTH: 31
<212> TYPE: DNA
<213> ORGANISM: Homo sapiens

```
<400> SEQUENCE: 106
gttactcaca ccccctatca gttgtcagct c                                    31

<210> SEQ ID NO 107
<211> LENGTH: 38
<212> TYPE: DNA
<213> ORGANISM: Homo sapiens

<400> SEQUENCE: 107
atatgcacct gtggccacga tgtccagggg gtcactgg                             38

<210> SEQ ID NO 108
<211> LENGTH: 30
<212> TYPE: DNA
<213> ORGANISM: Homo sapiens

<400> SEQUENCE: 108
gccgcaagtg acccactgct tgtttctgtc                                      30

<210> SEQ ID NO 109
<211> LENGTH: 40
<212> TYPE: DNA
<213> ORGANISM: Homo sapiens

<400> SEQUENCE: 109
ggcctctcct gcctgaaccg cggggcccgg ctgggctgag                           40

<210> SEQ ID NO 110
<211> LENGTH: 36
<212> TYPE: DNA
<213> ORGANISM: Homo sapiens

<400> SEQUENCE: 110
caggcaggag aggccgtgac cttgtcctgt agctcc                               36

<210> SEQ ID NO 111
<211> LENGTH: 33
<212> TYPE: DNA
<213> ORGANISM: Homo sapiens

<400> SEQUENCE: 111
ataggagctc gcggagctac aggacaaggt cac                                  33

<210> SEQ ID NO 112
<211> LENGTH: 33
<212> TYPE: DNA
<213> ORGANISM: Homo sapiens

<400> SEQUENCE: 112
tccgcgagct cctatgacat ctaccatctg tcc                                  33

<210> SEQ ID NO 113
<211> LENGTH: 42
<212> TYPE: DNA
<213> ORGANISM: Homo sapiens

<400> SEQUENCE: 113
atgggcctcc ccttccctgg acagatggta catgtcatag ga                        42

<210> SEQ ID NO 114
<211> LENGTH: 36
<212> TYPE: DNA
<213> ORGANISM: Homo sapiens
```

<400> SEQUENCE: 114 gaagggagg cccatgaacg taggctccct gcagtg        36

<210> SEQ ID NO 115
<211> LENGTH: 36
<212> TYPE: DNA
<213> ORGANISM: Homo sapiens

<400> SEQUENCE: 115
atgtgctcca ccttccctgg acagatggta gatgtc        36

<210> SEQ ID NO 116
<211> LENGTH: 36
<212> TYPE: DNA
<213> ORGANISM: Homo sapiens

<400> SEQUENCE: 116
gaaggtggag cacatgaacg taggctccgt gcagtg        36

<210> SEQ ID NO 117
<211> LENGTH: 36
<212> TYPE: DNA
<213> ORGANISM: Homo sapiens

<400> SEQUENCE: 117
tctgttgacc ttggccactg cacggagcct acgttc        36

<210> SEQ ID NO 118
<211> LENGTH: 30
<212> TYPE: DNA
<213> ORGANISM: Homo sapiens

<400> SEQUENCE: 118
gccaaggtca acagaacatt ccaggcagac        30

<210> SEQ ID NO 119
<211> LENGTH: 37
<212> TYPE: DNA
<213> ORGANISM: Homo sapiens

<400> SEQUENCE: 119
cgcggcgggc gcgtgacgga aagagccgaa gcatctg        37

<210> SEQ ID NO 120
<211> LENGTH: 35
<212> TYPE: DNA
<213> ORGANISM: Homo sapiens

<400> SEQUENCE: 120
cacgcgcccg ccgcgtggtc aaactcaagt gaccc        35

<210> SEQ ID NO 121
<211> LENGTH: 40
<212> TYPE: DNA
<213> ORGANISM: Homo sapiens

<400> SEQUENCE: 121
ctcgcagggc gagtgacgga aagagccgaa gcatctgtag        40

<210> SEQ ID NO 122
<211> LENGTH: 35
<212> TYPE: DNA

<213> ORGANISM: Homo sapiens

<400> SEQUENCE: 122
cactcgccct gcgagtggtc aaactcaagt gaccc                               35

<210> SEQ ID NO 123
<211> LENGTH: 30
<212> TYPE: DNA
<213> ORGANISM: Homo sapiens

<400> SEQUENCE: 123
gtagggcagg gcacggaaag agccgaagca                                     30

<210> SEQ ID NO 124
<211> LENGTH: 25
<212> TYPE: DNA
<213> ORGANISM: Homo sapiens

<400> SEQUENCE: 124
cccagacacc tgcatgttct gattg                                          25

<210> SEQ ID NO 125
<211> LENGTH: 41
<212> TYPE: DNA
<213> ORGANISM: HOMO SAPIENS

<400> SEQUENCE: 125
tgtggtcaca gggcccatga tgaagctctc ctggaatatt c                        41

<210> SEQ ID NO 126
<211> LENGTH: 36
<212> TYPE: DNA
<213> ORGANISM: HOMO SAPIENS

<400> SEQUENCE: 126
ggccctgtga ccacagcaca tgcagggacc tacaga                              36

<210> SEQ ID NO 127
<211> LENGTH: 39
<212> TYPE: DNA
<213> ORGANISM: HOMO SAPIENS

<400> SEQUENCE: 127
gtcactggga gctgacaact gataggggt gtgagtaac                            39

<210> SEQ ID NO 128
<211> LENGTH: 38
<212> TYPE: DNA
<213> ORGANISM: HOMO SAPIENS

<400> SEQUENCE: 128
tcagctccca gtgacccct ggacatcgtg atcacagg                             38

<210> SEQ ID NO 129
<211> LENGTH: 36
<212> TYPE: DNA
<213> ORGANISM: HOMO SAPIENS

<400> SEQUENCE: 129
gatatctgac caacattgca ggatgactgt ctctcc                              36

<210> SEQ ID NO 130
<211> LENGTH: 36

```
<212> TYPE: DNA
<213> ORGANISM: HOMO SAPIENS

<400> SEQUENCE: 130
tgttggtcag atatcatgtt tgagcacttc tttctg                                36

<210> SEQ ID NO 131
<211> LENGTH: 36
<212> TYPE: DNA
<213> ORGANISM: HOMO SAPIENS

<400> SEQUENCE: 131
ggaggaagga gcagaaccat aacatctgta ggttcc                                36

<210> SEQ ID NO 132
<211> LENGTH: 36
<212> TYPE: DNA
<213> ORGANISM: HOMO SAPIENS

<400> SEQUENCE: 132
tctgctcctt cctcccccta tcagttgtca gctccc                                36

<210> SEQ ID NO 133
<211> LENGTH: 33
<212> TYPE: DNA
<213> ORGANISM: HOMO SAPIENS

<400> SEQUENCE: 133
gatcaccagg gggttgctgg gagccgacca ccc                                   33

<210> SEQ ID NO 134
<211> LENGTH: 45
<212> TYPE: DNA
<213> ORGANISM: HOMO SAPIENS

<400> SEQUENCE: 134
aaccccctgg tgatcatggt cacaggaagc tccagaaaac cttcc                      45

<210> SEQ ID NO 135
<211> LENGTH: 45
<212> TYPE: DNA
<213> ORGANISM: HOMO SAPIENS

<400> SEQUENCE: 135
gtccaggggg tcactcccag ctgacaacgc atagggggag tgagg                      45

<210> SEQ ID NO 136
<211> LENGTH: 31
<212> TYPE: DNA
<213> ORGANISM: HOMO SAPIENS

<400> SEQUENCE: 136
agtgaccccc tggacatcgt gatcacaggt c                                     31

<210> SEQ ID NO 137
<211> LENGTH: 37
<212> TYPE: DNA
<213> ORGANISM: HOMO SAPIENS

<400> SEQUENCE: 137
agagatccca tctctgtgca gaaagaagga cgaaaac                               37

<210> SEQ ID NO 138
```

```
<211> LENGTH: 33
<212> TYPE: DNA
<213> ORGANISM: HOMO SAPIENS

<400> SEQUENCE: 138
agagatggga tctctgagga cccctcaagc ctc                                        33

<210> SEQ ID NO 139
<211> LENGTH: 33
<212> TYPE: DNA
<213> ORGANISM: HOMO SAPIENS

<400> SEQUENCE: 139
atggatcgat ccagcgaggc gtgaggggtc ctc                                        33

<210> SEQ ID NO 140
<211> LENGTH: 33
<212> TYPE: DNA
<213> ORGANISM: HOMO SAPIENS

<400> SEQUENCE: 140
gctggatcga tccatgatgg ggtctccaag gcc                                        33

<210> SEQ ID NO 141
<211> LENGTH: 45
<212> TYPE: DNA
<213> ORGANISM: HOMO SAPIENS

<400> SEQUENCE: 141
ctcagagatc ccatctctgt gcagaaagaa gtgctcaaac gcgac                           45

<210> SEQ ID NO 142
<211> LENGTH: 46
<212> TYPE: DNA
<213> ORGANISM: HOMO SAPIENS

<400> SEQUENCE: 142
gatgggatct ctgaggaccc ctcacgcctc gttggacagg cccatg                          46

<210> SEQ ID NO 143
<211> LENGTH: 35
<212> TYPE: DNA
<213> ORGANISM: HOMO SAPIENS

<400> SEQUENCE: 143
tcctcctcga ggcaccacag tgctgggcca ggcag                                      35

<210> SEQ ID NO 144
<211> LENGTH: 41
<212> TYPE: DNA
<213> ORGANISM: HOMO SAPIENS

<400> SEQUENCE: 144
gtgcctcgag gaggacacgt gactcttcgg tgtcactatc g                               41

<210> SEQ ID NO 145
<211> LENGTH: 34
<212> TYPE: DNA
<213> ORGANISM: HOMO SAPIENS

<400> SEQUENCE: 145
tggggtcaca gggctcatgt tgaagctctc ctgg                                       34
```

```
<210> SEQ ID NO 146
<211> LENGTH: 41
<212> TYPE: DNA
<213> ORGANISM: HOMO SAPIENS

<400> SEQUENCE: 146
agccctgtga ccccagcaca tgcagggacc tacagatgtc g                41

<210> SEQ ID NO 147
<211> LENGTH: 34
<212> TYPE: DNA
<213> ORGANISM: HOMO SAPIENS

<400> SEQUENCE: 147
ggcagccagg gagggtttgt cctgaccacc catg                        34

<210> SEQ ID NO 148
<211> LENGTH: 35
<212> TYPE: DNA
<213> ORGANISM: HOMO SAPIENS

<400> SEQUENCE: 148
ccctccctgg ctgcccggcc cagcactgtg gtgcc                       35

<210> SEQ ID NO 149
<211> LENGTH: 36
<212> TYPE: DNA
<213> ORGANISM: HOMO SAPIENS

<400> SEQUENCE: 149
cccacgacga taggaacact gaagagccac gtgtcc                      36

<210> SEQ ID NO 150
<211> LENGTH: 36
<212> TYPE: DNA
<213> ORGANISM: HOMO SAPIENS

<400> SEQUENCE: 150
tcctatcgtc gtggggctaa caatttcatg ctgtac                      36

<210> SEQ ID NO 151
<211> LENGTH: 34
<212> TYPE: DNA
<213> ORGANISM: HOMO SAPIENS

<400> SEQUENCE: 151
tatgctgccg tgggcgatgg gaacgtggct tctg                        34

<210> SEQ ID NO 152
<211> LENGTH: 33
<212> TYPE: DNA
<213> ORGANISM: HOMO SAPIENS

<400> SEQUENCE: 152
gcccacggca gcatattcca ggagagcttc atc                         33

<210> SEQ ID NO 153
<211> LENGTH: 35
<212> TYPE: DNA
<213> ORGANISM: HOMO SAPIENS

<400> SEQUENCE: 153
gaagctcgcc gagaatattc tgccgtggaa gatgg                       35
```

<210> SEQ ID NO 154
<211> LENGTH: 33
<212> TYPE: DNA
<213> ORGANISM: HOMO SAPIENS

<400> SEQUENCE: 154
ttctcggcga gcttcatcat gggccctgtg acc                                    33

<210> SEQ ID NO 155
<211> LENGTH: 36
<212> TYPE: DNA
<213> ORGANISM: HOMO SAPIENS

<400> SEQUENCE: 155
tcctcgaggc accacagtgg cggaccgggc agacag                                 36

<210> SEQ ID NO 156
<211> LENGTH: 37
<212> TYPE: DNA
<213> ORGANISM: HOMO SAPIENS

<400> SEQUENCE: 156
gtggtgcctc gaggaggatc cgtggctctt cagtgtc                                37

<210> SEQ ID NO 157
<211> LENGTH: 31
<212> TYPE: DNA
<213> ORGANISM: HOMO SAPIENS

<400> SEQUENCE: 157
gtcctcttgg atcccatctc tgtgcagaaa g                                      31

<210> SEQ ID NO 158
<211> LENGTH: 32
<212> TYPE: DNA
<213> ORGANISM: HOMO SAPIENS

<400> SEQUENCE: 158
gggatccaag aggacccctc acgcctcgtt gg                                     32

<210> SEQ ID NO 159
<211> LENGTH: 455
<212> TYPE: PRT
<213> ORGANISM: Homo sapiens

<400> SEQUENCE: 159

Met Ser Leu Thr Val Val Ser Met Ala Cys Val Gly Phe Phe Leu Leu
 1               5                  10                  15

Gln Gly Ala Trp Pro Leu Met Gly Gly Gln Asp Lys Pro Phe Leu Ser
            20                  25                  30

Ala Arg Pro Ser Thr Val Val Pro Arg Gly Gly His Val Ala Leu Gln
        35                  40                  45

Cys His Tyr Arg Arg Gly Phe Asn Asn Phe Met Leu Tyr Lys Glu Asp
    50                  55                  60

Arg Ser His Val Pro Ile Phe His Gly Arg Ile Phe Gln Glu Ser Phe
65                  70                  75                  80

Ile Met Gly Pro Val Thr Pro Ala His Ala Gly Thr Tyr Arg Cys Arg
                85                  90                  95

Gly Ser Arg Pro His Ser Leu Thr Gly Trp Ser Ala Pro Ser Asn Pro
            100                 105                 110

Leu Val Ile Met Val Thr Gly Asn His Arg Lys Pro Ser Leu Leu Ala
            115                 120                 125

His Pro Gly Pro Leu Leu Lys Ser Gly Glu Thr Val Ile Leu Gln Cys
        130                 135                 140

Trp Ser Asp Val Met Phe Glu His Phe Phe Leu His Arg Asp Gly Ile
145                 150                 155                 160

Ser Glu Asp Pro Ser Arg Leu Val Gly Gln Ile His Asp Gly Val Ser
                165                 170                 175

Lys Ala Asn Phe Ser Ile Gly Pro Leu Met Pro Val Leu Ala Gly Thr
            180                 185                 190

Tyr Arg Cys Tyr Gly Ser Val Pro His Ser Pro Tyr Gln Leu Ser Ala
        195                 200                 205

Pro Ser Asp Pro Leu Asp Ile Val Ile Thr Gly Leu Tyr Glu Lys Pro
    210                 215                 220

Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
                245                 250                 255

Arg Glu Gly Glu Ala His Glu Arg Arg Leu Arg Ala Val Pro Lys Val
            260                 265                 270

Asn Arg Thr Phe Gln Ala Asp Phe Pro Leu Gly Pro Ala Thr His Gly
        275                 280                 285

Gly Thr Tyr Arg Cys Phe Gly Ser Phe Arg Ala Leu Pro Cys Val Trp
    290                 295                 300

Ser Asn Ser Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Ile Cys
                325                 330                 335

Arg His Leu His Val Leu Ile Gly Thr Ser Val Val Ile Phe Leu Phe
            340                 345                 350

Ile Leu Leu Leu Phe Phe Leu Leu Tyr Arg Trp Cys Ser Asn Lys Lys
        355                 360                 365

Asn Ala Ala Val Met Asp Gln Glu Pro Ala Gly Asp Arg Thr Val Asn
370                 375                 380

Arg Gln Asp Ser Asp Glu Gln Asp Pro Gln Glu Val Thr Tyr Ala Gln
385                 390                 395                 400

Leu Asp His Cys Val Phe Ile Gln Arg Lys Ile Ser Arg Pro Ser Gln
                405                 410                 415

Arg Pro Lys Thr Pro Leu Thr Asp Thr Ser Val Tyr Thr Glu Leu Pro
            420                 425                 430

Asn Ala Glu Pro Arg Ser Lys Val Val Ser Cys Pro Arg Ala Pro Gln
        435                 440                 445

Ser Gly Leu Glu Gly Val Phe
    450                 455

<210> SEQ ID NO 160
<211> LENGTH: 455
<212> TYPE: PRT
<213> ORGANISM: HOMO SAPIENS

<400> SEQUENCE: 160

Met Ser Leu Thr Val Val Ser Met Ala Cys Val Gly Phe Phe Leu Leu
1               5                   10                  15

Gln Gly Ala Trp Pro Leu Met Gly Gly Gln Asp Lys Pro Phe Leu Ser
            20                  25                  30

```
Ala Arg Pro Ser Thr Val Val Pro Arg Gly His Val Ala Leu Gln
         35                  40                  45

Cys His Tyr Arg Arg Gly Phe Asn Asn Phe Met Leu Tyr Lys Glu Asp
 50                  55                  60

Arg Ser His Val Pro Ile Phe His Gly Arg Ile Phe Gln Glu Ser Phe
 65                  70                  75                  80

Ile Met Gly Pro Val Thr Pro Ala His Ala Gly Thr Tyr Arg Cys Arg
                 85                  90                  95

Gly Ser Arg Pro His Ser Leu Thr Gly Trp Ser Ala Pro Ser Asn Pro
             100                 105                 110

Leu Val Ile Met Val Thr Gly Asn His Arg Lys Pro Ser Leu Leu Ala
             115                 120                 125

His Pro Gly Pro Leu Leu Lys Ser Gly Glu Thr Val Ile Leu Gln Cys
 130                 135                 140

Trp Ser Asp Val Met Phe Glu His Phe Phe Leu His Arg Glu Gly Ile
145                 150                 155                 160

Ser Glu Asp Pro Ser Arg Leu Val Gly Gln Ile His Asp Gly Val Ser
                 165                 170                 175

Lys Ala Asn Phe Ser Ile Gly Pro Leu Met Pro Val Leu Ala Gly Thr
             180                 185                 190

Tyr Arg Cys Tyr Gly Ser Val Pro His Ser Pro Tyr Gln Leu Ser Ala
             195                 200                 205

Pro Ser Asp Pro Leu Asp Ile Val Ile Thr Gly Leu Tyr Glu Lys Pro
 210                 215                 220

Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
                 245                 250                 255

Arg Glu Gly Glu Ala His Glu Arg Arg Leu Arg Ala Val Pro Lys Val
             260                 265                 270

Asn Arg Thr Phe Gln Ala Asp Phe Pro Leu Gly Pro Ala Thr His Gly
             275                 280                 285

Gly Thr Tyr Arg Cys Phe Gly Ser Phe Arg Ala Leu Pro Cys Val Trp
             290                 295                 300

Ser Asn Ser Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Ile Cys
                 325                 330                 335

Arg His Leu His Val Leu Ile Gly Thr Ser Val Val Ile Phe Leu Phe
             340                 345                 350

Ile Leu Leu Leu Phe Phe Leu Leu Tyr Arg Trp Cys Ser Asn Lys Lys
             355                 360                 365

Asn Ala Ala Val Met Asp Gln Glu Pro Ala Gly Asp Arg Thr Val Asn
 370                 375                 380

Arg Gln Asp Ser Asp Glu Gln Asp Pro Gln Glu Val Thr Tyr Ala Gln
385                 390                 395                 400

Leu Asp His Cys Val Phe Ile Gln Arg Lys Ile Ser Arg Pro Ser Gln
                 405                 410                 415

Arg Pro Lys Thr Pro Leu Thr Asp Thr Ser Val Tyr Thr Glu Leu Pro
             420                 425                 430

Asn Ala Glu Pro Arg Ser Lys Val Val Ser Cys Pro Arg Ala Pro Gln
             435                 440                 445
```

```
Ser Gly Leu Glu Gly Val Phe
    450             455

<210> SEQ ID NO 161
<211> LENGTH: 455
<212> TYPE: PRT
<213> ORGANISM: Homo sapiens

<400> SEQUENCE: 161

Met Ser Leu Thr Val Val Ser Met Ala Cys Val Gly Phe Phe Leu Leu
1               5                   10                  15

Gln Gly Ala Trp Pro Leu Met Gly Gly Gln Asp Lys Pro Phe Leu Ser
            20                  25                  30

Ala Arg Pro Ser Thr Val Val Pro Arg Gly Gly His Val Ala Leu Gln
        35                  40                  45

Cys His Tyr Arg Arg Gly Phe Asn Asn Phe Met Leu Tyr Lys Glu Asp
    50                  55                  60

Arg Ser His Val Pro Ile Phe His Gly Arg Ile Phe Gln Glu Ser Phe
65                  70                  75                  80

Ile Met Gly Pro Val Thr Pro Ala His Ala Gly Thr Tyr Arg Cys Arg
                85                  90                  95

Gly Ser Arg Pro His Ser Leu Thr Gly Trp Ser Ala Pro Ser Asn Pro
            100                 105                 110

Val Val Ile Met Val Thr Gly Asn His Arg Lys Pro Ser Leu Leu Ala
        115                 120                 125

His Pro Gly Pro Leu Leu Lys Ser Gly Glu Thr Val Ile Leu Gln Cys
    130                 135                 140

Trp Ser Asp Val Met Phe Glu His Phe Phe Leu His Arg Glu Gly Ile
145                 150                 155                 160

Ser Glu Asp Pro Ser Arg Leu Val Gly Gln Ile His Asp Gly Val Ser
                165                 170                 175

Lys Ala Asn Phe Ser Ile Gly Pro Leu Met Pro Val Leu Ala Gly Thr
            180                 185                 190

Tyr Arg Cys Tyr Gly Ser Val Pro His Ser Pro Tyr Gln Leu Ser Ala
        195                 200                 205

Pro Ser Asp Pro Leu Asp Ile Val Ile Thr Gly Leu Tyr Glu Lys Pro
    210                 215                 220

Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
                245                 250                 255

Arg Glu Gly Glu Ala His Glu Arg Arg Leu Arg Ala Val Pro Lys Val
            260                 265                 270

Asn Arg Thr Phe Gln Ala Asp Phe Pro Leu Gly Pro Ala Thr His Gly
        275                 280                 285

Gly Thr Tyr Arg Cys Phe Gly Ser Phe Arg Ala Leu Pro Cys Val Trp
    290                 295                 300

Ser Asn Ser Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Ile Cys
                325                 330                 335

Arg His Leu His Val Leu Ile Gly Thr Ser Val Val Ile Phe Leu Phe
            340                 345                 350

Ile Leu Leu Leu Phe Phe Leu Leu Tyr Arg Trp Cys Ser Asn Lys Lys
        355                 360                 365
```

Asn Ala Ala Val Met Asp Gln Glu Pro Ala Gly Asp Arg Thr Val Asn
            370                 375                 380

Arg Gln Asp Ser Asp Glu Gln Asp Pro Gln Glu Val Thr Tyr Ala Gln
385                 390                 395                 400

Leu Asp His Cys Val Phe Ile Gln Arg Lys Ile Ser Arg Pro Ser Gln
                405                 410                 415

Arg Pro Lys Thr Pro Leu Thr Asp Thr Ser Val Tyr Thr Glu Leu Pro
            420                 425                 430

Asn Ala Glu Pro Arg Ser Lys Val Val Ser Cys Pro Arg Ala Pro Gln
        435                 440                 445

Ser Gly Leu Glu Gly Val Phe
    450                 455

<210> SEQ ID NO 162
<211> LENGTH: 455
<212> TYPE: PRT
<213> ORGANISM: HOMO SAPIENS

<400> SEQUENCE: 162

Met Ser Leu Thr Val Val Ser Met Ala Cys Val Gly Phe Phe Leu Leu
1               5                   10                  15

Gln Gly Ala Trp Pro Leu Met Gly Gly Gln Asp Lys Pro Phe Leu Ser
            20                  25                  30

Ala Arg Pro Ser Thr Val Val Ala Arg Gly Gly His Val Ala Leu Gln
        35                  40                  45

Cys His Tyr Arg Arg Gly Phe Asn Asn Phe Met Leu Tyr Lys Glu Asp
    50                  55                  60

Arg Ser His Val Pro Ile Phe His Gly Arg Ile Phe Gln Glu Ser Phe
65                  70                  75                  80

Ile Met Gly Pro Val Thr Pro Ala His Ala Gly Thr Tyr Arg Cys Arg
                85                  90                  95

Gly Ser Arg Pro His Ser Leu Thr Gly Trp Ser Ala Pro Ser Asn Pro
            100                 105                 110

Val Val Ile Met Val Thr Gly Asn His Arg Lys Pro Ser Leu Leu Ala
        115                 120                 125

His Pro Gly Pro Leu Leu Lys Ser Gly Glu Thr Val Ile Leu Gln Cys
    130                 135                 140

Trp Ser Asp Val Met Phe Glu His Phe Phe Leu His Arg Glu Gly Ile
145                 150                 155                 160

Ser Glu Asp Pro Ser His Leu Val Gly Gln Ile His Asp Gly Val Ser
                165                 170                 175

Lys Ala Asn Phe Ser Ile Gly Pro Leu Met Pro Val Leu Ala Gly Thr
            180                 185                 190

Tyr Arg Cys Tyr Gly Ser Val Pro His Ser Pro Tyr Gln Leu Ser Ala
        195                 200                 205

Pro Ser Asp Pro Leu Asp Ile Val Ile Thr Gly Leu Tyr Glu Lys Pro
    210                 215                 220

Ser Leu Ser Pro Gln Pro Gly Pro Thr Val Gln Ala Gly Glu Asn Val
225                 230                 235                 240

Thr Leu Ser Cys Ser Ser Trp Ser Ser Tyr Asp Thr Tyr His Leu Ser
                245                 250                 255

Arg Glu Gly Glu Ala His Glu Arg Arg Leu Arg Ala Val Pro Lys Val
            260                 265                 270

Asn Arg Thr Phe Gln Ala Asp Phe Pro Leu Gly Pro Ala Thr His Gly

```
                275                 280                 285
Gly Thr Tyr Arg Cys Phe Gly Ser Phe Arg Ala Leu Pro Cys Val Trp
    290                 295                 300
Ser Asn Ser Ser Asp Pro Leu Leu Val Ser Val Thr Gly Asn Pro Ser
305                 310                 315                 320
Ser Ser Trp Pro Ser Pro Thr Glu Pro Ser Lys Ser Gly Ile Cys
                    325                 330                 335
Arg His Leu His Val Leu Ile Gly Thr Ser Val Val Ile Phe Leu Phe
                340                 345                 350
Ile Leu Leu Leu Phe Phe Leu Leu Tyr Arg Trp Cys Ser Asn Lys Lys
                355                 360                 365
Asn Ala Ala Val Met Asp Gln Glu Pro Ala Gly Asp Arg Thr Val Asn
                370                 375                 380
Arg Gln Asp Ser Asp Glu Gln Asp Pro Gln Glu Val Thr Tyr Ala Gln
385                 390                 395                 400
Leu Asp His Cys Val Phe Ile Gln Arg Lys Ile Ser Arg Pro Ser Gln
                    405                 410                 415
Arg Pro Lys Thr Pro Leu Thr Asp Thr Ser Val Tyr Thr Glu Leu Pro
                420                 425                 430
Asn Ala Glu Pro Arg Ser Lys Val Val Ser Cys Pro Arg Ala Pro Gln
                435                 440                 445
Ser Gly Leu Glu Gly Val Phe
                450                 455

<210> SEQ ID NO 163
<211> LENGTH: 455
<212> TYPE: PRT
<213> ORGANISM: HOMO SAPIENS

<400> SEQUENCE: 163

Met Ser Leu Thr Val Val Ser Met Ala Cys Val Gly Phe Phe Leu Leu
1               5                   10                  15
Gln Gly Ala Trp Pro Leu Met Gly Gly Gln Asp Lys Pro Phe Leu Ser
                20                  25                  30
Ala Arg Pro Ser Thr Val Val Pro Arg Gly Gly His Val Ala Leu Gln
            35                  40                  45
Cys His Tyr Arg Arg Gly Phe Asn Asn Phe Met Leu Tyr Lys Glu Asp
    50                  55                  60
Arg Ser His Val Pro Ile Phe His Gly Arg Ile Phe Gln Glu Ser Phe
65                  70                  75                  80
Ile Met Gly Pro Val Thr Pro Ala His Ala Gly Thr Tyr Arg Cys Arg
                85                  90                  95
Gly Ser Arg Pro His Ser Leu Thr Gly Trp Ser Ala Pro Ser Asn Pro
            100                 105                 110
Val Val Ile Met Val Thr Gly Asn His Arg Lys Pro Ser Leu Leu Ala
        115                 120                 125
His Pro Gly Pro Leu Leu Lys Ser Gly Glu Thr Val Ile Leu Gln Cys
    130                 135                 140
Trp Ser Asp Val Met Phe Glu His Phe Phe Leu His Arg Glu Gly Ile
145                 150                 155                 160
Ser Glu Asp Pro Ser His Leu Val Gly Gln Ile His Asp Gly Val Ser
                165                 170                 175
Lys Ala Asn Phe Ser Ile Gly Pro Leu Met Pro Val Leu Ala Gly Thr
            180                 185                 190
```

Tyr Arg Cys Tyr Gly Ser Val Pro His Ser Pro Tyr Gln Leu Ser Ala
            195                 200                 205

Pro Ser Asp Pro Leu Asp Ile Val Ile Thr Gly Leu Tyr Glu Lys Pro
    210                 215                 220

Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
            245                 250                 255

Arg Glu Gly Glu Ala His Glu Arg Arg Leu Arg Ala Val Pro Lys Val
            260                 265                 270

Asn Arg Thr Phe Gln Ala Asp Phe Pro Leu Gly Pro Ala Thr His Gly
    275                 280                 285

Gly Thr Tyr Arg Cys Phe Gly Ser Phe Arg Ala Leu Pro Cys Val Trp
    290                 295                 300

Ser Asn Ser Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Ile Cys
            325                 330                 335

Arg His Leu His Val Leu Ile Gly Thr Ser Val Val Ile Phe Leu Phe
            340                 345                 350

Ile Leu Leu Leu Phe Phe Leu Leu Tyr Arg Trp Cys Ser Asn Lys Lys
            355                 360                 365

Asn Ala Ala Val Met Asp Gln Glu Pro Ala Gly Asp Arg Thr Val Asn
    370                 375                 380

Arg Gln Asp Ser Asp Glu Gln Asp Pro Gln Glu Val Thr Tyr Ala Gln
385                 390                 395                 400

Leu Asp His Cys Val Phe Ile Gln Arg Lys Ile Ser Arg Pro Ser Gln
            405                 410                 415

Arg Pro Lys Thr Pro Leu Thr Asp Thr Ser Val Tyr Thr Glu Leu Pro
            420                 425                 430

Asn Ala Glu Pro Arg Ser Lys Val Val Ser Cys Pro Arg Ala Pro Gln
    435                 440                 445

Ser Gly Leu Glu Gly Val Phe
    450                 455

<210> SEQ ID NO 164
<211> LENGTH: 428
<212> TYPE: PRT
<213> ORGANISM: Homo sapiens

<400> SEQUENCE: 164

Lys Pro Phe Leu Ser Ala Arg Pro Ser Thr Val Val Pro Arg Gly Gly
1               5                   10                  15

His Val Ala Leu Gln Cys His Tyr Arg Arg Gly Phe Asn Asn Phe Met
            20                  25                  30

Leu Tyr Lys Glu Asp Arg Ser His Val Pro Ile Phe His Gly Arg Ile
        35                  40                  45

Phe Gln Glu Ser Phe Ile Met Gly Pro Val Thr Pro Ala His Ala Gly
    50                  55                  60

Thr Tyr Arg Cys Arg Gly Ser Arg Pro His Ser Leu Thr Gly Trp Ser
65                  70                  75                  80

Thr Pro Ser Asn Pro Leu Val Ile Met Val Thr Gly Asn His Arg Lys
            85                  90                  95

Pro Ser Leu Leu Ala His Pro Gly Pro Leu Leu Lys Ser Gly Glu Thr
            100                 105                 110

```
Val Ile Leu Gln Cys Trp Ser Asp Val Met Phe Glu His Phe Leu
        115                 120                 125

His Arg Glu Gly Ile Ser Glu Asp Pro Ser Arg Leu Val Gly Gln Ile
        130                 135                 140

His Asp Gly Val Ser Lys Ala Asn Phe Ser Ile Gly Pro Leu Met Pro
145                 150                 155                 160

Val Leu Ala Gly Thr Tyr Arg Cys Tyr Gly Ser Val Pro His Ser Pro
                165                 170                 175

Tyr Gln Leu Ser Ala Pro Ser Asp Pro Leu Asp Ile Val Ile Thr Gly
                180                 185                 190

Leu Tyr Glu Lys Pro Ser Leu Ser Ala Gln Pro Gly Pro Thr Val Gln
                195                 200                 205

Ala Gly Glu Asn Val Thr Leu Ser Cys Ser Ser Trp Ser Ser Tyr Asp
        210                 215                 220

Ile Tyr His Leu Ser Arg Glu Gly Glu Ala His Glu Arg Arg Leu Arg
225                 230                 235                 240

Ala Val Pro Lys Val Asn Arg Thr Phe Gln Ala Asp Phe Pro Leu Gly
                245                 250                 255

Pro Ala Thr His Gly Gly Thr Tyr Arg Cys Phe Gly Ser Phe Arg Ala
                260                 265                 270

Leu Pro Cys Val Trp Ser Asn Ser Ser Asp Pro Leu Leu Val Ser Val
        275                 280                 285

Thr Gly Asn Pro Ser Ser Ser Trp Pro Ser Pro Thr Glu Pro Ser Ser
        290                 295                 300

Lys Ser Gly Ile Cys Arg His Leu His Val Leu Ile Gly Thr Ser Val
305                 310                 315                 320

Val Ile Phe Leu Phe Ile Leu Leu Leu Phe Phe Leu Leu Tyr Arg Trp
                325                 330                 335

Cys Ser Asn Lys Lys Asn Ala Ala Val Met Asp Gln Glu Pro Ala Gly
                340                 345                 350

Asp Arg Thr Val Asn Arg Gln Asp Ser Asp Glu Gln Asp Pro Gln Glu
        355                 360                 365

Val Thr Tyr Ala Gln Leu Asp His Cys Val Phe Ile Gln Arg Lys Ile
        370                 375                 380

Ser Arg Pro Ser Gln Arg Pro Lys Thr Pro Leu Thr Asp Thr Ser Val
385                 390                 395                 400

Tyr Thr Glu Leu Pro Asn Ala Glu Pro Arg Ser Lys Val Val Ser Cys
                405                 410                 415

Pro Arg Ala Pro Gln Ser Gly Leu Glu Gly Val Phe
                420                 425

<210> SEQ ID NO 165
<211> LENGTH: 428
<212> TYPE: PRT
<213> ORGANISM: Homo sapiens

<400> SEQUENCE: 165

Lys Pro Phe Leu Ser Ala Arg Pro Ser Thr Val Val Pro Arg Gly Gly
1               5                   10                  15

His Val Ala Leu Gln Cys His Tyr Arg Arg Gly Phe Asn Asn Phe Met
                20                  25                  30

Leu Tyr Lys Glu Asp Arg Ser His Val Pro Ile Phe His Gly Arg Ile
                35                  40                  45

Phe Gln Glu Ser Phe Ile Met Gly Pro Val Thr Pro Ala His Ala Gly
```

```
                50                  55                  60
Thr Tyr Arg Cys Arg Gly Ser Arg Pro His Ser Leu Thr Gly Trp Ser
 65                  70                  75                  80

Thr Pro Ser Asn Pro Leu Val Ile Met Val Thr Gly Asn His Arg Lys
                 85                  90                  95

Pro Ser Leu Leu Ala His Pro Gly Pro Leu Leu Lys Ser Gly Glu Thr
            100                 105                 110

Val Ile Leu Gln Cys Trp Ser Asp Val Met Phe Glu His Phe Phe Leu
        115                 120                 125

His Arg Glu Gly Ile Ser Glu Asp Pro Ser Arg Leu Val Gly Gln Ile
    130                 135                 140

His Asp Gly Val Ser Lys Ala Asn Phe Ser Ile Gly Pro Leu Met Pro
145                 150                 155                 160

Val Leu Ala Gly Thr Tyr Arg Cys Tyr Gly Ser Val Pro His Ser Pro
                165                 170                 175

Tyr Gln Leu Ser Ala Pro Ser Asp Pro Leu Asp Ile Val Ile Thr Gly
            180                 185                 190

Leu Tyr Glu Lys Pro Ser Leu Ser Ala Gln Pro Gly Pro Thr Val Gln
        195                 200                 205

Ala Gly Glu Asn Val Thr Leu Ser Cys Ser Ser Trp Ser Ser Tyr Asp
    210                 215                 220

Ile Tyr His Leu Ser Arg Glu Gly Glu Ala His Glu Arg Arg Leu Arg
225                 230                 235                 240

Ala Val Pro Lys Val Asn Arg Thr Phe Gln Ala Asp Phe Pro Leu Gly
                245                 250                 255

Pro Ala Thr His Gly Gly Thr Tyr Arg Cys Phe Gly Ser Phe Arg Ala
            260                 265                 270

Leu Pro Cys Val Trp Ser Asn Ser Ser Asp Pro Leu Leu Val Ser Val
        275                 280                 285

Thr Gly Asn Pro Ser Ser Ser Trp Pro Ser Pro Thr Glu Pro Ser Ser
    290                 295                 300

Lys Ser Gly Ile Cys Arg His Leu His Val Leu Ile Gly Thr Ser Val
305                 310                 315                 320

Val Ile Phe Leu Phe Ile Leu Leu Leu Phe Phe Leu Leu Tyr Arg Trp
                325                 330                 335

Cys Ser Asn Lys Lys Asn Ala Ala Val Met Asp Gln Glu Pro Ala Gly
            340                 345                 350

Asp Arg Thr Val Asn Arg Gln Asp Ser Asp Glu Gln Asp Pro Gln Glu
        355                 360                 365

Val Met Tyr Ala Gln Leu Asp His Cys Val Phe Ile Gln Arg Lys Ile
    370                 375                 380

Ser Arg Pro Ser Gln Arg Pro Lys Thr Pro Leu Thr Asp Thr Ser Val
385                 390                 395                 400

Tyr Thr Glu Leu Pro Asn Ala Glu Pro Arg Ser Lys Val Val Ser Cys
                405                 410                 415

Pro Arg Ala Pro Gln Ser Gly Leu Glu Gly Val Phe
            420                 425

<210> SEQ ID NO 166
<211> LENGTH: 455
<212> TYPE: PRT
<213> ORGANISM: homo sapiens

<400> SEQUENCE: 166
```

```
Met Ser Leu Thr Val Ser Met Ala Cys Val Gly Phe Phe Leu Leu
1               5                   10                  15

Gln Gly Ala Trp Pro Leu Met Gly Gly Gln Asp Lys Pro Phe Leu Ser
            20                  25                  30

Ala Arg Pro Ser Thr Val Val Pro Gln Gly Gly His Val Ala Leu Gln
            35                  40                  45

Cys His Tyr Arg Arg Gly Phe Asn Asn Phe Met Leu Tyr Lys Glu Asp
        50                  55                  60

Arg Ser His Val Pro Ile Phe His Gly Arg Ile Phe Gln Glu Ser Phe
65                  70                  75                  80

Ile Met Gly Pro Val Thr Pro Ala His Ala Gly Thr Tyr Arg Cys Arg
                85                  90                  95

Gly Ser Arg Pro His Ser Leu Thr Gly Trp Ser Ala Pro Ser Asn Pro
                100                 105                 110

Leu Val Ile Met Val Thr Gly Asn His Arg Lys Pro Ser Leu Leu Ala
            115                 120                 125

His Pro Gly Thr Leu Leu Lys Ser Gly Glu Thr Val Ile Leu Gln Cys
        130                 135                 140

Trp Ser Asp Val Met Phe Glu His Phe Phe Leu His Arg Glu Gly Ile
145                 150                 155                 160

Ser Glu Asp Pro Ser Arg Leu Val Gly Gln Ile His Asp Gly Val Ser
                165                 170                 175

Lys Ala Asn Phe Ser Ile Gly Pro Leu Met Pro Val Leu Ala Gly Thr
            180                 185                 190

Tyr Arg Cys Tyr Gly Ser Val Pro His Ser Pro Tyr Gln Leu Ser Ala
        195                 200                 205

Pro Ser Asp Pro Leu Asp Ile Val Ile Thr Gly Leu Tyr Glu Lys Pro
210                 215                 220

Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
                245                 250                 255

Arg Glu Gly Glu Ala His Glu Arg Arg Leu Arg Ala Val Pro Lys Val
            260                 265                 270

Asn Arg Thr Phe Gln Ala Asp Phe Pro Leu Gly Pro Ala Thr His Gly
        275                 280                 285

Gly Thr Tyr Arg Cys Phe Gly Ser Phe Arg Ala Leu Pro Cys Val Trp
        290                 295                 300

Ser Asn Ser Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Ile Cys
                325                 330                 335

Arg His Leu His Val Leu Ile Gly Thr Ser Val Val Ile Phe Leu Phe
            340                 345                 350

Ile Leu Leu Leu Phe Phe Leu Leu Tyr Arg Trp Cys Ser Asn Lys Lys
        355                 360                 365

Asn Ala Ala Val Met Asp Gln Glu Pro Ala Gly Asp Arg Thr Val Asn
        370                 375                 380

Arg Gln Asp Ser Asp Glu Gln Asp Pro Gln Glu Val Thr Tyr Ala Gln
385                 390                 395                 400

Leu Asp His Cys Val Phe Ile Gln Arg Lys Ile Ser Arg Pro Ser Gln
                405                 410                 415

Arg Pro Lys Thr Pro Pro Thr Asp Thr Ser Val Tyr Thr Glu Leu Pro
```

Asn Ala Glu Pro Arg Ser Lys Val Val Ser Cys Pro Arg Ala Pro Gln
            420             425                 430
Ser Gly Leu Glu Gly Val Phe
    435                 440                 445
            450                 455

<210> SEQ ID NO 167
<211> LENGTH: 455
<212> TYPE: PRT
<213> ORGANISM: HOMO SAPIENS

<400> SEQUENCE: 167

Met Ser Leu Thr Val Val Ser Met Ala Cys Val Gly Phe Phe Leu Leu
1               5                   10                  15

Gln Gly Ala Trp Pro Leu Met Gly Gly Gln Asp Lys Pro Phe Leu Ser
            20                  25                  30

Ala Arg Pro Ser Thr Val Val Pro Arg Gly Gly His Val Ala Leu Gln
        35                  40                  45

Cys His Tyr Arg Arg Gly Phe Asn Asn Phe Met Leu Tyr Lys Glu Asp
    50                  55                  60

Arg Ser His Val Pro Ile Phe His Gly Arg Ile Phe Gln Glu Ser Phe
65                  70                  75                  80

Ile Met Gly Pro Val Thr Pro Ala His Ala Gly Thr Tyr Arg Cys Arg
                85                  90                  95

Gly Ser Arg Pro His Ser Leu Thr Gly Trp Ser Ala Pro Ser Asn Pro
            100                 105                 110

Leu Val Ile Met Val Thr Gly Asn His Arg Lys Pro Ser Leu Leu Ala
        115                 120                 125

His Pro Gly Pro Leu Leu Lys Ser Gly Glu Thr Val Ile Leu Gln Cys
    130                 135                 140

Trp Ser Asp Val Met Phe Glu His Phe Phe Leu His Arg Glu Gly Ile
145                 150                 155                 160

Ser Glu Asp Pro Ser Arg Leu Val Gly Gln Ile His Asp Gly Val Ser
                165                 170                 175

Lys Ala Asn Phe Ser Ile Gly Pro Leu Met Pro Val Leu Ala Gly Thr
            180                 185                 190

Tyr Arg Cys Tyr Gly Ser Val Pro His Ser Pro Tyr Gln Leu Ser Ala
        195                 200                 205

Pro Ser Asp Pro Leu Asp Ile Val Ile Thr Gly Leu Tyr Glu Lys Pro
    210                 215                 220

Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
                245                 250                 255

Arg Glu Gly Glu Ala His Glu Arg Arg Leu Arg Ala Val Pro Lys Val
            260                 265                 270

Asn Arg Thr Phe Gln Ala Asp Phe Pro Leu Gly Pro Ala Thr His Gly
        275                 280                 285

Gly Thr Tyr Arg Cys Phe Gly Ser Phe His Ala Leu Pro Cys Val Trp
    290                 295                 300

Ser Asn Ser Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Ile Cys
                325                 330                 335

```
Arg His Leu His Val Leu Ile Gly Thr Ser Val Val Ile Phe Leu Phe
                340                 345                 350

Ile Leu Leu Leu Phe Phe Leu Leu Tyr Arg Trp Cys Ser Asn Lys Lys
            355                 360                 365

Asn Ala Ala Val Met Asp Gln Glu Pro Ala Gly Asp Arg Thr Val Asn
        370                 375                 380

Arg Gln Asp Ser Asp Glu Gln Asp Pro Gln Glu Val Thr Tyr Ala Gln
385                 390                 395                 400

Leu Asp His Cys Val Phe Ile Gln Arg Lys Ile Ser Arg Pro Ser Gln
                405                 410                 415

Arg Pro Lys Thr Pro Leu Thr Asp Thr Ser Val Tyr Thr Glu Leu Pro
            420                 425                 430

Asn Ala Glu Pro Arg Ser Lys Val Val Ser Cys Pro Arg Ala Pro Gln
        435                 440                 445

Ser Gly Leu Glu Gly Val Phe
        450                 455

<210> SEQ ID NO 168
<211> LENGTH: 455
<212> TYPE: PRT
<213> ORGANISM: HOMO SAPIENS

<400> SEQUENCE: 168

Met Ser Leu Thr Val Val Ser Met Ala Cys Val Gly Phe Phe Leu Leu
1               5                   10                  15

Gln Gly Ala Trp Pro Leu Met Gly Gly Gln Asp Lys Pro Phe Leu Ser
            20                  25                  30

Ala Arg Pro Ser Thr Val Val Pro Arg Gly Gly His Val Ala Leu Gln
        35                  40                  45

Cys His Tyr Arg Arg Gly Phe Asn Asn Phe Met Leu Tyr Lys Glu Asp
    50                  55                  60

Arg Ser His Val Pro Ile Phe His Gly Arg Ile Phe Gln Glu Ser Phe
65                  70                  75                  80

Ile Met Gly Pro Val Thr Pro Ala His Ala Gly Thr Tyr Arg Cys Arg
                85                  90                  95

Gly Ser Arg Pro His Ser Leu Thr Gly Trp Ser Ala Pro Ser Asn Pro
            100                 105                 110

Val Val Ile Met Val Thr Gly Asn His Arg Lys Pro Ser Leu Leu Ala
        115                 120                 125

His Pro Gly Pro Leu Leu Lys Ser Gly Glu Thr Val Ile Leu Gln Cys
    130                 135                 140

Trp Ser Asp Val Met Phe Glu His Phe Phe Leu His Arg Glu Gly Ile
145                 150                 155                 160

Ser Glu Asp Pro Ser Arg Leu Val Gly Gln Ile His Asp Gly Val Ser
                165                 170                 175

Lys Ala Asn Phe Ser Ile Gly Pro Leu Met Pro Val Leu Ala Gly Thr
            180                 185                 190

Tyr Arg Cys Tyr Gly Ser Val Pro His Ser Pro Tyr Gln Leu Ser Ala
        195                 200                 205

Pro Ser Asp Pro Leu Asp Ile Val Ile Thr Gly Leu Tyr Glu Lys Pro
    210                 215                 220

Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
                245                 250                 255
```

Arg Glu Gly Glu Ala His Glu Arg Leu Arg Ala Val Pro Lys Val
            260                 265                 270

Asn Arg Thr Phe Gln Ala Asp Phe Pro Leu Gly Pro Ala Thr His Gly
        275                 280                 285

Gly Thr Tyr Arg Cys Phe Gly Ser Phe Arg Ala Leu Pro Cys Val Trp
    290                 295                 300

Ser Asn Ser Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Ile Cys
            325                 330                 335

Arg His Leu His Val Leu Ile Gly Thr Ser Val Val Ile Phe Leu Phe
        340                 345                 350

Ile Leu Leu Leu Phe Phe Leu Leu Tyr Arg Trp Cys Ser Asn Lys Lys
    355                 360                 365

Asn Ala Ala Val Met Asp Gln Glu Pro Ala Gly Asp Arg Thr Val Asn
370                 375                 380

Arg Gln Asp Ser Asp Glu Gln Asp Pro Gln Glu Val Met Tyr Ala Gln
385                 390                 395                 400

Leu Asp His Cys Val Phe Ile Gln Arg Lys Ile Ser Arg Pro Ser Gln
            405                 410                 415

Arg Pro Lys Thr Pro Leu Thr Asp Thr Ser Val Tyr Thr Glu Leu Pro
        420                 425                 430

Asn Ala Glu Pro Arg Ser Lys Val Val Ser Cys Pro Arg Ala Pro Gln
    435                 440                 445

Ser Gly Leu Glu Gly Val Phe
        450                 455

<210> SEQ ID NO 169
<211> LENGTH: 444
<212> TYPE: PRT
<213> ORGANISM: homo sapiens

<400> SEQUENCE: 169

Met Ser Leu Met Val Val Ser Met Ala Cys Val Gly Leu Phe Leu Val
1               5                   10                  15

Gln Arg Ala Gly Pro His Met Gly Gly Gln Asp Lys Pro Phe Leu Ser
            20                  25                  30

Ala Trp Pro Ser Ala Val Val Pro Arg Gly Gly His Val Thr Leu Arg
        35                  40                  45

Cys His Tyr Arg His Arg Phe Asn Asn Phe Met Leu Tyr Lys Glu Asp
    50                  55                  60

Arg Ile His Ile Pro Ile Phe His Gly Arg Ile Phe Gln Glu Ser Phe
65                  70                  75                  80

Asn Met Ser Pro Val Thr Thr Ala His Ala Gly Asn Tyr Thr Cys Arg
            85                  90                  95

Gly Ser His Pro His Ser Pro Thr Gly Trp Ser Ala Pro Ser Asn Pro
        100                 105                 110

Val Val Ile Met Val Thr Gly Asn His Arg Lys Pro Ser Leu Leu Ala
    115                 120                 125

His Pro Gly Pro Leu Val Lys Ser Gly Glu Arg Val Ile Leu Gln Cys
130                 135                 140

Trp Ser Asp Ile Met Phe Glu His Phe Phe Leu His Lys Glu Gly Ile
145                 150                 155                 160

Ser Lys Asp Pro Ser Arg Leu Val Gly Gln Ile His Asp Gly Val Ser

```
                165                 170                 175
Lys Ala Asn Phe Ser Ile Gly Pro Met Met Leu Ala Leu Ala Gly Thr
            180                 185                 190

Tyr Arg Cys Tyr Gly Ser Val Thr His Thr Pro Tyr Gln Leu Ser Ala
        195                 200                 205

Pro Ser Asp Pro Leu Asp Ile Val Val Thr Gly Pro Tyr Glu Lys Pro
    210                 215                 220

Ser Leu Ser Ala Gln Pro Gly Pro Lys Val Gln Ala Gly Glu Ser Val
225                 230                 235                 240

Thr Leu Ser Cys Ser Ser Arg Ser Ser Tyr Asp Met Tyr His Leu Ser
            245                 250                 255

Arg Glu Gly Gly Ala His Glu Arg Arg Leu Pro Ala Val Arg Lys Val
        260                 265                 270

Asn Arg Thr Phe Gln Ala Asp Phe Pro Leu Gly Pro Ala Thr His Gly
    275                 280                 285

Gly Thr Tyr Arg Cys Phe Gly Ser Phe Arg His Ser Pro Tyr Glu Trp
290                 295                 300

Ser Asp Pro Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Asn Pro
            325                 330                 335

Arg His Leu His Ile Leu Ile Gly Thr Ser Val Val Ile Ile Leu Phe
        340                 345                 350

Ile Leu Leu Leu Phe Phe Leu Leu His Leu Trp Cys Ser Asn Lys Lys
    355                 360                 365

Asn Ala Ala Val Met Asp Gln Glu Pro Ala Gly Asn Arg Thr Ala Asn
    370                 375                 380

Ser Glu Asp Ser Asp Glu Gln Asp Pro Glu Glu Val Thr Tyr Ala Gln
385                 390                 395                 400

Leu Asp His Cys Val Phe Thr Gln Arg Lys Ile Thr Arg Pro Ser Gln
            405                 410                 415

Arg Pro Lys Thr Pro Pro Thr Asp Thr Ile Leu Tyr Thr Glu Leu Pro
        420                 425                 430

Asn Ala Lys Pro Arg Ser Lys Val Val Ser Cys Pro
    435                 440

<210> SEQ ID NO 170
<211> LENGTH: 118
<212> TYPE: PRT
<213> ORGANISM: Homo sapiens

<400> SEQUENCE: 170

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Ala Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
            85                  90                  95
```

Ala Arg Arg Tyr Asp Gly Tyr Tyr His Phe Asp Tyr Trp Gly Gln Gly
            100                 105                 110

Thr Thr Leu Thr Val Ser
        115

<210> SEQ ID NO 171
<211> LENGTH: 115
<212> TYPE: PRT
<213> ORGANISM: Homo sapiens

<400> SEQUENCE: 171

Asp Ile Val Met Thr Gln Ser Pro Ser Leu Ala Val Thr Ala Gly
1               5                   10                  15

Glu Lys Val Thr Met Ser Cys Lys Ser Ser Gln Ser Leu Leu Trp Ser
            20                  25                  30

Val Asn Gln Lys Asn Tyr Leu Ser Trp Tyr Gln Gln Lys Gln Arg Gln
            35                  40                  45

Pro Pro Lys Leu Leu Ile Tyr Gly Ala Ser Ile Arg Glu Ser Trp Val
        50                  55                  60

Pro Asp Arg Phe Thr Gly Ser Gly Ser Gly Thr Asp Phe Thr Leu Thr
65                  70                  75                  80

Ile Ser Asn Val His Ala Glu Asp Leu Ala Val Tyr Tyr Cys Gln His
                85                  90                  95

Asn His Gly Ser Phe Leu Pro Leu Thr Phe Gly Ser Gly Thr Lys Leu
            100                 105                 110

Glu Ile Lys
        115

<210> SEQ ID NO 172
<211> LENGTH: 5
<212> TYPE: PRT
<213> ORGANISM: Homo sapiens

<400> SEQUENCE: 172

Ser Tyr Trp Met Gln
1               5

<210> SEQ ID NO 173
<211> LENGTH: 6
<212> TYPE: PRT
<213> ORGANISM: Homo sapiens

<400> SEQUENCE: 173

Gly Tyr Thr Phe Thr Ser
1               5

<210> SEQ ID NO 174
<211> LENGTH: 10
<212> TYPE: PRT
<213> ORGANISM: Homo sapiens

<400> SEQUENCE: 174

Gly Tyr Thr Phe Thr Ser Tyr Trp Met Gln
1               5                   10

<210> SEQ ID NO 175
<211> LENGTH: 17
<212> TYPE: PRT
<213> ORGANISM: Homo sapiens

<400> SEQUENCE: 175

```
Ala Ile Tyr Pro Gly Asp Gly Asp Thr Arg Tyr Thr Gln Lys Phe Lys
1               5                   10                  15

Gly

<210> SEQ ID NO 176
<211> LENGTH: 10
<212> TYPE: PRT
<213> ORGANISM: Homo sapiens

<400> SEQUENCE: 176

Ala Ile Tyr Pro Gly Asp Gly Asp Thr Arg
1               5                   10

<210> SEQ ID NO 177
<211> LENGTH: 10
<212> TYPE: PRT
<213> ORGANISM: Homo sapiens

<400> SEQUENCE: 177

Arg Tyr Asp Gly Tyr Tyr His Phe Asp Tyr
1               5                   10

<210> SEQ ID NO 178
<211> LENGTH: 17
<212> TYPE: PRT
<213> ORGANISM: Homo sapiens

<400> SEQUENCE: 178

Lys Ser Ser Gln Ser Leu Leu Trp Ser Val Asn Gln Lys Asn Tyr Leu
1               5                   10                  15

Ser

<210> SEQ ID NO 179
<211> LENGTH: 7
<212> TYPE: PRT
<213> ORGANISM: Homo sapiens

<400> SEQUENCE: 179

Gly Ala Ser Ile Arg Glu Ser
1               5

<210> SEQ ID NO 180
<211> LENGTH: 11
<212> TYPE: PRT
<213> ORGANISM: Homo sapiens

<400> SEQUENCE: 180

Gln His Asn His Gly Ser Phe Leu Pro Leu Thr
1               5                   10

<210> SEQ ID NO 181
<211> LENGTH: 120
<212> TYPE: PRT
<213> ORGANISM: Homo sapiens

<400> SEQUENCE: 181

Gln Val Gln Leu Gln Gln Ser Gly Ala Glu Val Ala Arg Pro Gly Ala
1               5                   10                  15

Ser Val Lys Leu Ser Cys Lys Ser Ser Gly Phe Thr Phe Thr Thr Tyr
                20                  25                  30

Trp Met Gln Trp Val Lys Gln Arg Pro Gly Gln Gly Leu Glu Trp Ile
            35                  40                  45
```

```
Gly Ala Ile Tyr Pro Gly Asp Gly Asp Thr Arg Tyr Thr Gln Lys Phe
 50                  55                  60

Lys Gly Lys Ala Thr Leu Thr Ala Asp Lys Ser Ser Ile Thr Ala Tyr
 65                  70                  75                  80

Met Gln Leu Ser Ser Leu Ala Ser Glu Asp Ser Ala Val Tyr Tyr Cys
                 85                  90                  95

Ala Arg Arg Gly Asp Tyr Gly Asn Tyr Gly Met Asp Tyr Trp Gly Gln
            100                 105                 110

Gly Thr Ser Val Thr Val Ser Ser
            115                 120

<210> SEQ ID NO 182
<211> LENGTH: 112
<212> TYPE: PRT
<213> ORGANISM: Homo sapiens

<400> SEQUENCE: 182

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
                 20                  25                  30

Asn Gly Asn Thr Tyr Leu Glu Trp Tyr Leu Gln Lys Pro Gly Gln Ser
             35                  40                  45

Pro Lys Leu Leu Ile Tyr Lys Val Ser Asn His Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Pro Thr Phe Gly Gly Gly Thr Lys Leu Glu Ile Lys
            100                 105                 110

<210> SEQ ID NO 183
<211> LENGTH: 5
<212> TYPE: PRT
<213> ORGANISM: Homo sapiens

<400> SEQUENCE: 183

Thr Tyr Trp Met Gln
 1               5

<210> SEQ ID NO 184
<211> LENGTH: 6
<212> TYPE: PRT
<213> ORGANISM: Homo sapiens

<400> SEQUENCE: 184

Gly Phe Thr Phe Thr Thr
 1               5

<210> SEQ ID NO 185
<211> LENGTH: 10
<212> TYPE: PRT
<213> ORGANISM: Homo sapiens

<400> SEQUENCE: 185

Gly Phe Thr Phe Thr Thr Tyr Trp Met Gln
 1               5                  10

<210> SEQ ID NO 186
```

-continued

```
<211> LENGTH: 17
<212> TYPE: PRT
<213> ORGANISM: Homo sapiens

<400> SEQUENCE: 186

Ala Ile Tyr Pro Gly Asp Gly Asp Thr Arg Tyr Thr Gln Lys Phe Lys
1               5                   10                  15
Gly

<210> SEQ ID NO 187
<211> LENGTH: 10
<212> TYPE: PRT
<213> ORGANISM: Homo sapiens

<400> SEQUENCE: 187

Ala Ile Tyr Pro Gly Asp Gly Asp Thr Arg
1               5                   10

<210> SEQ ID NO 188
<211> LENGTH: 11
<212> TYPE: PRT
<213> ORGANISM: Homo sapiens

<400> SEQUENCE: 188

Arg Gly Asp Tyr Gly Asn Tyr Gly Met Asp Tyr
1               5                   10

<210> SEQ ID NO 189
<211> LENGTH: 16
<212> TYPE: PRT
<213> ORGANISM: Homo sapiens

<400> SEQUENCE: 189

Arg Ser Ser Gln Ser Ile Val His Ser Asn Gly Asn Thr Tyr Leu Glu
1               5                   10                  15

<210> SEQ ID NO 190
<211> LENGTH: 7
<212> TYPE: PRT
<213> ORGANISM: Homo sapiens

<400> SEQUENCE: 190

Lys Val Ser Asn His Phe Ser
1               5

<210> SEQ ID NO 191
<211> LENGTH: 9
<212> TYPE: PRT
<213> ORGANISM: Homo sapiens

<400> SEQUENCE: 191

Phe Gln Gly Ser His Val Pro Pro Thr
1               5

<210> SEQ ID NO 192
<211> LENGTH: 5
<212> TYPE: PRT
<213> ORGANISM: Artificial Sequence
<220> FEATURE:
<223> OTHER INFORMATION: sequence used to identify CDR-H1

<400> SEQUENCE: 192

Leu Glu Trp Ile Gly
1               5
```